US010428017B2

(12) United States Patent
Altenbach et al.

(10) Patent No.: US 10,428,017 B2
(45) Date of Patent: Oct. 1, 2019

(54) MODULATORS OF THE CYSTIC FIBROSIS TRANSMEMBRANE CONDUCTANCE REGULATOR PROTEIN AND METHODS OF USE

(71) Applicants: AbbVie S.à.r.l., Luxembourg (LU); Galapagos NV, Mechelen (BE)

(72) Inventors: Robert J. Altenbach, Chicago, IL (US); Andrew Bogdan, Evanston, IL (US); Nicolas Desroy, Romainville (FR); Gregory A. Gfesser, Lindenhurst, IL (US); Stephen N. Greszler, Vernon Hills, IL (US); Philip R. Kym, Libertyville, IL (US); Bo Liu, Waukegan, IL (US); Karine Fabienne Malagu, Saffron (GB); Nuria Merayo Merayo, Romainville (FR); Mathieu Rafaël Pizzonero, Romainville (FR); Xenia B. Searle, Grayslake, IL (US); Steven Emiel Van der Plas, Mechelen (BE); Xueqing Wang, Northbrook, IL (US); Ming C. Yeung, Grayslake, IL (US); Gang Zhao, Northbrook, IL (US)

(73) Assignees: AbbVie S.á.r.l., Luxembourg (LU); Galapagos NV, Mechelen (BE)

( * ) Notice: Subject to any disclaimer, the term of this patent is extended or adjusted under 35 U.S.C. 154(b) by 0 days.

(21) Appl. No.: 15/902,802

(22) Filed: Feb. 22, 2018

(65) Prior Publication Data
US 2018/0244640 A1 Aug. 30, 2018

Related U.S. Application Data

(60) Provisional application No. 62/463,019, filed on Feb. 24, 2017, provisional application No. 62/583,237, filed on Nov. 8, 2017.

(51) Int. Cl.

| C07D 405/12 | (2006.01) |
| C07C 311/51 | (2006.01) |
| A61P 11/00 | (2006.01) |
| C07D 215/48 | (2006.01) |
| C07D 307/81 | (2006.01) |
| C07D 311/04 | (2006.01) |
| C07D 311/76 | (2006.01) |
| C07D 317/68 | (2006.01) |
| C07D 319/22 | (2006.01) |
| C07C 317/14 | (2006.01) |
| C07D 407/12 | (2006.01) |
| C07D 307/16 | (2006.01) |

(52) U.S. Cl.
CPC ............ *C07C 311/51* (2013.01); *A61P 11/00* (2018.01); *C07C 317/14* (2013.01); *C07D 215/48* (2013.01); *C07D 307/16* (2013.01); *C07D 307/81* (2013.01); *C07D 311/04* (2013.01); *C07D 311/76* (2013.01); *C07D 317/68* (2013.01); *C07D 319/22* (2013.01); *C07D 405/12* (2013.01); *C07D 407/12* (2013.01); *C07C 2601/02* (2017.05); *C07C 2601/04* (2017.05); *C07C 2601/08* (2017.05); *C07C 2601/14* (2017.05); *C07C 2602/06* (2017.05); *C07C 2602/08* (2017.05); *C07C 2602/10* (2017.05)

(58) Field of Classification Search
CPC .. C07D 405/12; C07D 407/12; C07D 319/22; C07D 307/16; A61K 31/381; A61K 31/343
See application file for complete search history.

(56) References Cited

U.S. PATENT DOCUMENTS

| 5,889,045 | A | 3/1999 | Muller et al. |
| 8,999,976 | B2 | 4/2015 | Binch et al. |
| 2018/0099931 | A1 | 3/2018 | Altenbach et al. |
| 2018/0099932 | A1 | 3/2018 | Altenbach et al. |

FOREIGN PATENT DOCUMENTS

| EP | 0995742 A1 | 4/2000 |
| WO | 9533742 A1 | 12/1995 |
| WO | 9620193 A1 | 7/1996 |
| WO | 2005120497 A2 | 12/2005 |
| WO | 2006002421 A2 | 1/2006 |
| WO | 2008147952 A1 | 12/2008 |
| WO | 2009074575 A2 | 6/2009 |
| WO | 2009076593 A1 | 6/2009 |
| WO | 2010048573 A1 | 4/2010 |
| WO | 2011072241 A1 | 6/2011 |
| WO | 2011113894 A1 | 9/2011 |
| WO | 2013038373 A1 | 3/2013 |
| WO | 2013038378 A1 | 3/2013 |
| WO | 2013038381 A1 | 3/2013 |
| WO | 2013038386 A1 | 3/2013 |

(Continued)

OTHER PUBLICATIONS

Portevin et al., Dual inhibitors of Human Leukocyte Elastase and Lipid Peroxidation, J Med Chem, 40(12): 1906-1918 (1997).*
STN Registry RN 1808507-55-2 (Entered STN Sep. 29, 2015).*
STN Registry RN 1444312-15-5 (Entered STN Jul. 16, 2013).*
STN Registry RN 1333762-60-9 (Entered STN Sep. 29, 2011).*
Quinton, P.M., 1990. Cystic fibrosis: a disease in electrolyte transport. FASEB J. 4, 2709-2717.
Kerem, B., Rommens, J.M., Buchanan, J.A., Markiewicz, D., Cox, T.K., Chakravarti, A., Buchwald, M., Tsui, L.C., 1989. Identification of the cystic fibrosis gene: genetic analysis. Science 245, 1073-1080.

(Continued)

*Primary Examiner* — Deepak R Rao
(74) *Attorney, Agent, or Firm* — Quarles & Brady LLP

(57) ABSTRACT

The present invention relates to compounds and their use in the treatment of cystic fibrosis, methods for their production, pharmaceutical compositions comprising the same, and methods of treating cystic fibrosis by administering a compound of the invention.

19 Claims, No Drawings

(56) References Cited

FOREIGN PATENT DOCUMENTS

| WO | 2013038390 A1 | 3/2013 |
| WO | 2013043720 A1 | 3/2013 |
| WO | 2013125732 A1 | 8/2013 |
| WO | 2014180562 A1 | 12/2014 |
| WO | 2015018823 A1 | 2/2015 |
| WO | 2015138909 A1 | 9/2015 |
| WO | 2015138934 A1 | 9/2015 |
| WO | 2016069757 A1 | 5/2016 |
| WO | 2016069891 A1 | 5/2016 |
| WO | 2016193812 A1 | 12/2016 |
| WO | 2017009804 A1 | 1/2017 |
| WO | 2017060873 A1 | 4/2017 |
| WO | 2017060874 A1 | 4/2017 |
| WO | 2017187321 A1 | 11/2017 |
| WO | 2017208115 A1 | 12/2017 |

OTHER PUBLICATIONS

Bobadilla, J.L., Macek, M., Jr, Fine, J.P., Farrell, P.M., 2002. Cystic fibrosis: a worldwide analysis of CFTR mutations—correlation with incidence data and application to screening. Hum. Mutat. 19, 575-606. doi:10.1002/humu.10041.

Pasyk, E.A., Foskett, J.K., 1995. Mutant (ΔF508) Cystic Fibrosis Transmembrane Conductance Regulator Cl-Channel Is Functional When Retained in Endoplasmic Reticulum of Mammalian Cells. J. Biol. Chem. 270, 12347-12350.

Morello, J.-P., Bouvier, M., Petäjä-Repo, U.E., Bichet, D.G., 2000. Pharmacological chaperones: a new twist on receptor folding. Trends Pharmacol. Sci. 21, 466-469. doi:10.1016/S0165-6147(00)01575-3.

Shastry, B.S., 2003. Neurodegenerative disorders of protein aggregation. Neurochem. Int. 43, 1-7. doi:10.1016/S0197-0186(02)00196-1.

Zhang W., Fujii, N., Naren, A.P., 2012. Recent advances and new perspectives in targeting CFTR for therapy of cystic fibrosis and enterotoxin-induced secretory diarrheas. Future Med. Chem. 4, 329-345. doi:10.4155/fmc.12.1.

IUPAC 1974 Recommendations for Section E, Fundamental Stereochemistry, in Pure Appl. Chem., 1976, 45: 13-30.

S. M. Berge et al. J. Pharmaceutical Sciences, 1977, 66: 1-19.

Burch, J.D. "Structure-activity relationships and pharmacokinetic parameters of quinolone acylsulfonamides as potent and selective antagonists of the EP4 receptor", Bioorganic & Medical Chemistry Letters 18 (2008) 2048-2054.

ISR/WO from PCT/IB2018/051125; May 3, 2018, 12 pages.

ISR/WO from PCT/IB2018/051160; May 2, 2018, 13 pages.

First Office Action issued in corresponding Pakastani Patent Application No. 103/2018, dated Mar. 29, 2019, 2 pages.

* cited by examiner

MODULATORS OF THE CYSTIC FIBROSIS TRANSMEMBRANE CONDUCTANCE REGULATOR PROTEIN AND METHODS OF USE

CROSS REFERENCE TO RELATED APPLICATIONS

This application claims priority to U.S. Provisional Application No. 62/463,019, filed Feb. 24, 2017 and U.S. Provisional Application No. 62/583,237, filed Nov. 8, 2017, both of which are incorporated herein by reference for all purposes.

BACKGROUND OF THE INVENTION

Technical Field

This invention relates to compounds that are modulators of the Cystic Fibrosis Transmembrane Conductance Regulator (CFTR) protein, useful in treating diseases and conditions mediated and modulated by CFTR. This invention also relates to compositions containing compounds of the invention, processes for their preparation, and methods of treatment using them.

Description of Related Technology

ABC transporters are a family of homologous membrane transporter proteins regulating the transport of a wide variety of pharmacological agents (for example drugs, xenobiotics, anions, etc.) that bind and use cellular adenosine triphosphate (ATP) for their specific activities. Some of these transporters were found to defend malignant cancer cells against chemotherapeutic agents, acting as multidrug resistance proteins (like the MDR1-P glycoprotein, or the multidrug resistance protein, MRP 1). So far, 48 ABC transporters, grouped into 7 families based on their sequence identity and function, have been identified.

ABC transporters provide protection against harmful environmental compounds by regulating a variety of important physiological roles within the body, and therefore represent important potential drug targets for the treatment of diseases associated with transporter defects, outwards cell drug transport, and other diseases in which modulation of ABC transporter activity may be beneficial.

The cAMP/ATP-mediated anion channel, CFTR, is one member of the ABC transporter family commonly associated with diseases, which is expressed in a variety of cell types, including absorptive and secretory epithelia cells, where it regulates anion flux across the membrane, as well as the activity of other ion channels and proteins. The activity of CFTR in epithelial cells is essential for the maintenance of electrolyte transport throughout the body, including respiratory and digestive tissue (Quinton, P. M., 1990. Cystic fibrosis: a disease in electrolyte transport. FASEB J. 4, 2709-2717).

The gene encoding CFTR has been identified and sequenced (Kerem, B., Rommens, J. M., Buchanan, J. A., Markiewicz, D., Cox, T. K., Chakravarti, A., Buchwald, M., Tsui, L. C., 1989. Identification of the cystic fibrosis gene: genetic analysis. Science 245, 1073-1080). CFTR comprises about 1480 amino acids that encode a protein made up of a tandem repeat of transmembrane domains, each containing six transmembrane helices and a nucleotide binding domain. The pair of transmembrane domains is linked by a large, polar, regulatory (R)-domain with multiple phosphorylation sites that regulate channel activity and cellular trafficking.

Cystic fibrosis (CF) is caused by a defect in this gene which induces mutations in CFTR. Cystic fibrosis is the most common fatal genetic disease in humans, and affects ~0.04% of white individuals (Bobadilla, J. L., Macek, M., Jr, Fine, J. P., Farrell, P. M., 2002. Cystic fibrosis: a worldwide analysis of CFTR mutations—correlation with incidence data and application to screening. Hum. Mutat. 19, 575-606. doi: 10.1002/humu.10041), for example, in the United States, about one in every 2,500 infants is affected, and up to 10 million people carry a single copy of the defective gene without apparent ill effects; moreover subjects bearing a single copy of the gene exhibit increased resistance to cholera and to dehydration resulting from diarrhea. This effect might explain the relatively high frequency of the CF gene within the population.

In contrast, individuals with two copies of the CF associated gene suffer from the debilitating and fatal effects of CF, including chronic lung infections.

In cystic fibrosis patients, mutations in endogenous respiratory epithelial CFTR fails to confer chloride and bicarbonate permeability to epithelial cells in lung and other tissues, thus leading to reduced apical anion secretion and disruptions of the ion and fluid transport. This decrease in anion transport causes an enhanced mucus and pathogenic agent accumulation in the lung triggering microbial infections that ultimately cause death in CF patients.

Beyond respiratory disease, CF patients also suffer from gastrointestinal problems and pancreatic insufficiency that result in death if left untreated. Furthermore, female subjects with cystic fibrosis suffer from decreased fertility, whilst males with cystic fibrosis are infertile.

A variety of disease causing mutations has been identified through sequence analysis of the CFTR gene of CF chromosomes (Kerem, B., Rommens, J. M., Buchanan, J. A., Markiewicz, D., Cox, T. K., Chakravarti, A., Buchwald, M., Tsui, L. C., 1989. Identification of the cystic fibrosis gene: genetic analysis. Science 245, 1073-1080). F508delCFTR, the most common CF mutation (present in at least 1 allele in ~90% of CF patients) and occurring in approximately 70% of the cases of cystic fibrosis, contains a single amino acid deletion of phenylalanine 508. This deletion prevents the nascent protein from folding correctly, which protein in turn cannot exit the endoplasmic reticulum (ER) and traffic to the plasma membrane, and then is rapidly degraded. As a result, the number of channels present in the membrane is far less than in cells expressing wild-type CFTR. In addition to impaired trafficking, the mutation results in defective channel gating. Indeed, even if F508delCFTR is allowed to reach the cell plasma membrane by low-temperature (27° C.) rescue where it can function as a cAMP-activated chloride channel, its activity is decreased significantly compared with WT-CFTR (Pasyk, E. A., Foskett, J. K., 1995. Mutant (F508delCTFR) Cystic Fibrosis Transmembrane Conductance Regulator Cl⁻ channel is functional when retained in Endoplasmic Reticulum of mammalian cells. J. Biol. Chem. 270, 12347-12350).

Other mutations with lower incidence have also been identified that alter the channel regulation or the channel conductance. In case of the channel regulation mutants, the mutated protein is properly trafficked and localized to the plasma membrane but either cannot be activated or cannot function as a chloride channel (e.g. missense mutations located within the nucleotide binding domains), examples of these mutations are G551D, G178R, and G1349D. Mutations affecting chloride conductance have a CFTR protein that is correctly trafficked to the cell membrane but that generates reduced chloride flow (e.g. missense mutations located within the membrane-spanning domain), examples of these mutations are R117H and R334W.

In addition to cystic fibrosis, CFTR activity modulation may be beneficial for other diseases not directly caused by mutations in CFTR, such as, for example, chronic obstructive pulmonary disease (COPD), dry eye disease, and Sjögren's syndrome.

COPD is characterized by a progressive and non-reversible airflow limitation, which is due to mucus hypersecretion, bronchiolitis, and emphysema. A potential treatment of mucus hypersecretion and impaired mucociliary clearance that is common in COPD could consist in using activators of mutant or wild-type CFTR. In particular, the anion secretion increase across CFTR may facilitate fluid transport into the airway surface liquid to hydrate the mucus and optimize periciliary fluid viscosity. The resulting enhanced mucociliary clearance would help in reducing the symptoms associated with COPD.

Dry eye disease is characterized by a decrease in tear production and abnormal tear film lipid, protein and mucin profiles. Many factors may cause dry eye disease, some of which include age, arthritis, Lasik eye surgery, chemical/thermal burns, medications, allergies, and diseases, such as cystic fibrosis and Sjögren's syndrome. Increasing anion secretion via CFTR could enhance fluid transport from the corneal endothelial cells and secretory glands surrounding the eye, and eventually improve corneal hydration, thus helping to alleviate dry eye disease associated symptoms. Sjögren's syndrome is an autoimmune disease where the immune system harms moisture-producing glands throughout the body, including the eye, mouth, skin, respiratory tissue, liver, vagina, and gut. The ensuing symptoms, include, dry eye, mouth, and vagina, as well as lung disease. Sjögren's syndrome is also associated with rheumatoid arthritis, systemic lupus, systemic sclerosis, and polymyositis/dermatomyositis. The cause of the disease is believed to lie in defective protein trafficking, for which treatment options are limited. As a consequence, modulation of CFTR activity may help hydrating the various organs and help to elevate the associated symptoms.

In addition to CF, the defective protein trafficking induced by the 508delCFTR has been shown to be the underlying basis for a wide range of other diseases, in particular diseases where the defective functioning of the endoplasmic reticulum (ER) may either prevent the CFTR protein to exit the cell, and/or the misfolded protein is degraded (Morello, J.-P., Bouvier, M., Petaja-Repo, U. E., Bichet, D. G., 2000. Pharmacological chaperones: a new twist on receptor folding. Trends Pharmacol. Sci. 21, 466-469. doi: 10.1016/S0165-6147(00)01575-3; Shastry, B. S., 2003. Neurodegenerative disorders of protein aggregation. Neurochem. Int. 43, 1-7. doi:10.1016/S0197-0186(02)00196-1; Zhang, W., Fujii, N., Naren, A. P., 2012. Recent advances and new perspectives in targeting CFTR for therapy of cystic fibrosis and enterotoxin-induced secretory diarrheas. (Future Med. Chem. 4, 329-345. doi:10.4155/fmc.12.1).

A number of genetic diseases are associated with a defective ER processing equivalent to the defect observed with CFTR in CF such as glycanosis CDG type 1, hereditary emphysema (α-1-antitrypsin (PiZ variant)), congenital hyperthyroidism, osteogenesis imperfecta (Type I, II, or IV procollagen), hereditary hypofibrinogenemia (fibrinogen), ACT deficiency (α-1-antichymotrypsin), diabetes insipidus (DI), neurophyseal DI (vasopvessin hormoneN2-receptor), neprogenic DI (aquaporin II), Charcot-Marie Tooth syndrome (peripheral myelin protein 22), Perlizaeus-Merzbacher disease, neurodegenerative diseases such as Alzheimer's disease (APP and presenilins), Parkinson's disease, amyotrophic lateral sclerosis, progressive supranuclear palsy, Pick's disease, several polyglutamine neurological disorders such as Huntington's disease, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (prion protein processing defect), Fabry disease (lysosomal α-galactosidase A), Straussler-Scheinker syndrome, chronic obstructive pulmonary disease (COPD), dry eye disease, and Sjögren's syndrome.

In addition to up-regulation of the activity of CFTR, anion secretion reduction by CFTR modulators may be beneficial for the treatment of secretory diarrheas, in which epithelial water transport is dramatically increased as a result of secretagogue activated chloride transport. The mechanism involves elevation of cAMP and stimulation of CFTR.

Regardless of the cause, excessive chloride transport is seen in all diarrheas, and results in dehydration, acidosis, impaired growth and death. Acute and chronic diarrheas remain a major medical problem worldwide, and are a significant factor in malnutrition, leading to death in children of less than five years old (5,000,000 deaths/year). Furthermore, in patients with chronic inflammatory bowel disease (IBD) and/or acquired immunodeficiency syndrome (AIDS), diarrhea is a dangerous condition.

Accordingly, there is a need for novel compounds able to modulate CFTR. In particular, the present invention discloses compounds that may act as CFTR modulators for the treatment of cystic fibrosis. The present invention also provides methods for the preparation of these compounds, pharmaceutical compositions comprising these compounds and methods for the treatment of cystic fibrosis by administering the compounds of the invention.

SUMMARY

In one aspect, the invention provides for compounds of Formula (I)

(I)

wherein

A$^1$ is selected from the group consisting of

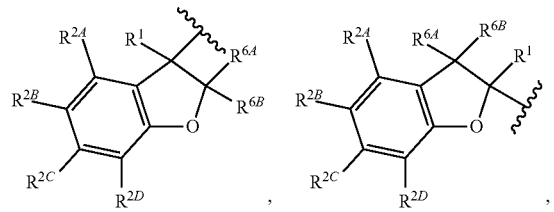

,

-continued

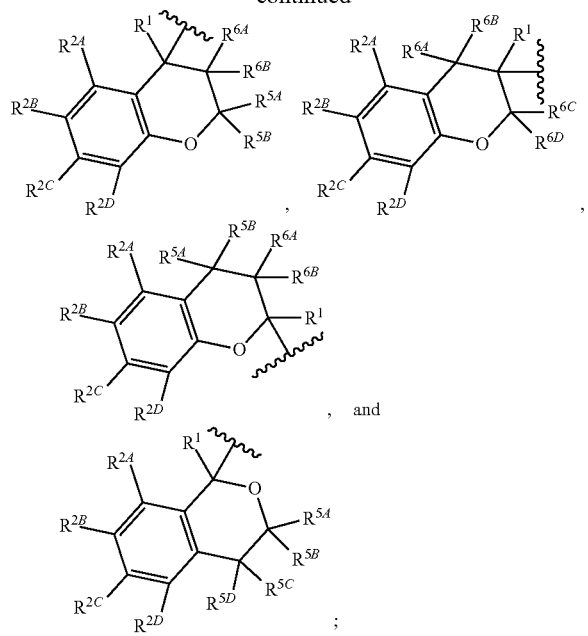

R¹ is selected from the group consisting of hydrogen, OH, CN, $C_1$-$C_6$ alkyl, $C_2$-$C_6$ alkenyl, $C_2$-$C_6$ alkynyl, $C_1$-$C_6$ alkoxy, 6-10 membered aryl, 5-11 membered heteroaryl, $C_3$-$C_{11}$cycloalkyl, $C_4$-$C_{11}$ cycloalkenyl, and 4-12 membered heterocyclyl; wherein the R¹ $C_1$-$C_6$ alkyl, $C_2$-$C_6$ alkenyl, $C_2$-$C_6$ alkynyl, and $C_1$-$C_6$ alkoxy are optionally substituted with one or more substituents independently selected from the group consisting of $R^7$, $OR^7$, $SR^7$, $NHR^7$, $N(R^7)_2$, $NH_2$, C(O)OH, OH, CN, $NO_2$, F, Cl, Br and I; wherein the R¹ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $C_1$-$C_6$ alkyl, $C_1$-$C_6$ haloalkyl, $C_1$-$C_6$ alkoxy, $C_1$-$C_6$ haloalkoxy, C(O)OH, OH, oxo, CN, $NO_2$, F, Cl, Br and I;

one of $R^{2A}$, $R^{2B}$, $R^{2C}$, and $R^{2D}$ is hydrogen, and the remaining are independently selected from the group consisting of hydrogen, $R^8$, $OR^8$, $C(O)R^8$, $C(O)OR^8$, $SO_2R^8$, $NHR^8$, $N(R^8)_2$, $NH_2$, C(O)OH, OH, CN, $NO_2$, F, Cl, Br and I; or two of $R^{2A}$, $R^{2B}$, $R^{2C}$, and $R^{2D}$ on adjacent carbons form a fused ring selected from the group consisting of phenyl, 5-6 membered heteroaryl, $C_3$-$C_7$ cycloalkyl, $C_4$-$C_7$ cycloalkenyl, and 4-7 membered heterocyclyl; and the remaining are independently selected from the group consisting of hydrogen, $R^8$, $OR^8$, $C(O)R^8$, $OC(O)R^8$, $C(O)OR^8$, $SO_2R^8$, $NHR^8$, $N(R^8)_2$, $NH_2$, C(O)OH, OH, CN, $NO_2$, F, Cl, Br and I; wherein the phenyl, 5-6 membered heteroaryl, $C_3$-$C_7$ cycloalkyl, $C_4$-$C_7$ cycloalkenyl, and 4-7 membered heterocyclyl are optionally substituted with one or more substituents independently selected from the group consisting of $R^8$, $OR^8$, $C(O)R^8$, $OC(O)R^8$, $C(O)OR^8$, $SO_2R^8$, $NHR^8$, $N(R^8)_2$, $NH_2$, C(O)OH, OH, CN, $NO_2$, F, Cl, Br and I;

R³ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the R³ $C_2$-$C_6$ alkyl, $C_2$-$C_6$ alkenyl, and $C_2$-$C_6$ alkynyl are optionally substituted with one or more substituents independently selected from the group consisting of $C_1$-$C_6$ alkoxy, phenyl, OH, oxo, CN, $NO_2$, F, Cl, Br and I; wherein the R³ 6-10 membered aryl, 5-11 membered heteroaryl, $C_3$-$C_{11}$cycloalkyl, $C_4$-$C_{11}$ cycloalkenyl, and 4-12 membered heterocyclyl are optionally substituted with one or more substituents independently selected from the group consisting of $R^9$, $OR^9$, $C(O)R^9$, $OC(O)R^9$, $C(O)OR^9$, $SO_2R^9$, $C(O)NH_2$, $C(O)NHR^9$, $C(O)N(R^9)_2$, $NHC(O)R^9$, $NHR^9$, $N(R^9)_2$, $NH_2$, C(O)OH, OH, oxo, CN, $NO_2$, F, Cl, Br and I;

R⁴ is selected from the group consisting of hydrogen and $C_1$-$C_6$ alkyl; wherein the R⁴ $C_1$-$C_6$ alkyl is optionally substituted with one or more substituents independently selected from the group consisting of $R^{10}$, $OR^{10}$, $SR^{10}$, $NHR^{10}$, $N(R^{10})_2$, $NH_2$, C(O)OH, OH, oxo, CN, $NO_2$, F, Cl, Br and I;

$R^{5A}$, $R^{5B}$, $R^{5C}$, and $R^{5D}$ are each independently selected from the group consisting of hydrogen, $C_1$-$C_6$ alkyl, $C_2$-$C_6$ alkenyl, $C_2$-$C_6$ alkynyl, $C_1$-$C_6$ alkoxy, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^{5A}$, $R^{5B}$, $R^{5C}$, and $R^{5D}$ $C_1$-$C_6$ alkyl, $C_2$-$C_6$ alkenyl, $C_2$-$C_6$ alkynyl, and $C_1$-$C_6$ alkoxy are optionally substituted with one or more substituents independently selected from the group consisting of 6-10 membered aryl, 5-11 membered heteroaryl, $C_3$-$C_{11}$ cycloalkyl, $C_4$-$C_{11}$ cycloalkenyl, 4-12 membered heterocyclyl, $C_1$-$C_6$ thioalkyl, OH, oxo, CN, $NO_2$, F, Cl, Br and I; wherein the $R^{5A}$, $R^{5B}$, $R^{5C}$, and $R^{5D}$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $C_1$-$C_6$ alkyl, C(O)OH, $NH_2$, OH, oxo, CN, $NO_2$, F, Cl, Br and I; or $R^{5A}$ and $R^{5B}$, together with the carbon atom to which they are attached, form a $C_3$-$C_7$ monocyclic cycloalkyl or a 4-7 membered monocyclic heterocycle; wherein the $C_3$-$C_7$ monocyclic cycloalkyl and the 4-7 membered monocyclic heterocycle are each optionally substituted with one or more substituents independently selected from the group consisting of $C_1$-$C_6$ alkyl, C(O)OH, $NH_2$, OH, oxo, CN, $NO_2$, F, Cl, Br and I; and $R^{5C}$ and $R^{5D}$ are each independently selected from the group consisting of hydrogen, $C_1$-$C_6$ alkyl, $C_2$-$C_6$ alkenyl, $C_2$-$C_6$ alkynyl, $C_1$-$C_6$ alkoxy, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^{5C}$ and $R^{5D}$ $C_1$-$C_6$ alkyl, $C_2$-$C_6$ alkenyl, $C_2$-$C_6$ alkynyl, and $C_1$-$C_6$ alkoxy are optionally substituted with one or more substituents independently selected from the group consisting of 6-10 membered aryl, 5-11 membered heteroaryl, $C_3$-$C_{11}$ cycloalkyl, $C_4$-$C_{11}$ cycloalkenyl, 4-12 membered heterocyclyl, $C_1$-$C_6$ thioalkyl, OH, oxo, CN, $NO_2$, F, Cl, Br and I; wherein the $R^{5C}$ and $R^{5D}$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $C_1$-$C_6$ alkyl, C(O)OH, $NH_2$, OH, oxo, CN, $NO_2$, F, Cl, Br and I; or $R^{5C}$ and $R^{5D}$, together with the carbon atom to which they are attached, form a $C_3$-$C_7$ monocyclic cycloalkyl or a 4-7 membered monocyclic heterocycle; wherein the $C_3$-$C_7$ monocyclic cycloalkyl and the 4-7 membered monocyclic heterocycle are each optionally substituted with one or more substituents independently selected from the group consisting of $C_1$-$C_6$ alkyl, C(O)OH, $NH_2$, OH, oxo, CN, $NO_2$, F, Cl, Br and I; and $R^{5A}$ and $R^{5B}$ are each independently selected from the group consisting of hydrogen, $C_1$-$C_6$ alkyl, $C_2$-$C_6$ alkenyl, $C_2$-$C_6$ alkynyl, $C_1$-$C_6$ alkoxy, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^{5A}$ and $R^{5B}$ $C_1$-$C_6$ alkyl, $C_2$-$C_6$ alkenyl, $C_2$-$C_6$ alkynyl, and $C_1$-$C_6$ alkoxy are optionally substituted with one or more substituents independently selected from the group consisting of 6-10 membered aryl, 5-11 membered heteroaryl, $C_3$-$C_{11}$ cycloalkyl, $C_4$-$C_{11}$ cycloalkenyl, 4-12 membered heterocyclyl, $C_1$-$C_6$ thioalkyl, OH, oxo, CN, $NO_2$, F, Cl, Br and I; wherein the $R^{5A}$ and $R^{5B}$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $C_1$-$C_6$ alkyl, C(O)OH, $NH_2$, OH, oxo, CN, $NO_2$, F, Cl, Br and I;

$R^{6A}$, $R^{6B}$, $R^{6C}$, and $R^{6D}$ are each hydrogen;

$R^7$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^7$ $C_1$-$C_6$ alkyl, $C_2$-$C_6$ alkenyl, and $C_2$-$C_6$ alkynyl is optionally substituted with one or more substituents independently selected from the group consisting of $C_1$-$C_6$ alkoxy, OH, oxo, CN, $NO_2$, F, Cl, Br and I; wherein each $R^7$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, oxo, OH, CN, $NO_2$, F, Cl, Br and I;

$R^8$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of $R^{11}$, $OR^{11}$, $C(O)OR^{11}$, $NHR^{11}$, $N(R^{11})_2$, $NH_2$, C(O)OH, OH, CN, $NO_2$, F, Cl, Br and I; wherein each $R^8$ $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{12}$, $OR^{12}$, $C(O)OR^{12}$, $NHR^{12}$, $N(R^{12})_2$, $NH_2$, C(O)OH, OH, oxo, CN, $NO_2$, F, Cl, Br and I;

$R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{13}$, $OR^{13}$, $SR^{13}$, $C(O)R^{13}$, $NHR^{13}$, $N(R^{13})_2$, C(O)OH, OH, CN, $NO_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^{14}$, $OR^{14}$, $C(O)R^{14}$, $OC(O)R^{14}$, $C(O)OR^{14}$, $SO_2R^{14}$, $NHR^{14}$, $N(R^{14})_2$, $NH_2$, C(O)OH, OH, oxo, CN, $NO_2$, F, Cl, Br and I;

$R^{10}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{10}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{10}$ $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I;

$R^{11}$, at each occurrence, is independently selected from the group consisting of $C_1$-$C_6$ alkyl, $C_1$-$C_6$ alkoxy, $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl; wherein each $R^{11}$ $C_1$-$C_6$ alkyl and $C_1$-$C_6$ alkoxy is optionally substituted with one or more substituents independently selected from the group consisting of OH, oxo, CN, $NO_2$, F, Cl, Br and I; wherein each $R^{11}$ $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl is optionally substituted with one or more substituents independently selected from the group consisting of $C_1$-$C_6$ alkyl, $C_1$-$C_6$ alkoxy, F, Cl, Br and I;

$R^{12}$, at each occurrence, is independently selected from the group consisting of $C_1$-$C_6$ alkyl, $C_1$-$C_6$ alkoxy, $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl; wherein each $R^{12}$ $C_1$-$C_6$ alkyl and $C_1$-$C_6$ alkoxy is optionally substituted with one or more substituents independently selected from the group consisting of OH, oxo, CN, $NO_2$, F, Cl, Br and I; wherein each $R^{12}$ $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl is optionally substituted with one or more substituents independently selected from the group consisting of $C_1$-$C_6$ alkyl, $C_1$-$C_6$ alkoxy, F, Cl, Br and I;

$R^{13}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{13}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{13}$ $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I; and $R^{14}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$cycloalkyl, $C_4$-$C_{11}$ cycloalkenyl, and 4-12 membered heterocyclyl; wherein each $R^{14}$ $C_1$-$C_6$ alkyl, $C_2$-$C_6$ alkenyl, and $C_2$-$C_6$ alkynyl is optionally substituted with one or more substituents independently selected from the group consisting of $C_1$-$C_6$ alkyl, $C_1$-$C_6$ alkoxy, 5-6 membered heteroaryl, 4-12 membered heterocyclyl, OH, oxo, CN, $NO_2$, F, Cl, Br and I;

with the proviso that $R^3$ is not $C_1$-alkyl or thienyl;

with the proviso that, when $R^{2A}$, $R^{2B}$, $R^{2C}$, and $R^{2D}$ are each hydrogen, $R^1$ is not hydrogen;

with the proviso that, when $R^3$ is imidazolyl, $R^9$ is not $CH_2CH(CH_3)_2$;

with the proviso that when $R^{2B}$ is Cl, $R^3$ is not 2,4-dimethyl-5-thiazolyl or 2-cyano-3-fluorophenyl;

with the proviso that, when $R^3$ is cyclohexyl, $R^{2C}$ is not $OCH_3$;

with the proviso that, when $R^3$ is 3-pyridinyl, $R^{2C}$ is not Cl; and with the proviso that, when $R^3$ is phenyl, $R^{13}$ is not $C(O)CH_3$.

One aspect pertains to a compound of Formula (I), or a pharmaceutically acceptable salt thereof, wherein $R^4$ is hydrogen. Another aspect pertains to a compound of Formula (I), or a pharmaceutically acceptable salt thereof, wherein $R^4$ is hydrogen; and $A^1$ is

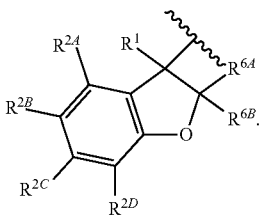

Another aspect pertains to a compound of Formula (I), or a pharmaceutically acceptable salt thereof, wherein $R^4$ is hydrogen; and $A^1$ is

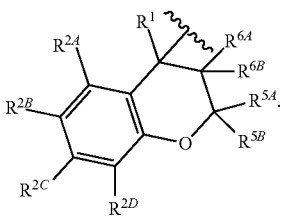

Another aspect pertains to a compound of Formula (I), or a pharmaceutically acceptable salt thereof, wherein $R^4$ is hydrogen; $A^1$ is

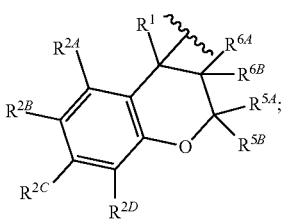

wherein two of $R^{2A}$, $R^{2B}$, $R^{2C}$, and $R^{2D}$ are hydrogen and the remaining are independently selected from the group consisting of $R^8$ and $OR^8$; and $R^8$, at each occurrence, is independently selected from the group consisting of $C_1$-$C_6$ alkyl and $C_3$-$C_{11}$ cycloalkyl. Another aspect pertains to a compound of Formula (I), or a pharmaceutically acceptable salt thereof, wherein $R^4$ is hydrogen; $A^1$ is

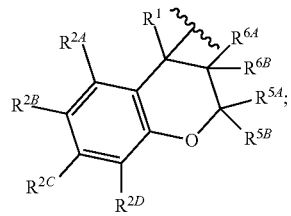

wherein two of $R^{2A}$, $R^{2B}$, $R^{2C}$, and $R^{2D}$ are hydrogen and the remaining are independently selected from the group consisting of $R^8$ and $OR^8$; $R^8$, at each occurrence, is independently selected from the group consisting of $C_1$-$C_6$ alkyl and $C_3$-$C_{11}$ cycloalkyl; and $R^1$ is hydrogen. Another aspect pertains to a compound of Formula (I), or a pharmaceutically acceptable salt thereof, wherein $R^4$ is hydrogen; $A^1$ is

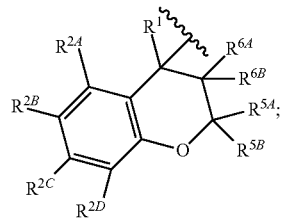

wherein two of $R^{2A}$, $R^{2B}$, $R^{2C}$, and $R^{2D}$ are hydrogen and the remaining are independently selected from the group consisting of $R^8$ and $OR^8$; $R^8$, at each occurrence, is independently selected from the group consisting of $C_1$-$C_6$ alkyl and $C_3$-$C_{11}$ cycloalkyl; $R^1$ is hydrogen; and $R^{5A}$, $R^{5B}$, $R^{6A}$, and $R^{6B}$ are hydrogen. Another aspect pertains to a compound of Formula (I), or a pharmaceutically acceptable salt thereof, wherein $R^4$ is hydrogen; $A^1$ is

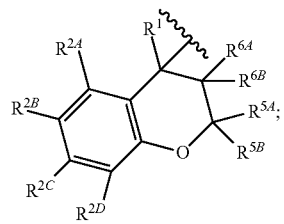

wherein two of $R^{2A}$, $R^{2B}$, $R^{2C}$, and $R^{2D}$ are hydrogen and the remaining are independently selected from the group consisting of $R^8$ and $OR^8$; $R^8$, at each occurrence, is independently selected from the group consisting of $C_1$-$C_6$ alkyl and $C_3$-$C_{11}$ cycloalkyl; $R^1$ is hydrogen; $R^{5A}$, $R^{5B}$, $R^{6A}$, and $R^{6B}$ are hydrogen; and $R^3$ is quinolinyl; wherein the $R^3$ quinolinyl is optionally substituted with one or more $R^9$; and $R^9$ is $C_1$-$C_6$ alkyl. Another aspect pertains to a compound of Formula (I), or a pharmaceutically acceptable salt thereof, wherein $A^1$ is

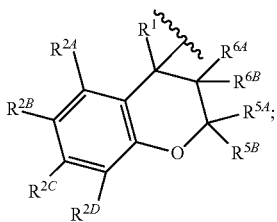

R¹ is hydrogen; two of R$^{2A}$, R$^{2B}$, R$^{2C}$, and R$^{2D}$ are hydrogen and the remaining are independently selected from the group consisting of R$^8$ and OR$^8$; R$^3$ is 5-11 membered heteroaryl; wherein the R$^3$ 5-11 membered heteroaryl is optionally substituted with one or more R$^9$; R$^4$ is hydrogen; R$^{5A}$ and R$^{5B}$ are each independently hydrogen; R$^{6A}$ and R$^{6B}$ are each independently hydrogen; R$^8$, at each occurrence, is independently selected from the group consisting of C$_1$-C$_6$ alkyl and C$_3$-C$_{11}$ cycloalkyl; and R$^9$, at each occurrence, is independently C$_1$-C$_6$ alkyl.

Another aspect pertains to a compound of Formula (I), or a pharmaceutically acceptable salt thereof, wherein the compound is selected from the group consisting of:
6-bromo-N-(naphthalene-1-sulfonyl)-4-phenyl-3,4-dihydro-2H-1-benzopyran-4-carboxamide;
(2R,4R)-2-[(ethylsulfanyl)methyl]-N-(naphthalene-1-sulfonyl)-4-phenyl-3,4-dihydro-2H-1-benzopyran-4-carboxamide;
6-methoxy-2,2-dimethyl-N-(naphthalene-1-sulfonyl)-4-phenyl-3,4-dihydro-2H-1-benzopyran-4-carboxamide;
6-methoxy-N-(naphthalene-1-sulfonyl)-4-phenyl-3,4-dihydro-2H-1-benzopyran-4-carboxamide;
6-benzoyl-5,7-dimethyl-N-(naphthalene-1-sulfonyl)-3,4-dihydro-2H-1-benzopyran-4-carboxamide;
N-(naphthalene-1-sulfonyl)-3-phenyl-2,3-dihydro-1-benzofuran-3-carboxamide;
8-chloro-N-(naphthalene-1-sulfonyl)-3,4-dihydro-2H-1-benzopyran-4-carboxamide;
3-ethyl-4-methoxy-N-(naphthalene-1-sulfonyl)-2,3-dihydro-1-benzofuran-3-carboxamide;
5-methoxy-N-(naphthalene-1-sulfonyl)-3,4-dihydro-2H-1-benzopyran-4-carboxamide;
4-ethyl-5-methoxy-N-(naphthalene-1-sulfonyl)-3,4-dihydro-2H-1-benzopyran-4-carboxamide;
8-bromo-5-methoxy-N-(naphthalene-1-sulfonyl)-3,4-dihydro-2H-1-benzopyran-4-carboxamide;
6,8-dibromo-5-methoxy-N-(naphthalene-1-sulfonyl)-3,4-dihydro-2H-1-benzopyran-4-carboxamide;
8-cyclobutyl-5-methoxy-N-(naphthalene-1-sulfonyl)-3,4-dihydro-2H-1-benzopyran-4-carboxamide;
8-cyclopentyl-5-methoxy-N-(naphthalene-1-sulfonyl)-3,4-dihydro-2H-1-benzopyran-4-carboxamide;
3-ethyl-7-methoxy-N-(naphthalene-1-sulfonyl)-2,3-dihydro-1-benzofuran-3-carboxamide;
2-methyl-N-(2-methylbenzene-1-sulfonyl)-2,3-dihydro-1-benzofuran-2-carboxamide;
N-(2-methylbenzene-1-sulfonyl)-2,3-dihydro-1-benzofuran-2-carboxamide;
6-methyl-N-(naphthalene-1-sulfonyl)-4-phenyl-3,4-dihydro-2H-1-benzopyran-4-carboxamide;
6-chloro-N-(naphthalene-1-sulfonyl)-4-phenyl-3,4-dihydro-2H-1-benzopyran-4-carboxamide;
4-methoxy-N-(naphthalene-1-sulfonyl)-2,3-dihydro-1-benzofuran-3-carboxamide;
7-bromo-N-(naphthalene-1-sulfonyl)-2,3-dihydro-1-benzofuran-3-carboxamide;
7-bromo-3-ethyl-N-(naphthalene-1-sulfonyl)-2,3-dihydro-1-benzofuran-3-carboxamide;
3-ethyl-N-(naphthalene-1-sulfonyl)-2,3-dihydro-1-benzofuran-3-carboxamide;
N-(naphthalene-1-sulfonyl)-3,4-dihydro-2H-1-benzopyran-4-carboxamide;
7-methoxy-N-(naphthalene-1-sulfonyl)-2,3-dihydro-1-benzofuran-3-carboxamide;
2-methyl-N-[4-(propan-2-yl)benzene-1-sulfonyl]-2,3-dihydro-1-benzofuran-2-carboxamide;
5-chloro-N-(2-methylbenzene-1-sulfonyl)-2,3-dihydro-1-benzofuran-3-carboxamide;
5-chloro-N-(propane-1-sulfonyl)-2,3-dihydro-1-benzofuran-3-carboxamide;
N-(2-methylbenzene-1-sulfonyl)-2,3-dihydro-1-benzofuran-3-carboxamide;
N-(2-methylbenzene-1-sulfonyl)-3,4-dihydro-2H-1-benzopyran-4-carboxamide;
(2S)—N-(naphthalene-1-sulfonyl)-4-phenyl-2-[(pyrrolidin-1-yl)methyl]-3,4-dihydro-2H-1-benzopyran-4-carboxamide;
(7S)-2,2-difluoro-7-methyl-N-(naphthalene-1-sulfonyl)-6,7-dihydro-2H-furo[2,3-f][1,3]benzodioxole-7-carboxamide;
(7R)-2,2-difluoro-7-methyl-N-(naphthalene-1-sulfonyl)-6,7-dihydro-2H-furo[2,3-f][1,3]benzodioxole-7-carboxamide;
N-(naphthalene-1-sulfonyl)-2,3-dihydro-1-benzofuran-3-carboxamide;
(4S)-8-bromo-5-methoxy-N-(naphthalene-1-sulfonyl)-3,4-dihydro-2H-1-benzopyran-4-carboxamide;
(4R)-8-bromo-5-methoxy-N-(naphthalene-1-sulfonyl)-3,4-dihydro-2H-1-benzopyran-4-carboxamide;
4-bromo-7-methoxy-N-(naphthalene-1-sulfonyl)-2,3-dihydro-1-benzofuran-3-carboxamide;
5-methoxy-N-(naphthalene-1-sulfonyl)-3,4-dihydrospiro[1-benzopyran-2,1'-cyclohexane]-4-carboxamide;
7-bromo-4-methoxy-N-(naphthalene-1-sulfonyl)-2,3-dihydro-1-benzofuran-3-carboxamide;
4-methoxy-N-(naphthalene-1-sulfonyl)-5-(trifluoromethyl)-2,3-dihydro-1-benzofuran-3-carboxamide and 4-methoxy-N-(naphthalene-1-sulfonyl)-7-(trifluoromethyl)-2,3-dihydro-1-benzofuran-3-carboxamide;
8-bromo-5-methoxy-N-(naphthalene-1-sulfonyl)-3,4-dihydrospiro[1-benzopyran-2,1'-cyclohexane]-4-carboxamide;
8-bromo-5-methoxy-N-(quinoline-8-sulfonyl)-3,4-dihydro-2H-1-benzopyran-4-carboxamide;
7-chloro-N-(naphthalene-1-sulfonyl)-2,3-dihydro-1-benzofuran-3-carboxamide;
7-chloro-3-ethyl-N-(naphthalene-1-sulfonyl)-2,3-dihydro-1-benzofuran-3-carboxamide;
N-(naphthalene-1-sulfonyl)-7-(trifluoromethyl)-2,3-dihydro-1-benzofuran-3-carboxamide;
8-bromo-5-methoxy-2,2-dimethyl-N-(quinoline-5-sulfonyl)-3,4-dihydro-2H-1-benzopyran-4-carboxamide;
5-methoxy-2,2-dimethyl-N-(quinoline-8-sulfonyl)-3,4-dihydro-2H-1-benzopyran-4-carboxamide;
5-methoxy-2,2-dimethyl-N-(quinoline-5-sulfonyl)-3,4-dihydro-2H-1-benzopyran-4-carboxamide;
5-methoxy-2,2-dimethyl-N-(naphthalene-1-sulfonyl)-3,4-dihydro-2H-1-benzopyran-4-carboxamide;
8-cyano-5-methoxy-2,2-dimethyl-N-(naphthalene-1-sulfonyl)-3,4-dihydro-2H-1-benzopyran-4-carboxamide;
8-chloro-5-methoxy-2,2-dimethyl-N-(naphthalene-1-sulfonyl)-3,4-dihydro-2H-1-benzopyran-4-carboxamide;

8-bromo-5-methoxy-2,2-dimethyl-N-(naphthalene-1-sulfonyl)-3,4-dihydro-2H-1-benzopyran-4-carboxamide;
5-methoxy-N-(naphthalene-1-sulfonyl)-8-(trifluoromethyl)-3,4-dihydro-2H-1-benzopyran-4-carboxamide;
8-cyclobutyl-5-methoxy-N-(quinoline-5-sulfonyl)-3,4-dihydro-2H-1-benzopyran-4-carboxamide;
(4S)-8-cyclobutyl-5-methoxy-N-(naphthalene-1-sulfonyl)-3,4-dihydro-2H-1-benzopyran-4-carboxamide;
(4R)-8-cyclobutyl-5-methoxy-N-(naphthalene-1-sulfonyl)-3,4-dihydro-2H-1-benzopyran-4-carboxamide;
(4S)-5-methoxy-N-(naphthalene-1-sulfonyl)-8-(trifluoromethyl)-3,4-dihydro-2H-1-benzopyran-4-carboxamide;
(4R)-5-methoxy-N-(naphthalene-1-sulfonyl)-8-(trifluoromethyl)-3,4-dihydro-2H-1-benzopyran-4-carboxamide;
(4S)-8-cyclobutyl-5-methoxy-N-(quinoline-5-sulfonyl)-3,4-dihydro-2H-1-benzopyran-4-carboxamide;
(4R)-8-cyclobutyl-5-methoxy-N-(quinoline-5-sulfonyl)-3,4-dihydro-2H-1-benzopyran-4-carboxamide;
3-ethyl-N-(naphthalene-1-sulfonyl)-7-(trifluoromethyl)-2,3-dihydro-1-benzofuran-3-carboxamide;
4,7-dimethoxy-N-(naphthalene-1-sulfonyl)-2,3-dihydro-1-benzofuran-3-carboxamide;
7-chloro-4-methoxy-N-(naphthalene-1-sulfonyl)-2,3-dihydro-1-benzofuran-3-carboxamide;
8-cyclopropyl-5-methoxy-N-(naphthalene-1-sulfonyl)-3,4-dihydro-2H-1-benzopyran-4-carboxamide;
(3S)-7-cyclobutyl-4-methoxy-N-(naphthalene-1-sulfonyl)-2,3-dihydro-1-benzofuran-3-carboxamide;
(3R)-7-cyclobutyl-4-methoxy-N-(naphthalene-1-sulfonyl)-2,3-dihydro-1-benzofuran-3-carboxamide;
(3R)-7-chloro-4-methoxy-N-(naphthalene-1-sulfonyl)-2,3-dihydro-1-benzofuran-3-carboxamide;
(3S)-7-chloro-4-methoxy-N-(naphthalene-1-sulfonyl)-2,3-dihydro-1-benzofuran-3-carboxamide;
(4S)-8-bromo-5-methoxy-N-(1-methyl-1H-indazole-7-sulfonyl)-3,4-dihydro-2H-1-benzopyran-4-carboxamide;
(4R)-8-bromo-5-methoxy-N-(1-methyl-1H-indazole-7-sulfonyl)-3,4-dihydro-2H-1-benzopyran-4-carboxamide;
(4S)-8-bromo-5-methoxy-2,2-dimethyl-N-(quinoline-5-sulfonyl)-3,4-dihydro-2H-1-benzopyran-4-carboxamide;
(4R)-8-bromo-5-methoxy-2,2-dimethyl-N-(quinoline-5-sulfonyl)-3,4-dihydro-2H-1-benzopyran-4-carboxamide;
(3R)-7-bromo-4-methoxy-N-(1-naphthylsulfonyl)-2,3-dihydrobenzofuran-3-carboxamide;
(3S)-7-bromo-4-methoxy-N-(1-naphthylsulfonyl)-2,3-dihydrobenzofuran-3-carboxamide;
8-cyclobutyl-5-methoxy-N-(2-methylquinoline-5-sulfonyl)-3,4-dihydro-2H-1-benzopyran-4-carboxamide;
(4S)-8-cyclobutyl-5-methoxy-N-(2-methylquinoline-5-sulfonyl)-3,4-dihydro-2H-1-benzopyran-4-carboxamide;
(4R)-8-cyclobutyl-5-methoxy-N-(2-methylquinoline-5-sulfonyl)-3,4-dihydro-2H-1-benzopyran-4-carboxamide;
5-bromo-8-methoxy-N-(naphthalene-1-sulfonyl)-3,4-dihydro-1H-2-benzopyran-1-carboxamide;
5-cyclobutyl-8-methoxy-N-(naphthalene-1-sulfonyl)-3,4-dihydro-1H-2-benzopyran-1-carboxamide;
7-cyclobutyl-4-methoxy-N-(quinoline-5-sulfonyl)-2,3-dihydro-1-benzofuran-3-carboxamide;
5-cyclobutyl-8-methoxy-N-(quinoline-5-sulfonyl)-3,4-dihydro-1H-2-benzopyran-1-carboxamide;
(3R)-7-cyclobutyl-4-methoxy-N-(quinoline-5-sulfonyl)-2,3-dihydro-1-benzofuran-3-carboxamide;
(3S)-7-cyclobutyl-4-methoxy-N-(quinoline-5-sulfonyl)-2,3-dihydro-1-benzofuran-3-carboxamide;
5-cyclobutyl-8-methoxy-1-methyl-N-(naphthalene-1-sulfonyl)-3,4-dihydro-1H-2-benzopyran-1-carboxamide;
8-cyclobutyl-5-methoxy-N-(1,2,3,4-tetrahydroquinoline-5-sulfonyl)-3,4-dihydro-2H-1-benzopyran-4-carboxamide;
(4R)-8-cyclobutyl-5-methoxy-2,2-dimethyl-N-(quinoline-5-sulfonyl)-3,4-dihydro-2H-1-benzopyran-4-carboxamide;
7-cyclobutyl-4-methoxy-N-(1-methyl-1H-benzimidazole-7-sulfonyl)-2,3-dihydro-1-benzofuran-3-carboxamide;
7-cyclobutyl-4-methoxy-N-(pyrazolo[1,5-a]pyridine-4-sulfonyl)-2,3-dihydro-1-benzofuran-3-carboxamide;
7-cyclobutyl-4-methoxy-N-(1,2,3,4-tetrahydroquinoline-5-sulfonyl)-2,3-dihydro-1-benzofuran-3-carboxamide;
7-cyclobutyl-4-methoxy-N-(1,2,3,4-tetrahydroquinoline-8-sulfonyl)-2,3-dihydro-1-benzofuran-3-carboxamide;
(4S)-8-cyclobutyl-5-methoxy-N-(1,2,3,4-tetrahydroquinoline-5-sulfonyl)-3,4-dihydro-2H-1-benzopyran-4-carboxamide;
(4R)-8-cyclobutyl-5-methoxy-N-(1,2,3,4-tetrahydroquinoline-5-sulfonyl)-3,4-dihydro-2H-1-benzopyran-4-carboxamide;
8-cyclobutyl-5-methoxy-2,2-dimethyl-N-(1,2,3,4-tetrahydroquinoline-5-sulfonyl)-3,4-dihydro-2H-1-benzopyran-4-carboxamide;
(3R)-7-cyclobutyl-4-methoxy-N-(1-methyl-1H-indazole-7-sulfonyl)-2,3-dihydro-1-benzofuran-3-carboxamide;
(3S)-7-cyclobutyl-4-methoxy-N-(1-methyl-1H-indazole-7-sulfonyl)-2,3-dihydro-1-benzofuran-3-carboxamide;
(4S)-8-cyclobutyl-5-methoxy-2,2-dimethyl-N-(1,2,3,4-tetrahydroquinoline-5-sulfonyl)-3,4-dihydro-2H-1-benzopyran-4-carboxamide;
(4R)-8-cyclobutyl-5-methoxy-2,2-dimethyl-N-(1,2,3,4-tetrahydroquinoline-5-sulfonyl)-3,4-dihydro-2H-1-benzopyran-4-carboxamide;
(3R)-7-cyclobutyl-4-methoxy-N-(1,2,3,4-tetrahydroquinoline-8-sulfonyl)-2,3-dihydro-1-benzofuran-3-carboxamide;
(3S)-7-cyclobutyl-4-methoxy-N-(1,2,3,4-tetrahydroquinoline-8-sulfonyl)-2,3-dihydro-1-benzofuran-3-carboxamide;
(3R)-7-cyclobutyl-4-methoxy-N-(1,2,3,4-tetrahydroquinoline-5-sulfonyl)-2,3-dihydro-1-benzofuran-3-carboxamide;
(3S)-7-cyclobutyl-4-methoxy-N-(1,2,3,4-tetrahydroquinoline-5-sulfonyl)-2,3-dihydro-1-benzofuran-3-carboxamide;
8-cyclobutyl-N-(1H-indole-4-sulfonyl)-5-methoxy-3,4-dihydro-2H-1-benzopyran-4-carboxamide;
(4S)-8-cyclobutyl-N-(1H-indole-4-sulfonyl)-5-methoxy-3,4-dihydro-2H-1-benzopyran-4-carboxamide;
(4R)-8-cyclobutyl-N-(1H-indole-4-sulfonyl)-5-methoxy-3,4-dihydro-2H-1-benzopyran-4-carboxamide;
5-cyclobutyl-8-methoxy-N-(quinoline-5-sulfonyl)-3,4-dihydro-2H-1-benzopyran-4-carboxamide;
(4R)-5-cyclobutyl-8-methoxy-N-(quinoline-5-sulfonyl)-3,4-dihydro-2H-1-benzopyran-4-carboxamide;
(4S)-5-cyclobutyl-8-methoxy-N-(quinoline-5-sulfonyl)-3,4-dihydro-2H-1-benzopyran-4-carboxamide;
8-bromo-5-methoxy-N-(naphthalene-1-sulfonyl)-3,4-dihydro-1H-2-benzopyran-1-carboxamide;
N-(naphthalene-1-sulfonyl)-7-(trifluoromethoxy)-3,4-dihydro-1H-2-benzopyran-1-carboxamide;
5-methoxy-N-(naphthalene-1-sulfonyl)-3,4-dihydro-1H-2-benzopyran-1-carboxamide; and pharmaceutically acceptable salts thereof.

One aspect pertains to 8-cyclobutyl-5-methoxy-N-(2-methylquinoline-5-sulfonyl)-3,4-dihydro-2H-1-benzopyran-4-carboxamide, or a pharmaceutically acceptable salt thereof. One aspect pertains to (4S)-8-cyclobutyl-5- methoxy-N-(2-methylquinoline-5-sulfonyl)-3,4-dihydro-2H-1-benzopyran-4-carboxamide; or a pharmaceutically acceptable salt thereof. One aspect pertains to (4R)-8-cyclobutyl-5-methoxy-N-(2-methylquinoline-5-sulfonyl)-3,4-dihydro-2H-1-benzopyran-4-carboxamide; or a pharmaceutically acceptable salt thereof. One aspect pertains to 8-cyclobutyl-N-(1H-indole-4-sulfonyl)-5-methoxy-3,4-dihydro-2H-1-benzopyran-4-carboxamide; or a pharmaceutically acceptable salt thereof. One aspect pertains to (4S)-8-cyclobutyl-N-(1H-indole-4-sulfonyl)-5-methoxy-3,4-dihydro-2H-1-benzopyran-4-carboxamide; or a pharmaceutically acceptable salt thereof. One aspect pertains to (4R)-8-cyclobutyl-N-(1H-indole-4-sulfonyl)-5-methoxy-3,4-dihydro-2H-1-benzopyran-4-carboxamide; or a pharmaceutically acceptable salt thereof. One aspect pertains to 5-cyclobutyl-8-methoxy-N-(quinoline-5-sulfonyl)-3,4-dihydro-2H-1-benzopyran-4-carboxamide; or a pharmaceutically acceptable salt thereof. One aspect pertains to (4R)-5-cyclobutyl-8-methoxy-N-(quinoline-5-sulfonyl)-3,4-dihydro-2H-1-benzopyran-4-carboxamide; or a pharmaceutically acceptable salt thereof. One aspect pertains to (4S)-5-cyclobutyl-8-methoxy-N-(quinoline-5-sulfonyl)-3,4-dihydro-2H-1-benzopyran-4-carboxamide; or a pharmaceutically acceptable salt thereof.

Another aspect of the invention relates to pharmaceutical compositions comprising a compound of the invention, and a pharmaceutical carrier. Such compositions can be administered in accordance with a method of the invention, typically as part of a therapeutic regimen for treatment or prevention of conditions and disorders related to Cystic Fibrosis Transmembrane Conductance Regulator activity. In a particular aspect, the pharmaceutical compositions may additionally comprise further therapeutically active ingredients suitable for use in combination with the compounds of the invention. In a more particular aspect, the further therapeutically active ingredient is an agent for the treatment of cystic fibrosis.

Moreover, the compounds of the invention, useful in the pharmaceutical compositions and treatment methods disclosed herein, are pharmaceutically acceptable as prepared and used.

Yet another aspect of the invention relates to a method for treating, or preventing conditions and disorders related to Cystic Fibrosis Transmembrane Conductance Regulator activity in mammals. More particularly, the method is useful for treating or preventing conditions and disorders related to cystic fibrosis, Sjögren's syndrome, pancreatic insufficiency, chronic obstructive lung disease, or chronic obstructive airway disease. Accordingly, the compounds and compositions of the invention are useful as a medicament for treating or preventing Cystic Fibrosis Transmembrane Conductance Regulator modulated disease.

The compounds, compositions comprising the compounds, methods for making the compounds, and methods for treating or preventing conditions and disorders by administering the compounds are further described herein.

In a particular aspect, the compounds of the invention are provided for use in the treatment of cystic fibrosis. In a particular aspect, the compounds of the invention are provided for use in the treatment of cystic fibrosis caused by class I, II, III, IV, V, and/or VI mutations.

The present invention also provides pharmaceutical compositions comprising a compound of the invention, and a suitable pharmaceutical carrier for use in medicine. In a particular aspect, the pharmaceutical composition is for use in the treatment of cystic fibrosis.

These and other objects of the invention are described in the following paragraphs. These objects should not be deemed to narrow the scope of the invention.

DETAILED DESCRIPTION OF THE INVENTION

Described herein are compounds of Formula (I)

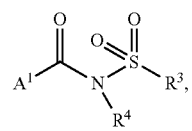

(I)

wherein $A^1$, $R^3$, and $R^4$ are defined above in the Summary and below in the Detailed Description. Further, compositions comprising such compounds and methods for treating conditions and disorders using such compounds and compositions are also included.

Compounds included herein may contain one or more variable(s) that occur more than one time in any substituent or in the formulae herein. Definition of a variable on each occurrence is independent of its definition at another occurrence. Further, combinations of substituents are permissible only if such combinations result in stable compounds. Stable compounds are compounds which can be isolated from a reaction mixture.

Definitions

It is noted that, as used in this specification and the intended claims, the singular form "a," "an," and "the" include plural referents unless the context clearly dictates otherwise. Thus, for example, reference to "a compound" includes a single compound as well as one or more of the same or different compounds; reference to "a pharmaceutically acceptable carrier" means a single pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "$C_2$-$C_6$ alkenyl" means an alkenyl group containing 2-6 carbon atoms. Non-limiting examples of $C_2$-$C_6$ alkenyl include buta-1,3-dienyl, ethenyl, 2-propenyl, 2-methyl-2-propenyl, 3-butenyl, 4-pentenyl, and 5-hexenyl.

The term "alkoxy" as used herein, means a alkyl group, as defined herein, appended to the parent molecular moiety through an oxygen atom. The term "$C_1$-$C_6$ alkoxy" as used herein, means a $C_1$-$C_6$ alkyl group, as defined herein, appended to the parent molecular moiety through an oxygen atom. The term "$C_1$-$C_3$ alkoxy" as used herein, means a $C_1$-$C_3$ alkyl group, as defined herein, appended to the parent molecular moiety through an oxygen atom. Non-limiting examples of alkoxy include methoxy, ethoxy, propoxy, 2-propoxy, butoxy, tert-butoxy, pentyloxy, and hexyloxy.

The term "$C_1$-$C_6$ thioalkyl" as used herein, means a $C_1$-$C_6$ alkyl group, as defined herein, appended to the parent molecular moiety through a sulfur atom.

The term "alkyl" as used herein, means a saturated, straight or branched hydrocarbon chain radical. In some instances, the number of carbon atoms in an alkyl moiety is indicated by the prefix "$C_x$-$C_y$", wherein x is the minimum and y is the maximum number of carbon atoms in the substituent. Thus, for example, "$C_1$-$C_6$ alkyl" means an alkyl substituent containing from 1 to 6 carbon atoms and "$C_1$-$C_3$ alkyl" means an alkyl substituent containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 3,3-dimethylbutyl, 1,1-dimethylpropyl, 1,2-dimethylpropyl, 2,2-dimethylpropyl, 1-methylpropyl, 2-methylpropyl, 1-ethylpropyl, and 1,2,2-trimethylpropyl. The terms "alkyl," "$C_1$-$C_6$ alkyl," "$C_1$-$C_4$ alkyl," and "$C_1$-$C_3$ alkyl" used herein are unsubstituted, unless otherwise indicated.

The term "alkylene" or "alkylenyl" means a divalent radical derived from a straight or branched, saturated hydrocarbon chain, for example, of 1 to 10 carbon atoms or of 1 to 6 carbon atoms ($C_1$-$C_6$ alkylenyl) or of 1 to 4 carbon atoms or of 1 to 3 carbon atoms ($C_1$-$C_3$ alkylenyl) or of 2 to 6 carbon atoms ($C_2$-$C_6$ alkylenyl). Examples of $C_1$-$C_6$ alkylenyl include, but are not limited to, —$CH_2$—, —$CH_2CH_2$—, —$C(CH_3)_2$—$CH_2CH_2$—, —$C(CH_3)_2$—$CH_2CH_2$—, —$CH_2CH_2CH_2$—, and —$CH_2CH(CH_3)CH_2$—.

The term "alkynyl" as used herein, means a straight or branched chain hydrocarbon radical containing at least one carbon-carbon triple bond. The term "$C_2$-$C_6$ alkynyl" as used herein, means a straight or branched chain hydrocarbon radical containing from 2 to 6 carbon atoms and containing at least one carbon-carbon triple bond. Representative examples of $C_2$-$C_6$ alkynyl include, but are not limited, to acetylenyl, 1-propynyl, 2-propynyl, 3-butynyl, 2-pentynyl, and 1-butynyl.

The term "$C_3$-$C_{11}$ cycloalkyl" as used herein, means a hydrocarbon ring radical containing 3-11 carbon atoms, zero heteroatoms, and zero double bonds. The $C_3$-$C_{11}$ cycloalkyl group may be a single-ring (monocyclic) or have two or more rings (polycyclic or bicyclic). Monocyclic cycloalkyl groups typically contain from 3 to 8 carbon ring atoms ($C_3$-$C_8$ monocyclic cycloalkyl), and even more typically 3-6 carbon ring atoms ($C_3$-$C_6$ monocyclic cycloalkyl). Examples of monocyclic cycloalkyls include cyclopropyl, cyclobutyl, cyclopentyl, cyclohexyl, cycloheptyl, and cyclooctyl. Polycyclic cycloalkyl groups contain two or more rings, and bicyclic cycloalkyls contain two rings. In certain embodiments, the polycyclic cycloalkyl groups contain 2 or 3 rings. The rings within the polycyclic and the bicyclic cycloalkyl groups may be in a bridged, fused, or spiro orientation, or combinations thereof. In a spirocyclic cycloalkyl, one atom is common to two different rings. Examples of a spirocyclic cycloalkyl include spiro[2.5]octanyl and spiro[4.5]decanyl. In a bridged cycloalkyl, the rings share at least two non-adjacent atoms. Examples of bridged cycloalkyls include, but are not limited to bicyclo[1.1.1]pentanyl, bicyclo[2.2.2]octyl, bicyclo[3.2.1]octyl, bicyclo[3.1.1]heptyl, bicyclo[2.2.1]heptyl, bicyclo[3.2.2]nonyl, bicyclo[3.3.1]nonyl, and bicyclo[4.2.1]nonyl, tricyclo[3.3.1.0$^{3,7}$]nonyl (octahydro-2,5-methanopentalenyl or noradamantyl), tricyclo[3.3.1.1$^{3,7}$]decyl (adamantyl), and tricyclo[4.3.1.1$^{3,8}$]undecyl (homoadamantyl). In a fused ring cycloalkyl, the rings share one common bond. Examples of fused-ring cycloalkyl include, but not limited to, decalin (decahydronaphthyl), bicyclo[3.1.0]hexanyl, and bicyclo[2.2.0]octyl.

The term "$C_3$-$C_7$ cycloalkyl" as used herein, means a hydrocarbon ring radical containing 3-7 carbon atoms, zero heteroatoms, and zero double bonds. The $C_3$-$C_7$ cycloalkyl group may be a single-ring (monocyclic) or have two rings (bicyclic) unless otherwise indicated.

The term "$C_4$-$C_7$ cycloalkenyl" as used herein, means a non-aromatic hydrocarbon ring radical containing 4-7 carbon atoms, zero heteroatoms, and one or more double bonds. The $C_4$-$C_7$ cycloalkenyl group may be a single-ring (monocyclic) or have two or more rings (polycyclic or bicyclic). Examples of monocyclic cycloalkenyl include cyclobutenyl, cyclopentenyl, cyclohexenyl, cyclohexadienyl, and cycloheptyl.

The term "$C_4$-$C_{11}$ cycloalkenyl" as used herein, means a non-aromatic hydrocarbon ring radical containing 4-11 carbon atoms, zero heteroatoms, and one or more double bonds. The $C_4$-$C_{11}$ cycloalkenyl group may be a single-ring (monocyclic) or have two or more rings (polycyclic or bicyclic). Examples of monocyclic cycloalkenyl include cyclobutenyl, cyclopentenyl, cyclohexenyl, cyclohexadienyl, cycloheptyl, cyclooctenyl, and cyclooctadienyl. Examples of bicyclic cycloalkenyl include bicyclo[2.2.1]hept-2-enyl.

The term "$C_4$-$C_8$ monocyclic cycloalkenyl" as used herein, means cyclobutenyl, cyclopentenyl, cyclohexenyl, cyclohexadienyl, cycloheptyl, cycloheptadienyl, cyclooctenyl, and cyclooctadienyl.

The term "$C_4$-$C_7$ monocyclic cycloalkenyl" as used herein, means cyclobutenyl, cyclopentenyl, cyclohexenyl, cyclohexadienyl, and cycloheptyl.

The term "halo" or "halogen" as used herein, means Cl, Br, I, and F.

The term "haloalkyl" as used herein, means an alkyl group, as defined herein, in which one, two, three, four, five or six hydrogen atoms are replaced by halogen. The term "$C_1$-$C_6$ haloalkyl" means a $C_1$-$C_6$ alkyl group, as defined herein, in which one, two, three, four, five, or six hydrogen atoms are replaced by halogen. The term "$C_1$-$C_3$ haloalkyl" means a $C_1$-$C_3$ alkyl group, as defined herein, in which one, two, three, four, or five hydrogen atoms are replaced by halogen. Representative examples of haloalkyl include, but are not limited to, chloromethyl, 2-fluoroethyl, 2,2-difluoroethyl, fluoromethyl, 2,2,2-trifluoroethyl, trifluoromethyl, difluoromethyl, pentafluoroethyl, 2-chloro-3-fluoropentyl, trifluorobutyl, and trifluoropropyl.

The term "haloalkoxy" as used herein, means an alkoxy group, as defined herein, in which one, two, three, four, five or six hydrogen atoms are replaced by halogen. The term "$C_1$-$C_6$ haloalkoxy" means a $C_1$-$C_6$ alkoxy group, as defined herein, in which one, two, three, four, five, or six hydrogen atoms are replaced by halogen. The term "$C_1$-$C_3$ haloalkoxy" means a $C_1$-$C_3$ alkoxy group, as defined herein, in which one, two, three, four, or five hydrogen atoms are replaced by halogen.

The term "4-12 membered heterocyclyl" as used herein, means a hydrocarbon ring radical of 4-12 carbon ring atoms wherein at least one carbon atom is replaced by a heteroatom(s) independently selected from the group consisting of O, N, and S. The 4-12 membered heterocycle ring may be a single ring (monocyclic) or have two or more rings (bicyclic or polycyclic). In certain embodiments, the monocyclic heterocycle is a four-, five-, six-, seven-, or eight-membered hydrocarbon ring wherein at least one carbon ring atom is replaced by a heteroatom(s) independently selected from the group consisting of O, N, and S. In certain embodiments, the monocyclic heterocycle is a 4-7 membered hydrocarbon ring wherein at least one carbon ring atom is replaced by a heteroatom(s). A four-membered monocyclic heterocycle contains zero or one double bond, and one heteroatom selected from the group consisting of O, N, and S. A five-membered monocyclic heterocycle contains zero or one double bond and one, two, or three heteroatoms selected from the group consisting of O, N, and S. Examples of five-membered monocyclic heterocycles include those containing in the ring: 1 O; 1 S; 1 N; 2 N; 3 N; 1 S and 1 N; 1 S, and 2 N; 1 O and 1 N; or 1 O and 2 N. Non limiting examples of 5-membered monocyclic heterocyclic groups include 1,3-dioxolanyl, tetrahydrofuranyl, dihydrofuranyl, tetrahydrothienyl, dihydrothienyl, imidazolidinyl, oxazolidinyl, imidazolinyl, imidazolidinyl, isoxazolidinyl, pyrazolidinyl, pyrazolinyl, pyrrolidinyl, 2-pyrrolinyl, 3-pyrrolinyl, thiazolinyl, and thiazolidinyl. A six-membered monocyclic heterocycle contains zero, one, or two double bonds and one, two, or three heteroatoms selected from the group consisting of O, N, and S. Examples of six-membered monocyclic heterocycles include those containing in the ring: 1 O; 2 O; 1 S; 2 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Examples of six-membered monocyclic heterocycles include dihydropyranyl, 1,4-dioxanyl, 1,3-dioxanyl, 1,4-dithianyl, hexahydropyrimidine, morpholinyl, 1,4-dihydropyridinyl, piperazinyl, piperidinyl, tetrahydropyranyl, 1,2,3,6-tetrahydropyridinyl, tetrahydrothiopyranyl, thiomorpholinyl, thioxanyl, and trithianyl. Seven- and eight-membered monocyclic heterocycles contains zero, one, two, or three double bonds and one, two, or three heteroatoms selected from the group consisting of O, N, and S. Examples of monocyclic heterocycles include, but are not limited to, azetidinyl, azepanyl, aziridinyl, 1,4-diazepanyl, dihydropyranyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxazepanyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyridinyl, tetrahydropyranyl, tetrahydrothienyl, thiadiazolinyl, thiadiazolidinyl, thiazolinyl, thiazolidinyl, thiomorpholinyl, thiopyranyl, and trithianyl. Polycyclic heterocycle groups contain two or more rings, and bicyclic heterocycles contain two rings. In certain embodiments, the polycyclic heterocycle groups contain 2 or 3 rings. The rings within the polycyclic and the bicyclic heterocycle groups may be in a bridged, fused, or spiro orientation, or combinations thereof. In a spirocyclic heterocycle, one atom is common to two different rings. Non limiting examples of the spirocyclic heterocycle include 6-oxaspiro[2.5]octanyl, 2-azaspiro[3.3]heptyl, 5-azaspiro[2.4]heptyl, 5-azaspiro[2.5]octyl, 2-azaspiro[3.5] nonyl, 2-azaspiro[3.4]octyl, 3-azaspiro[5.5]undecyl, 5-azaspiro[3.4]octyl, 2-oxaspiro[3.3]heptyl, 2-oxa-6-azaspiro[3.3]heptyl, 6-oxa-2-azaspiro[3.4]octyl, 6-azaspiro[3.4]octyl, 7-azaspiro[3.5]nonyl, 8-azaspiro[4.5]decyl, 1-oxa-7-azaspiro[4.4]nonyl, 1-oxa-7-azaspiro[3.5]nonyl, 1-oxa-8-azaspiro[4.5]decyl, 1-oxa-3,8-diazaspiro[4.5]decyl, 1-oxa-4,9-diazaspiro[5.5]undecyl, 2-oxa-7-azaspiro[3.5] nonyl, 5-oxa-2-azaspiro[3.5]nonyl, 6-oxa-2-azaspiro[3.5] nonyl, 7-oxa-2-azaspiro[3.5]nonyl, 8-oxa-2-azaspiro[4.5] decyl, 2,7-diazaspiro[4.4]nonyl, 1,4-dioxa-8-azaspiro[4.5] decyl, 1,3,8-triazaspiro[4.5]decyl. In a fused ring heterocycle, the rings share one common bond. Examples of fused bicyclic heterocycles are a 4-6 membered monocyclic heterocycle fused to a phenyl group, or a 4-6 membered monocyclic heterocycle fused to a $C_3$-$C_6$ monocyclic cycloalkyl, or a 4-6 membered monocyclic heterocycle fused to a $C_4$-$C_7$ monocyclic cycloalkenyl, or a 4-6 membered monocyclic heterocycle fused to a 4-7 membered monocyclic heterocycle. Examples of fused bicyclic heterocycles include, but are not limited to, 1,2-dihydrophthalazinyl, 3,4-dihydro-2H-benzo[b][1,4]dioxepinyl, chromanyl, chromenyl, isochromanyl, 2,3-dihydrobenzo[b][1,4]dioxinyl, isoindolinyl, 2,3-dihydrobenzo[b]thienyl, hexahydro-1H-cyclopenta[c]furanyl, 3-oxabicyclo[3.1.0]hexanyl, 3-azabicyclo[3.1.0]hexyl, benzopyranyl, benzothiopyranyl, indolinyl, decahydropyrrolo[3,4-b]azepinyl, 2,3-dihydrobenzofuranyl, 2,3-dihydrobenzothienyl, 2,3-dihydro-1H-indolyl, 3,4-dihydroisoquinolin-2(1H)-yl, 2,3,4,6-tetrahydro-1H-pyrido[1,2-a]pyrazin-2-yl, hexahydropyrano[3,4-b][1,4]oxazin-1(5H)-yl, hexahydropyrrolo[3,4-c]pyrrol-2 (1H)-yl, hexahydrocyclopenta[c]pyrrol-3a(1H)-yl, hexahydro-1H-oxazolo[3,4-a]pyrazinyl, octahydropyrrolo [3,4-b][1,4]oxazinyl, octahydroimidazo[1,5-a]pyrazinyl, octahydropyrrolo[1,2-a]pyrazinyl, octahydro-1H-pyrrolo[3,2-c]pyridinyl, and octahydropyrrolo[3,4-c]pyrrolyl. In a bridged heterocycle, the rings share at least two non-adjacent atoms. Examples of such bridged heterocycles include, but are not limited to, 8-oxabicyclo[3.2.1]octanyl, 7-oxabicyclo[2.2.1]heptanyl, azabicyclo[2.2.1]heptyl (including 2-azabicyclo[2.2.1]hept-2-yl), 8-azabicyclo[3.2.1]oct-8-yl, octahydro-2,5-epoxypentalene, 8-oxa-3-azabicyclo[3.2.1] octyl, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). The nitrogen and sulfur heteroatoms in the heterocycle rings may optionally be oxidized (e.g. 1,1-dioxidotetrahydrothienyl, 1,1-dioxido-1,2-thiazolidinyl, 1,1-dioxidothiomorpholinyl)) and the nitrogen atoms may optionally be quaternized. Non limiting examples of the polycyclic heterocycle include 6,7-dihydro-[1,3]dioxolo[4,5-f]benzofuranyl.

The term "4-7 membered heterocyclyl" as used herein, means a hydrocarbon ring radical of 4-7 carbon ring atoms wherein at least one carbon atom is replaced by a heteroatom (s) independently selected from the group consisting of O, N, and S. A four-membered monocyclic heterocycle contains zero or one double bond, and one heteroatom selected from the group consisting of O, N, and S. A five-membered monocyclic heterocycle contains zero or one double bond and one, two, or three heteroatoms selected from the group consisting of O, N, and S. Examples of five-membered monocyclic heterocycles include those containing in the ring: 1 O; 1 S; 1 N; 2 N; 3 N; 1 S and 1 N; 1 S, and 2 N; 1 O and 1 N; or 1 O and 2 N. Non limiting examples of 5-membered monocyclic heterocyclic groups include 1,3-dioxolanyl, tetrahydrofuranyl, dihydrofuranyl, tetrahydrothienyl, dihydrothienyl, imidazolidinyl, oxazolidinyl, imidazolinyl, imidazolidinyl, isoxazolidinyl, pyrazolidinyl, pyrazolinyl, pyrrolidinyl, 2-pyrrolinyl, 3-pyrrolinyl, thiazolinyl, and thiazolidinyl. A six-membered monocyclic heterocycle contains zero, one, or two double bonds and one, two, or three heteroatoms selected from the group consisting of O, N, and S. Examples of six-membered monocyclic heterocycles include those containing in the ring: 1 O; 2 O; 1 S; 2 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Examples of six-membered monocyclic heterocycles include dihydropyranyl, 1,4-dioxanyl, 1,3-dioxanyl, 1,4-dithianyl, hexahydropyrimidine, morpholinyl, 1,4-dihydropyridinyl, piperazinyl, piperidinyl, tetrahydropyranyl, 1,2,3,6-tetrahydropyridinyl, tetrahydrothiopyranyl, thiomorpholinyl, thioxanyl, and trithianyl. Seven- and eight-membered monocyclic heterocycles contains zero, one, two, or three double bonds and one, two, or three heteroatoms selected from the group consisting of O, N, and S.

The term "5-11 membered heteroaryl" as used herein, means a monocyclic heteroaryl and a bicyclic heteroaryl. The "5-6 membered heteroaryl" is a five- or six-membered ring. The five-membered ring contains two double bonds. The five membered ring may contain one heteroatom selected from O or S; or one, two, three, or four nitrogen atoms and optionally one oxygen or one sulfur atom. The six-membered ring contains three double bonds and one, two, three or four nitrogen atoms. Examples of 5-6 membered monocyclic heteroaryl include, but are not limited to, furanyl, imidazolyl, isoxazolyl, isothiazolyl, oxadiazolyl, 1,3-oxazolyl, pyridazinonyl, pyridinonyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a $C_3$-$C_6$ monocyclic cycloalkyl, or a monocyclic heteroaryl fused to $C_4$-$C_7$ monocyclic cycloalkenyl, or a monocyclic heteroaryl fused to a monocyclic heteroaryl, or a monocyclic heteroaryl fused to a 4-7 membered monocyclic heterocycle. Representative examples of bicyclic heteroaryl groups include, but are not limited to, 4H-furo[3,2-b]pyrrolyl, benzofuranyl, benzothienyl, benzoisoxazolyl, benzoxazolyl, benzimidazolyl, benzoxadiazolyl, phthalazinyl, 2,6-dihydropyrrolo[3,4-c]pyrazol-5(4H)-yl, 6,7-dihydro-pyrazolo[1,5-a]pyrazin-5(4H)-yl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, 4,5,6,7-tetrahydropyrazolo[1,5-a]pyridinyl, 2,4,6,7-tetrahydro-5H-pyrazolo[4,3-c]pyridin-5-yl, thiazolo[5,4-b]pyridin-2-yl, thiazolo[5,4-d]pyrimidin-2-yl, and 5,6,7,8-tetrahydroquinolin-5-yl. The nitrogen atom in the heteroaryl rings may optionally be oxidized and may optionally be alkylated.

The term "6-10 membered aryl", as used herein, means a hydrocarbon ring radical containing 6-10 carbon atoms, zero heteroatoms, and one or more aromatic rings. The 6-10 membered aryl group may be a single-ring (monocyclic) or have two rings (bicyclic). The bicyclic aryl is naphthyl, or a phenyl fused to a monocyclic cycloalkyl, or a phenyl fused to a monocyclic cycloalkenyl. Representative examples of 6-10 membered aryl groups include, but are not limited to, phenyl, indenyl, tetrahydronaphthalenyl, dihydroindenyl (indanyl), naphthyl, and the like.

The aryls, the cycloalkyls, the cycloalkenyls, the heterocycles, and the heteroaryls, including the exemplary rings, are optionally substituted unless otherwise indicated; and are attached to the parent molecular moiety through any substitutable atom contained within the ring system.

The term "heteroatom" as used herein, means a nitrogen, oxygen, and sulfur.

The term "oxo" as used herein, means a =O group.

The term "radiolabel" means a compound of the invention in which at least one of the atoms is a radioactive atom or a radioactive isotope, wherein the radioactive atom or isotope spontaneously emits gamma rays or energetic particles, for example alpha particles or beta particles, or positrons. Examples of such radioactive atoms include, but are not limited to, $^3$H (tritium), $^{14}$C, $^{11}$C, $^{15}$O, $^{18}$F, $^{35}$S, $^{123}$I, and $^{125}$I.

A moiety is described as "substituted" when a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The terms "treat", "treating", and "treatment" refer to a method of alleviating or abrogating a disease and/or its attendant symptoms. In certain embodiments, "treat," "treating," and "treatment" refer to ameliorating at least one physical parameter, which may not be discernible by the subject. In yet another embodiment, "treat", "treating", and "treatment" refer to modulating the disease or disorder, either physically (for example, stabilization of a discernible symptom), physiologically (for example, stabilization of a physical parameter), or both. In a further embodiment, "treat", "treating", and "treatment" refer to slowing the progression of the disease or disorder.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring or developing a disease or disorder.

The phrase "therapeutically effective amount" means an amount of a compound, or a pharmaceutically acceptable salt thereof, sufficient to prevent the development of or to alleviate to some extent one or more of the symptoms of the condition or disorder being treated when administered alone or in conjunction with another therapeutic agent for treatment in a particular subject or subject population. The "therapeutically effective amount" may vary depending on the compound, the disease and its severity, and the age, weight, health, etc., of the subject to be treated. For example in a human or other mammal, a therapeutically effective amount may be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, pigs, horses, dogs, cats, rabbits, rats, mice and the like. In one embodiment, the subject is a human. The terms "human," "patient," and "subject" are used interchangeably herein.

The term "one or more" refers to one to eight. In one embodiment it refers to one to eight. In one embodiment it refers to one to seven. In one embodiment it refers to one to six. In one embodiment it refers to one to five. In one embodiment it refers to one to four. In one embodiment it refers to one or three. In another embodiment it refers to one to three. In a further embodiment it refers to one to two. In yet other embodiment it refers to two. In yet other further embodiment it refers to one.

As used herein, "Class I mutation(s)" refers to mutations which interfere with protein synthesis. They result in the introduction of a premature signal of termination of translation (stop codon) in the mRNA. The truncated CFTR proteins are unstable and rapidly degraded, so, the net effect is that there is no protein at the apical membrane. In particular, Class I mutation(s) refers to p.Gly542X (G542X), W1282X, c.489+1G>T (621+1G>T), or c.579+1G>T (711+1G>T) mutation. More particularly, Class I mutation(s) refers to G542X; or W1282X mutations.

As used herein, "Class II mutation(s)" refers to mutations which affect protein maturation. These lead to the production of a CFTR protein that cannot be correctly folded and/or trafficked to its site of function on the apical membrane. In particular, Class II mutation(s) refers to p.Phe508del (F508del), p.Ile507del, or p.Asn1303Lys (N1303K) mutations. More particularly, Class II mutation(s) refers to F508del or N1303K mutations.

As used herein, "Class III mutation(s)" refers to mutations which alter the regulation of the CFTR channel. The mutated CFTR protein is properly trafficked and localized to the plasma membrane but cannot be activated, or it cannot function as a chloride channel. In particular, Class III mutation(s) refers to p.Gly551Asp (G551D), G551S, R553G, G1349D, S1251N, G178R, S549N mutations. More particularly, Class III mutation(s) refers to G551D, R553G, G1349D, S1251N, G178R, or S549N mutations.

As used herein, "Class IV mutation(s)" refers to mutations which affect chloride conductance. The CFTR protein is correctly trafficked to the cell membrane but generates reduced chloride flow or a "gating defect" (most are missense mutations located within the membrane-spanning domain). In particular, Class IV mutation(s) refers to p.Arg117His (R117H), R347P, or p.Arg334Trp (R334W) mutations.

As used herein, "Class V mutation(s)" refers to mutations which reduce the level of normally functioning CFTR at the apical membrane or result in a "conductance defect" (for example partially aberrant splicing mutations or inefficient trafficking missense mutations). In particular, Class V mutation(s) refers to c.1210-12T[5] (5T allele), c.S3140-26A>G (3272-26A>G), c.3850-2477C>T (3849+10kbC>T) mutations.

As used herein, "Class VI mutation(s)" refers to mutations which decrease the stability of the CFTR which is present or which affect the regulation of other channels, resulting in inherent instability of the CFTR protein. In effect, although functional, the CFTR protein is unstable at the cell surface and it is rapidly removed and degraded by cell machinery. In particular, Class VI mutation(s) refers to Rescued F508del, 120del23, N287Y, 4326dellTC, or 4279insA mutations. More particularly, Class VI mutation(s) refers to Rescued F508del mutations.

Compounds

Compounds of the invention are described herein.

Particular values of variable groups are as follows. Such values may be used where appropriate with any of the other values, definitions, claims or embodiments defined hereinbefore or hereinafter.

Formula (I)

One embodiment pertains to compounds of Formula (I), or a pharmaceutically acceptable salt thereof,

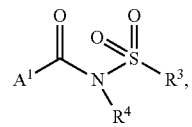

$A^1$ is selected from the group consisting of

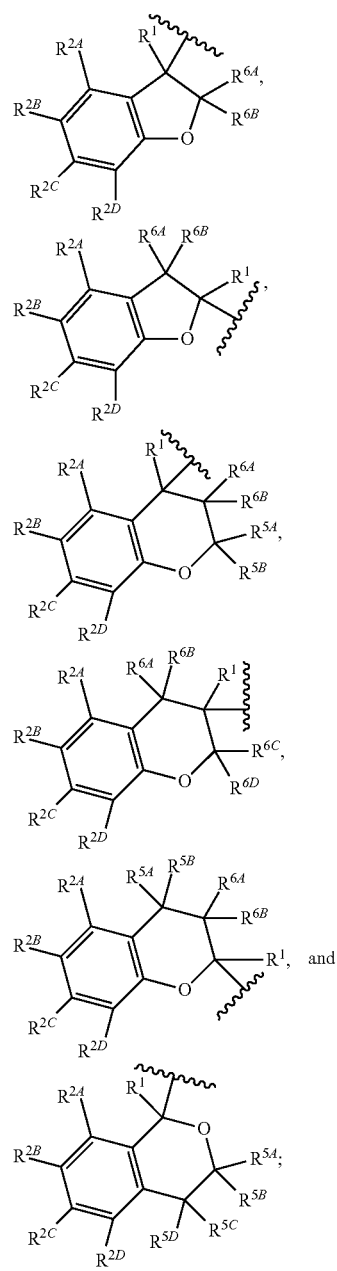

$R^1$ is selected from the group consisting of hydrogen, OH, CN, $C_1$-$C_6$ alkyl, $C_2$-$C_6$ alkenyl, $C_2$-$C_6$ alkynyl, $C_1$-$C_6$ alkoxy, 6-10 membered aryl, 5-11 membered heteroaryl, $C_3$-$C_{11}$cycloalkyl, $C_4$-$C_{11}$ cycloalkenyl, and 4-12 membered heterocyclyl; wherein the $R^1$ $C_1$-$C_6$ alkyl, $C_2$-$C_6$ alkenyl, $C_2$-$C_6$ alkynyl, and $C_1$-$C_6$ alkoxy are optionally substituted with one or more substituents independently selected from the group consisting of $R^7$, $OR^7$, $SR^7$, $NHR^7$, $N(R^7)_2$, $NH_2$, $C(O)OH$, $OH$, $CN$, $NO_2$, F, Cl, Br and I; wherein the $R^1$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $C_1$-$C_6$ alkyl, $C_1$-$C_6$ haloalkyl, $C_1$-$C_6$ alkoxy, $C_1$-$C_6$ haloalkoxy, $C(O)OH$, $OH$, oxo, $CN$, $NO_2$, F, Cl, Br and I;

one of $R^{2A}$, $R^{2B}$, $R^{2C}$, and $R^{2D}$ is hydrogen, and the remaining are independently selected from the group consisting of hydrogen, $R^8$, $OR^8$, $C(O)R^8$, $C(O)OR^8$, $SO_2R^8$, $NHR^8$, $N(R^8)_2$, $NH_2$, $C(O)OH$, $OH$, $CN$, $NO_2$, F, Cl, Br and I; or two of $R^{2A}$, $R^{2B}$, $R^{2C}$, and $R^{2D}$ on adjacent carbons form a fused ring selected from the group consisting of phenyl, 5-6 membered heteroaryl, $C_3$-$C_7$ cycloalkyl, $C_4$-$C_7$ cycloalkenyl, and 4-7 membered heterocyclyl; and the remaining are independently selected from the group consisting of hydrogen, $R^8$, $OR^8$, $C(O)R^8$, $OC(O)R^8$, $C(O)OR^8$, $SO_2R^8$, $NHR^8$, $N(R^8)_2$, $NH_2$, $C(O)OH$, $OH$, $CN$, $NO_2$, F, Cl, Br and I; wherein the phenyl, 5-6 membered heteroaryl, $C_3$-$C_7$ cycloalkyl, $C_4$-$C_7$ cycloalkenyl, and 4-7 membered heterocyclyl are optionally substituted with one or more substituents independently selected from the group consisting of $R^8$, $OR^8$, $C(O)R^8$, $OC(O)R^8$, $C(O)OR^8$, $SO_2R^8$, $NHR^8$, $N(R^8)_2$, $NH_2$, $C(O)OH$, $OH$, $CN$, $NO_2$, F, Cl, Br and I;

$R^3$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^3$ $C_2$-$C_6$ alkyl, $C_2$-$C_6$ alkenyl, and $C_2$-$C_6$ alkynyl are optionally substituted with one or more substituents independently selected from the group consisting of $C_1$-$C_6$ alkoxy, phenyl, $OH$, oxo, $CN$, $NO_2$, F, Cl, Br and I; wherein the $R^3$ 6-10 membered aryl, 5-11 membered heteroaryl, $C_3$-$C_{11}$cycloalkyl, $C_4$-$C_{11}$ cycloalkenyl, and 4-12 membered heterocyclyl are optionally substituted with one or more substituents independently selected from the group consisting of $R^9$, $OR^9$, $C(O)R^9$, $OC(O)R^9$, $C(O)OR^9$, $SO_2R^9$, $C(O)NH_2$, $C(O)NHR^9$, $C(O)N(R^9)_2$, $NHC(O)R^9$, $NHR^9$, $N(R^9)_2$, $NH_2$, $C(O)OH$, $OH$, oxo, $CN$, $NO_2$, F, Cl, Br and I;

$R^4$ is selected from the group consisting of hydrogen and $C_1$-$C_6$ alkyl; wherein the $R^4$ $C_1$-$C_6$ alkyl is optionally substituted with one or more substituents independently selected from the group consisting of $R^{10}$, $OR^{10}$, $SR^{10}$, $NHR^{10}$, $N(R^{10})_2$, $NH_2$, $C(O)OH$, $OH$, oxo, $CN$, $NO_2$, F, Cl, Br and I;

$R^{5A}$, $R^{5B}$, $R^{5C}$, and $R^{5D}$ are each independently selected from the group consisting of hydrogen, $C_1$-$C_6$ alkyl, $C_2$-$C_6$ alkenyl, $C_2$-$C_6$ alkynyl, $C_1$-$C_6$ alkoxy, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^{5A}$, $R^{5B}$, $R^{5C}$, and $R^{5D}$ $C_1$-$C_6$ alkyl, $C_2$-$C_6$ alkenyl, $C_2$-$C_6$ alkynyl, and $C_1$-$C_6$ alkoxy are optionally substituted with one or more substituents independently selected from the group consisting of 6-10 membered aryl, 5-11 membered heteroaryl, $C_3$-$C_{11}$ cycloalkyl, $C_4$-$C_{11}$ cycloalkenyl, 4-12 membered heterocyclyl, $C_1$-$C_6$ thioalkyl, $OH$, oxo, $CN$, $NO_2$, F, Cl, Br and I; wherein the $R^{5A}$, $R^{5B}$, $R^{5C}$, and $R^{5D}$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $C_1$-$C_6$ alkyl, $C(O)OH$, $NH_2$, $OH$, oxo, $CN$, $NO_2$, F, Cl, Br and I; or $R^{5A}$ and $R^{5B}$, together with the carbon atom to which they are attached, form a $C_3$-$C_7$ monocyclic cycloalkyl or a 4-7 membered monocyclic heterocycle; wherein the $C_3$-$C_7$ monocyclic cycloalkyl and the 4-7 membered monocyclic heterocycle are each optionally substituted with one or more substituents independently selected from the group consisting of $C_1$-$C_6$ alkyl, $C(O)OH$, $NH_2$, $OH$, oxo, $CN$, $NO_2$, F, Cl, Br and I; and $R^{5C}$ and $R^{5D}$ are each independently selected from the group consisting of hydrogen, $C_1$-$C_6$ alkyl, $C_2$-$C_6$ alkenyl, $C_2$-$C_6$ alkynyl, $C_1$-$C_6$ alkoxy, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^{5C}$ and $R^{5D}$ $C_1$-$C_6$ alkyl, $C_2$-$C_6$ alkenyl, $C_2$-$C_6$ alkynyl, and $C_1$-$C_6$ alkoxy are optionally substituted with one or more substituents independently selected from the group consisting of 6-10 membered aryl, 5-11 membered heteroaryl, $C_3$-$C_{11}$ cycloalkyl, $C_4$-$C_{11}$ cycloalkenyl, 4-12 membered heterocyclyl, $C_1$-$C_6$ thioalkyl, $OH$, oxo, $CN$, $NO_2$, F, Cl, Br and I; wherein the $R^{5C}$ and $R^{5D}$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $C_1$-$C_6$ alkyl, $C(O)OH$, $NH_2$, $OH$, oxo, $CN$, $NO_2$, F, Cl, Br and I; or $R^{5C}$ and $R^{5D}$, together with the carbon atom to which they are attached, form a $C_3$-$C_7$ monocyclic cycloalkyl or a 4-7 membered monocyclic heterocycle; wherein the $C_3$-$C_7$ monocyclic cycloalkyl and the 4-7 membered monocyclic heterocycle are each optionally substituted with one or more substituents independently selected from the group consisting of $C_1$-$C_6$ alkyl, $C(O)OH$, $NH_2$, $OH$, oxo, $CN$, $NO_2$, F, Cl, Br and I; and $R^{5A}$ and $R^{5B}$ are each independently selected from the group consisting of hydrogen, $C_1$-$C_6$ alkyl, $C_2$-$C_6$ alkenyl, $C_2$-$C_6$ alkynyl, $C_1$-$C_6$ alkoxy, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^{5A}$ and $R^{5B}$ $C_1$-$C_6$ alkyl, $C_2$-$C_6$ alkenyl, $C_2$-$C_6$ alkynyl, and $C_1$-$C_6$ alkoxy are optionally substituted with one or more substituents independently selected from the group consisting of 6-10 membered aryl, 5-11 membered heteroaryl, $C_3$-$C_{11}$ cycloalkyl, $C_4$-$C_{11}$ cycloalkenyl, 4-12 membered heterocyclyl, $C_1$-$C_6$ thioalkyl, $OH$, oxo, $CN$, $NO_2$, F, Cl, Br and I; wherein the $R^{5A}$ and $R^{5B}$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $C_1$-$C_6$ alkyl, $C(O)OH$, $NH_2$, $OH$, oxo, $CN$, $NO_2$, F, Cl, Br and I;

$R^{6A}$, $R^{6B}$, $R^{6C}$, and $R^{6D}$ are each independently hydrogen;

$R^7$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^7$ $C_1$-$C_6$ alkyl, $C_2$-$C_6$ alkenyl, and $C_2$-$C_6$ alkynyl is optionally substituted with one or more substituents independently selected from the group consisting of $C_1$-$C_6$ alkoxy, OH, oxo, CN, $NO_2$, F, Cl, Br and I; wherein each $R^7$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, oxo, OH, CN, $NO_2$, F, Cl, Br and I;

$R^8$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$cycloalkyl, $C_4$-$C_{11}$ cycloalkenyl, and 4-12 membered heterocyclyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of $R^{11}$, $OR^{11}$, $C(O)OR^{11}$, $NHR^{11}$, $N(R^{11})_2$, $NH_2$, C(O)OH, OH, CN, $NO_2$, F, Cl, Br and I; wherein each $R^8$ $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{12}$, $OR^{12}$, $C(O)OR^{12}$, $NHR^{12}$, $N(R^{12})_2$, $NH_2$, C(O)OH, OH, oxo, CN, $NO_2$, F, Cl, Br and I;

$R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{13}$, $OR^{13}$, $SR^{13}$, $C(O)R^{13}$, $NHR^{13}$, $N(R^{13})_2$, C(O)OH, OH, CN, $NO_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^{14}$, $OR^{14}$, $C(O)R^{14}$, $OC(O)R^{14}$, $C(O)OR^{14}$, $SO_2R^{14}$, $NHR^{14}$, $N(R^{14})_2$, $NH_2$, C(O)OH, OH, oxo, CN, $NO_2$, F, Cl, Br and I;

$R^{10}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$cycloalkyl, $C_4$-$C_{11}$ cycloalkenyl, and 4-12 membered heterocyclyl; wherein each $R^{10}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{10}$ $C_6$-$C_{10}$ membered aryl, 5-11 membered heteroaryl, $C_3$-$C_{11}$cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I;

$R^{11}$, at each occurrence, is independently selected from the group consisting of $C_1$-$C_6$ alkyl, $C_1$-$C_6$ alkoxy, $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl; wherein each $R^{11}$ $C_1$-$C_6$ alkyl and $C_1$-$C_6$ alkoxy is optionally substituted with one or more substituents independently selected from the group consisting of OH, oxo, CN, $NO_2$, F, Cl, Br and I; wherein each $R^{11}$ $C_6$-$C_{10}$ membered aryl, $C_3$-$C_{11}$ cycloalkyl, 4-12 membered heterocyclyl, $C_4$-$C_{11}$cycloalkenyl, and 5-6 membered heteroaryl is optionally substituted with one or more substituents independently selected from the group consisting of $C_1$-$C_6$ alkyl, $C_1$-$C_6$ alkoxy, F, Cl, Br and I;

$R^{12}$, at each occurrence, is independently selected from the group consisting of $C_1$-$C_6$ alkyl, $C_1$-$C_6$ alkoxy, $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl; wherein each $R^{12}$ $C_1$-$C_6$ alkyl and $C_1$-$C_6$ alkoxy is optionally substituted with one or more substituents independently selected from the group consisting of OH, oxo, CN, $NO_2$, F, Cl, Br and I; wherein each $R^{12}$ $C_6$-$C_{10}$ membered aryl, $C_3$-$C_{11}$ cycloalkyl, 4-12 membered heterocyclyl, $C_4$-$C_{11}$cycloalkenyl, and 5-6 membered heteroaryl is optionally substituted with one or more substituents independently selected from the group consisting of $C_1$-$C_6$ alkyl, $C_1$-$C_6$ alkoxy, F, Cl, Br and I;

$R^{13}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^3$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{13}$ $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I; and $R^{14}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{14}$ $C_1$-$C_6$ alkyl, $C_2$-$C_6$ alkenyl, and $C_2$-$C_6$ alkynyl is optionally substituted with one or more substituents independently selected from the group consisting of $C_1$-$C_6$ alkyl, $C_1$-$C_6$ alkoxy, 5-6 membered heteroaryl, 4-12 membered heterocyclyl, OH, oxo, CN, $NO_2$, F, Cl, Br and I;

with the proviso that $R^3$ is not $C_1$-alkyl or thienyl;

with the proviso that, when $R^{2A}$, $R^{2B}$, $R^{2C}$, and $R^{2D}$ are each hydrogen, $R^1$ is not hydrogen;

with the proviso that, when $R^3$ is imidazolyl, $R^9$ is not $CH_2CH(CH_3)_2$;

with the proviso that when $R^{2B}$ is Cl, $R^3$ is not 2,4-dimethyl-5-thiazolyl or 2-cyano-3-fluorophenyl;

with the proviso that, when $R^3$ is cyclohexyl, $R^{2C}$ is not $OCH_3$;

with the proviso that, when $R^3$ is 3-pyridinyl, $R^{2C}$ is not Cl; and with the proviso that, when $R^3$ is phenyl, $R^{13}$ is not $C(O)CH_3$.

In one embodiment of Formula (I), $A^1$ is selected from the group consisting of

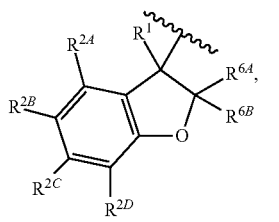
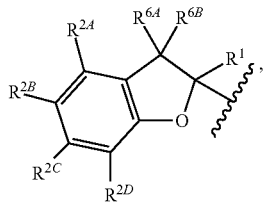
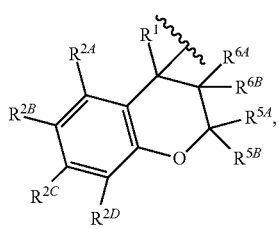
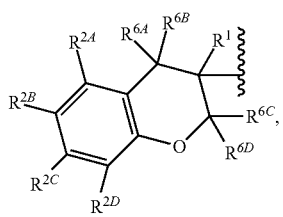
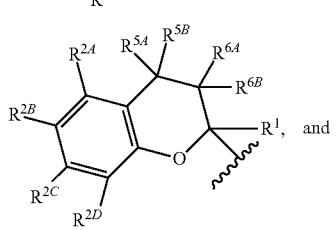
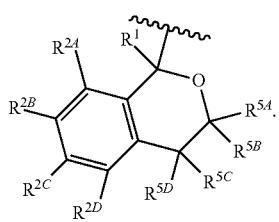
In another embodiment of Formula (I), A is selected from the group consisting of
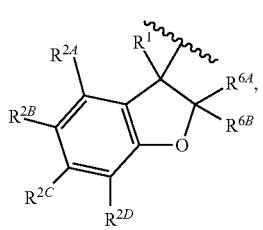
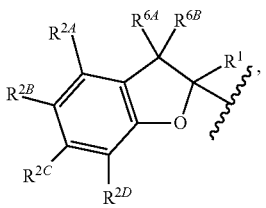
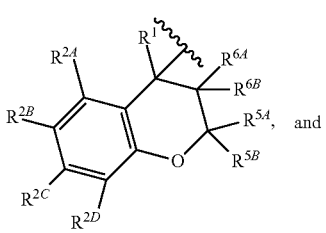
-continued
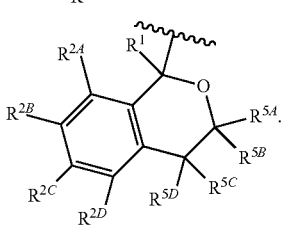
In another embodiment of Formula (I), $A^1$ is
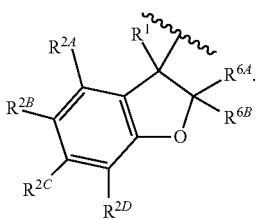
In another embodiment of Formula (I), $A^1$ is
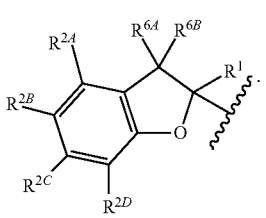
In another embodiment of Formula (I), $A^1$ is
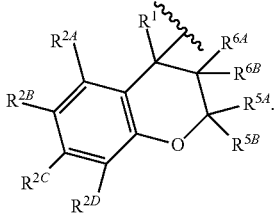

In another embodiment of Formula (I), $A^1$ is

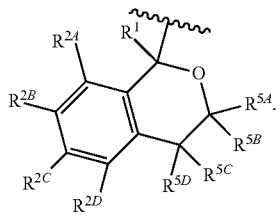

In one embodiment of Formula (I), $R^1$ is selected from the group consisting of hydrogen, OH, CN, $C_1$-$C_6$ alkyl, $C_2$-$C_6$ alkenyl, $C_2$-$C_6$ alkynyl, $C_1$-$C_6$ alkoxy, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^1$ $C_1$-$C_6$ alkyl, $C_2$-$C_6$ alkenyl, $C_2$-$C_6$ alkynyl, and $C_1$-$C_6$ alkoxy are optionally substituted with one or more substituents independently selected from the group consisting of $R^7$, $OR^7$, $SR^7$, $NHR^7$, $N(R^7)_2$, $NH_2$, $C(O)OH$, OH, CN, $NO_2$, F, Cl, Br and I; wherein the $R^1$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $C_1$-$C_6$ alkyl, $C_1$-$C_6$ haloalkyl, $C_1$-$C_6$ alkoxy, $C_1$-$C_6$ haloalkoxy, $C(O)OH$, OH, oxo, CN, $NO_2$, F, Cl, Br and I. In another embodiment of Formula (I), $R^1$ is selected from the group consisting of hydrogen, $C_1$-$C_6$ alkyl, and 6-10 membered aryl. In another embodiment of Formula (I), $R^1$ is hydrogen. In another embodiment of Formula (I), $R^1$ is $C_1$-$C_6$ alkyl. In another embodiment of Formula (I), $R^1$ is $CH_3$. In another embodiment of Formula (I), $R^1$ is $CH_2CH_3$. In another embodiment of Formula (I), $R^1$ is 6-10 membered aryl. In another embodiment of Formula (I), $R^1$ is phenyl.

In one embodiment of Formula (I), one of $R^{2A}$, $R^{2B}$, $R^{2C}$, and $R^{2D}$ is hydrogen, and the remaining are independently selected from the group consisting of hydrogen, $R^8$, $OR^8$, $C(O)R^8$, $C(O)OR^8$, $SO_2R^8$, $NHR^8$, $N(R^8)_2$, $NH_2$, $C(O)OH$, OH, CN, $NO_2$, F, Cl, Br and I; or two of $R^{2A}$, $R^{2B}$, $R^{2C}$, and $R^{2D}$ on adjacent carbons form a fused ring selected from the group consisting of phenyl, 5-6 membered heteroaryl, $C_3$-$C_7$ cycloalkyl, $C_4$-$C_7$ cycloalkenyl, and 4-7 membered heterocyclyl; and the remaining are independently selected from the group consisting of hydrogen, $R^8$, $OR^8$, $C(O)R^8$, $OC(O)R^8$, $C(O)OR^8$, $SO_2R^8$, $NHR^8$, $N(R^8)_2$, $NH_2$, $C(O)OH$, OH, CN, $NO_2$, F, Cl, Br and I; wherein the phenyl, 5-6 membered heteroaryl, $C_3$-$C_7$ cycloalkyl, $C_4$-$C_7$ cycloalkenyl, and 4-7 membered heterocyclyl are optionally substituted with one or more substituents independently selected from the group consisting of $R^8$, $OR^8$, $C(O)R^8$, $OC(O)R^8$, $C(O)OR^8$, $SO_2R^8$, $NHR^8$, $N(R^8)_2$, $NH_2$, $C(O)OH$, OH, CN, $NO_2$, F, Cl, Br and I. In one embodiment of Formula (I), one of $R^{2A}$, $R^{2B}$, $R^{2C}$, and $R^{2D}$ is hydrogen, and the remaining are independently selected from the group consisting of hydrogen, $R^8$, $OR^8$, $C(O)R^8$, $C(O)OR^8$, $SO_2R^8$, $NHR^8$, $N(R^8)_2$, $NH_2$, $C(O)OH$, OH, CN, $NO_2$, F, Cl, Br and I. In another embodiment of Formula (I), $R^{2A}$, $R^{2B}$, $R^{2C}$, and $R^{2D}$ are each independently hydrogen. In another embodiment of Formula (I), three of $R^{2A}$, $R^{2B}$, $R^{2C}$, and $R^{2D}$ are hydrogen, and the remaining is independently selected from the group consisting of hydrogen, $R^8$, $OR^8$, $C(O)R^8$, CN, Cl, and Br. In another embodiment of Formula (I), two of $R^{2A}$, $R^{2B}$, $R^{2C}$, and $R^{2D}$ are hydrogen, and the remaining are independently selected from the group consisting of hydrogen, $R^8$, $OR^8$, $C(O)R^8$, CN, Cl, and Br. In another embodiment of Formula (I), three of $R^{2A}$, $R^{2B}$, $R^{2C}$, and $R^{2D}$ are hydrogen, and the remaining is independently selected from the group consisting of hydrogen, $R^8$, $OR^8$, $C(O)R^8$, CN, Cl, and Br. In another embodiment of Formula (I), two of $R^{2A}$, $R^{2B}$, $R^{2C}$, and $R^{2D}$ on adjacent carbons form a fused 4-7 membered heterocyclyl; and the remaining are independently hydrogen; wherein the 4-7 membered heterocyclyl is optionally substituted with one or more F.

In one embodiment of Formula (I), $R^3$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^3$ $C_2$-$C_6$ alkyl, $C_2$-$C_6$ alkenyl, and $C_2$-$C_6$ alkynyl are optionally substituted with one or more substituents independently selected from the group consisting of $C_1$-$C_6$ alkoxy, phenyl, OH, oxo, CN, $NO_2$, F, Cl, Br and I; wherein the $R^3$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^9$, $OR^9$, $C(O)R^9$, $OC(O)R^9$, $C(O)OR^9$, $SO_2R^9$, $C(O)NH_2$, $C(O)NHR^9$, $C(O)N(R^9)_2$, $NHC(O)R^9$, $NHR^9$, $N(R^9)_2$, $NH_2$, $C(O)OH$, OH, oxo, CN, $NO_2$, F, Cl, Br and I. In another embodiment of Formula (I), $R^3$ is selected from the group consisting of $C_1$-$C_6$ alkyl, 6-10 membered aryl, 5-11 membered heteroaryl, and 4-12 membered heterocyclyl; wherein the $R^3$ 6-10 membered aryl, 5-11 membered heteroaryl, and 4-12 membered heterocyclyl are optionally substituted with one or more $R^9$. In another embodiment of Formula (I), $R^3$ is $C_1$-$C_6$ alkyl. In another embodiment of Formula (I), $R^3$ is 6-10 membered aryl; wherein the $R^3$ 6-10 membered aryl is optionally substituted with one or more $R^9$. In another embodiment of Formula (I), $R^3$ is phenyl or napthyl; wherein the $R^3$ phenyl or napthyl is optionally substituted with one or more $R^9$; and $R^9$ is $C_1$-$C_6$ alkyl. In another embodiment of Formula (I), $R^3$ is phenyl; wherein the $R^3$ phenyl is unsubstituted. In another embodiment of Formula (I), $R^3$ is napthyl; wherein the $R^3$ napthyl is unsubstituted. In another embodiment of Formula (I), $R^3$ is 5-11 membered heteroaryl; wherein the $R^3$ 5-11 membered heteroaryl is optionally substituted with one or more $R^9$. In another embodiment of Formula (I), $R^3$ is indazolyl or quinolinyl; wherein the $R^3$ indazolyl or quinolinyl is optionally substituted with one or more $R^9$; and $R^9$ is $C_1$-$C_6$ alkyl. In another embodiment of Formula (I), $R^3$ is quinolinyl; wherein the quinolinyl is unsubstituted. In another embodiment of Formula (I), $R^3$ is quinolinyl; wherein the quinolinyl is substituted with one $CH_3$.

In one embodiment of Formula (I), $R^4$ is selected from the group consisting of hydrogen and $C_1$-$C_6$ alkyl; wherein the $R^4$ $C_1$-$C_6$ alkyl is optionally substituted with one or more substituents independently selected from the group consisting of $R^{10}$, $OR^{10}$, $SR^{10}$, $NHR^{10}$, $N(R^{10})_2$, $NH_2$, $C(O)OH$, OH, oxo, CN, $NO_2$, F, Cl, Br and I. In another embodiment of Formula (I), $R^4$ is hydrogen.

In one embodiment of Formula (I), $R^{6A}$, $R^{6B}$, $R^{6C}$, and $R^{6D}$ are each independently hydrogen.

In one embodiment of Formula (I), $R^{5A}$, $R^{5B}$, $R^{5C}$, and $R^{5D}$ are each independently selected from the group consisting of hydrogen, $C_1$-$C_6$ alkyl, $C_2$-$C_6$ alkenyl, $C_2$-$C_6$ alkynyl, $C_1$-$C_6$ alkoxy, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^{5A}$, $R^{5B}$, $R^{5C}$, and $R^{5D}$ $C_1$-$C_6$ alkyl, $C_2$-$C_6$ alkenyl, $C_2$-$C_6$ alkynyl, and $C_1$-$C_6$ alkoxy are optionally substituted with one or more substituents independently selected from the group consisting of 6-10 membered aryl, 5-11 membered heteroaryl, $C_3$-$C_{11}$ cycloalkyl, $C_4$-$C_{11}$ cycloalkenyl, 4-12 membered heterocyclyl, $C_1$-$C_6$ thioalkyl, OH, oxo, CN, $NO_2$, F, Cl, Br and I; wherein the $R^{5A}$, $R^{5B}$, $R^{5C}$, and $R^{5D}$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $C_1$-$C_6$ alkyl, C(O)OH, $NH_2$, OH, oxo, CN, $NO_2$, F, Cl, Br and I. In another embodiment of Formula (I), $R^{5A}$, $R^{5B}$, $R^{5C}$, and $R^{5D}$ are each independently selected from the group consisting of hydrogen and $C_1$-$C_6$ alkyl; wherein the $R^{5A}$, $R^{5B}$, $R^{5C}$, and $R^{5D}$ $C_1$-$C_6$ alkyl is optionally substituted with one or more substituents independently selected from the group consisting of 4-12 membered heterocyclyl and $C_1$-$C_6$ thioalkyl.

In one embodiment of Formula (I), $R^{5A}$ and $R^{5B}$, together with the carbon atom to which they are attached, form a $C_3$-$C_7$ monocyclic cycloalkyl or a 4-7 membered monocyclic heterocycle; wherein the $C_3$-$C_7$ monocyclic cycloalkyl and the 4-7 membered monocyclic heterocycle are each optionally substituted with one or more substituents independently selected from the group consisting of $C_1$-$C_6$ alkyl, C(O)OH, $NH_2$, OH, oxo, CN, $NO_2$, F, Cl, Br and I; and $R^{5C}$ and $R^{5D}$ are each independently selected from the group consisting of hydrogen, $C_1$-$C_6$ alkyl, $C_2$-$C_6$ alkenyl, $C_2$-$C_6$ alkynyl, $C_1$-$C_6$ alkoxy, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^{5C}$ and $R^{5D}$ $C_1$-$C_6$ alkyl, $C_2$-$C_6$ alkenyl, $C_2$-$C_6$ alkynyl, and $C_1$-$C_6$ alkoxy are optionally substituted with one or more substituents independently selected from the group consisting of 6-10 membered aryl, 5-11 membered heteroaryl, $C_3$-$C_{11}$ cycloalkyl, $C_4$-$C_{11}$ cycloalkenyl, 4-12 membered heterocyclyl, $C_1$-$C_6$ thioalkyl, OH, oxo, CN, $NO_2$, F, Cl, Br and I; wherein the $R^{5C}$ and $R^{5D}$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $C_1$-$C_6$ alkyl, C(O)OH, $NH_2$, OH, oxo, CN, $NO_2$, F, Cl, Br and I. In another embodiment of Formula (I), $R^{5A}$ and $R^{5B}$, together with the carbon atom to which they are attached, form a $C_3$-$C_7$ monocyclic cycloalkyl; and $R^{5C}$ and $R^{5D}$ are each independently hydrogen.

In one embodiment of Formula (I), $R^{5C}$ and $R^{5D}$, together with the carbon atom to which they are attached, form a $C_3$-$C_7$ monocyclic cycloalkyl or a 4-7 membered monocyclic heterocycle; wherein the $C_3$-$C_7$ monocyclic cycloalkyl and the 4-7 membered monocyclic heterocycle are each optionally substituted with one or more substituents independently selected from the group consisting of $C_1$-$C_6$ alkyl, C(O)OH, $NH_2$, OH, oxo, CN, $NO_2$, F, Cl, Br and I; and $R^{5A}$ and $R^{5B}$ are each independently selected from the group consisting of hydrogen, $C_1$-$C_6$ alkyl, $C_2$-$C_6$ alkenyl, $C_2$-$C_6$ alkynyl, $C_1$-$C_6$ alkoxy, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^{5A}$ and $R^{5B}$ $C_1$-$C_6$ alkyl, $C_2$-$C_6$ alkenyl, $C_2$-$C_6$ alkynyl, and $C_1$-$C_6$ alkoxy are optionally substituted with one or more substituents independently selected from the group consisting of 6-10 membered aryl, 5-11 membered heteroaryl, $C_3$-$C_{11}$cycloalkyl, $C_4$-$C_{11}$ cycloalkenyl, 4-12 membered heterocyclyl, $C_1$-$C_6$ thioalkyl, OH, oxo, CN, $NO_2$, F, Cl, Br and I; wherein the $R^{5A}$ and $R^{5B}$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $C_1$-$C_6$ alkyl, C(O)OH, $NH_2$, OH, oxo, CN, $NO_2$, F, Cl, Br and I.

In another embodiment of Formula (I), $R^{5A}$, $R^{5B}$, $R^{5C}$, and $R^{5D}$ are each independently hydrogen. In another embodiment of Formula (I), $R^{5A}$ and $R^{5B}$ are each independently hydrogen. In another embodiment of Formula (I), $R^{5A}$ and $R^{5B}$ are each independently methyl. In another embodiment of Formula (I), $R^{5A}$ and $R^{5B}$, together with the carbon atom to which they are attached, form a $C_3$-$C_7$ monocyclic cycloalkyl. In another embodiment of Formula (I), $R^{5A}$ and $R^{5B}$, together with the carbon atom to which they are attached, form cyclohexyl.

In one embodiment of Formula (I), $R^8$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of $R^{11}$, $OR^{11}$, $C(O)OR^{11}$, $NHR^{11}$, $N(R^{11})_2$, $NH_2$, C(O)OH, OH, CN, $NO_2$, F, Cl, Br and I; wherein each $R^8$ $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{12}$, $OR^{12}$, $C(O)OR^{12}$, $NHR^{12}$, $N(R^{12})_2$, $NH_2$, C(O)OH, OH, oxo, CN, $NO_2$, F, Cl, Br and I. In another embodiment of Formula (I), $R^8$, at each occurrence, is independently selected from the group consisting of $C_1$-$C_6$ alkyl, $C_6$-$C_{10}$ membered aryl, and $C_3$-$C_{11}$ cycloalkyl; wherein each $R^8$ $C_1$-$C_6$ alkyl is optionally substituted with one or more F. In another embodiment of Formula (I), $R^8$, at each occurrence, is independently $CH_3$. In another embodiment of Formula (I), $R^8$, at each occurrence, is independently $CF_3$. In another embodiment of Formula (I), $R^8$, at each occurrence, is independently phenyl. In another embodiment of Formula (I), $R^8$, at each occurrence, is independently cyclopropyl. In another embodiment of Formula (I), $R^8$, at each occurrence, is independently cyclobutyl. In another embodiment of Formula (I), $R^8$, at each occurrence, is independently cyclopentyl.

Another embodiment pertains to compounds of Formula (I), or a pharmaceutically acceptable salt thereof,

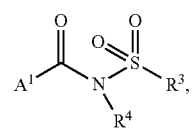

wherein $A^1$ is selected from the group consisting of

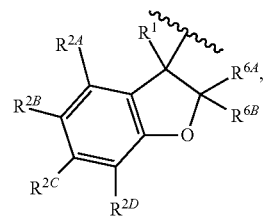

-continued

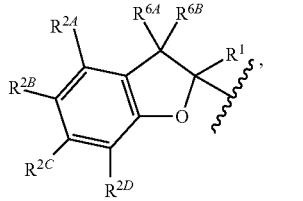

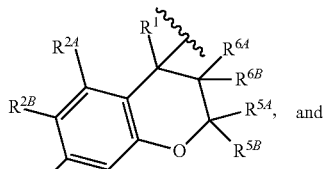, and

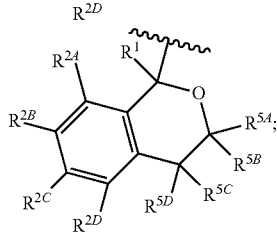

$R^1$ is selected from the group consisting of hydrogen, $C_1$-$C_6$ alkyl, and 6-10 membered aryl;
one of $R^{2A}$, $R^{2B}$, $R^{2C}$, and $R^{2D}$ is hydrogen, and the remaining are independently selected from the group consisting of hydrogen, $R^8$, $OR^8$, $C(O)R^8$, CN, Cl, and Br; or
two of $R^{2A}$, $R^{2B}$, $R^{2C}$, and $R^{2D}$ on adjacent carbons form a 4-7 membered heterocyclyl; and the remaining are independently hydrogen; wherein the 4-7 membered heterocyclyl is optionally substituted with one or more F;
$R^3$ is selected from the group consisting of $C_1$-$C_6$ alkyl, 6-10 membered aryl, 5-11 membered heteroaryl, and 4-12 membered heterocyclyl; wherein the $R^3$ 6-10 membered aryl, 5-11 membered heteroaryl, and 4-12 membered heterocyclyl are optionally substituted with one or more $R^9$;
$R^4$ is hydrogen;
$R^{5A}$, $R^{5B}$, $R^{5C}$, and $R^{5D}$ are each independently selected from the group consisting of hydrogen, and $C_1$-$C_6$ alkyl; wherein the $R^{5A}$, $R^{5B}$, $R^{5C}$, and $R^{5D}$ $C_1$-$C_6$ alkyl is optionally substituted with one or more substituents independently selected from the group consisting of 4-12 membered heterocyclyl, and $C_1$-$C_6$ thioalkyl; or
$R^{5A}$ and $R^{5B}$, together with the carbon atom to which they are attached, form a $C_3$-$C_7$ monocyclic cycloalkyl; and $R^{5C}$ and $R^{5D}$ are each independently selected from the group consisting of hydrogen;
$R^{6A}$ and $R^{6B}$ are each independently hydrogen;
$R^8$, at each occurrence, is independently selected from the group consisting of $C_1$-$C_6$ alkyl, $C_6$-$C_{10}$ membered aryl, and $C_3$-$C_{11}$ cycloalkyl; wherein each $R^8$ $C_1$-$C_6$ alkyl is optionally substituted with one or more F; and
$R^9$, at each occurrence, is independently $C_1$-$C_6$ alkyl; wherein each $R^9$ $C_1$-$C_6$ alkyl is optionally substituted with one or more F;
with the proviso that $R^3$ is not $C_1$-alkyl or thienyl;
with the proviso that, when $R^{2A}$, $R^{2B}$, $R^{2C}$, and $R^{2D}$ are each hydrogen, $R^1$ is not hydrogen;
with the proviso that, when $R^3$ is imidazolyl, $R^9$ is not $CH_2CH(CH_3)_2$;
with the proviso that, when $R^{2B}$ is Cl, $R^3$ is not 2,4-dimethyl-5-thiazolyl; and
with the proviso that, when $R^3$ is 3-pyridinyl, $R^{2C}$ is not Cl.

Another embodiment pertains to compounds of Formula (I), or a pharmaceutically acceptable salt thereof,

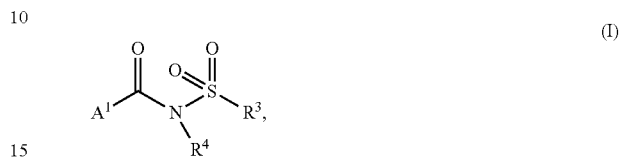 (I)

wherein
$A^1$ is R

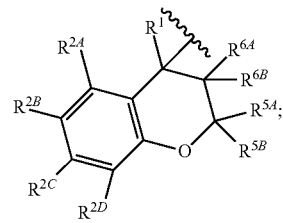

$R^1$ is hydrogen;
one of $R^{2A}$, $R^{2B}$, $R^{2C}$, and $R^{2D}$ is hydrogen, and the remaining are independently selected from the group consisting of hydrogen, $R^8$, and $OR^8$;
$R^3$ is 5-11 membered heteroaryl; wherein the $R^3$ 5-11 membered heteroaryl is substituted with one or more $R^9$;
$R^4$ is hydrogen;
$R^{5A}$ and $R^{5B}$ are each independently hydrogen;
$R^{6A}$ and $R^{6B}$ are each independently hydrogen;
$R^8$, at each occurrence, is independently selected from the group consisting of $C_1$-$C_6$ alkyl and $C_3$-$C_{11}$ cycloalkyl; and
$R^9$, at each occurrence, is independently $C_1$-$C_6$ alkyl;
with the proviso that $R^3$ is not thienyl;
with the proviso that, at least one of $R^{2A}$, $R^{2B}$, $R^{2C}$, and $R^{2D}$ is not hydrogen; and
with the proviso that, when $R^3$ is imidazolyl, $R^9$ is not $CH_2CH(CH_3)_2$.

One embodiment pertains to a compound of Formula (I), or a pharmaceutically acceptable salt thereof, wherein $R^4$ is hydrogen. Another embodiment pertains to a compound of Formula (I), or a pharmaceutically acceptable salt thereof, wherein $R^4$ is hydrogen; and $A^1$ is

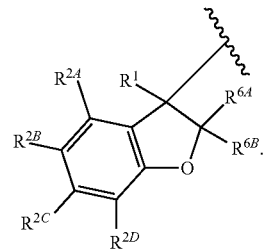

Another embodiment pertains to a compound of Formula (I), or a pharmaceutically acceptable salt thereof, wherein $R^4$ is hydrogen; and $A^1$ is

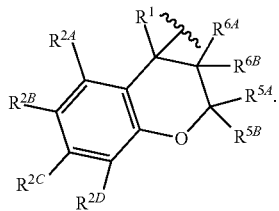

Another embodiment pertains to a compound of Formula (I), or a pharmaceutically acceptable salt thereof, wherein $R^4$ is hydrogen; $A^1$ is

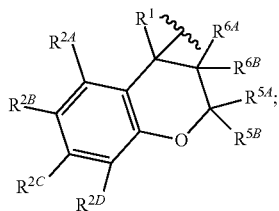

wherein two of $R^{2A}$, $R^{2B}$, $R^{2C}$, and $R^{2D}$ are hydrogen and the remaining are independently selected from the group consisting of $R^8$ and $OR^8$; and $R^8$, at each occurrence, is independently selected from the group consisting of $C_1$-$C_6$ alkyl and $C_3$-$C_{11}$ cycloalkyl. Another embodiment pertains to a compound of Formula (I), or a pharmaceutically acceptable salt thereof, wherein $R^4$ is hydrogen; $A^1$ is

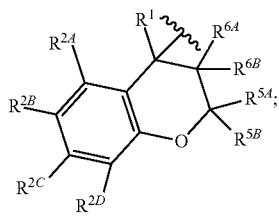

wherein two of $R^{2A}$, $R^{2B}$, $R^{2C}$, and $R^{2D}$ are hydrogen and the remaining are independently selected from the group consisting of $R^8$ and $OR^8$; $R^8$, at each occurrence, is independently selected from the group consisting of $C_1$-$C_6$ alkyl and $C_3$-$C_{11}$ cycloalkyl; and $R^1$ is hydrogen. Another embodiment pertains to a compound of Formula (I), or a pharmaceutically acceptable salt thereof, wherein $R^4$ is hydrogen; $A^1$ is

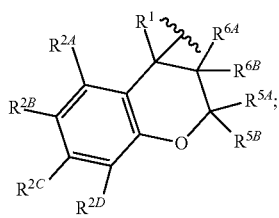

wherein two of $R^{2A}$, $R^{2B}$, $R^{2C}$, and $R^{2D}$ are hydrogen and the remaining are independently selected from the group consisting of $R^8$ and $OR^8$; $R^8$, at each occurrence, is independently selected from the group consisting of $C_1$-$C_6$ alkyl and $C_3$-$C_{11}$ cycloalkyl; $R^1$ is hydrogen; and $R^{5A}$, $R^{5B}$, $R^{6A}$, and $R^{6B}$ are hydrogen. Another embodiment pertains to a compound of Formula (I), or a pharmaceutically acceptable salt thereof, wherein $R^4$ is hydrogen; $A^1$ is

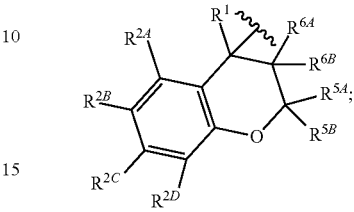

wherein two of $R^{2A}$, $R^{2B}$, $R^{2C}$, and $R^{2D}$ are hydrogen and the remaining are independently selected from the group consisting of $R^8$ and $OR^8$; $R^8$, at each occurrence, is independently selected from the group consisting of $C_1$-$C_6$ alkyl and $C_3$-$C_{11}$ cycloalkyl; $R^1$ is hydrogen; $R^{5A}$, $R^{5B}$, $R^{6A}$, and $R^{6B}$ are hydrogen; and $R^3$ is quinolinyl; wherein the $R^3$ quinolinyl is optionally substituted with one or more $R^9$; and $R^9$ is $C_1$-$C_6$ alkyl. Another embodiment pertains to a compound of Formula (I), or a pharmaceutically acceptable salt thereof, wherein $A^1$ is

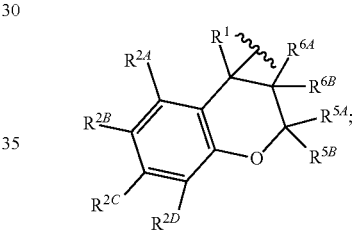

$R^1$ is hydrogen; two of $R^{2A}$, $R^{2B}$, $R^{2C}$, and $R^{2D}$ are hydrogen and the remaining are independently selected from the group consisting of $R^8$ and $OR^8$; $R^3$ is 5-11 membered heteroaryl; wherein the $R^3$ 5-11 membered heteroaryl is optionally substituted with one or more $R^9$; $R^4$ is hydrogen; $R^{5A}$ and $R^{5B}$ are each independently hydrogen; $R^{6A}$ and $R^{6B}$ are each independently hydrogen; $R^8$, at each occurrence, is independently selected from the group consisting of $C_1$-$C_6$ alkyl and $C_3$-$C_{11}$ cycloalkyl; and $R^9$, at each occurrence, is independently $C_1$-$C_6$ alkyl.

Exemplary compounds of Formula (I) include, but are not limited to:
6-bromo-N-(naphthalene-1-sulfonyl)-4-phenyl-3,4-dihydro-2H-1-benzopyran-4-carboxamide;
(2R,4R)-2-[(ethylsulfanyl)methyl]-N-(naphthalene-1-sulfonyl)-4-phenyl-3,4-dihydro-2H-1-benzopyran-4-carboxamide;
6-methoxy-2,2-dimethyl-N-(naphthalene-1-sulfonyl)-4-phenyl-3,4-dihydro-2H-1-benzopyran-4-carboxamide;
6-methoxy-N-(naphthalene-1-sulfonyl)-4-phenyl-3,4-dihydro-2H-1-benzopyran-4-carboxamide;
6-benzoyl-5,7-dimethyl-N-(naphthalene-1-sulfonyl)-3,4-dihydro-2H-1-benzopyran-4-carboxamide;
N-(naphthalene-1-sulfonyl)-3-phenyl-2,3-dihydro-1-benzofuran-3-carboxamide;
8-chloro-N-(naphthalene-1-sulfonyl)-3,4-dihydro-2H-1-benzopyran-4-carboxamide;

3-ethyl-4-methoxy-N-(naphthalene-1-sulfonyl)-2,3-dihydro-1-benzofuran-3-carboxamide;
5-methoxy-N-(naphthalene-1-sulfonyl)-3,4-dihydro-2H-1-benzopyran-4-carboxamide;
4-ethyl-5-methoxy-N-(naphthalene-1-sulfonyl)-3,4-dihydro-2H-1-benzopyran-4-carboxamide;
8-bromo-5-methoxy-N-(naphthalene-1-sulfonyl)-3,4-dihydro-2H-1-benzopyran-4-carboxamide;
6,8-dibromo-5-methoxy-N-(naphthalene-1-sulfonyl)-3,4-dihydro-2H-1-benzopyran-4-carboxamide;
8-cyclobutyl-5-methoxy-N-(naphthalene-1-sulfonyl)-3,4-dihydro-2H-1-benzopyran-4-carboxamide;
8-cyclopentyl-5-methoxy-N-(naphthalene-1-sulfonyl)-3,4-dihydro-2H-1-benzopyran-4-carboxamide;
3-ethyl-7-methoxy-N-(naphthalene-1-sulfonyl)-2,3-dihydro-1-benzofuran-3-carboxamide;
2-methyl-N-(2-methylbenzene-1-sulfonyl)-2,3-dihydro-1-benzofuran-2-carboxamide;
6-methyl-N-(naphthalene-1-sulfonyl)-4-phenyl-3,4-dihydro-2H-1-benzopyran-4-carboxamide;
6-chloro-N-(naphthalene-1-sulfonyl)-4-phenyl-3,4-dihydro-2H-1-benzopyran-4-carboxamide;
4-methoxy-N-(naphthalene-1-sulfonyl)-2,3-dihydro-1-benzofuran-3-carboxamide;
7-bromo-N-(naphthalene-1-sulfonyl)-2,3-dihydro-1-benzofuran-3-carboxamide;
7-bromo-3-ethyl-N-(naphthalene-1-sulfonyl)-2,3-dihydro-1-benzofuran-3-carboxamide;
3-ethyl-N-(naphthalene-1-sulfonyl)-2,3-dihydro-1-benzofuran-3-carboxamide;
7-methoxy-N-(naphthalene-1-sulfonyl)-2,3-dihydro-1-benzofuran-3-carboxamide;
2-methyl-N-[4-(propan-2-yl)benzene-1-sulfonyl]-2,3-dihydro-1-benzofuran-2-carboxamide;
5-chloro-N-(2-methylbenzene-1-sulfonyl)-2,3-dihydro-1-benzofuran-3-carboxamide;
5-chloro-N-(propane-1-sulfonyl)-2,3-dihydro-1-benzofuran-3-carboxamide;
(2S)—N-(naphthalene-1-sulfonyl)-4-phenyl-2-[(pyrrolidin-1-yl)methyl]-3,4-dihydro-2H-1-benzopyran-4-carboxamide;
(7S)-2,2-difluoro-7-methyl-N-(naphthalene-1-sulfonyl)-6,7-dihydro-2H-furo[2,3-f][1,3]benzodioxole-7-carboxamide;
(7R)-2,2-difluoro-7-methyl-N-(naphthalene-1-sulfonyl)-6,7-dihydro-2H-furo[2,3-f][1,3]benzodioxole-7-carboxamide;
(4S)-8-bromo-5-methoxy-N-(naphthalene-1-sulfonyl)-3,4-dihydro-2H-1-benzopyran-4-carboxamide;
(4R)-8-bromo-5-methoxy-N-(naphthalene-1-sulfonyl)-3,4-dihydro-2H-1-benzopyran-4-carboxamide;
4-bromo-7-methoxy-N-(naphthalene-1-sulfonyl)-2,3-dihydro-1-benzofuran-3-carboxamide;
5-methoxy-N-(naphthalene-1-sulfonyl)-3,4-dihydrospiro[1-benzopyran-2,1'-cyclohexane]-4-carboxamide;
7-bromo-4-methoxy-N-(naphthalene-1-sulfonyl)-2,3-dihydro-1-benzofuran-3-carboxamide;
4-methoxy-N-(naphthalene-1-sulfonyl)-5-(trifluoromethyl)-2,3-dihydro-1-benzofuran-3-carboxamide and
4-methoxy-N-(naphthalene-1-sulfonyl)-7-(trifluoromethyl)-2,3-dihydro-1-benzofuran-3-carboxamide;
8-bromo-5-methoxy-N-(naphthalene-1-sulfonyl)-3,4-dihydrospiro[1-benzopyran-2,1'-cyclohexane]-4-carboxamide;
8-bromo-5-methoxy-N-(quinoline-8-sulfonyl)-3,4-dihydro-2H-1-benzopyran-4-carboxamide;
7-chloro-N-(naphthalene-1-sulfonyl)-2,3-dihydro-1-benzofuran-3-carboxamide;
7-chloro-3-ethyl-N-(naphthalene-1-sulfonyl)-2,3-dihydro-1-benzofuran-3-carboxamide;
N-(naphthalene-1-sulfonyl)-7-(trifluoromethyl)-2,3-dihydro-1-benzofuran-3-carboxamide;
8-bromo-5-methoxy-2,2-dimethyl-N-(quinoline-5-sulfonyl)-3,4-dihydro-2H-1-benzopyran-4-carboxamide;
5-methoxy-2,2-dimethyl-N-(quinoline-8-sulfonyl)-3,4-dihydro-2H-1-benzopyran-4-carboxamide;
5-methoxy-2,2-dimethyl-N-(quinoline-5-sulfonyl)-3,4-dihydro-2H-1-benzopyran-4-carboxamide;
5-methoxy-2,2-dimethyl-N-(naphthalene-1-sulfonyl)-3,4-dihydro-2H-1-benzopyran-4-carboxamide;
8-cyano-5-methoxy-2,2-dimethyl-N-(naphthalene-1-sulfonyl)-3,4-dihydro-2H-1-benzopyran-4-carboxamide;
8-chloro-5-methoxy-2,2-dimethyl-N-(naphthalene-1-sulfonyl)-3,4-dihydro-2H-1-benzopyran-4-carboxamide;
8-bromo-5-methoxy-2,2-dimethyl-N-(naphthalene-1-sulfonyl)-3,4-dihydro-2H-1-benzopyran-4-carboxamide;
5-methoxy-N-(naphthalene-1-sulfonyl)-8-(trifluoromethyl)-3,4-dihydro-2H-1-benzopyran-4-carboxamide;
8-cyclobutyl-5-methoxy-N-(quinoline-5-sulfonyl)-3,4-dihydro-2H-1-benzopyran-4-carboxamide;
(4S)-8-cyclobutyl-5-methoxy-N-(naphthalene-1-sulfonyl)-3,4-dihydro-2H-1-benzopyran-4-carboxamide;
(4R)-8-cyclobutyl-5-methoxy-N-(naphthalene-1-sulfonyl)-3,4-dihydro-2H-1-benzopyran-4-carboxamide;
(4S)-5-methoxy-N-(naphthalene-1-sulfonyl)-8-(trifluoromethyl)-3,4-dihydro-2H-1-benzopyran-4-carboxamide;
(4R)-5-methoxy-N-(naphthalene-1-sulfonyl)-8-(trifluoromethyl)-3,4-dihydro-2H-1-benzopyran-4-carboxamide;
(4S)-8-cyclobutyl-5-methoxy-N-(quinoline-5-sulfonyl)-3,4-dihydro-2H-1-benzopyran-4-carboxamide;
(4R)-8-cyclobutyl-5-methoxy-N-(quinoline-5-sulfonyl)-3,4-dihydro-2H-1-benzopyran-4-carboxamide;
3-ethyl-N-(naphthalene-1-sulfonyl)-7-(trifluoromethyl)-2,3-dihydro-1-benzofuran-3-carboxamide;
4,7-dimethoxy-N-(naphthalene-1-sulfonyl)-2,3-dihydro-1-benzofuran-3-carboxamide;
7-chloro-4-methoxy-N-(naphthalene-1-sulfonyl)-2,3-dihydro-1-benzofuran-3-carboxamide;
8-cyclopropyl-5-methoxy-N-(naphthalene-1-sulfonyl)-3,4-dihydro-2H-1-benzopyran-4-carboxamide;
(3S)-7-cyclobutyl-4-methoxy-N-(naphthalene-1-sulfonyl)-2,3-dihydro-1-benzofuran-3-carboxamide;
(3R)-7-cyclobutyl-4-methoxy-N-(naphthalene-1-sulfonyl)-2,3-dihydro-1-benzofuran-3-carboxamide;
(3R)-7-chloro-4-methoxy-N-(naphthalene-1-sulfonyl)-2,3-dihydro-1-benzofuran-3-carboxamide;
(3S)-7-chloro-4-methoxy-N-(naphthalene-1-sulfonyl)-2,3-dihydro-1-benzofuran-3-carboxamide;
(4S)-8-bromo-5-methoxy-N-(1-methyl-1H-indazole-7-sulfonyl)-3,4-dihydro-2H-1-benzopyran-4-carboxamide;
(4R)-8-bromo-5-methoxy-N-(1-methyl-1H-indazole-7-sulfonyl)-3,4-dihydro-2H-1-benzopyran-4-carboxamide;
(4S)-8-bromo-5-methoxy-2,2-dimethyl-N-(quinoline-5-sulfonyl)-3,4-dihydro-2H-1-benzopyran-4-carboxamide;
(4R)-8-bromo-5-methoxy-2,2-dimethyl-N-(quinoline-5-sulfonyl)-3,4-dihydro-2H-1-benzopyran-4-carboxamide;
(3R)-7-bromo-4-methoxy-N-(1-naphthylsulfonyl)-2,3-dihydrobenzofuran-3-carboxamide;
(3S)-7-bromo-4-methoxy-N-(1-naphthylsulfonyl)-2,3-dihydrobenzofuran-3-carboxamide;
8-cyclobutyl-5-methoxy-N-(2-methylquinoline-5-sulfonyl)-3,4-dihydro-2H-1-benzopyran-4-carboxamide;

(4S)-8-cyclobutyl-5-methoxy-N-(2-methylquinoline-5-sulfonyl)-3,4-dihydro-2H-1-benzopyran-4-carboxamide;
(4R)-8-cyclobutyl-5-methoxy-N-(2-methylquinoline-5-sulfonyl)-3,4-dihydro-2H-1-benzopyran-4-carboxamide;
5-bromo-8-methoxy-N-(naphthalene-1-sulfonyl)-3,4-dihydro-1H-2-benzopyran-1-carboxamide;
5-cyclobutyl-8-methoxy-N-(naphthalene-1-sulfonyl)-3,4-dihydro-1H-2-benzopyran-1-carboxamide;
7-cyclobutyl-4-methoxy-N-(quinoline-5-sulfonyl)-2,3-dihydro-1-benzofuran-3-carboxamide;
5-cyclobutyl-8-methoxy-N-(quinoline-5-sulfonyl)-3,4-dihydro-1H-2-benzopyran-1-carboxamide;
(3R)-7-cyclobutyl-4-methoxy-N-(quinoline-5-sulfonyl)-2,3-dihydro-1-benzofuran-3-carboxamide;
(3S)-7-cyclobutyl-4-methoxy-N-(quinoline-5-sulfonyl)-2,3-dihydro-1-benzofuran-3-carboxamide;
5-cyclobutyl-8-methoxy-1-methyl-N-(naphthalene-1-sulfonyl)-3,4-dihydro-1H-2-benzopyran-1-carboxamide;
8-cyclobutyl-5-methoxy-N-(1,2,3,4-tetrahydroquinoline-5-sulfonyl)-3,4-dihydro-2H-1-benzopyran-4-carboxamide;
(4R)-8-cyclobutyl-5-methoxy-2,2-dimethyl-N-(quinoline-5-sulfonyl)-3,4-dihydro-2H-1-benzopyran-4-carboxamide;
7-cyclobutyl-4-methoxy-N-(1-methyl-1H-benzimidazole-7-sulfonyl)-2,3-dihydro-1-benzofuran-3-carboxamide;
7-cyclobutyl-4-methoxy-N-(pyrazolo[1,5-a]pyridine-4-sulfonyl)-2,3-dihydro-1-benzofuran-3-carboxamide;
7-cyclobutyl-4-methoxy-N-(1,2,3,4-tetrahydroquinoline-5-sulfonyl)-2,3-dihydro-1-benzofuran-3-carboxamide;
7-cyclobutyl-4-methoxy-N-(1,2,3,4-tetrahydroquinoline-8-sulfonyl)-2,3-dihydro-1-benzofuran-3-carboxamide;
(4S)-8-cyclobutyl-5-methoxy-N-(1,2,3,4-tetrahydroquinoline-5-sulfonyl)-3,4-dihydro-2H-1-benzopyran-4-carboxamide;
(4R)-8-cyclobutyl-5-methoxy-N-(1,2,3,4-tetrahydroquinoline-5-sulfonyl)-3,4-dihydro-2H-1-benzopyran-4-carboxamide;
8-cyclobutyl-5-methoxy-2,2-dimethyl-N-(1,2,3,4-tetrahydroquinoline-5-sulfonyl)-3,4-dihydro-2H-1-benzopyran-4-carboxamide;
(3R)-7-cyclobutyl-4-methoxy-N-(1-methyl-1H-indazole-7-sulfonyl)-2,3-dihydro-1-benzofuran-3-carboxamide;
(3S)-7-cyclobutyl-4-methoxy-N-(1-methyl-1H-indazole-7-sulfonyl)-2,3-dihydro-1-benzofuran-3-carboxamide;
(4S)-8-cyclobutyl-5-methoxy-2,2-dimethyl-N-(1,2,3,4-tetrahydroquinoline-5-sulfonyl)-3,4-dihydro-2H-1-benzopyran-4-carboxamide;
(4R)-8-cyclobutyl-5-methoxy-2,2-dimethyl-N-(1,2,3,4-tetrahydroquinoline-5-sulfonyl)-3,4-dihydro-2H-1-benzopyran-4-carboxamide;
(3R)-7-cyclobutyl-4-methoxy-N-(1,2,3,4-tetrahydroquinoline-8-sulfonyl)-2,3-dihydro-1-benzofuran-3-carboxamide;
(3S)-7-cyclobutyl-4-methoxy-N-(1,2,3,4-tetrahydroquinoline-8-sulfonyl)-2,3-dihydro-1-benzofuran-3-carboxamide;
(3R)-7-cyclobutyl-4-methoxy-N-(1,2,3,4-tetrahydroquinoline-5-sulfonyl)-2,3-dihydro-1-benzofuran-3-carboxamide;
(3S)-7-cyclobutyl-4-methoxy-N-(1,2,3,4-tetrahydroquinoline-5-sulfonyl)-2,3-dihydro-1-benzofuran-3-carboxamide;
8-cyclobutyl-N-(1H-indole-4-sulfonyl)-5-methoxy-3,4-dihydro-2H-1-benzopyran-4-carboxamide;
(4S)-8-cyclobutyl-N-(1H-indole-4-sulfonyl)-5-methoxy-3,4-dihydro-2H-1-benzopyran-4-carboxamide;
(4R)-8-cyclobutyl-N-(1H-indole-4-sulfonyl)-5-methoxy-3,4-dihydro-2H-1-benzopyran-4-carboxamide;
5-cyclobutyl-8-methoxy-N-(quinoline-5-sulfonyl)-3,4-dihydro-2H-1-benzopyran-4-carboxamide;
(4R)-5-cyclobutyl-8-methoxy-N-(quinoline-5-sulfonyl)-3,4-dihydro-2H-1-benzopyran-4-carboxamide;
(4S)-5-cyclobutyl-8-methoxy-N-(quinoline-5-sulfonyl)-3,4-dihydro-2H-1-benzopyran-4-carboxamide;
8-bromo-5-methoxy-N-(naphthalene-1-sulfonyl)-3,4-dihydro-1H-2-benzopyran-1-carboxamide;
N-(naphthalene-1-sulfonyl)-7-(trifluoromethoxy)-3,4-dihydro-1H-2-benzopyran-1-carboxamide;
5-methoxy-N-(naphthalene-1-sulfonyl)-3,4-dihydro-1H-2-benzopyran-1-carboxamide; and pharmaceutically acceptable salts thereof.

One embodiment pertains to a compound selected from the group consisting of:
N-(2-methylbenzene-1-sulfonyl)-2,3-dihydro-1-benzofuran-2-carboxamide;
N-(naphthalene-1-sulfonyl)-3,4-dihydro-2H-1-benzopyran-4-carboxamide;
N-(2-methylbenzene-1-sulfonyl)-2,3-dihydro-1-benzofuran-3-carboxamide;
N-(2-methylbenzene-1-sulfonyl)-3,4-dihydro-2H-1-benzopyran-4-carboxamide;
N-(naphthalene-1-sulfonyl)-2,3-dihydro-1-benzofuran-3-carboxamide; and pharmaceutically acceptable salts thereof.

One embodiment pertains to 8-cyclobutyl-5-methoxy-N-(2-methylquinoline-5-sulfonyl)-3,4-dihydro-2H-1-benzopyran-4-carboxamide, or a pharmaceutically acceptable salt thereof.

One embodiment pertains to (4S)-8-cyclobutyl-5-methoxy-N-(2-methylquinoline-5-sulfonyl)-3,4-dihydro-2H-1-benzopyran-4-carboxamide; or a pharmaceutically acceptable salt thereof.

One embodiment pertains to (4R)-8-cyclobutyl-5-methoxy-N-(2-methylquinoline-5-sulfonyl)-3,4-dihydro-2H-1-benzopyran-4-carboxamide; or a pharmaceutically acceptable salt thereof.

One embodiment pertains to 8-cyclobutyl-N-(1H-indole-4-sulfonyl)-5-methoxy-3,4-dihydro-2H-1-benzopyran-4-carboxamide; or a pharmaceutically acceptable salt thereof.

One embodiment pertains to (4S)-8-cyclobutyl-N-(1H-indole-4-sulfonyl)-5-methoxy-3,4-dihydro-2H-1-benzopyran-4-carboxamide; or a pharmaceutically acceptable salt thereof.

One embodiment pertains to (4R)-8-cyclobutyl-N-(1H-indole-4-sulfonyl)-5-methoxy-3,4-dihydro-2H-1-benzopyran-4-carboxamide; or a pharmaceutically acceptable salt thereof.

One embodiment pertains to 5-cyclobutyl-8-methoxy-N-(quinoline-5-sulfonyl)-3,4-dihydro-2H-1-benzopyran-4-carboxamide; or a pharmaceutically acceptable salt thereof.

One embodiment pertains to (4R)-5-cyclobutyl-8-methoxy-N-(quinoline-5-sulfonyl)-3,4-dihydro-2H-1-benzopyran-4-carboxamide; or a pharmaceutically acceptable salt thereof.

One embodiment pertains to (4S)-5-cyclobutyl-8-methoxy-N-(quinoline-5-sulfonyl)-3,4-dihydro-2H-1-benzopyran-4-carboxamide; or a pharmaceutically acceptable salt thereof.

One embodiment pertains to a compound selected from the group consisting of:
6-bromo-N-(naphthalene-1-sulfonyl)-4-phenyl-3,4-dihydro-2H-1-benzopyran-4-carboxamide;

(2R,4R)-2-[(ethylsulfanyl)methyl]-N-(naphthalene-1-sulfonyl)-4-phenyl-3,4-dihydro-2H-1-benzopyran-4-carboxamide;
6-methoxy-2,2-dimethyl-N-(naphthalene-1-sulfonyl)-4-phenyl-3,4-dihydro-2H-1-benzopyran-4-carboxamide;
6-methoxy-N-(naphthalene-1-sulfonyl)-4-phenyl-3,4-dihydro-2H-1-benzopyran-4-carboxamide;
6-benzoyl-5,7-dimethyl-N-(naphthalene-1-sulfonyl)-3,4-dihydro-2H-1-benzopyran-4-carboxamide;
N-(naphthalene-1-sulfonyl)-3-phenyl-2,3-dihydro-1-benzofuran-3-carboxamide;
8-chloro-N-(naphthalene-1-sulfonyl)-3,4-dihydro-2H-1-benzopyran-4-carboxamide;
3-ethyl-4-methoxy-N-(naphthalene-1-sulfonyl)-2,3-dihydro-1-benzofuran-3-carboxamide;
5-methoxy-N-(naphthalene-1-sulfonyl)-3,4-dihydro-2H-1-benzopyran-4-carboxamide;
4-ethyl-5-methoxy-N-(naphthalene-1-sulfonyl)-3,4-dihydro-2H-1-benzopyran-4-carboxamide;
8-bromo-5-methoxy-N-(naphthalene-1-sulfonyl)-3,4-dihydro-2H-1-benzopyran-4-carboxamide;
6,8-dibromo-5-methoxy-N-(naphthalene-1-sulfonyl)-3,4-dihydro-2H-1-benzopyran-4-carboxamide;
8-cyclobutyl-5-methoxy-N-(naphthalene-1-sulfonyl)-3,4-dihydro-2H-1-benzopyran-4-carboxamide;
8-cyclopentyl-5-methoxy-N-(naphthalene-1-sulfonyl)-3,4-dihydro-2H-1-benzopyran-4-carboxamide;
3-ethyl-7-methoxy-N-(naphthalene-1-sulfonyl)-2,3-dihydro-1-benzofuran-3-carboxamide;
2-methyl-N-(2-methylbenzene-1-sulfonyl)-2,3-dihydro-1-benzofuran-2-carboxamide;
N-(2-methylbenzene-1-sulfonyl)-2,3-dihydro-1-benzofuran-2-carboxamide;
6-methyl-N-(naphthalene-1-sulfonyl)-4-phenyl-3,4-dihydro-2H-1-benzopyran-4-carboxamide;
6-chloro-N-(naphthalene-1-sulfonyl)-4-phenyl-3,4-dihydro-2H-1-benzopyran-4-carboxamide;
4-methoxy-N-(naphthalene-1-sulfonyl)-2,3-dihydro-1-benzofuran-3-carboxamide;
7-bromo-N-(naphthalene-1-sulfonyl)-2,3-dihydro-1-benzofuran-3-carboxamide;
7-bromo-3-ethyl-N-(naphthalene-1-sulfonyl)-2,3-dihydro-1-benzofuran-3-carboxamide;
3-ethyl-N-(naphthalene-1-sulfonyl)-2,3-dihydro-1-benzofuran-3-carboxamide;
N-(naphthalene-1-sulfonyl)-3,4-dihydro-2H-1-benzopyran-4-carboxamide;
7-methoxy-N-(naphthalene-1-sulfonyl)-2,3-dihydro-1-benzofuran-3-carboxamide;
2-methyl-N-[4-(propan-2-yl)benzene-1-sulfonyl]-2,3-dihydro-1-benzofuran-2-carboxamide;
5-chloro-N-(2-methylbenzene-1-sulfonyl)-2,3-dihydro-1-benzofuran-3-carboxamide;
5-chloro-N-(propane-1-sulfonyl)-2,3-dihydro-1-benzofuran-3-carboxamide;
N-(2-methylbenzene-1-sulfonyl)-2,3-dihydro-1-benzofuran-3-carboxamide;
N-(2-methylbenzene-1-sulfonyl)-3,4-dihydro-2H-1-benzopyran-4-carboxamide;
(2S)—N-(naphthalene-1-sulfonyl)-4-phenyl-2-[(pyrrolidin-1-yl)methyl]-3,4-dihydro-2H-1-benzopyran-4-carboxamide;
(7S)-2,2-difluoro-7-methyl-N-(naphthalene-1-sulfonyl)-6,7-dihydro-2H-furo[2,3-f][1,3]benzodioxole-7-carboxamide;
(7R)-2,2-difluoro-7-methyl-N-(naphthalene-1-sulfonyl)-6,7-dihydro-2H-furo[2,3-f][1,3]benzodioxole-7-carboxamide;
N-(naphthalene-1-sulfonyl)-2,3-dihydro-1-benzofuran-3-carboxamide;
(4S)-8-bromo-5-methoxy-N-(naphthalene-1-sulfonyl)-3,4-dihydro-2H-1-benzopyran-4-carboxamide;
(4R)-8-bromo-5-methoxy-N-(naphthalene-1-sulfonyl)-3,4-dihydro-2H-1-benzopyran-4-carboxamide;
4-bromo-7-methoxy-N-(naphthalene-1-sulfonyl)-2,3-dihydro-1-benzofuran-3-carboxamide;
5-methoxy-N-(naphthalene-1-sulfonyl)-3,4-dihydrospiro[1-benzopyran-2,1'-cyclohexane]-4-carboxamide;
7-bromo-4-methoxy-N-(naphthalene-1-sulfonyl)-2,3-dihydro-1-benzofuran-3-carboxamide;
4-methoxy-N-(naphthalene-1-sulfonyl)-5-(trifluoromethyl)-2,3-dihydro-1-benzofuran-3-carboxamide and
4-methoxy-N-(naphthalene-1-sulfonyl)-7-(trifluoromethyl)-2,3-dihydro-1-benzofuran-3-carboxamide;
8-bromo-5-methoxy-N-(naphthalene-1-sulfonyl)-3,4-dihydrospiro[1-benzopyran-2,1'-cyclohexane]-4-carboxamide;
8-bromo-5-methoxy-N-(quinoline-8-sulfonyl)-3,4-dihydro-2H-1-benzopyran-4-carboxamide;
7-chloro-N-(naphthalene-1-sulfonyl)-2,3-dihydro-1-benzofuran-3-carboxamide;
7-chloro-3-ethyl-N-(naphthalene-1-sulfonyl)-2,3-dihydro-1-benzofuran-3-carboxamide;
N-(naphthalene-1-sulfonyl)-7-(trifluoromethyl)-2,3-dihydro-1-benzofuran-3-carboxamide;
8-bromo-5-methoxy-2,2-dimethyl-N-(quinoline-5-sulfonyl)-3,4-dihydro-2H-1-benzopyran-4-carboxamide;
5-methoxy-2,2-dimethyl-N-(quinoline-8-sulfonyl)-3,4-dihydro-2H-1-benzopyran-4-carboxamide;
5-methoxy-2,2-dimethyl-N-(quinoline-5-sulfonyl)-3,4-dihydro-2H-1-benzopyran-4-carboxamide;
5-methoxy-2,2-dimethyl-N-(naphthalene-1-sulfonyl)-3,4-dihydro-2H-1-benzopyran-4-carboxamide;
8-cyano-5-methoxy-2,2-dimethyl-N-(naphthalene-1-sulfonyl)-3,4-dihydro-2H-1-benzopyran-4-carboxamide;
8-chloro-5-methoxy-2,2-dimethyl-N-(naphthalene-1-sulfonyl)-3,4-dihydro-2H-1-benzopyran-4-carboxamide;
8-bromo-5-methoxy-2,2-dimethyl-N-(naphthalene-1-sulfonyl)-3,4-dihydro-2H-1-benzopyran-4-carboxamide;
5-methoxy-N-(naphthalene-1-sulfonyl)-8-(trifluoromethyl)-3,4-dihydro-2H-1-benzopyran-4-carboxamide;
8-cyclobutyl-5-methoxy-N-(quinoline-5-sulfonyl)-3,4-dihydro-2H-1-benzopyran-4-carboxamide;
(4S)-8-cyclobutyl-5-methoxy-N-(naphthalene-1-sulfonyl)-3,4-dihydro-2H-1-benzopyran-4-carboxamide;
(4R)-8-cyclobutyl-5-methoxy-N-(naphthalene-1-sulfonyl)-3,4-dihydro-2H-1-benzopyran-4-carboxamide;
(4S)-5-methoxy-N-(naphthalene-1-sulfonyl)-8-(trifluoromethyl)-3,4-dihydro-2H-1-benzopyran-4-carboxamide;
(4R)-5-methoxy-N-(naphthalene-1-sulfonyl)-8-(trifluoromethyl)-3,4-dihydro-2H-1-benzopyran-4-carboxamide;
(4S)-8-cyclobutyl-5-methoxy-N-(quinoline-5-sulfonyl)-3,4-dihydro-2H-1-benzopyran-4-carboxamide;
(4R)-8-cyclobutyl-5-methoxy-N-(quinoline-5-sulfonyl)-3,4-dihydro-2H-1-benzopyran-4-carboxamide;
3-ethyl-N-(naphthalene-1-sulfonyl)-7-(trifluoromethyl)-2,3-dihydro-1-benzofuran-3-carboxamide;
4,7-dimethoxy-N-(naphthalene-1-sulfonyl)-2,3-dihydro-1-benzofuran-3-carboxamide;
7-chloro-4-methoxy-N-(naphthalene-1-sulfonyl)-2,3-dihydro-1-benzofuran-3-carboxamide;

8-cyclopropyl-5-methoxy-N-(naphthalene-1-sulfonyl)-3,4-dihydro-2H-1-benzopyran-4-carboxamide;
(3S)-7-cyclobutyl-4-methoxy-N-(naphthalene-1-sulfonyl)-2,3-dihydro-1-benzofuran-3-carboxamide;
(3R)-7-cyclobutyl-4-methoxy-N-(naphthalene-1-sulfonyl)-2,3-dihydro-1-benzofuran-3-carboxamide;
(3R)-7-chloro-4-methoxy-N-(naphthalene-1-sulfonyl)-2,3-dihydro-1-benzofuran-3-carboxamide;
(3S)-7-chloro-4-methoxy-N-(naphthalene-1-sulfonyl)-2,3-dihydro-1-benzofuran-3-carboxamide;
(4S)-8-bromo-5-methoxy-N-(1-methyl-1H-indazole-7-sulfonyl)-3,4-dihydro-2H-1-benzopyran-4-carboxamide;
(4R)-8-bromo-5-methoxy-N-(1-methyl-1H-indazole-7-sulfonyl)-3,4-dihydro-2H-1-benzopyran-4-carboxamide;
(4S)-8-bromo-5-methoxy-2,2-dimethyl-N-(quinoline-5-sulfonyl)-3,4-dihydro-2H-1-benzopyran-4-carboxamide;
(4R)-8-bromo-5-methoxy-2,2-dimethyl-N-(quinoline-5-sulfonyl)-3,4-dihydro-2H-1-benzopyran-4-carboxamide;
(3R)-7-bromo-4-methoxy-N-(1-naphthylsulfonyl)-2,3-dihydrobenzofuran-3-carboxamide;
(3S)-7-bromo-4-methoxy-N-(1-naphthylsulfonyl)-2,3-dihydrobenzofuran-3-carboxamide;
8-cyclobutyl-5-methoxy-N-(2-methylquinoline-5-sulfonyl)-3,4-dihydro-2H-1-benzopyran-4-carboxamide;
(4S)-8-cyclobutyl-5-methoxy-N-(2-methylquinoline-5-sulfonyl)-3,4-dihydro-2H-1-benzopyran-4-carboxamide;
(4R)-8-cyclobutyl-5-methoxy-N-(2-methylquinoline-5-sulfonyl)-3,4-dihydro-2H-1-benzopyran-4-carboxamide;
5-bromo-8-methoxy-N-(naphthalene-1-sulfonyl)-3,4-dihydro-1H-2-benzopyran-1-carboxamide;
5-cyclobutyl-8-methoxy-N-(naphthalene-1-sulfonyl)-3,4-dihydro-1H-2-benzopyran-1-carboxamide;
7-cyclobutyl-4-methoxy-N-(quinoline-5-sulfonyl)-2,3-dihydro-1-benzofuran-3-carboxamide;
5-cyclobutyl-8-methoxy-N-(quinoline-5-sulfonyl)-3,4-dihydro-1H-2-benzopyran-1-carboxamide;
(3R)-7-cyclobutyl-4-methoxy-N-(quinoline-5-sulfonyl)-2,3-dihydro-1-benzofuran-3-carboxamide;
(3S)-7-cyclobutyl-4-methoxy-N-(quinoline-5-sulfonyl)-2,3-dihydro-1-benzofuran-3-carboxamide;
5-cyclobutyl-8-methoxy-1-methyl-N-(naphthalene-1-sulfonyl)-3,4-dihydro-1H-2-benzopyran-1-carboxamide;
8-cyclobutyl-5-methoxy-N-(1,2,3,4-tetrahydroquinoline-5-sulfonyl)-3,4-dihydro-2H-1-benzopyran-4-carboxamide;
(4R)-8-cyclobutyl-5-methoxy-2,2-dimethyl-N-(quinoline-5-sulfonyl)-3,4-dihydro-2H-1-benzopyran-4-carboxamide;
7-cyclobutyl-4-methoxy-N-(1-methyl-1H-benzimidazole-7-sulfonyl)-2,3-dihydro-1-benzofuran-3-carboxamide;
7-cyclobutyl-4-methoxy-N-(pyrazolo[1,5-a]pyridine-4-sulfonyl)-2,3-dihydro-1-benzofuran-3-carboxamide;
7-cyclobutyl-4-methoxy-N-(1,2,3,4-tetrahydroquinoline-5-sulfonyl)-2,3-dihydro-1-benzofuran-3-carboxamide;
7-cyclobutyl-4-methoxy-N-(1,2,3,4-tetrahydroquinoline-8-sulfonyl)-2,3-dihydro-1-benzofuran-3-carboxamide;
(4S)-8-cyclobutyl-5-methoxy-N-(1,2,3,4-tetrahydroquinoline-5-sulfonyl)-3,4-dihydro-2H-1-benzopyran-4-carboxamide;
(4R)-8-cyclobutyl-5-methoxy-N-(1,2,3,4-tetrahydroquinoline-5-sulfonyl)-3,4-dihydro-2H-1-benzopyran-4-carboxamide;
8-cyclobutyl-5-methoxy-2,2-dimethyl-N-(1,2,3,4-tetrahydroquinoline-5-sulfonyl)-3,4-dihydro-2H-1-benzopyran-4-carboxamide;
(3R)-7-cyclobutyl-4-methoxy-N-(1-methyl-1H-indazole-7-sulfonyl)-2,3-dihydro-1-benzofuran-3-carboxamide;
(3S)-7-cyclobutyl-4-methoxy-N-(1-methyl-1H-indazole-7-sulfonyl)-2,3-dihydro-1-benzofuran-3-carboxamide;
(4S)-8-cyclobutyl-5-methoxy-2,2-dimethyl-N-(1,2,3,4-tetrahydroquinoline-5-sulfonyl)-3,4-dihydro-2H-1-benzopyran-4-carboxamide;
(4R)-8-cyclobutyl-5-methoxy-2,2-dimethyl-N-(1,2,3,4-tetrahydroquinoline-5-sulfonyl)-3,4-dihydro-2H-1-benzopyran-4-carboxamide;
(3R)-7-cyclobutyl-4-methoxy-N-(1,2,3,4-tetrahydroquinoline-8-sulfonyl)-2,3-dihydro-1-benzofuran-3-carboxamide;
(3S)-7-cyclobutyl-4-methoxy-N-(1,2,3,4-tetrahydroquinoline-8-sulfonyl)-2,3-dihydro-1-benzofuran-3-carboxamide;
(3R)-7-cyclobutyl-4-methoxy-N-(1,2,3,4-tetrahydroquinoline-5-sulfonyl)-2,3-dihydro-1-benzofuran-3-carboxamide;
(3S)-7-cyclobutyl-4-methoxy-N-(1,2,3,4-tetrahydroquinoline-5-sulfonyl)-2,3-dihydro-1-benzofuran-3-carboxamide;
8-cyclobutyl-N-(1H-indole-4-sulfonyl)-5-methoxy-3,4-dihydro-2H-1-benzopyran-4-carboxamide;
(4S)-8-cyclobutyl-N-(1H-indole-4-sulfonyl)-5-methoxy-3,4-dihydro-2H-1-benzopyran-4-carboxamide;
(4R)-8-cyclobutyl-N-(1H-indole-4-sulfonyl)-5-methoxy-3,4-dihydro-2H-1-benzopyran-4-carboxamide;
5-cyclobutyl-8-methoxy-N-(quinoline-5-sulfonyl)-3,4-dihydro-2H-1-benzopyran-4-carboxamide;
(4R)-5-cyclobutyl-8-methoxy-N-(quinoline-5-sulfonyl)-3,4-dihydro-2H-1-benzopyran-4-carboxamide;
(4S)-5-cyclobutyl-8-methoxy-N-(quinoline-5-sulfonyl)-3,4-dihydro-2H-1-benzopyran-4-carboxamide;
8-bromo-5-methoxy-N-(naphthalene-1-sulfonyl)-3,4-dihydro-1H-2-benzopyran-1-carboxamide;
N-(naphthalene-1-sulfonyl)-7-(trifluoromethoxy)-3,4-dihydro-1H-2-benzopyran-1-carboxamide;
5-methoxy-N-(naphthalene-1-sulfonyl)-3,4-dihydro-1H-2-benzopyran-1-carboxamide; and pharmaceutically acceptable salts thereof.

Formula (II)

One embodiment pertains to compounds of Formula (II), or a pharmaceutically acceptable salt thereof,

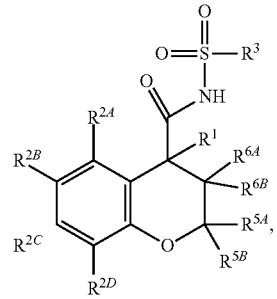

(II)

wherein
R$^1$ is selected from the group consisting of hydrogen, OH, CN, C$_1$-C$_6$ alkyl, C$_2$-C$_6$ alkenyl, C$_2$-C$_6$ alkynyl, C$_1$-C$_6$ alkoxy, 6-10 membered aryl, 5-11 membered heteroaryl, C$_3$-C$_{11}$cycloalkyl, C$_4$-C$_{11}$ cycloalkenyl, and 4-12 membered heterocyclyl; wherein the R$^1$ C$_1$-C$_6$ alkyl, C$_2$-C$_6$ alkenyl, C$_2$-C$_6$ alkynyl, and C$_1$-C$_6$ alkoxy are optionally substituted with one or more substituents independently selected from the group consisting of R$^7$, OR$^7$, SR$^7$, NHR$^7$, N(R$^7$)$_2$, NH$_2$, C(O)OH, OH, CN, NO$_2$, F, Cl, Br and I; wherein the R$^1$ 6-10 membered aryl, 5-11 membered heteroaryl, C$_3$-C$_{11}$ cycloalkyl, C$_4$-C$_{11}$ cycloalkenyl, and 4-12 membered heterocyclyl are optionally substituted with one or more substituents independently selected from the group consisting of C$_1$-C$_6$ alkyl, C$_1$-C$_6$ haloalkyl, C$_1$-C$_6$ alkoxy, C$_1$-C$_6$ haloalkoxy, C(O)OH, OH, oxo, CN, NO$_2$, F, Cl, Br and I;

one of R$^{2A}$, R$^{2B}$, R$^{2C}$, and R$^{2D}$ is hydrogen, and the remaining are independently selected from the group consisting of hydrogen, R$^8$, OR$^8$, C(O)R$^8$, C(O)OR$^8$, SO$_2$R$^8$, NHR$^8$, N(R$^8$)$_2$, NH$_2$, C(O)OH, OH, CN, NO$_2$, F, Cl, Br and I; or two of R$^{2A}$, R$^{2B}$, R$^{2C}$, and R$^{2D}$ on adjacent carbons form a fused ring selected from the group consisting of phenyl, 5-6 membered heteroaryl, C$_3$-C$_7$ cycloalkyl, C$_4$-C$_7$ cycloalkenyl, and 4-7 membered heterocyclyl; and the remaining are independently selected from the group consisting of hydrogen, R$^8$, OR$^8$, C(O)R$^8$, OC(O)R$^8$, C(O)OR$^8$, SO$_2$R$^8$, NHR$^8$, N(R)$_2$, NH$_2$, C(O)OH, OH, CN, NO$_2$, F, Cl, Br and I; wherein the phenyl, 5-6 membered heteroaryl, C$_3$-C$_7$ cycloalkyl, C$_4$-C$_7$ cycloalkenyl, and 4-7 membered heterocyclyl are optionally substituted with one or more substituents independently selected from the group consisting of R$^8$, OR$^8$, C(O)R$^8$, OC(O)R$^8$, C(O)OR$^8$, SO$_2$R$^8$, NHR$^8$, N(R)$_2$, NH$_2$, C(O)OH, OH, CN, NO$_2$, F, Cl, Br and I;

R$^3$ is selected from the group consisting of C$_1$-C$_6$ alkyl, C$_2$-C$_6$ alkenyl, C$_2$-C$_6$ alkynyl, 6-10 membered aryl, 5-11 membered heteroaryl, C$_3$-C$_{11}$ cycloalkyl, C$_4$-C$_{11}$ cycloalkenyl, and 4-12 membered heterocyclyl; wherein the R$^3$ C$_2$-C$_6$ alkyl, C$_2$-C$_6$ alkenyl, and C$_2$-C$_6$ alkynyl are optionally substituted with one or more substituents independently selected from the group consisting of C$_1$-C$_6$ alkoxy, phenyl, OH, oxo, CN, NO$_2$, F, Cl, Br and I; wherein the R$^3$ 6-10 membered aryl, 5-11 membered heteroaryl, C$_3$-C$_{11}$cycloalkyl, C$_4$-C$_{11}$ cycloalkenyl, and 4-12 membered heterocyclyl are optionally substituted with one or more substituents independently selected from the group consisting of R$^9$, OR$^9$, C(O)R$^9$, OC(O)R$^9$, C(O)OR$^9$, SO$_2$R$^9$, C(O)NH$_2$, C(O)NHR$^9$, C(O)N(R$^9$)$_2$, NHC(O)R$^9$, NHR$^9$, N(R$^9$)$_2$, NH$_2$, C(O)OH, OH, oxo, CN, NO$_2$, F, Cl, Br and I;

R$^{5A}$ and R$^{5B}$ are each independently selected from the group consisting of hydrogen, C$_1$-C$_6$ alkyl, C$_2$-C$_6$ alkenyl, C$_2$-C$_6$ alkynyl, C$_1$-C$_6$ alkoxy, 6-10 membered aryl, 5-11 membered heteroaryl, C$_3$-C$_{11}$ cycloalkyl, C$_4$-C$_{11}$ cycloalkenyl, and 4-12 membered heterocyclyl; wherein the R$^{5A}$ and R$^{5B}$ C$_1$-C$_6$ alkyl, C$_2$-C$_6$ alkenyl, C$_2$-C$_6$ alkynyl, and C$_1$-C$_6$ alkoxy are optionally substituted with one or more substituents independently selected from the group consisting of 6-10 membered aryl, 5-11 membered heteroaryl, C$_3$-C$_{11}$ cycloalkyl, C$_4$-C$_{11}$ cycloalkenyl, 4-12 membered heterocyclyl, C$_1$-C$_6$ thioalkyl, OH, oxo, CN, NO$_2$, F, Cl, Br and I; wherein the R$^{5A}$ and R$^{5B}$ 6-10 membered aryl, 5-11 membered heteroaryl, C$_3$-C$_{11}$ cycloalkyl, C$_4$-C$_{11}$ cycloalkenyl, and 4-12 membered heterocyclyl are optionally substituted with one or more substituents independently selected from the group consisting of C$_1$-C$_6$ alkyl, C(O)OH, NH$_2$, OH, oxo, CN, NO$_2$, F, Cl, Br and I; or R$^{5A}$ and R$^{5B}$, together with the carbon atom to which they are attached, form a C$_3$-C$_7$ monocyclic cycloalkyl or a 4-7 membered monocyclic heterocycle; wherein the C$_3$-C$_7$ monocyclic cycloalkyl and the 4-7 membered monocyclic heterocycle are each optionally substituted with one or more substituents independently selected from the group consisting of C$_1$-C$_6$ alkyl, C(O)OH, NH$_2$, OH, oxo, CN, NO$_2$, F, Cl, Br and I;

R$^{6A}$ and R$^{6B}$ are each independently hydrogen;

R$^7$, at each occurrence, is independently selected from the group consisting of C$_1$-C$_6$ alkyl, C$_2$-C$_6$ alkenyl, C$_2$-C$_6$ alkynyl, 6-10 membered aryl, 5-11 membered heteroaryl, C$_3$-C$_{11}$ cycloalkyl, C$_4$-C$_{11}$ cycloalkenyl, and 4-12 membered heterocyclyl; wherein each R$^7$ C$_1$-C$_6$ alkyl, C$_2$-C$_6$ alkenyl, and C$_2$-C$_6$ alkynyl is optionally substituted with one or more substituents independently selected from the group consisting of C$_1$-C$_6$ alkoxy, OH, oxo, CN, NO$_2$, F, Cl, Br and I; wherein each R$^7$ 6-10 membered aryl, 5-11 membered heteroaryl, C$_3$-C$_{11}$ cycloalkyl, C$_4$-C$_{11}$ cycloalkenyl, and 4-12 membered heterocyclyl is optionally substituted with one or more substituents independently selected from the group consisting of C$_1$-C$_6$ alkyl, C$_1$-C$_6$ alkoxy, C$_1$-C$_6$ haloalkyl, oxo, OH, CN, NO$_2$, F, Cl, Br and I;

R$^8$, at each occurrence, is independently selected from the group consisting of C$_1$-C$_6$ alkyl, C$_2$-C$_6$ alkenyl, C$_2$-C$_6$ alkynyl, C$_6$-C$_{10}$ membered aryl, 5-11 membered heteroaryl, C$_3$-C$_{11}$cycloalkyl, C$_4$-C$_{11}$ cycloalkenyl, and 4-12 membered heterocyclyl; wherein each R$^8$ C$_1$-C$_6$ alkyl, C$_2$-C$_6$ alkenyl, and C$_2$-C$_6$ alkynyl is optionally substituted with one or more substituents independently selected from the group consisting of R$^{11}$, OR$^{11}$, C(O)OR$^{11}$, NHR$^{11}$, N(R$^{11}$)$_2$, NH$_2$, C(O)OH, OH, CN, NO$_2$, F, Cl, Br and I; wherein each R$^8$ C$_6$-C$_{10}$ membered aryl, 5-11 membered heteroaryl, C$_3$-C$_{11}$ cycloalkyl, C$_4$-C$_{11}$ cycloalkenyl, and 4-12 membered heterocyclyl is optionally substituted with one or more substituents independently selected from the group consisting of R$^{12}$, OR$^{12}$, C(O)OR$^{12}$, NHR$^{12}$, N(R$^{12}$)$_2$, NH$_2$, C(O)OH, OH, oxo, CN, NO$_2$, F, Cl, Br and I;

R$^9$, at each occurrence, is independently selected from the group consisting of C$_1$-C$_6$ alkyl, C$_2$-C$_6$ alkenyl, C$_2$-C$_6$ alkynyl, 6-10 membered aryl, 5-11 membered heteroaryl, C$_3$-C$_{11}$ cycloalkyl, C$_4$-C$_{11}$ cycloalkenyl, and 4-12 membered heterocyclyl; wherein each R$^9$ C$_1$-C$_6$ alkyl, C$_2$-C$_6$ alkenyl, and C$_2$-C$_6$ alkynyl is optionally substituted with one or more substituents independently selected from the group consisting of R$^{13}$, OR$^{13}$, SR$^{13}$, C(O)R$^{13}$, NHR$^{13}$, N(R$^{13}$)$_2$, C(O)OH, OH, CN, NO$_2$, F, Cl, Br and I; wherein each R$^9$ 6-10 membered aryl, 5-11 membered heteroaryl, C$_3$-C$_{11}$ cycloalkyl, C$_4$-C$_{11}$ cycloalkenyl, and 4-12 membered heterocyclyl are optionally substituted with one or more substituents independently selected from the group consisting of R$^{14}$, OR$^{14}$, C(O)R$^{14}$, OC(O)R$^{14}$, C(O)OR$^{14}$, SO$_2$R$^{14}$, NHR$^{14}$, N(R$^{14}$)$_2$, NH$_2$, C(O)OH, OH, oxo, CN, NO$_2$, F, Cl, Br and I;

R$^{11}$, at each occurrence, is independently selected from the group consisting of C$_1$-C$_6$ alkyl, C$_1$-C$_6$ alkoxy, C$_6$-C$_{10}$ membered aryl, C$_3$-C$_{11}$ cycloalkyl, 4-12 membered heterocyclyl, C$_4$-C$_{11}$ cycloalkenyl, and 5-6 membered heteroaryl; wherein each R$^{11}$ C$_1$-C$_6$ alkyl and C$_1$-C$_6$ alkoxy is optionally substituted with one or more substituents independently selected from the group consisting of OH, oxo, CN, NO$_2$, F, Cl, Br and I; wherein each R$^{11}$ C$_6$-C$_{10}$ membered aryl, C$_3$-C$_{11}$ cycloalkyl, 4-12 membered heterocyclyl, C$_4$-C$_{11}$cycloalkenyl, and 5-6 membered heteroaryl is optionally substituted with one or more substituents independently selected from the group consisting of C$_1$-C$_6$ alkyl, C$_1$-C$_6$ alkoxy, F, Cl, Br and I;

$R^{12}$, at each occurrence, is independently selected from the group consisting of $C_1$-$C_6$ alkyl, $C_1$-$C_6$ alkoxy, $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl; wherein each $R^{12}$ $C_1$-$C_6$ alkyl and $C_1$-$C_6$ alkoxy is optionally substituted with one or more substituents independently selected from the group consisting of OH, oxo, CN, $NO_2$, F, Cl, Br and I; wherein each $R^{12}$ $C_6$-$C_{10}$ membered aryl, $C_3$-$C_{11}$ cycloalkyl, 4-12 membered heterocyclyl, $C_4$-$C_{11}$cycloalkenyl, and 5-6 membered heteroaryl is optionally substituted with one or more substituents independently selected from the group consisting of $C_1$-$C_6$ alkyl, $C_1$-$C_6$ alkoxy, F, Cl, Br and I;

$R^{13}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{13}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{13}$ $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I; and $R^{14}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$cycloalkyl, $C_4$-$C_{11}$ cycloalkenyl, and 4-12 membered heterocyclyl; wherein each $R^{14}$ $C_1$-$C_6$ alkyl, $C_2$-$C_6$ alkenyl, and $C_2$-$C_6$ alkynyl is optionally substituted with one or more substituents independently selected from the group consisting of $C_1$-$C_6$ alkyl, $C_1$-$C_6$ alkoxy, 5-6 membered heteroaryl, 4-12 membered heterocyclyl, OH, oxo, CN, $NO_2$, F, Cl, Br and I;

with the proviso that $R^3$ is not $C_1$-alkyl or thienyl;
with the proviso that, when $R^{2A}$, $R^{2B}$, $R^{2C}$, and $R^{2D}$ are each hydrogen, $R^1$ is not hydrogen;
with the proviso that, when $R^3$ is imidazolyl, $R^9$ is not $CH_2CH(CH_3)_2$;
with the proviso that, when $R^{2B}$ is Cl, $R^3$ is not 2,4-dimethyl-5-thiazolyl or 2-cyano-3-fluorophenyl;
with the proviso that, when $R^3$ is cyclohexyl, $R^{2C}$ is not $OCH_3$;
with the proviso that, when $R^3$ is 3-pyridinyl, $R^{2C}$ is not Cl; and
with the proviso that, when $R^3$ is phenyl, $R^{13}$ is not $C(O)CH_3$.

In one embodiment of Formula (II), $R^1$ is selected from the group consisting of hydrogen, OH, CN, $C_1$-$C_6$ alkyl, $C_2$-$C_6$ alkenyl, $C_2$-$C_6$ alkynyl, $C_1$-$C_6$ alkoxy, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^1$ $C_1$-$C_6$ alkyl, $C_2$-$C_6$ alkenyl, $C_2$-$C_6$ alkynyl, and $C_1$-$C_6$ alkoxy are optionally substituted with one or more substituents independently selected from the group consisting of $R^7$, $OR^7$, $SR^7$, $NHR^7$, $N(R^7)_2$, $NH_2$, C(O)OH, OH, CN, $NO_2$, F, Cl, Br and I; wherein the $R^1$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $C_1$-$C_6$ alkyl, $C_1$-$C_6$ haloalkyl, $C_1$-$C_6$ alkoxy, $C_1$-$C_6$ haloalkoxy, C(O)OH, OH, oxo, CN, $NO_2$, F, Cl, Br and I. In another embodiment of Formula (II), $R^1$ is selected from the group consisting of hydrogen, $C_1$-$C_6$ alkyl, and 6-10 membered aryl. In another embodiment of Formula (II), $R^1$ is hydrogen. In another embodiment of Formula (II), $R^1$ is $C_1$-$C_6$ alkyl. In another embodiment of Formula (II), $R^1$ is $CH_3$. In another embodiment of Formula (II), $R^1$ is $CH_2CH_3$. In another embodiment of Formula (II), $R^1$ is 6-10 membered aryl. In another embodiment of Formula (II), $R^1$ is phenyl.

In one embodiment of Formula (II), one of $R^{2A}$, $R^{2B}$, $R^{2C}$, and $R^{2D}$ is hydrogen, and the remaining are independently selected from the group consisting of hydrogen, $R^8$, $OR^8$, $C(O)R^8$, $C(O)OR^8$, $SO_2R^8$, $NHR^8$, $N(R^8)_2$, $NH_2$, C(O)OH, OH, CN, $NO_2$, F, Cl, Br and I; or two of $R^{2A}$, $R^{2B}$, $R^{2C}$, and $R^{2D}$ on adjacent carbons form a fused ring selected from the group consisting of phenyl, 5-6 membered heteroaryl, $C_3$-$C_7$ cycloalkyl, $C_4$-$C_7$ cycloalkenyl, and 4-7 membered heterocyclyl; and the remaining are independently selected from the group consisting of hydrogen, $R^8$, $OR^8$, $C(O)R^8$, $OC(O)R^8$, $C(O)OR^8$, $SO_2R^8$, $NHR^8$, $N(R^8)_2$, $NH_2$, C(O)OH, OH, CN, $NO_2$, F, Cl, Br and I; wherein the phenyl, 5-6 membered heteroaryl, $C_3$-$C_7$ cycloalkyl, $C_4$-$C_7$ cycloalkenyl, and 4-7 membered heterocyclyl are optionally substituted with one or more substituents independently selected from the group consisting of $R^8$, $OR^8$, $C(O)R^8$, $OC(O)R^8$, $C(O)OR^8$, $SO_2R^8$, $NHR^8$, $N(R^8)_2$, $NH_2$, C(O)OH, OH, CN, $NO_2$, F, Cl, Br and I. In one embodiment of Formula (II), one of $R^{2A}$, $R^{2B}$, $R^{2C}$, and $R^{2D}$ is hydrogen, and the remaining are independently selected from the group consisting of hydrogen, $R^8$, $OR^8$, $C(O)R^8$, $C(O)OR^8$, $SO_2R^8$, $NHR^8$, $N(R^8)_2$, $NH_2$, C(O)OH, OH, CN, $NO_2$, F, Cl, Br and I. In another embodiment of Formula (II), $R^{2A}$, $R^{2B}$, $R^{2C}$, and $R^{2D}$ are each independently hydrogen. In another embodiment of Formula (II), three of $R^{2A}$, $R^{2B}$, $R^{2C}$, and $R^{2D}$ are hydrogen, and the remaining are independently selected from the group consisting of hydrogen, $R^8$, $OR^8$, $C(O)R^8$, CN, Cl, and Br. In another embodiment of Formula (II), two of $R^{2A}$, $R^{2B}$, $R^{2C}$, and $R^{2D}$ are hydrogen, and the remaining are independently selected from the group consisting of hydrogen, $R^8$, $OR^8$, $C(O)R^8$, CN, Cl, and Br. In another embodiment of Formula (II), three of $R^{2A}$, $R^{2B}$, $R^{2C}$, and $R^{2D}$ are hydrogen, and the remaining is independently selected from the group consisting of hydrogen, $R^8$, $OR^8$, $C(O)R^8$, CN, Cl, and Br. In another embodiment of Formula (II), two of $R^{2A}$, $R^{2B}$, $R^{2C}$, and $R^{2D}$ on adjacent carbons form a fused 4-7 membered heterocyclyl; and the remaining are independently hydrogen; wherein the 4-7 membered heterocyclyl is optionally substituted with one or more F.

In one embodiment of Formula (II), $R^3$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$cycloalkenyl, and 4-12 membered heterocyclyl; wherein the $R^3$ $C_2$-$C_6$ alkyl, $C_2$-$C_6$ alkenyl, and $C_2$-$C_6$ alkynyl are optionally substituted with one or more substituents independently selected from the group consisting of $C_1$-$C_6$ alkoxy, phenyl, OH, oxo, CN, $NO_2$, F, Cl, Br and I; wherein the $R^3$ 6-10 membered aryl, 5-11 membered heteroaryl, $C_3$-$C_{11}$cycloalkyl, $C_4$-$C_{11}$ cycloalkenyl, and 4-12 membered heterocyclyl are optionally substituted with one or more substituents independently selected from the group consisting of $R^9$, $OR^9$, $C(O)R^9$, $OC(O)R^9$, $C(O)OR^9$, $SO_2R^9$, $C(O)NH_2$, $C(O)NHR^9$, $C(O)N(R^9)_2$, $NHC(O)R^9$, $NHR^9$, $N(R^9)_2$, $NH_2$, C(O)OH, OH, oxo, CN, $NO_2$, F, Cl, Br and I. In another embodiment of Formula (II), $R^3$ is selected from the group consisting of $C_1$-$C_6$ alkyl, 6-10 membered aryl, 5-11 membered heteroaryl, and 4-12 membered heterocyclyl; wherein the $R^3$ 6-10 membered aryl, 5-11 membered heteroaryl, and 4-12 membered heterocyclyl are optionally substituted with one or more $R^9$. In another embodiment of Formula (II), $R^3$ is $C_1$-$C_6$ alkyl. In another embodiment of Formula (II), $R^3$ is 6-10 membered aryl; wherein the $R^3$ 6-10 membered aryl is optionally substituted with one or more $R^9$. In another embodiment of Formula (II), $R^3$ is phenyl or napthyl; wherein the $R^3$ phenyl or napthyl is optionally substituted with one or more $R^9$; and $R^9$ is $C_1$-$C_6$ alkyl. In another embodiment of Formula (II), $R^3$ is phenyl; wherein the $R^3$ phenyl is unsubstituted. In another embodiment of Formula (II), $R^3$ is napthyl; wherein the $R^3$ napthyl is unsubstituted. In another embodiment of Formula (II), $R^3$ is 5-11 membered heteroaryl; wherein the $R^3$ 5-11 membered heteroaryl is optionally substituted with one or more $R^9$. In another embodiment of Formula (II), $R^3$ is indazolyl or quinolinyl; wherein the $R^3$ indazolyl or quinolinyl is optionally substituted with one or more $R^9$; and $R^9$ is $C_1$-$C_6$ alkyl. In another embodiment of Formula (II), $R^3$ is quinolinyl; wherein the quinolinyl is unsubstituted. In another embodiment of Formula (II), $R^3$ is quinolinyl; wherein the quinolinyl is substituted with one $CH_3$.

In one embodiment of Formula (II), $R^{5A}$ and $R^{5B}$ are each independently selected from the group consisting of hydrogen, $C_1$-$C_6$ alkyl, $C_2$-$C_6$ alkenyl, $C_2$-$C_6$ alkynyl, $C_1$-$C_6$ alkoxy, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^{5A}$ and $R^{5B}$ $C_1$-$C_6$ alkyl, $C_2$-$C_6$ alkenyl, $C_2$-$C_6$ alkynyl, and $C_1$-$C_6$ alkoxy are optionally substituted with one or more substituents independently selected from the group consisting of 6-10 membered aryl, 5-11 membered heteroaryl, $C_3$-$C_{11}$ cycloalkyl, $C_4$-$C_{11}$ cycloalkenyl, 4-12 membered heterocyclyl, $C_1$-$C_6$ thioalkyl, OH, oxo, CN, $NO_2$, F, Cl, Br and I; wherein the $R^{5A}$ and $R^{5B}$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $C_1$-$C_6$ alkyl, C(O)OH, $NH_2$, OH, oxo, CN, $NO_2$, F, Cl, Br and I; or $R^{5A}$ and $R^{5B}$, together with the carbon atom to which they are attached, form a $C_3$-$C_7$ monocyclic cycloalkyl or a 4-7 membered monocyclic heterocycle; wherein the $C_3$-$C_7$ monocyclic cycloalkyl and the 4-7 membered monocyclic heterocycle are each optionally substituted with one or more substituents independently selected from the group consisting of $C_1$-$C_6$ alkyl, C(O)OH, $NH_2$, OH, oxo, CN, $NO_2$, F, Cl, Br and I. In another embodiment of Formula (II), $R^{5A}$ and $R^{5B}$ are each independently selected from the group consisting of hydrogen and $C_1$-$C_6$ alkyl; wherein the $R^{5A}$ and $R^{5B}$ $C_1$-$C_6$ alkyl is optionally substituted with one or more substituents independently selected from the group consisting of 4-12 membered heterocyclyl and $C_1$-$C_6$ thioalkyl. In another embodiment of Formula (II), $R^{5A}$ and $R^{5B}$ are each independently hydrogen. In another embodiment of Formula (II), $R^{5A}$ and $R^{5B}$ are each independently methyl. In another embodiment of Formula (II), $R^{5A}$ and $R^{5B}$, together with the carbon atom to which they are attached, form a $C_3$-$C_7$ monocyclic cycloalkyl. In another embodiment of Formula (II), $R^{5A}$ and $R^{5B}$, together with the carbon atom to which they are attached, form cyclohexyl.

In one embodiment of Formula (II), $R^{6A}$ and $R^{6B}$ are each independently hydrogen.

In one embodiment of Formula (II), $R^8$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of $R^{11}$, $OR^{11}$, $C(O)OR^{11}$, $NHR^{11}$, $N(R^{11})_2$, $NH_2$, C(O)OH, OH, CN, $NO_2$, F, Cl, Br and I; wherein each $R^8$ $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{12}$, $OR^{12}$, $C(O)OR^{12}$, $NHR^{12}$, $N(R^{12})_2$, $NH_2$, C(O)OH, OH, oxo, CN, $NO_2$, F, Cl, Br and I. In another embodiment of Formula (II), $R^8$, at each occurrence, is independently selected from the group consisting of $C_1$-$C_6$ alkyl, $C_6$-$C_{10}$ membered aryl, and $C_3$-$C_{11}$ cycloalkyl; wherein each $R^8$ $C_1$-$C_6$ alkyl is optionally substituted with one or more F. In another embodiment of Formula (II), $R^8$, at each occurrence, is independently $CH_3$. In another embodiment of Formula (II), $R^8$, at each occurrence, is independently $CF_3$. In another embodiment of Formula (II), $R^8$, at each occurrence, is independently phenyl. In another embodiment of Formula (II), $R^8$, at each occurrence, is independently cyclopropyl. In another embodiment of Formula (II), $R^8$, at each occurrence, is independently cyclobutyl. In another embodiment of Formula (II), $R^8$, at each occurrence, is independently cyclopentyl.

Another embodiment pertains to compounds of Formula (II), or a pharmaceutically acceptable salt thereof,

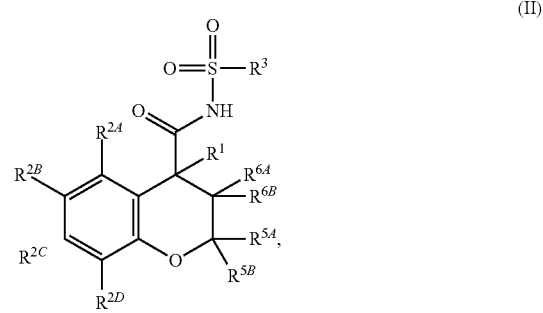

(II)

wherein
$R^1$ is selected from the group consisting of hydrogen, $C_1$-$C_6$ alkyl, and 6-10 membered aryl;
one of $R^{2A}$, $R^{2B}$, $R^{2C}$, and $R^{2D}$ is hydrogen, and the remaining are independently selected from the group consisting of hydrogen, $R^8$, $OR^8$, $C(O)R^8$, CN, Cl, and Br; or
two of $R^{2A}$, $R^{2B}$, $R^{2C}$, and $R^{2D}$ on adjacent carbons form a 4-7 membered heterocyclyl; and the remaining are independently hydrogen; wherein the 4-7 membered heterocyclyl is optionally substituted with one or more F;
$R^3$ is selected from the group consisting of $C_1$-$C_6$ alkyl, 6-10 membered aryl, 5-11 membered heteroaryl, and 4-12 membered heterocyclyl; wherein the $R^3$ 6-10 membered aryl, 5-11 membered heteroaryl, and 4-12 membered heterocyclyl are optionally substituted with one or more $R^9$;
$R^{5A}$ and $R^{5B}$ are each independently selected from the group consisting of hydrogen and $C_1$-$C_6$ alkyl; wherein the $R^{5A}$ and $R^{5B}$ $C_1$-$C_6$ alkyl is optionally substituted with one or more substituents independently selected from the group consisting of 4-12 membered heterocyclyl and $C_1$-$C_6$ thioalkyl; or $R^{5A}$ and $R^{5B}$, together with the carbon atom to which they are attached, form a $C_3$-$C_7$ monocyclic cycloalkyl;

$R^{6A}$ and $R^{6B}$ are each independently hydrogen;

$R^8$, at each occurrence, is independently selected from the group consisting of $C_1$-$C_6$ alkyl, $C_6$-$C_{10}$ membered aryl, and $C_3$-$C_{11}$ cycloalkyl; wherein each $R^8$ $C_1$-$C_6$ alkyl is optionally substituted with one or more F; and $R^9$, at each occurrence, is independently $C_1$-$C_6$ alkyl; wherein each $R^9$ $C_1$-$C_6$ alkyl is optionally substituted with one or more F;

with the proviso that $R^3$ is not $C_1$-alkyl or thienyl;

with the proviso that, when $R^{2A}$, $R^{2B}$, $R^{2C}$, and $R^{2D}$ are each hydrogen, $R^1$ is not hydrogen;

with the proviso that, when $R^3$ is imidazolyl, $R^9$ is not $CH_2CH(CH_3)_2$;

with the proviso that, when $R^{2B}$ is Cl, $R^3$ is not 2,4-dimethyl-5-thiazolyl; and with the proviso that, when $R^3$ is 3-pyridinyl, $R^{2C}$ is not Cl.

Exemplary compounds of Formula (II) include, but are not limited to:

6-bromo-N-(naphthalene-1-sulfonyl)-4-phenyl-3,4-dihydro-2H-1-benzopyran-4-carboxamide;
(2R,4R)-2-[(ethylsulfanyl)methyl]-N-(naphthalene-1-sulfonyl)-4-phenyl-3,4-dihydro-2H-1-benzopyran-4-carboxamide;
6-methoxy-2,2-dimethyl-N-(naphthalene-1-sulfonyl)-4-phenyl-3,4-dihydro-2H-1-benzopyran-4-carboxamide;
6-methoxy-N-(naphthalene-1-sulfonyl)-4-phenyl-3,4-dihydro-2H-1-benzopyran-4-carboxamide;
6-benzoyl-5,7-dimethyl-N-(naphthalene-1-sulfonyl)-3,4-dihydro-2H-1-benzopyran-4-carboxamide;
8-chloro-N-(naphthalene-1-sulfonyl)-3,4-dihydro-2H-1-benzopyran-4-carboxamide;
3-ethyl-4-methoxy-N-(naphthalene-1-sulfonyl)-2,3-dihydro-1-benzofuran-3-carboxamide;
5-methoxy-N-(naphthalene-1-sulfonyl)-3,4-dihydro-2H-1-benzopyran-4-carboxamide;
4-ethyl-5-methoxy-N-(naphthalene-1-sulfonyl)-3,4-dihydro-2H-1-benzopyran-4-carboxamide;
8-bromo-5-methoxy-N-(naphthalene-1-sulfonyl)-3,4-dihydro-2H-1-benzopyran-4-carboxamide;
6,8-dibromo-5-methoxy-N-(naphthalene-1-sulfonyl)-3,4-dihydro-2H-1-benzopyran-4-carboxamide;
8-cyclobutyl-5-methoxy-N-(naphthalene-1-sulfonyl)-3,4-dihydro-2H-1-benzopyran-4-carboxamide;
8-cyclopentyl-5-methoxy-N-(naphthalene-1-sulfonyl)-3,4-dihydro-2H-1-benzopyran-4-carboxamide;
6-methyl-N-(naphthalene-1-sulfonyl)-4-phenyl-3,4-dihydro-2H-1-benzopyran-4-carboxamide;
6-chloro-N-(naphthalene-1-sulfonyl)-4-phenyl-3,4-dihydro-2H-1-benzopyran-4-carboxamide;
N-(2-methylbenzene-1-sulfonyl)-3,4-dihydro-2H-1-benzopyran-4-carboxamide;
(2S)—N-(naphthalene-1-sulfonyl)-4-phenyl-2-[(pyrrolidin-1-yl)methyl]-3,4-dihydro-2H-1-benzopyran-4-carboxamide;
(4S)-8-bromo-5-methoxy-N-(naphthalene-1-sulfonyl)-3,4-dihydro-2H-1-benzopyran-4-carboxamide;
(4R)-8-bromo-5-methoxy-N-(naphthalene-1-sulfonyl)-3,4-dihydro-2H-1-benzopyran-4-carboxamide;
5-methoxy-N-(naphthalene-1-sulfonyl)-3,4-dihydrospiro[1-benzopyran-2,1'-cyclohexane]-4-carboxamide;
8-bromo-5-methoxy-N-(naphthalene-1-sulfonyl)-3,4-dihydrospiro[1-benzopyran-2,1'-cyclohexane]-4-carboxamide;
8-bromo-5-methoxy-N-(quinoline-8-sulfonyl)-3,4-dihydro-2H-1-benzopyran-4-carboxamide;
8-bromo-5-methoxy-2,2-dimethyl-N-(quinoline-5-sulfonyl)-3,4-dihydro-2H-1-benzopyran-4-carboxamide;
5-methoxy-2,2-dimethyl-N-(quinoline-8-sulfonyl)-3,4-dihydro-2H-1-benzopyran-4-carboxamide;
5-methoxy-2,2-dimethyl-N-(quinoline-5-sulfonyl)-3,4-dihydro-2H-1-benzopyran-4-carboxamide;
5-methoxy-2,2-dimethyl-N-(naphthalene-1-sulfonyl)-3,4-dihydro-2H-1-benzopyran-4-carboxamide;
8-cyano-5-methoxy-2,2-dimethyl-N-(naphthalene-1-sulfonyl)-3,4-dihydro-2H-1-benzopyran-4-carboxamide;
8-chloro-5-methoxy-2,2-dimethyl-N-(naphthalene-1-sulfonyl)-3,4-dihydro-2H-1-benzopyran-4-carboxamide;
8-bromo-5-methoxy-2,2-dimethyl-N-(naphthalene-1-sulfonyl)-3,4-dihydro-2H-1-benzopyran-4-carboxamide;
5-methoxy-N-(naphthalene-1-sulfonyl)-8-(trifluoromethyl)-3,4-dihydro-2H-1-benzopyran-4-carboxamide;
8-cyclobutyl-5-methoxy-N-(quinoline-5-sulfonyl)-3,4-dihydro-2H-1-benzopyran-4-carboxamide;
(4S)-8-cyclobutyl-5-methoxy-N-(naphthalene-1-sulfonyl)-3,4-dihydro-2H-1-benzopyran-4-carboxamide;
(4R)-8-cyclobutyl-5-methoxy-N-(naphthalene-1-sulfonyl)-3,4-dihydro-2H-1-benzopyran-4-carboxamide;
(4S)-5-methoxy-N-(naphthalene-1-sulfonyl)-8-(trifluoromethyl)-3,4-dihydro-2H-1-benzopyran-4-carboxamide;
(4R)-5-methoxy-N-(naphthalene-1-sulfonyl)-8-(trifluoromethyl)-3,4-dihydro-2H-1-benzopyran-4-carboxamide;
(4S)-8-cyclobutyl-5-methoxy-N-(quinoline-5-sulfonyl)-3,4-dihydro-2H-1-benzopyran-4-carboxamide;
(4R)-8-cyclobutyl-5-methoxy-N-(quinoline-5-sulfonyl)-3,4-dihydro-2H-1-benzopyran-4-carboxamide;
8-cyclopropyl-5-methoxy-N-(naphthalene-1-sulfonyl)-3,4-dihydro-2H-1-benzopyran-4-carboxamide;
(4S)-8-bromo-5-methoxy-N-(1-methyl-1H-indazole-7-sulfonyl)-3,4-dihydro-2H-1-benzopyran-4-carboxamide;
(4R)-8-bromo-5-methoxy-N-(1-methyl-1H-indazole-7-sulfonyl)-3,4-dihydro-2H-1-benzopyran-4-carboxamide;
(4S)-8-bromo-5-methoxy-2,2-dimethyl-N-(quinoline-5-sulfonyl)-3,4-dihydro-2H-1-benzopyran-4-carboxamide;
(4R)-8-bromo-5-methoxy-2,2-dimethyl-N-(quinoline-5-sulfonyl)-3,4-dihydro-2H-1-benzopyran-4-carboxamide;
8-cyclobutyl-5-methoxy-N-(2-methylquinoline-5-sulfonyl)-3,4-dihydro-2H-1-benzopyran-4-carboxamide;
(4S)-8-cyclobutyl-5-methoxy-N-(2-methylquinoline-5-sulfonyl)-3,4-dihydro-2H-1-benzopyran-4-carboxamide;
(4R)-8-cyclobutyl-5-methoxy-N-(2-methylquinoline-5-sulfonyl)-3,4-dihydro-2H-1-benzopyran-4-carboxamide;
8-cyclobutyl-5-methoxy-N-(1,2,3,4-tetrahydroquinoline-5-sulfonyl)-3,4-dihydro-2H-1-benzopyran-4-carboxamide;
(4R)-8-cyclobutyl-5-methoxy-2,2-dimethyl-N-(quinoline-5-sulfonyl)-3,4-dihydro-2H-1-benzopyran-4-carboxamide;
(4S)-8-cyclobutyl-5-methoxy-N-(1,2,3,4-tetrahydroquinoline-5-sulfonyl)-3,4-dihydro-2H-1-benzopyran-4-carboxamide;
(4R)-8-cyclobutyl-5-methoxy-N-(1,2,3,4-tetrahydroquinoline-5-sulfonyl)-3,4-dihydro-2H-1-benzopyran-4-carboxamide;
8-cyclobutyl-5-methoxy-2,2-dimethyl-N-(1,2,3,4-tetrahydroquinoline-5-sulfonyl)-3,4-dihydro-2H-1-benzopyran-4-carboxamide;

(4S)-8-cyclobutyl-5-methoxy-2,2-dimethyl-N-(1,2,3,4-tet-rahydroquinoline-5-sulfonyl)-3,4-dihydro-2H-1-benzo-pyran-4-carboxamide;
(4R)-8-cyclobutyl-5-methoxy-2,2-dimethyl-N-(1,2,3,4-tet-rahydroquinoline-5-sulfonyl)-3,4-dihydro-2H-1-benzo-pyran-4-carboxamide;
8-cyclobutyl-N-(1H-indole-4-sulfonyl)-5-methoxy-3,4-di-hydro-2H-1-benzopyran-4-carboxamide;
(4S)-8-cyclobutyl-N-(1H-indole-4-sulfonyl)-5-methoxy-3,4-dihydro-2H-1-benzopyran-4-carboxamide;
(4R)-8-cyclobutyl-N-(1H-indole-4-sulfonyl)-5-methoxy-3,4-dihydro-2H-1-benzopyran-4-carboxamide;
5-cyclobutyl-8-methoxy-N-(quinoline-5-sulfonyl)-3,4-di-hydro-2H-1-benzopyran-4-carboxamide;
(4R)-5-cyclobutyl-8-methoxy-N-(quinoline-5-sulfonyl)-3,4-dihydro-2H-1-benzopyran-4-carboxamide;
(4S)-5-cyclobutyl-8-methoxy-N-(quinoline-5-sulfonyl)-3,4-dihydro-2H-1-benzopyran-4-carboxamide; and pharmaceutically acceptable salts thereof.

Formula (III)

One embodiment pertains to compounds of Formula (III), or a pharmaceutically acceptable salt thereof,

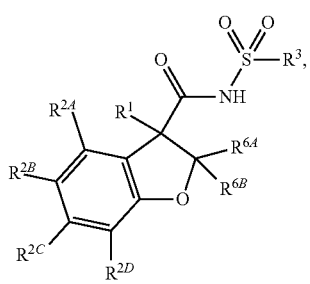

(III)

wherein
R$^1$ is selected from the group consisting of hydrogen, OH, CN, C$_1$-C$_6$ alkyl, C$_2$-C$_6$ alkenyl, C$_2$-C$_6$ alkynyl, C$_1$-C$_6$ alkoxy, 6-10 membered aryl, 5-11 membered heteroaryl, C$_3$-C$_{11}$cycloalkyl, C$_4$-C$_{11}$ cycloalkenyl, and 4-12 membered heterocyclyl; wherein the R$^1$ C$_1$-C$_6$ alkyl, C$_2$-C$_6$ alkenyl, C$_2$-C$_6$ alkynyl, and C$_1$-C$_6$ alkoxy are optionally substituted with one or more substituents independently selected from the group consisting of R$^7$, OR$^7$, SR$^7$, NHR$^7$, N(R$^7$)$_2$, NH$_2$, C(O)OH, OH, CN, NO$_2$, F, Cl, Br and I; wherein the R$^1$ 6-10 membered aryl, 5-11 membered heteroaryl, C$_3$-C$_{11}$ cycloalkyl, C$_4$-C$_{11}$ cycloalkenyl, and 4-12 membered heterocyclyl are optionally substituted with one or more substituents independently selected from the group consisting of C$_1$-C$_6$ alkyl, C$_1$-C$_6$ haloalkyl, C$_1$-C$_6$ alkoxy, C$_1$-C$_6$ haloalkoxy, C(O)OH, OH, oxo, CN, NO$_2$, F, Cl, Br and I;
one of R$^{2A}$, R$^{2B}$, R$^{2C}$, and R$^{2D}$ is hydrogen, and the remaining are independently selected from the group consisting of hydrogen, R$^8$, OR$^8$, C(O)R$^8$, C(O)OR$^8$, SO$_2$R$^8$, NHR$^8$, N(R$^8$)$_2$, NH$_2$, C(O)OH, OH, CN, NO$_2$, F, Cl, Br and I; or
two of R$^{2A}$, R$^{2B}$, R$^{2C}$, and R$^{2D}$ on adjacent carbons form a fused ring selected from the group consisting of phenyl, 5-6 membered heteroaryl, C$_3$-C$_7$ cycloalkyl, C$_4$-C$_7$ cycloalkenyl, and 4-7 membered heterocyclyl; and the remaining are independently selected from the group consisting of hydrogen, R$^8$, OR$^8$, C(O)R$^8$, OC(O)R$^8$, C(O)OR$^8$, SO$_2$R$^8$, NHR$^8$, N(R$^8$)$_2$, NH$_2$, C(O)OH, OH, CN, NO$_2$, F, Cl, Br and I; wherein the phenyl, 5-6 membered heteroaryl, C$_3$-C$_7$ cycloalkyl, C$_4$-C$_7$ cycloalkenyl, and 4-7 membered heterocyclyl are optionally substituted with one or more substituents independently selected from the group consisting of R$^8$, OR$^8$, C(O)R$^8$, OC(O)R$^8$, C(O)OR$^8$, SO$_2$R$^8$, NHR$^8$, N(R$^8$)$_2$, NH$_2$, C(O)OH, OH, CN, NO$_2$, F, Cl, Br and I;
R$^3$ is selected from the group consisting of C$_1$-C$_6$ alkyl, C$_2$-C$_6$ alkenyl, C$_2$-C$_6$ alkynyl, 6-10 membered aryl, 5-11 membered heteroaryl, C$_3$-C$_{11}$ cycloalkyl, C$_4$-C$_{11}$ cycloalkenyl, and 4-12 membered heterocyclyl; wherein the R$^3$ C$_2$-C$_6$ alkyl, C$_2$-C$_6$ alkenyl, and C$_2$-C$_6$ alkynyl are optionally substituted with one or more substituents independently selected from the group consisting of C$_1$-C$_6$ alkoxy, phenyl, OH, oxo, CN, NO$_2$, F, Cl, Br and I; wherein the R$^3$ 6-10 membered aryl, 5-11 membered heteroaryl, C$_3$-C$_{11}$cycloalkyl, C$_4$-C$_{11}$ cycloalkenyl, and 4-12 membered heterocyclyl are optionally substituted with one or more substituents independently selected from the group consisting of R$^9$, OR$^9$, C(O)R$^9$, OC(O)R$^9$, C(O)OR$^9$, SO$_2$R$^9$, C(O)NH$_2$, C(O)NHR$^9$, C(O)N(R$^9$)$_2$, NHC(O)R$^9$, NHR$^9$, N(R$^9$)$_2$, NH$_2$, C(O)OH, OH, oxo, CN, NO$_2$, F, Cl, Br and I;
R$^{6A}$ and R$^{6B}$ are each independently hydrogen;
R$^7$, at each occurrence, is independently selected from the group consisting of C$_1$-C$_6$ alkyl, C$_2$-C$_6$ alkenyl, C$_2$-C$_6$ alkynyl, 6-10 membered aryl, 5-11 membered heteroaryl, C$_3$-C$_{11}$cycloalkyl, C$_4$-C$_{11}$ cycloalkenyl, and 4-12 membered heterocyclyl; wherein each R$^7$ C$_1$-C$_6$ alkyl, C$_2$-C$_6$ alkenyl, and C$_2$-C$_6$ alkynyl is optionally substituted with one or more substituents independently selected from the group consisting of C$_1$-C$_6$ alkoxy, OH, oxo, CN, NO$_2$, F, Cl, Br and I; wherein each R$^7$ 6-10 membered aryl, 5-11 membered heteroaryl, C$_3$-C$_{11}$ cycloalkyl, C$_4$-C$_{11}$ cycloalkenyl, and 4-12 membered heterocyclyl is optionally substituted with one or more substituents independently selected from the group consisting of C$_1$-C$_6$ alkyl, C$_1$-C$_6$ alkoxy, C$_1$-C$_6$ haloalkyl, oxo, OH, CN, NO$_2$, F, Cl, Br and I;
R$^8$, at each occurrence, is independently selected from the group consisting of C$_1$-C$_6$ alkyl, C$_2$-C$_6$ alkenyl, C$_2$-C$_6$ alkynyl, C$_6$-C$_{10}$ membered aryl, 5-11 membered heteroaryl, C$_3$-C$_{11}$cycloalkyl, C$_4$-C$_{11}$ cycloalkenyl, and 4-12 membered heterocyclyl; wherein each R$^8$ C$_1$-C$_6$ alkyl, C$_2$-C$_6$ alkenyl, and C$_2$-C$_6$ alkynyl is optionally substituted with one or more substituents independently selected from the group consisting of R$^{11}$, OR$^{11}$, C(O)OR$^{11}$, NHR$^{11}$, N(R$^{11}$)$_2$, NH$_2$, C(O)OH, OH, CN, NO$_2$, F, Cl, Br and I; wherein each R$^8$ C$_6$-C$_{10}$ membered aryl, 5-11 membered heteroaryl, C$_3$-C$_{11}$ cycloalkyl, C$_4$-C$_{11}$ cycloalkenyl, and 4-12 membered heterocyclyl is optionally substituted with one or more substituents independently selected from the group consisting of R$^{12}$, OR$^{12}$, C(O)OR$^{12}$, NHR$^{12}$, N(R$^{12}$)$_2$, NH$_2$, C(O)OH, OH, oxo, CN, NO$_2$, F, Cl, Br and I;
R$^9$, at each occurrence, is independently selected from the group consisting of C$_1$-C$_6$ alkyl, C$_2$-C$_6$ alkenyl, C$_2$-C$_6$ alkynyl, 6-10 membered aryl, 5-11 membered heteroaryl, C$_3$-C$_{11}$cycloalkyl, C$_4$-C$_{11}$ cycloalkenyl, and 4-12 membered heterocyclyl; wherein each R$^9$ C$_1$-C$_6$ alkyl, C$_2$-C$_6$ alkenyl, and C$_2$-C$_6$ alkynyl is optionally substituted with one or more substituents independently selected from the group consisting of R$^{13}$, OR$^{13}$, SR$^{13}$, C(O)R$^{13}$, NHR$^{13}$, N(R$^{13}$)$_2$, C(O)OH, OH, CN, NO$_2$, F, Cl, Br and I; wherein each R$^9$ 6-10 membered aryl, 5-11 membered heteroaryl, C$_3$-C$_{11}$ cycloalkyl, C$_4$-C$_{11}$ cycloalkenyl, and 4-12 membered heterocyclyl are optionally substituted with one or more substituents independently selected from the group consisting of $R^{14}$, $OR^{14}$, $C(O)R^{14}$, $OC(O)R^{14}$, $C(O)OR^{14}$, $SO_2R^{14}$, $NHR^{14}$, $N(R^{14})_2$, $NH_2$, $C(O)OH$, $OH$, oxo, $CN$, $NO_2$, F, Cl, Br and I;

$R^{11}$, at each occurrence, is independently selected from the group consisting of $C_1$-$C_6$ alkyl, $C_1$-$C_6$ alkoxy, $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl; wherein each $R^{11}$ $C_1$-$C_6$ alkyl and $C_1$-$C_6$ alkoxy is optionally substituted with one or more substituents independently selected from the group consisting of OH, oxo, CN, $NO_2$, F, Cl, Br and I; wherein each $R^{11}$ $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl is optionally substituted with one or more substituents independently selected from the group consisting of $C_1$-$C_6$ alkyl, $C_1$-$C_6$ alkoxy, F, Cl, Br and I;

$R^{12}$, at each occurrence, is independently selected from the group consisting of $C_1$-$C_6$ alkyl, $C_1$-$C_6$ alkoxy, $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl; wherein each $R^{12}$ $C_1$-$C_6$ alkyl and $C_1$-$C_6$ alkoxy is optionally substituted with one or more substituents independently selected from the group consisting of OH, oxo, CN, $NO_2$, F, Cl, Br and I; wherein each $R^{12}$ $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl is optionally substituted with one or more substituents independently selected from the group consisting of $C_1$-$C_6$ alkyl, $C_1$-$C_6$ alkoxy, F, Cl, Br and I;

$R^{13}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{13}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{13}$ $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I; and $R^{14}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^4$ $C_1$-$C_6$ alkyl, $C_2$-$C_6$ alkenyl, and $C_2$-$C_6$ alkynyl is optionally substituted with one or more substituents independently selected from the group consisting of $C_1$-$C_6$ alkyl, $C_1$-$C_6$ alkoxy, 5-6 membered heteroaryl, 4-12 membered heterocyclyl, OH, oxo, CN, $NO_2$, F, Cl, Br and I;

with the proviso that $R^3$ is not $C_1$-alkyl or thienyl;
with the proviso that, when $R^{2A}$, $R^{2B}$, $R^{2C}$, and $R^{2D}$ are each hydrogen, $R^1$ is not hydrogen;
with the proviso that, when $R^3$ is imidazolyl, $R^9$ is not $CH_2CH(CH_3)_2$;
with the proviso that, when $R^{2B}$ is Cl, $R^3$ is not 2,4-dimethyl-5-thiazolyl or 2-cyano-3-fluorophenyl;
with the proviso that, when $R^3$ is cyclohexyl, $R^{2C}$ is not $OCH_3$;
with the proviso that, when $R^3$ is 3-pyridinyl, $R^{2C}$ is not Cl; and
with the proviso that, when $R^3$ is phenyl, $R^{13}$ is not $C(O)CH_3$.

In one embodiment of Formula (III), $R^1$ is selected from the group consisting of hydrogen, OH, CN, $C_1$-$C_6$ alkyl, $C_2$-$C_6$ alkenyl, $C_2$-$C_6$ alkynyl, $C_1$-$C_6$ alkoxy, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^1$ $C_1$-$C_6$ alkyl, $C_2$-$C_6$ alkenyl, $C_2$-$C_6$ alkynyl, and $C_1$-$C_6$ alkoxy are optionally substituted with one or more substituents independently selected from the group consisting of $R^7$, $OR^7$, $SR^7$, $NHR^7$, $N(R^7)_2$, $NH_2$, $C(O)OH$, OH, CN, $NO_2$, F, Cl, Br and I; wherein the $R^1$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $C_1$-$C_6$ alkyl, $C_1$-$C_6$ haloalkyl, $C_1$-$C_6$ alkoxy, $C_1$-$C_6$ haloalkoxy, $C(O)OH$, OH, oxo, CN, $NO_2$, F, Cl, Br and I. In another embodiment of Formula (III), $R^1$ is selected from the group consisting of hydrogen, $C_1$-$C_6$ alkyl, and 6-10 membered aryl. In another embodiment of Formula (III), $R^1$ is hydrogen. In another embodiment of Formula (III), $R^1$ is $C_1$-$C_6$ alkyl. In another embodiment of Formula (III), $R^1$ is $CH_3$. In another embodiment of Formula (III), $R^1$ is $CH_2CH_3$. In another embodiment of Formula (III), $R^1$ is 6-10 membered aryl. In another embodiment of Formula (III), $R^1$ is phenyl.

In one embodiment of Formula (III), one of $R^{2A}$, $R^{2B}$, $R^{2C}$, and $R^{2D}$ is hydrogen, and the remaining are independently selected from the group consisting of hydrogen, $R^8$, $OR^8$, $C(O)R^8$, $C(O)OR^8$, $SO_2R^8$, $NHR^8$, $N(R^8)_2$, $NH_2$, $C(O)OH$, OH, CN, $NO_2$, F, Cl, Br and I; or two of $R^{2A}$, $R^{2B}$, $R^{2C}$, and $R^{2D}$ on adjacent carbons form a fused ring selected from the group consisting of phenyl, 5-6 membered heteroaryl, $C_3$-$C_7$ cycloalkyl, $C_4$-$C_7$ cycloalkenyl, and 4-7 membered heterocyclyl; and the remaining are independently selected from the group consisting of hydrogen, $R^8$, $OR^8$, $C(O)R^8$, $OC(O)R^8$, $C(O)OR^8$, $SO_2R^8$, $NHR^8$, $N(R^8)_2$, $NH_2$, $C(O)OH$, OH, CN, $NO_2$, F, Cl, Br and I; wherein the phenyl, 5-6 membered heteroaryl, $C_3$-$C_7$ cycloalkyl, $C_4$-$C_7$ cycloalkenyl, and 4-7 membered heterocyclyl are optionally substituted with one or more substituents independently selected from the group consisting of $R^8$, $OR^8$, $C(O)R^8$, $OC(O)R^8$, $C(O)OR^8$, $SO_2R^8$, $NHR^8$, $N(R^8)_2$, $NH_2$, $C(O)OH$, OH, CN, $NO_2$, F, Cl, Br and I. In one embodiment of Formula (III), one of $R^{2A}$, $R^{2B}$, $R^{2C}$, and $R^{2D}$ is hydrogen, and the remaining are independently selected from the group consisting of hydrogen, $R^8$, $OR^8$, $C(O)R^8$, $C(O)OR^8$, $SO_2R^8$, $NHR^8$, $N(R^8)_2$, $NH_2$, $C(O)OH$, OH, CN, $NO_2$, F, Cl, Br and I. In another embodiment of Formula (III), $R^{2A}$, $R^{2B}$, $R^{2C}$, and $R^{2D}$ are each independently hydrogen. In another embodiment of Formula (III), three of $R^{2A}$, $R^{2B}$, $R^{2C}$, and $R^{2D}$ are hydrogen, and the remaining are independently selected from the group consisting of hydrogen, $R^8$, $OR^8$, $C(O)R^8$, CN, Cl, and Br. In another embodiment of Formula (III), two of $R^{2A}$, $R^{2B}$, $R^{2C}$, and $R^{2D}$ are hydrogen, and the remaining are independently selected from the group consisting of hydrogen, $R^8$, $OR^8$, $C(O)R^8$, CN, Cl, and Br. In another embodiment of Formula (III), three of $R^{2A}$, $R^{2B}$, $R^{2C}$, and $R^{2D}$ are hydrogen, and the remaining is independently selected from the group consisting of hydrogen, $R^8$, $OR^8$, $C(O)R^8$, CN, Cl, and Br. In another embodiment of Formula (III), two of $R^{2A}$, $R^{2B}$, $R^{2C}$, and $R^{2D}$ on adjacent carbons form a fused 4-7 membered heterocyclyl; and the remaining are independently hydrogen; wherein the 4-7 membered heterocyclyl is optionally substituted with one or more F.

In one embodiment of Formula (III), $R^3$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^3$ $C_2$-$C_6$ alkyl, $C_2$-$C_6$ alkenyl, and $C_2$-$C_6$ alkynyl are optionally substituted with one or more substituents independently selected from the group consisting of $C_1$-$C_6$ alkoxy, phenyl, OH, oxo, CN, $NO_2$, F, Cl, Br and I; wherein the $R^3$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^9$, $OR^9$, $C(O)R^9$, $OC(O)R^9$, $C(O)OR^9$, $SO_2R^9$, $C(O)NH_2$, $C(O)NHR^9$, $C(O)N(R^9)_2$, $NHC(O)R^9$, $NHR^9$, $N(R^9)_2$, $NH_2$, $C(O)OH$, OH, oxo, CN, $NO_2$, F, Cl, Br and I. In another embodiment of Formula (III), $R^3$ is selected from the group consisting of $C_1$-$C_6$ alkyl, 6-10 membered aryl, 5-11 membered heteroaryl, and 4-12 membered heterocyclyl; wherein the $R^3$ 6-10 membered aryl, 5-11 membered heteroaryl, and 4-12 membered heterocyclyl are optionally substituted with one or more $R^9$. In another embodiment of Formula (III), $R^3$ is $C_1$-$C_6$ alkyl. In another embodiment of Formula (III), $R^3$ is 6-10 membered aryl; wherein the $R^3$ 6-10 membered aryl is optionally substituted with one or more $R^9$. In another embodiment of Formula (III), $R^3$ is phenyl or napthyl; wherein the $R^3$ phenyl or napthyl is optionally substituted with one or more $R^9$; and $R^9$ is $C_1$-$C_6$ alkyl. In another embodiment of Formula (III), $R^3$ is phenyl; wherein the $R^3$ phenyl is unsubstituted. In another embodiment of Formula (III), $R^3$ is napthyl; wherein the $R^3$ napthyl is unsubstituted. In another embodiment of Formula (III), $R^3$ is 5-11 membered heteroaryl; wherein the $R^3$ 5-11 membered heteroaryl is optionally substituted with one or more $R^9$. In another embodiment of Formula (III), $R^3$ is indazolyl or quinolinyl; wherein the $R^3$ indazolyl or quinolinyl is optionally substituted with one or more $R^9$; and $R^9$ is $C_1$-$C_6$ alkyl. In another embodiment of Formula (III), $R^3$ is quinolinyl; wherein the quinolinyl is unsubstituted. In another embodiment of Formula (III), $R^3$ is quinolinyl; wherein the quinolinyl is substituted with one $CH_3$.

In one embodiment of Formula (III), $R^{6A}$ and $R^{6B}$ are each independently hydrogen.

In one embodiment of Formula (III), $R^8$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of $R^{11}$, $OR^{11}$, $C(O)OR^{11}$, $NHR^{11}$, $N(R^{11})_2$, $NH_2$, $C(O)OH$, OH, CN, $NO_2$, F, Cl, Br and I; wherein each $R^8$ $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{12}$, $OR^{12}$, $C(O)OR^{12}$, $NHR^{12}$, $N(R^{12})_2$, $NH_2$, $C(O)OH$, OH, oxo, CN, $NO_2$, F, Cl, Br and I. In another embodiment of Formula (III), $R^8$, at each occurrence, is independently selected from the group consisting of $C_1$-$C_6$ alkyl, $C_6$-$C_{10}$ membered aryl, and $C_3$-$C_{11}$ cycloalkyl; wherein each $R^8$ $C_1$-$C_6$ alkyl is optionally substituted with one or more F. In another embodiment of Formula (III), $R^8$, at each occurrence, is independently $CH_3$. In another embodiment of Formula (III), $R^8$, at each occurrence, is independently $CF_3$. In another embodiment of Formula (III), $R^8$, at each occurrence, is independently phenyl. In another embodiment of Formula (III), $R^8$, at each occurrence, is independently cyclopropyl. In another embodiment of Formula (III), $R^8$, at each occurrence, is independently cyclobutyl. In another embodiment of Formula (III), $R^8$, at each occurrence, is independently cyclopentyl.

Another embodiment pertains to compounds of Formula (III), or a pharmaceutically acceptable salt thereof,

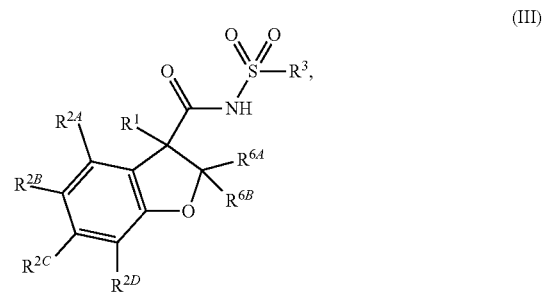

(III)

wherein
$R^1$ is selected from the group consisting of hydrogen, $C_1$-$C_6$ alkyl, and 6-10 membered aryl;
one of $R^{2A}$, $R^{2B}$, $R^{2C}$, and $R^{2D}$ is hydrogen, and the remaining are independently selected from the group consisting of hydrogen, $R^8$, $OR^8$, $C(O)R^8$, CN, Cl, and Br; or
two of $R^{2A}$, $R^{2B}$, $R^{2C}$, and $R^{2D}$ on adjacent carbons form a 4-7 membered heterocyclyl; and the remaining are independently hydrogen; wherein the 4-7 membered heterocyclyl is optionally substituted with one or more F;
$R^3$ is selected from the group consisting of $C_1$-$C_6$ alkyl, 6-10 membered aryl, 5-11 membered heteroaryl, and 4-12 membered heterocyclyl; wherein the $R^3$ 6-10 membered aryl, 5-11 membered heteroaryl, and 4-12 membered heterocyclyl are optionally substituted with one or more $R^9$;
$R^{6A}$ and $R^{6B}$ are each independently hydrogen;
$R^8$, at each occurrence, is independently selected from the group consisting of $C_1$-$C_6$ alkyl, $C_6$-$C_{10}$ membered aryl, and $C_3$-$C_{11}$ cycloalkyl; wherein each $R^8$ $C_1$-$C_6$ alkyl is optionally substituted with one or more F; and
$R^9$, at each occurrence, is independently $C_1$-$C_6$ alkyl; wherein each $R^9$ $C_1$-$C_6$ alkyl is optionally substituted with one or more F;
with the proviso that $R^3$ is not $C_1$-alkyl or thienyl;
with the proviso that, when $R^{2A}$, $R^{2B}$, $R^{2C}$, and $R^{2D}$ are each hydrogen, $R^1$ is not hydrogen;
with the proviso that, when $R^3$ is imidazolyl, $R^9$ is not $CH_2CH(CH_3)_2$;
with the proviso that, when $R^{2B}$ is Cl, $R^3$ is not 2,4-dimethyl-5-thiazolyl; and
with the proviso that, when $R^3$ is 3-pyridinyl, $R^{2C}$ is not Cl.

Exemplary compounds of Formula (III) include, but are not limited to:
N-(naphthalene-1-sulfonyl)-3-phenyl-2,3-dihydro-1-benzofuran-3-carboxamide;
3-ethyl-4-methoxy-N-(naphthalene-1-sulfonyl)-2,3-dihydro-1-benzofuran-3-carboxamide;
3-ethyl-7-methoxy-N-(naphthalene-1-sulfonyl)-2,3-dihydro-1-benzofuran-3-carboxamide;

4-methoxy-N-(naphthalene-1-sulfonyl)-2,3-dihydro-1-benzofuran-3-carboxamide;
7-bromo-N-(naphthalene-1-sulfonyl)-2,3-dihydro-1-benzofuran-3-carboxamide;
7-bromo-3-ethyl-N-(naphthalene-1-sulfonyl)-2,3-dihydro-1-benzofuran-3-carboxamide;
3-ethyl-N-(naphthalene-1-sulfonyl)-2,3-dihydro-1-benzofuran-3-carboxamide;
7-methoxy-N-(naphthalene-1-sulfonyl)-2,3-dihydro-1-benzofuran-3-carboxamide;
5-chloro-N-(2-methylbenzene-1-sulfonyl)-2,3-dihydro-1-benzofuran-3-carboxamide;
5-chloro-N-(propane-1-sulfonyl)-2,3-dihydro-1-benzofuran-3-carboxamide;
(7S)-2,2-difluoro-7-methyl-N-(naphthalene-1-sulfonyl)-6,7-dihydro-2H-furo[2,3-f][1,3]benzodioxole-7-carboxamide;
(7R)-2,2-difluoro-7-methyl-N-(naphthalene-1-sulfonyl)-6,7-dihydro-2H-furo[2,3-f][1,3]benzodioxole-7-carboxamide;
4-bromo-7-methoxy-N-(naphthalene-1-sulfonyl)-2,3-dihydro-1-benzofuran-3-carboxamide;
7-bromo-4-methoxy-N-(naphthalene-1-sulfonyl)-2,3-dihydro-1-benzofuran-3-carboxamide;
4-methoxy-N-(naphthalene-1-sulfonyl)-5-(trifluoromethyl)-2,3-dihydro-1-benzofuran-3-carboxamide and 4-methoxy-N-(naphthalene-1-sulfonyl)-7-(trifluoromethyl)-2,3-dihydro-1-benzofuran-3-carboxamide;
7-chloro-N-(naphthalene-1-sulfonyl)-2,3-dihydro-1-benzofuran-3-carboxamide;
7-chloro-3-ethyl-N-(naphthalene-1-sulfonyl)-2,3-dihydro-1-benzofuran-3-carboxamide;
N-(naphthalene-1-sulfonyl)-7-(trifluoromethyl)-2,3-dihydro-1-benzofuran-3-carboxamide;
3-ethyl-N-(naphthalene-1-sulfonyl)-7-(trifluoromethyl)-2,3-dihydro-1-benzofuran-3-carboxamide;
4,7-dimethoxy-N-(naphthalene-1-sulfonyl)-2,3-dihydro-1-benzofuran-3-carboxamide;
7-chloro-4-methoxy-N-(naphthalene-1-sulfonyl)-2,3-dihydro-1-benzofuran-3-carboxamide;
(3S)-7-cyclobutyl-4-methoxy-N-(naphthalene-1-sulfonyl)-2,3-dihydro-1-benzofuran-3-carboxamide;
(3R)-7-cyclobutyl-4-methoxy-N-(naphthalene-1-sulfonyl)-2,3-dihydro-1-benzofuran-3-carboxamide;
(3R)-7-chloro-4-methoxy-N-(naphthalene-1-sulfonyl)-2,3-dihydro-1-benzofuran-3-carboxamide;
(3S)-7-chloro-4-methoxy-N-(naphthalene-1-sulfonyl)-2,3-dihydro-1-benzofuran-3-carboxamide;
(3R)-7-bromo-4-methoxy-N-(1-naphthylsulfonyl)-2,3-dihydrobenzofuran-3-carboxamide;
(3S)-7-bromo-4-methoxy-N-(1-naphthylsulfonyl)-2,3-dihydrobenzofuran-3-carboxamide;
7-cyclobutyl-4-methoxy-N-(quinoline-5-sulfonyl)-2,3-dihydro-1-benzofuran-3-carboxamide;
(3R)-7-cyclobutyl-4-methoxy-N-(quinoline-5-sulfonyl)-2,3-dihydro-1-benzofuran-3-carboxamide;
(3S)-7-cyclobutyl-4-methoxy-N-(quinoline-5-sulfonyl)-2,3-dihydro-1-benzofuran-3-carboxamide;
7-cyclobutyl-4-methoxy-N-(1-methyl-1H-benzimidazole-7-sulfonyl)-2,3-dihydro-1-benzofuran-3-carboxamide;
7-cyclobutyl-4-methoxy-N-(pyrazolo[1,5-a]pyridine-4-sulfonyl)-2,3-dihydro-1-benzofuran-3-carboxamide;
7-cyclobutyl-4-methoxy-N-(1,2,3,4-tetrahydroquinoline-5-sulfonyl)-2,3-dihydro-1-benzofuran-3-carboxamide;
7-cyclobutyl-4-methoxy-N-(1,2,3,4-tetrahydroquinoline-8-sulfonyl)-2,3-dihydro-1-benzofuran-3-carboxamide;
(3R)-7-cyclobutyl-4-methoxy-N-(1-methyl-1H-indazole-7-sulfonyl)-2,3-dihydro-1-benzofuran-3-carboxamide;
(3S)-7-cyclobutyl-4-methoxy-N-(1-methyl-1H-indazole-7-sulfonyl)-2,3-dihydro-1-benzofuran-3-carboxamide;
(3R)-7-cyclobutyl-4-methoxy-N-(1,2,3,4-tetrahydroquinoline-8-sulfonyl)-2,3-dihydro-1-benzofuran-3-carboxamide;
(3S)-7-cyclobutyl-4-methoxy-N-(1,2,3,4-tetrahydroquinoline-8-sulfonyl)-2,3-dihydro-1-benzofuran-3-carboxamide;
(3R)-7-cyclobutyl-4-methoxy-N-(1,2,3,4-tetrahydroquinoline-5-sulfonyl)-2,3-dihydro-1-benzofuran-3-carboxamide;
(3S)-7-cyclobutyl-4-methoxy-N-(1,2,3,4-tetrahydroquinoline-5-sulfonyl)-2,3-dihydro-1-benzofuran-3-carboxamide; and pharmaceutically acceptable salts thereof.

Compounds of the invention were named using Name 2016.1.1 (File Version N30E41, Build 86668, 25 May, 2016) naming algorithm by Advanced Chemical Development, Inc., or Struct=Name naming algorithm as part of CHEMDRAW® ULTRA v. 12.0.2.1076 or Professional Version 15.0.0.106.

Compounds of the invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds of the invention may exist as cis or trans isomers, wherein substituents on a ring may attached in such a manner that they are on the same side of the ring (cis) relative to each other, or on opposite sides of the ring relative to each other (trans). For example, cyclobutane may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well-known to those of ordinary skill in the art, and may include separation of isomers by recrystallization or chromatography.

It should be understood that the compounds of the invention may possess tautomeric forms, as well as geometric isomers, and that these also constitute an aspect of the invention.

The present disclosure includes all pharmaceutically acceptable isotopically-labelled compounds of Formula (I) wherein one or more atoms are replaced by atoms having the same atomic number, but an atomic mass or mass number different from the atomic mass or mass number which predominates in nature. Examples of isotopes suitable for inclusion in the compounds of the disclosure include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S. Certain isotopically-labelled compounds of Formula (I) for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of Formula (I) may generally be prepared by conventional techniques known to those skilled in the art or by processes analogous to those described in the accompanying Examples using an appropriate isotopically-labeled reagents in place of the non-labeled reagent previously employed.

Thus, the formula drawings within this specification can represent only one of the possible tautomeric, geometric, or stereoisomeric forms. It is to be understood that the invention encompasses any tautomeric, geometric, or stereoisomeric form, and mixtures thereof, and is not to be limited merely to any one tautomeric, geometric, or stereoisomeric form utilized within the formula drawings.

Compounds of Formula (I) may be used in the form of pharmaceutically acceptable salts. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts have been described in S. M. Berge et al. J. Pharmaceutical Sciences, 1977, 66: 1-19.

Compounds of Formula (I) may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid, and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, refers to derivatives of the compounds of the invention which have cleavable groups. Such derivatives become, by solvolysis or under physiological conditions, the compounds of the invention which are pharmaceutically active in vivo. Prodrugs of the compounds of the invention are, within the scope of sound medical judgement, suitable for use in contact with the tissues of humans and lower animals without undue toxicity, irritation, allergic response, and the like, commensurate with a reasonable benefit/risk ratio, and effective for their intended use.

The invention contemplates compounds of Formula (I) formed by synthetic means or formed by in vivo biotransformation of a prodrug.

Compounds described herein may exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

Pharmaceutical Compositions

When employed as a pharmaceutical, a compound of the invention is typically administered in the form of a pharmaceutical composition. Such compositions can be prepared in a manner well known in the pharmaceutical art and comprise a therapeutically effective amount of a compound of Formula (I), or a pharmaceutically acceptable salt thereof together with a pharmaceutically acceptable carrier. The phrase "pharmaceutical composition" refers to a composition suitable for administration in medical or veterinary use.

The term "pharmaceutically acceptable carrier" as used herein, means a non-toxic, inert solid, semi-solid or liquid filler, diluent, encapsulating material or formulation auxiliary of any type.

Methods of Use

The compounds and compositions using any amount and any route of administration may be administered to a subject for the treatment or prevention of cystic fibrosis, pancreatic insufficiency, Sjögren's syndrome (SS), chronic obstructive lung disease (COLD), or chronic obstructive airway disease (COAD).

The term "administering" refers to the method of contacting a compound with a subject. Thus, the compounds may be administered by injection, that is, intravenously, intramuscularly, intracutaneously, subcutaneously, intraduodenally, parentally, or intraperitoneally. Also, the compounds described herein may be administered by inhalation, for example, intranasally. Additionally, the compounds may be administered transdermally, topically, and via implantation. In certain embodiments, the compounds and compositions thereof may be delivered orally. The compounds may also be delivered rectally, bucally, intravaginally, ocularly, or by insufflation. CFTR-modulated disorders and conditions may be treated prophylactically, acutely, and chronically using compounds and compositions thereof, depending on the nature of the disorder or condition. Typically, the host or subject in each of these methods is human, although other mammals may also benefit from the administration of compounds and compositions thereof as set forth hereinabove.

Compounds of the invention are useful as modulators of CFTR. Thus, the compounds and compositions are particularly useful for treating or lessening the severity or progression of a disease, disorder, or a condition where hyperactivity or inactivity of CFTR is involved. Accordingly, the invention provides a method for treating cystic fibrosis, pancreatic insufficiency, Sjögren's syndrome (SS), chronic obstructive lung disease (COLD), or chronic obstructive airway disease (COAD) in a subject, wherein the method comprises the step of administering to said subject a therapeutically effective amount of a compound of Formula (I), or a pharmaceutically acceptable salt thereof, or a preferred embodiment thereof as set forth above, with or without a pharmaceutically acceptable carrier. Particularly, the method is for the treatment or prevention of cystic fibrosis. In a more particular embodiment, the cystic fibrosis is caused by a Class I, II, III, IV, V, and/or VI mutation.

In a particular embodiment, the present invention provides compounds of the invention, or a pharmaceutically acceptable salt thereof, or a pharmaceutical composition comprising a compound of the invention, for use in medicine. In a particular embodiment, the present invention provides compounds of the invention, or a pharmaceutically acceptable salt thereof, or pharmaceutical compositions comprising a compound of the invention, for use in the treatment of cystic fibrosis, pancreatic insufficiency, Sjögren's syndrome (SS), chronic obstructive lung disease (COLD) or chronic obstructive airway disease (COAD). In a more particular embodiment, the present invention provides compounds of the invention or pharmaceutical compositions comprising a compound of the invention, for use in the treatment of cystic fibrosis. In a more particular embodiment, the cystic fibrosis is caused by a Class I, II, III, IV, V, and/or VI mutation.

One embodiment is directed to the use of a compound according to Formula (I) or a pharmaceutically acceptable salt thereof in the preparation of a medicament. The medicament optionally can comprise one or more additional therapeutic agents. In some embodiments, the medicament is for use in the treatment of cystic fibrosis, pancreatic insufficiency, Sjögren's syndrome (SS), chronic obstructive lung disease (COLD) or chronic obstructive airway disease (COAD). In a particular embodiment, the medicament is for use in the treatment of cystic fibrosis. In a more particular embodiment, the cystic fibrosis is caused by a Class I, II, III, IV, V, and/or VI mutation.

This invention also is directed to the use of a compound according to Formula (I) or a pharmaceutically acceptable salt thereof in the manufacture of a medicament for the treatment of cystic fibrosis, Sjögren's syndrome, pancreatic insufficiency, chronic obstructive lung disease, and chronic obstructive airway disease. The medicament optionally can comprise one or more additional therapeutic agents. In a particular embodiment, the invention is directed to the use of a compound according to Formula (I) or a pharmaceutically acceptable salt thereof in the manufacture of a medicament for the treatment of cystic fibrosis. In a more particular embodiment, the cystic fibrosis is caused by a Class I, II, III, IV, V, and/or VI mutation.

In one embodiment, the present invention provides pharmaceutical compositions comprising a compound of the invention, or a pharmaceutically acceptable salt thereof, and one or more additional therapeutic agents. In another embodiment, the present invention provides pharmaceutical compositions comprising a compound of the invention, or a pharmaceutically acceptable salt thereof, and one or more additional therapeutic agents wherein the additional therapeutic agents are selected from the group consisting of CFTR modulators and CFTR amplifiers. In another embodiment, the present invention provides pharmaceutical compositions comprising a compound of the invention, or a pharmaceutically acceptable salt thereof, and one or more additional therapeutic agents wherein the additional therapeutic agents are CFTR modulators.

In one embodiment, the present invention provides pharmaceutical compositions comprising a compound of the invention, or a pharmaceutically acceptable salt thereof, and one or more additional therapeutic agents. In one embodiment, the present invention provides pharmaceutical compositions comprising a compound of the invention, or a pharmaceutically acceptable salt thereof, one potentiator, and one or more additional correctors. In one embodiment, the present invention provides pharmaceutical compositions comprising a compound of the invention, and another therapeutic agent. In a particular embodiment, the other therapeutic agent is a cystic fibrosis treatment agent. In one embodiment, the present invention provides a method for treating cystic fibrosis in a subject comprising administering a compound of the invention, or a pharmaceutically acceptable salt thereof, and one or more additional therapeutic agents. In another embodiment, the present invention provides a method for treating cystic fibrosis in a subject comprising administering a compound of the invention, or a pharmaceutically acceptable salt thereof, and one or more additional therapeutic agents wherein the additional therapeutic agents are selected from the group consisting of CFTR modulators and CFTR amplifiers. In one embodiment, the present invention provides a method for treating cystic fibrosis in a subject comprising administering a compound of the invention, or a pharmaceutically acceptable salt thereof, and one or more additional therapeutic agents wherein the additional therapeutic agents are CFTR modulators. In one embodiment, the present invention provides a method for treating cystic fibrosis in a subject comprising administering a compound of the invention, or a pharmaceutically acceptable salt thereof, and, and another therapeutic agent. In a particular embodiment, the other therapeutic agent is a cystic fibrosis treatment agent. In one embodiment, the present invention provides a method for treating cystic fibrosis in a subject comprising administering a therapeutically effective amount of a compound of the invention, or a pharmaceutically acceptable salt thereof. In a particular embodiment, the additional therapeutic agent(s) are one potentiator, and one or more additional correctors. In another embodiment, the additional therapeutic agent(s) is selected from the group consisting of CFTR modulators and CFTR amplifiers. In another embodiment, the other therapeutic agent(s) is a CFTR modulator. In a more particular embodiment, the cystic fibrosis is caused by a Class I, II, III, IV, V, and/or VI mutation.

The present compounds or pharmaceutically acceptable salts thereof may be administered as the sole active agent or it may be co-administered with other therapeutic agents, including other compounds or pharmaceutically acceptable salts thereof, that demonstrate the same or a similar therapeutic activity and that are determined to be safe and efficacious for such combined administration. The present compounds may be co-administered to a subject. The term "co-administered" means the administration of two or more different therapeutic agents to a subject in a single pharmaceutical composition or in separate pharmaceutical compositions. Thus co-administration involves administration at the same time of a single pharmaceutical composition comprising two or more therapeutic agents or administration of two or more different compositions to the same subject at the same or different times.

The compounds of the invention or pharmaceutically acceptable salts thereof may be co-administered with a therapeutically effective amount of one or more additional therapeutic agents to treat a CFTR mediated disease, where examples of the therapeutic agents include, but are not limited to antibiotics (for example, aminoglycosides, colistin, aztreonam, ciprofloxacin, and azithromycin), expectorants (for example, hypertonic saline, acetylcysteine, dornase alfa, and denufosol), pancreatic enzyme supplements (for example, pancreatin, and pancrelipase), epithelial sodium channel blocker (ENaC) inhibitors, CFTR modulators (for example, CFTR potentiators, CFTR correctors), and CFTR amplifiers. In one embodiment, the CFTR mediated disease is cystic fibrosis, chronic obstructive pulmonary disease (COPD), dry eye disease, pancreatic insufficiency, or Sjögren's syndrome. In one embodiment, the CFTR mediated disease is cystic fibrosis.

In one embodiment, the compounds of the invention or pharmaceutically acceptable salts thereof may be co-administered with one or two CFTR modulators and one CFTR amplifier. In one embodiment, the compounds of the invention or pharmaceutically acceptable salts thereof may be co-administered with one potentiator, one or more correctors, and one CFTR amplifier. In one embodiment, the compounds of the invention or pharmaceutically acceptable salts thereof may be co-administered with one or more CFTR modulators. In one embodiment, the compounds of the invention or pharmaceutically acceptable salts thereof may be co-administered with one CFTR modulators. In one embodiment, the compounds of the invention or pharmaceutically acceptable salts thereof may be co-administered with two CFTR modulators. In one embodiment, the compounds of the invention or pharmaceutically acceptable salts thereof may be co-administered with three CFTR modulators. In embodiment, the compounds of the invention or pharmaceutically acceptable salts thereof may be co-administered with one potentiator and one or more correctors. In one embodiment, the compounds of the invention or pharmaceutically acceptable salts thereof may be co-administered with one potentiator and two correctors. In one embodiment, the compounds of the invention or pharmaceutically acceptable salts thereof may be co-administered with one potentiator. In one embodiment, the compounds of the invention or pharmaceutically acceptable salts thereof may be co-administered with one or more correctors. In one embodiment, the compounds of the invention or pharmaceutically acceptable salts thereof may be co-administered with one corrector. In one embodiment, the compounds of the invention or pharmaceutically acceptable salts thereof may be co-administered with two correctors.

Examples of CFTR potentiators include, but are not limited to, Ivacaftor (VX-770), CTP-656, NVS-QBW251, FD1860293, GLPG2451, GLPG3067, GLPG1837, PTI-808, N-(3-carbamoyl-5,5,7,7-tetramethyl-5,7-dihydro-4H-thieno[2,3-c]pyran-2-yl)-1H-pyrazole-5-carboxamide, and 3-amino-N-[(2S)-2-hydroxypropyl]-5-{[4-(trifluoromethoxy)phenyl]sulfonyl}pyridine-2-carboxamide. Examples of potentiators are also disclosed in publications: WO2005120497, WO2008147952, WO2009076593, WO2010048573, WO2006002421, WO2008147952, WO2011072241, WO2011113894, WO2013038373, WO2013038378, WO2013038381, WO2013038386, WO2013038390, WO2014180562, WO2015018823, WO2014/180562, WO2015018823, WO 2016193812 and WO2017208115.

In one embodiment, the potentiator can be selected from the group consisting of
Ivacaftor (VX-770, N-(2,4-di-tert-butyl-5-hydroxyphenyl)-4-oxo-1,4-dihydroquinoline-3-carboxamide);
GLPG1837;
GLP-2451;
PTI-808;
CTP-656;
NVS-QBW251;
FD1860293
GLPG3067;
2-(2-fluorobenzamido)-5,5,7,7-tetramethyl-5,7-dihydro-4H-thieno[2,3-c]pyran-3-carboxamide;
N-(3-carbamoyl-5,5,7,7-tetramethyl-4,7-dihydro-5H-thieno[2,3-c]pyran-2-yl)-1H-pyrazole-5-carboxamide;
2-(2-hydroxybenzamido)-5,5,7,7-tetramethyl-5,7-dihydro-4H-thieno[2,3-c]pyran-3-carboxamide
2-(1-hydroxycyclopropanecarboxamido)-5,5,7,7-tetramethyl-5,7-dihydro-4H-thieno[2,3-c]pyran-3-carboxamide;
5,5,7,7-tetramethyl-2-(2-(trifluoromethyl)benzamido)-5,7-dihydro-4H-thieno[2,3-c]pyran-3-carboxamide;
2-(2-hydroxy-2-methylpropanamido)-5,5,7,7-tetramethyl-5,7-dihydro-4H-thieno[2,3-c]pyran-3-carboxamide;
2-(1-(hydroxymethyl)cyclopropanecarboxamido)-5,5,7,7-tetramethyl-5,7-dihydro-4H-thieno[2,3-c]pyran-3-carboxamide;
2-(3-hydroxy-2,2-dimethylpropanamido)-5,5,7,7-tetramethyl-5,7-dihydro-4H-thieno[2,3-c]pyran-3-carboxamide;
N-(3-carbamoyl-5,5,7,7-tetramethyl-5,7-dihydro-4H-thieno[2,3-c]pyran-2-yl)-5-methyl-1H-pyrazole-3-carboxamide;
N-(3-carbamoyl-5,5,7,7-tetramethyl-5,7-dihydro-4H-thieno[2,3-c]pyran-2-yl)-5-cyclopropyl-1H-pyrazole-3-carboxamide;
N-(3-carbamoyl-5,5,7,7-tetramethyl-5,7-dihydro-4H-thieno[2,3-c]pyran-2-yl)-5-isopropyl-1H-pyrazole-3-carboxamide;

N-(3-carbamoyl-5,5,7,7-tetramethyl-5,7-dihydro-4H-thieno[2,3-c]pyran-2-yl)-5-(trifluoromethyl)-1H-pyrazole-3-carboxamide;

5-tert-butyl-N-(3-carbamoyl-5,5,7,7-tetramethyl-5,7-dihydro-4H-thieno[2,3-c]pyran-2-yl)-1H-pyrazole-3-carboxamide;

N-(3-carbamoyl-5,5,7,7-tetramethyl-5,7-dihydro-4H-thieno[2,3-c]pyran-2-yl)-5-ethyl-1H-pyrazole-3-carboxamide;

N-(3-carbamoyl-5,5,7,7-tetramethyl-5,7-dihydro-4H-thieno[2,3-c]pyran-2-yl)-3-ethyl-4-methyl-1H-pyrazole-5-carboxamide;

2-(2-hydroxypropanamido)-5,5,7,7-tetramethyl-5,7-dihydro-4H-thieno[2,3-c]pyran-3-carboxamide;

N-(3-carbamoyl-5,5,7,7-tetramethyl-5,7-dihydro-4H-thieno[2,3-c]pyran-2-yl)-4-chloro-1H-pyrazole-3-carboxamide;

N-(3-carbamoyl-5,5,7,7-tetramethyl-5,7-dihydro-4H-thieno[2,3-c]pyran-2-yl)-1,4,6,7-tetrahydropyrano[4,3-c]pyrazole-3-carboxamide;

4-bromo-N-(3-carbamoyl-5,5,7,7-tetramethyl-5,7-dihydro-4H-thieno[2,3-c]pyran-2-yl)-1H-pyrazole-3-carboxamide;

N-(3-carbamoyl-5,5,7,7-tetramethyl-5,7-dihydro-4H-thieno[2,3-c]pyran-2-yl)-4-chloro-5-methyl-1H-pyrazole-3-carboxamide;

N-(3-carbamoyl-5,5,7,7-tetramethyl-5,7-dihydro-4H-thieno[2,3-c]pyran-2-yl)-4-methyl-1H-pyrazole-3-carboxamide;

2-(2-hydroxy-3,3-dimethylbutanamido)-5,5,7,7-tetramethyl-5,7-dihydro-4H-thieno[2,3-c]pyran-3-carboxamide;

2-[(2-hydroxy-4-methyl-pentanoyl)amino]-5,5,7,7-tetramethyl-4H-thieno[2,3-c]pyran-3-carboxamide;

5-(2-methoxy-ethoxy)-1H-pyrazole-3-carboxylic acid (3-carbamoyl-5,5,7,7-tetramethyl-4,7-dihydro-5H-thieno[2,3-c]pyran-2-yl)-amide;

N-(3-carbamoyl-5,5,7,7-tetramethyl-4H-thieno[2,3-c]pyran-2-yl)-4-(3-methoxypropyl)-1H-pyrazole-3-carboxamide;

N-(3-carbamoyl-5,5,7,7-tetramethyl-4H-thieno[2,3-c]pyran-2-yl)-4-(2-ethoxyethyl)-1H-pyrazole-3-carboxamide;

2-[[(2S)-2-hydroxy-3,3-dimethyl-butanoyl]amino]-5,5,7,7-tetramethyl-4H-thieno[2,3-c]pyran-3-carboxamide;

2-[[(2R)-2-hydroxy-3,3-dimethyl-butanoyl]amino]-5,5,7,7-tetramethyl-4H-thieno[2,3-c]pyran-3-carboxamide;

2-[(2-hydroxy-2,3,3-trimethyl-butanoyl)amino]-5,5,7,7-tetramethyl-4H-thieno[2,3-c]pyran-3-carboxamide;

[5-[(3-carbamoyl-5,5,7,7-tetramethyl-4H-thieno[2,3-c]pyran-2-yl)carbamoyl]pyrazol-1-yl]methyl dihydrogen phosphate;

[3-[(3-carbamoyl-5,5,7,7-tetramethyl-4H-thieno[2,3-c]pyran-2-yl)carbamoyl]pyrazol-1-yl]methyl dihydrogen phosphate;

N-(3-carbamoyl-5,5,7,7-tetramethyl-4H-thieno[2,3-c]pyran-2-yl)-4-(1,4-dioxan-2-yl)-1H-pyrazole-3-carboxamide;

5,5,7,7-tetramethyl-2-[[(2S)-3,3,3-trifluoro-2-hydroxy-2-methyl-propanoyl]amino]-4H-thieno[2,3-c]pyran-3-carboxamide;

2-[[(2S)-2-hydroxypropanoyl]amino]-5,5,7,7-tetramethyl-4H-thieno[2,3-c]pyran-3-carboxamide;

3-amino-N-(2-hydroxy-2-methylpropyl)-5-{[4-(trifluoromethoxy)phenyl]sulfonyl}pyridine-2-carboxamide;

3-amino-N-[(4-hydroxy-1-methylpiperidin-4-yl)methyl]-5-{[4-(trifluoromethoxy)phenyl]sulfonyl}pyridine-2-carboxamide;

3-amino-N-(3-hydroxy-2,2-dimethylpropyl)-5-{[4-(trifluoromethoxy)phenyl]sulfonyl}pyridine-2-carboxamide;

3-amino-5-[(4-fluorophenyl)sulfonyl]-N-[(1-hydroxycyclopropyl)methyl]pyridine-2-carboxamide;

3-amino-5-[(4-fluorophenyl)sulfonyl]-N-[(2R)-3,3,3-trifluoro-2-hydroxypropyl]pyridine-2-carboxamide;

3-amino-5-[(3-fluorophenyl)sulfonyl]-N-(2-hydroxy-2-methylpropyl)pyridine-2-carboxamide;

3-amino-N-[2-(cyclopropylamino)-2-oxoethyl]-5-{[4-(trifluoromethoxy)phenyl]sulfonyl}pyridine-2-carboxamide;

(3-amino-5-{[4-(trifluoromethoxy)phenyl]sulfonyl}pyridin-2-yl)(azetidin-1-yl)methanone;

(3-amino-5-{[4-(trifluoromethoxy)phenyl]sulfonyl}pyridin-2-yl)[3-(hydroxymethyl)azetidin-1-yl]methanone;

(3-amino-5-{[4-(trifluoromethoxy)phenyl]sulfonyl}pyridin-2-yl)(3-fluoroazetidin-1-yl)methanone;

3-amino-N-[(2R)-2-hydroxy-3-methoxypropyl]-5-{[4-(trifluoromethyl)phenyl]sulfonyl}pyridine-2-carboxamide;

(3-amino-5-{[2-fluoro-4-(trifluoromethoxy)phenyl]sulfonyl}pyridin-2-yl)(3-hydroxyazetidin-1-yl)methanone;

(3-amino-5-{[2-(trifluoromethoxy)phenyl]sulfonyl}pyridin-2-yl)(3,3-difluoroazetidin-1-yl)methanone;

rac-3-amino-N-[(3R,4S)-4-hydroxytetrahydro-2H-pyran-3-yl]-5-{[2-(trifluoromethoxy)phenyl]sulfonyl}pyridine-2-carboxamide;

3-amino-5-[(4,4-difluoropiperidin-1-yl)sulfonyl]-N-(3,3,3-trifluoro-2-hydroxypropyl)pyridine-2-carboxamide;

(3-amino-5-{[2-(trifluoromethoxy)phenyl]sulfonyl}pyridin-2-yl)[3-hydroxy-3-(trifluoromethyl)azetidin-1-yl]methanone;

3-amino-N-(2-hydroxy-4-methylpentyl)-5-{[4-(trifluoromethoxy)phenyl]sulfonyl}pyridine-2-carboxamide;

(3-amino-5-{[4-(trifluoromethyl)phenyl]sulfonyl}pyridin-2-yl)(3-hydroxy-3-methylazetidin-1-yl)methanone;

3-amino-N-(3,3,3-trifluoro-2-hydroxypropyl)-5-{[4-(trifluoromethyl)piperidin-1-yl]sulfonyl}pyridine-2-carboxamide;

3-amino-N-[2-hydroxy-1-(4-methoxyphenyl)ethyl]-S-{[4-(trifluoromethoxy)phenyl]sulfonyl}pyridine-2-carboxamide;

3-amino-5-[(3,3-difluoroazetidin-1-yl)sulfonyl]-N-(3,3,3-trifluoro-2-hydroxypropyl)pyridine-2-carboxamide;

3-amino-5-{[2-fluoro-4-(trifluoromethyl)phenyl]sulfonyl}-N-[(2S)-2-hydroxypropyl]pyridine-2-carboxamide;

3-amino-5-{[2-fluoro-4-(trifluoromethyl)phenyl]sulfonyl}-N-[(2R)-2-hydroxy-3-methoxypropyl]pyridine-2-carboxamide;

3-amino-N-[2-oxo-2-(propan-2-ylamino)ethyl]-5-{[4-(trifluoromethyl)phenyl]sulfonyl}pyridine-2-carboxamide;

(3-amino-5-{[4-(trifluoromethyl)phenyl]sulfonyl}pyridin-2-yl)[3-hydroxy-3-(trifluoromethyl)azetidin-1-yl]methanone;

3-amino-5-{[2-fluoro-4-(trifluoromethyl)phenyl]sulfonyl}-N-[(3R)-tetrahydrofuran-3-ylmethyl]pyridine-2-carboxamide;

(3-amino-5-{[2-fluoro-4-(trifluoromethyl)phenyl]sulfonyl}pyridin-2-yl)[3-hydroxy-3-(trifluoromethyl)azetidin-1-yl]methanone;

3-amino-5-{[2-fluoro-4-(trifluoromethyl)phenyl]sulfonyl}-N-[(3S)-tetrahydrofuran-3-ylmethyl]pyridine-2-carboxamide;

3-amino-5-{[2-fluoro-4-(trifluoromethoxy)phenyl]sulfonyl}-N-[(3S)-tetrahydrofuran-3-ylmethyl]pyridine-2-carboxamide;

3-amino-N-[2-hydroxy-3-(2,2,2-trifluoroethoxy)propyl]-5-{[4-(trifluoromethyl)phenyl]sulfonyl}pyridine-2-carboxamide;
3-amino-N-(3-tert-butoxy-2-hydroxypropyl)-5-{[2-fluoro-4-(trifluoromethyl)phenyl]sulfonyl}pyridine-2-carboxamide;
[3-amino-5-(phenylsulfonyl)pyridin-2-yl][3-hydroxy-3-(trifluoromethyl)azetidin-1-yl]methanone;
{3-amino-5-[(3-fluorophenyl)sulfonyl]pyridin-2-yl}[3-hydroxy-3-(trifluoromethyl)azetidin-1-yl]methanone; and
3-amino-N-[(2S)-2-hydroxypropyl]-5-{[4-(trifluoromethoxy)phenyl]sulfonyl}pyridine-2-carboxamide.

Non-limiting examples of correctors include Lumacaftor (VX-809), 1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropanecarboxamide (VX-661), VX-983, GLPG2851, GLPG2222, GLPG2665, GLPG2737, GLPG3221, PTI-801, VX-152, VX-440, VX-445, VX-659, FDL169, FDL304, FD2052160, and FD2035659. Examples of correctors are also disclosed in WO2016069757, WO2016069891, WO2017009804, WO2017060874, WO2017060873, WO2017187321 and U.S. patent application Ser. Nos. 15/723,896, 15/726,075 and PCT Patent Application No. PCT/IB2017/058179.

In one embodiment, the corrector(s) can be selected from the group consisting of
Lumacaftor (VX-809);
1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropanecarboxamide (VX-661);
PTI-801;
VX-983;
GLPG2665;
GLPG2851;
GLPG2222;
GLPG2737;
GLPG3221;
VX-152;
VX-440;
VX-659;
VX-445;
FDL169
FDL304;
FD2052160;
FD2035659;
3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-6-methyl-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-6-methoxy-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]cyclohexanecarboxylic acid;
3-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-7-methoxy-3,4-dihydro-2H-chromen-2-yl]cyclohexanecarboxylic acid;
3-[(2R,4R)-4-({[1-(2,2-difluoro-1,3-benzodioxol-5-yl)cyclopropyl]carbonyl}amino)-7-fluoro-3,4-dihydro-2H-chromen-2-yl]benzoic acid;
3-({3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoyl}amino)-1-methylcyclopentanecarboxylic acid;
3-[(2R,4R)-4-({[1-(2,2-difluoro-1,3-benzodioxol-5-yl)cyclopropyl]carbonyl}amino)-7-methyl-3,4-dihydro-2H-chromen-2-yl]-N-[(2R)-2,3-dihydroxypropyl]benzamide;
3-[(2R,4R)-4-({[1-(2,2-difluoro-1,3-benzodioxol-5-yl)cyclopropyl]carbonyl}amino)-7-(2-methoxyethoxy)-3,4-dihydro-2H-chromen-2-yl]benzoic acid;
3-[(2R,4R)-7-(benzyloxy)-4-({[1-(2,2-difluoro-1,3-benzodioxol-5-yl)cyclopropyl]carbonyl}amino)-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-7-(2-fluoroethoxy)-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]cyclohexanecarboxylic acid;
4-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-8-fluoro-3,4-dihydro-2H-chromen-2-yl]benzoic acid;
4-[(2R,4R)-4-({[1-(2,2-difluoro-1,3-benzodioxol-5-yl)cyclopropyl]carbonyl}amino)-3,4-dihydro-2H-chromen-2-yl]benzoic acid;
4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid;
rac-3-[(2R,4S)-4-({[1-(2,2-difluoro-1,3-benzodioxol-5-yl)cyclopropyl]carbonyl}amino)tetrahydro-2H-pyran-2-yl]benzoic acid;
rac-4-[(2R,4S)-4-({[1-(2,2-difluoro-1,3-benzodioxol-5-yl)cyclopropyl]carbonyl}amino)tetrahydro-2H-pyran-2-yl]benzoic acid;
3-[(2S,4R)-4-({[1-(2,2-difluoro-1,3-benzodioxol-5-yl)cyclopropyl]carbonyl}amino)tetrahydro-2H-pyran-2-yl]benzoic acid;
3-[(2R,4S)-4-({[1-(2,2-difluoro-1,3-benzodioxol-5-yl)cyclopropyl]carbonyl}amino)tetrahydro-2H-pyran-2-yl]benzoic acid;
rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid;
3-[(2S,4R,6R)-4-({[1-(2,2-difluoro-1,3-benzodioxol-5-yl)cyclopropyl]carbonyl}amino)-6-phenyltetrahydro-2H-pyran-2-yl]benzoic acid;
3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid;
4-[(2R,4S)-4-({[1-(2,2-difluoro-1,3-benzodioxol-5-yl)cyclopropyl]carbonyl}amino)tetrahydro-2H-pyran-2-yl]
3-cyclobutyl-4-[4-(morpholin-4-yl)piperidin-1-yl]-1-phenyl-1H-pyrazolo[3,4-b]pyridine-6-carboxylic acid;

3-cyclobutyl-1-phenyl-4-{4-[(pyrrolidin-1-yl)methyl]piperidin-1-yl}-1H-pyrazolo[3,4-b]pyridine-6-carboxylic acid;

5-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyrazine-2-carboxylic acid;

6-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]pyridine-3-carboxylic acid;

trans-4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid;

6-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]pyridine-3-carboxylic acid;

trans-4-[(2S,4S)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid;

ethyl trans-4-[(2S,4S)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylate;

cis-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid;

trans-4-[(2S,4S)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylic acid;

1-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclopropane-1-carboxylic acid;

trans-4-[(2R,4R)-4-{[(5S)-2,2-difluoro-5-methyl-6,7-dihydro-2H,5H-indeno[5,6-d][1,3]dioxole-5-carbonyl]amino}-7-(trifluoromethoxy)-3,4-dihydro-2H-1-benzopyran-2-yl]cyclohexane-1-carboxylic acid;

trans-4-[(2R,4R)-4-{[(5S)-2,2-difluoro-5-methyl-6,7-dihydro-2H,5H-indeno[5,6-d][1,3]dioxole-5-carbonyl]amino}-7-methoxy-3,4-dihydro-2H-1-benzopyran-2-yl]cyclohexane-1-carboxylic acid;

trans-4-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid;

trans-4-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylic acid; and trans-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid.

In one embodiment, the additional therapeutic agent is a CFTR amplifier. CFTR amplifiers enhance the effect of known CFTR modulators, such as potentiators and correctors. Examples of CFTR amplifiers are PTI130 and PTI-428. Examples of amplifiers are also disclosed in International Patent Publication Nos.: WO2015138909 and WO2015138934.

In one embodiment, the additional therapeutic agent is a CFTR stabilizer. CFTR stabilizers enhance the stability of corrected CFTR that has been treated with a corrector, corrector/potentiator or other CFTR modulator combination(s). An example of a CFTR stabilizer is cavosonstat (N91115). Examples of stabilizers are also disclosed in International Patent Publication No.: WO2012048181.

In one embodiment, the additional therapeutic agent is an agent that reduces the activity of the epithelial sodium channel blocker (ENaC) either directly by blocking the channel or indirectly by modulation of proteases that lead to an increase in ENaC activity (e.g., serine proteases, channel-activating proteases). Exemplary of such agents include camostat (a trypsin-like protease inhibitor), QAU145, 552-02, GS-9411, INO-4995, Aerolytic, amiloride, and VX-371. Additional agents that reduce the activity of the epithelial sodium channel blocker (ENaC) can be found, for example, in International Patent Publication Nos. WO2009074575 and WO2013043720; and U.S. Pat. No. 8,999,976.

In one embodiment, the ENaC inhibitor is VX-371.

In one embodiment, the ENaC inhibitor is SPX-101 (S18).

In one embodiment, the present invention provides pharmaceutical compositions comprising a compound of the invention, or a pharmaceutically acceptable salt thereof, and one or more additional therapeutic agents. In a particular embodiment, the additional therapeutic agents are selected from the group consisting of CFTR modulators and CFTR amplifiers. In a further embodiment, the additional therapeutic agents are CFTR modulators. In one embodiment, the present invention provides pharmaceutical compositions comprising a compound of the invention, or a pharmaceutically acceptable salt thereof, one potentiator, and one or more additional correctors.

This invention also is directed to kits that comprise one or more compounds and/or salts of the invention, and, optionally, one or more additional therapeutic agents.

This invention also is directed to methods of use of the compounds, salts, compositions, and/or kits of the invention to, with or without one or more additional therapeutic agents, for example, modulate the Cystic Fibrosis Transmembrane Conductance Regulator (CFTR) protein, and treat a disease treatable by modulating the Cystic Fibrosis Transmembrane Conductance Regulator (CFTR) protein (including cystic fibrosis, Sjögren's syndrome, pancreatic insufficiency, chronic obstructive lung disease, and chronic obstructive airway disease).

Chemical Synthetic Procedures

General

The compounds of the invention can be prepared from readily available starting materials using the following general methods and procedures. It will be appreciated that where typical or preferred process conditions (i.e. reaction temperatures, times, mole ratios of reactants, solvents, pressures, etc.) were given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art (*Protective Groups in Organic Synthesis Third Edition*; Greene, T W and Wuts, P G M, Eds.; Wiley-Interscience: New York, 1991).

The following methods are presented with details as to the preparation of a compound of the invention as defined hereinabove and the comparative examples. A compound of the invention may be prepared from known or commercially available starting materials and reagents by one skilled in the art of organic synthesis.

All reagents were of commercial grade and were used as received without further purification, unless otherwise stated. Commercially available anhydrous solvents were used for reactions conducted under inert atmosphere. Reagent grade solvents were used in all other cases, unless otherwise specified. Column chromatography was performed on silica gel 60 (35-70 μm). Thin layer chromatography was carried out using pre-coated silica gel F-254 plates (thickness 0.25 mm). $^1$H NMR spectra were recorded on a Bruker Advance 300 NMR spectrometer (300 MHz), an Agilent 400 MHz NMR spectrometer or a 500 MHz spectrometer. Chemical shifts (δ) for $^1$H NMR spectra were reported in parts per million (ppm) relative to tetramethylsilane (δ 0.00) or the appropriate residual solvent peak, i.e. CHCl$_3$ (δ 7.27), as internal reference. Multiplicities were given as singlet (s), doublet (d), doublet of doublets (dd), doublet of doublets of doublets (ddd), doublet of doublets of doublets of doublets (dddd), doublet of doublets of quartets (ddq), doublet of doublets of triplets (ddt), doublet of quartets (dq), doublet of triplets of doublets (dtd), heptet (hept), triplet (t), triplet of doublets of doublets (tdd), triplet of quartets (tq), quartet (q), quartet of doublets (qd), quartet of triplets (qt), quintuplet (quin), multiplet (m) and broad (br). Electrospray MS spectra were obtained on a Waters platform LC/MS spectrometer or with Waters Acquity H-Class UPLC coupled to a Waters Mass detector 3100 spectrometer. Columns used: Waters Acquity UPLC BEH C18 1.7 μm, 2.1 mm ID×50 mm L, Waters Acquity UPLC BEH C18 1.7 μm, 2.1 mm ID×30 mm L, or Waters Xterra® MS 5 μm C18, 100×4.6 mm. The methods were using either MeCN/H$_2$O gradients (H$_2$O contains either 0.1% TFA or 0.1% NH$_3$) or CH$_3$OH/H$_2$O gradients (H$_2$O contains 0.05% TFA). Microwave heating was performed with a Biotage® Initiator.

Racemic mixtures were separated on an Agilent HP1100 system with UV detection. Column used: Chiralpak® IA (10×250 mm, 5 μm). Solvents used: iPrOH and tBME. Enantiomeric purity was determined on an Agilent HP1100 system with UV detection. Column used: Chiralpak® IA (4.6×250 mm, 5 μm). Solvents used: iPrOH and tBME.

Reverse Phase Purification Methods

Prep LC/MS Method TFA6

Samples were purified by reverse phase preparative HPLC on a Phenomenex® Luna® C8(2) 5 um 100 Å AXIA™ column (50 mm×21.2 mm). A gradient of acetonitrile (A) and 0.1% trifluoroacetic acid in water (B) was used, at a flow rate of 40 mL/minute (0-0.5 minute 15% A, 0.5-8.0 minute linear gradient 15-100% A, 8.0-9.0 minute 100% A, 7.0-8.9 minute 100% A, 9.0-9.1 minute linear gradient 100-15% A, 9.1-10 minute 15% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Prep LC/MS Method TFA7

Samples were purified by reverse phase preparative HPLC on a Phenomenex® Luna® C8(2) 5 um 100 Å AXIA™ column (50 mm×21.2 mm). A gradient of acetonitrile (A) and 0.1% trifluoroacetic acid in water (B) was used, at a flow rate of 40 mL/minute (0-0.5 minute 25% A, 0.5-8.0 minute linear gradient 25-100% A, 8.0-9.0 minute 100% A, 7.0-8.9 minute 100% A, 9.0-9.1 minute linear gradient 100-25% A, 9.1-10 minute 25% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Prep LC/MS Method TFA8

Samples were purified by reverse phase preparative HPLC on a Phenomenex® Luna® C8(2) 5 um 100 Å AXIA™ column (50 mm×21.2 mm). A gradient of acetonitrile (A) and 0.1% trifluoroacetic acid in water (B) was used, at a flow rate of 40 mL/minute (0-0.5 minute 35% A, 0.5-8.0 minute linear gradient 35-100% A, 8.0-9.0 minute 100% A, 7.0-8.9 minute 100% A, 9.0-9.1 minute linear gradient 100-35% A, 9.1-10 minute 35% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Prep LC/MS Method TFA10

Samples were purified by reverse phase preparative HPLC on a Phenomenex® Luna® C8(2) 5 um 100 Å AXIA™ column (50 mm×21.2 mm). A gradient of acetonitrile (A) and 0.1% trifluoroacetic acid in water (B) was used, at a flow rate of 30 mL/minute (0-0.2 minute 5% A, 0.2-3.0 minute linear gradient 5-100% A, 4.1-4.5 minute 100-5% A, 4.5-5.0 minute 5% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Prep LC/MS Method AA6

Samples were purified by reverse phase preparative HPLC on a Phenomenex® Luna® C8(2) 5 um 100 Å AXIA™ column (50 mm×21.2 mm). A gradient of acetonitrile (A) and 0.1% ammonium acetate in water (B) was used, at a flow rate of 40 mL/minute (0-0.5 minute 15% A, 0.5-8.0 minute linear gradient 15-100% A, 8.0-9.0 minute 100% A, 7.0-8.9 minute 100% A, 9.0-9.1 minute linear gradient 100-15% A, 9.1-10 minute 15% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Prep LC/MS Method AA7

Samples were purified by reverse phase preparative HPLC on a Phenomenex® Luna® C8(2) 5 um 100 Å AXIA™ column (50 mm×21.2 mm). A gradient of acetonitrile (A) and 0.1% ammonium acetate in water (B) was used, at a flow rate of 40 mL/minute (0-0.5 minute 25% A, 0.5-8.0 minute linear gradient 25-100% A, 8.0-9.0 minute 100% A, 7.0-8.9 minute 100% A, 9.0-9.1 minute linear gradient 100-25% A, 9.1-10 minute 25% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Prep LC/MS Method AA8

Samples were purified by reverse phase preparative HPLC on a Phenomenex® Luna® C8(2) 5 um 100 Å AXIA™ column (50 mm×21.2 mm). A gradient of acetonitrile (A) and 0.1% ammonium acetate in water (B) was used, at a flow rate of 40 mL/minute (0-0.5 minute 35% A, 0.5-8.0 minute linear gradient 35-100% A, 8.0-9.0 minute 100% A, 7.0-8.9 minute 100% A, 9.0-9.1 minute linear gradient 100-35% A, 9.1-10 minute 35% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Stereochemistry of final compounds was arbitrarily assigned in some cases, based on the order of elution and/or activity with respect to existing analogs.

List of abbreviations used in the experimental section:

| Abbreviation | Definition |
|---|---|
| MeCN | acetonitrile |
| TFA | trifluoroacetic acid |
| NMR | nuclear magnetic resonance |
| DMSO | dimethyl sulfoxide |
| LC/MS or LCMS | liquid chromatography-mass spectrometry |
| MeOH | methanol |
| tBME | tert-butyl methyl ether |
| s | singlet |
| br s | broad singlet |
| d | duplet or doublet |
| dd | double duplet or doublet of doublets |
| m | multiplet |
| min | minute |
| mL | milliliter |
| μL | microliter |
| g | gram |
| mg | milligram |
| mmol | millimoles |
| HPLC | high pressure liquid chromatography |
| ppm | parts per million |
| μm | micrometer |

Synthetic Preparation of the Compounds of the Invention

Schemes

The compounds of the present disclosure can be better understood in connection with the following synthetic schemes and methods which illustrate a means by which the compounds can be prepared. The compounds of this disclosure can be prepared by a variety of synthetic procedures.

Scheme 1

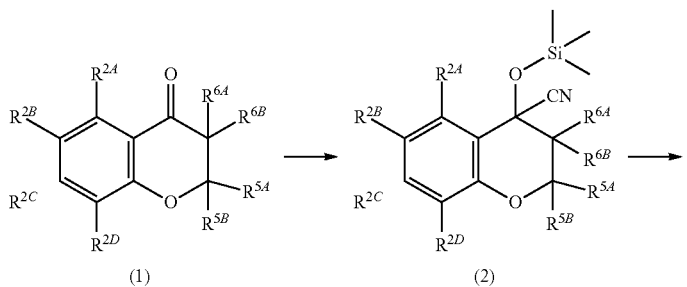

-continued

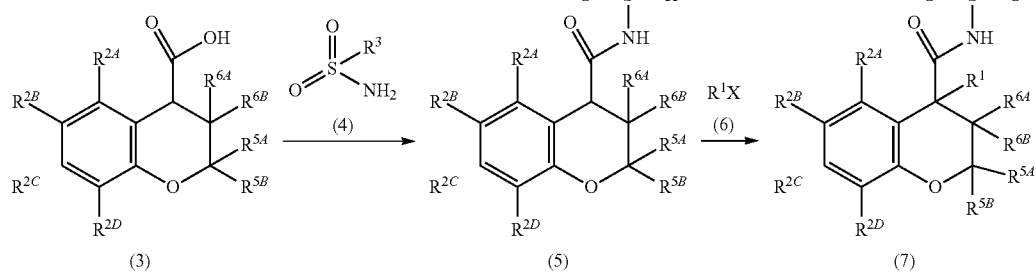

(3) → (5) → (7)

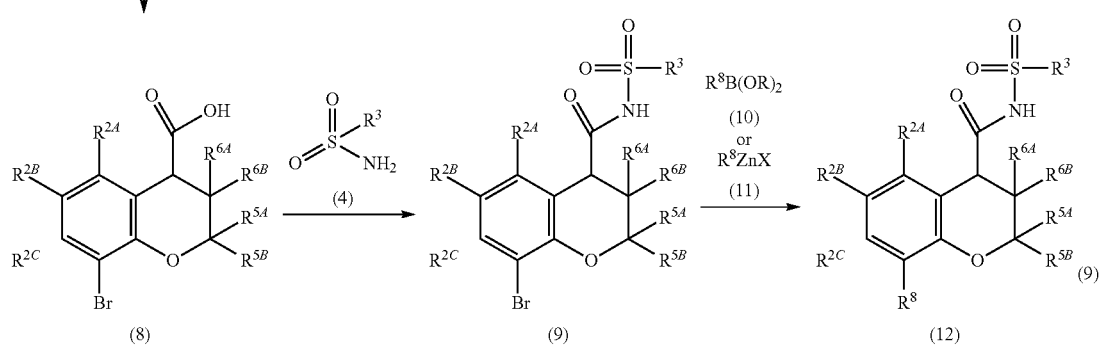

(8) → (9) → (12)

As shown in Scheme 1, compounds of formula (12) and compounds of formula (7), wherein $R^{2A}$, $R^{2B}$, $R^{2C}$, $R^{2D}$, $R^{3}$, $R^{6A}$, $R^{6B}$, $R^{5A}$, and $R^{5B}$ are as described herein, can be prepared from compounds of formula (1). Chromanones of formula (1) can be treated with zinc(II) iodide followed by trimethylsilanecarbonitrile to provide intermediates of formula (2). The addition is typically performed at low temperature in a solvent such as, but not limited to, dichloromethane before warming to ambient temperature. Compounds of formula (2) can be treated with tin(II) chloride hydrate in an aqueous hydrochloric acid/acetic acid mixture to provide carboxylic acids of formula (3). The reaction is typically performed an elevated temperature, such as about 130° C.

Carboxylic acids of formula (3) can be coupled with sulfonamides of formula (4), wherein $R^3$ is as described herein, to provide compounds of formula (5). Examples of conditions known to generate compounds of formula (5) from a mixture of a carboxylic acid and a sulfonamide include, but are not limited to, adding a coupling reagent such as, but not limited to, N-(3-dimethylaminopropyl)-N'-ethylcarbodiimide or 1-(3-dimethylaminopropyl)-3-ethyl-carbodiimide (EDC, EDAC or EDCI) or the corresponding hydrochloride salt, 1,3-dicyclohexylcarbodiimide (DCC), bis(2-oxo-3-oxazolidinyl)phosphinic chloride (BOPCl), N-[(dimethylamino)-1H-1,2,3-triazolo-[4,5-b]pyridin-1-yl-methylene]-N-methylmethanaminium hexafluorophosphate N-oxide or 2-(7-azabenzotriazol-1-yl)-N,N,N',N'-tetramethyluronium hexafluorophosphate or 1-[bis(dimethylamino)methylene]-1H-1,2,3-triazolo[4,5-b]pyridinium 3-oxid hexafluorophosphate (HATU), O-(benzotriazol-1-yl)-N,N,N',N'-tetramethyluronium tetrafluoroborate (TBTU), 2-(1H-benzo[d][1,2,3]triazol-1-yl)-1,1,3,3-tetramethylisouronium hexafluorophosphate(V) (HBTU), and 2,4,6-tripropyl-1,3,5,2,4,6-trioxatriphosphinane 2,4,6-trioxide (T3P®). The coupling reagents may be added as a solid, a solution, or as the reagent bound to a solid support resin. In addition to the coupling reagents, auxiliary-coupling reagents may facilitate the coupling reaction. Auxiliary coupling reagents that are often used in the coupling reactions include but are not limited to 4-(dimethylamino) pyridine (DMAP), 1-hydroxy-7-azabenzotriazole (HOAT) and 1-hydroxybenzotriazole (HOBT). The reaction may be carried out optionally in the presence of a base such as, but not limited to, triethylamine, N,N-diisopropylethylamine or pyridine. The coupling reaction may be carried out in solvents such as, but not limited to, tetrahydrofuran, N,N-dimethylformamide, N,N-dimethylacetamide, dimethyl sulfoxide, dichloromethane, and ethyl acetate. The reactions may be carried out at ambient temperature or an elevated temperature. The heating can be accomplished either conventionally or with microwave irradiation.

Compounds of formula (7), which are representative of compounds of Formula (I), can be prepared from compounds of formula (5) by treating the former with a base such as a potassium tert-butoxide, followed by compounds of formula (6), wherein $R^1$ is as described herein. The additions are typically performed in a solvent such as, but not limited to, N,N-dimethylformamide at a low temperature, such as about −60° C. for the potassium tert-butoxide addition and about 0° C. for the addition of compounds of formula (6).

Compounds of formula (3), wherein one or more of $R^{2A}$, $R^{2B}$, $R^{2C}$, $R^{2D}$ is hydrogen, can be treated with bromine in carbon disulfide to provide compounds of formula (4), wherein one or more of $R^{2A}$, $R^{2B}$, $R^{2C}$, $R^{2D}$, is bromine. The reaction is typically performed at ambient temperature.

Carboxylic acids of formula (8) can be coupled with sulfonamides of formula (4), wherein $R^3$ is as described herein, using examples of coupling conditions described above to provide compounds of formula (9). Compounds of formula (9) can be reacted with boronic acids of formula (10) (or the boronic ester equivalent) or zinc halides of formula (11) wherein $R^8$ is as described herein and X is I, Br, Cl or triflate, to provide compounds of formula (12), which are representative of compounds of Formula (I). For example, compounds of formula (12) can be prepared by reacting compounds of formula (9) wherein X is I, Br, Cl or triflate with boronic acid compounds of formula (10), wherein $R^8$ is as described herein (or the boronic ester equivalents), under Suzuki coupling conditions known to those skilled in the art and widely available in the literature. The reaction typically requires the use of a base and a catalyst. Examples of bases include, but are not limited to, potassium carbonate, potassium t-butoxide, sodium carbonate, cesium carbonate, and cesium fluoride. Examples of catalysts include, but are not limited to, tetrakis(triphenylphosphine)palladium(0), [1,1'-bis(diphenylphosphino)ferrocene]dichloropalladium(II) dichloromethane, bis(triphenylphosphine)palladium(II) dichloride, and tris(dibenzylideneacetone)dipalladium(0). The reaction may be conducted in a solvent such as, but not limited to, water, dioxane, 1,2-dimethoxyethane, N,N-dimethylformamide, toluene, ethanol, tetrahydrofuran and the like, or mixtures thereof. The reaction may be conducted at ambient or elevated temperatures, and optionally in a microwave oven.

Compounds of formula (12) can also be prepared by reacting compounds of formula (9) wherein X is I, Br, Cl or triflate with organozinc compounds of formula (11), wherein $R^8$ is as described herein, under Negishi coupling conditions known to those skilled in the art and widely available in the literature. The reaction typically requires the use of a palladium or nickel catalyst. Examples of catalysts include, but are not limited to, dichloro[4,5-dichloro-1,3-bis(2,6-di-3-pentylphenyl)imidazol-2-ylidene](3-chloropyridyl)palladium(II) (PEPPSI-IPentCl), tetrakis(triphenylphosphine)nickel(0), tetrakis(triphenylphosphine)palladium(0), bis(triphenylphosphine)palladium(II) dichloride, [1,1'-bis(diphenylphosphino)ferrocene]dichloropalladium(II) dichloromethane, tris(dibenzylideneacetone)dipalladium(0), and palladium(II) acetate. The reaction may be conducted in a solvent such as, but not limited to, water, dioxane, 1-methyl-2-pyrrolidinone, N,N-dimethylacetamide, 1,2-dimethoxyethane, N,N-dimethylformamide, toluene, ethanol, tetrahydrofuran and the like, or mixtures thereof. The reaction may be conducted at ambient or elevated temperatures, and optionally in a microwave oven.

Scheme 2

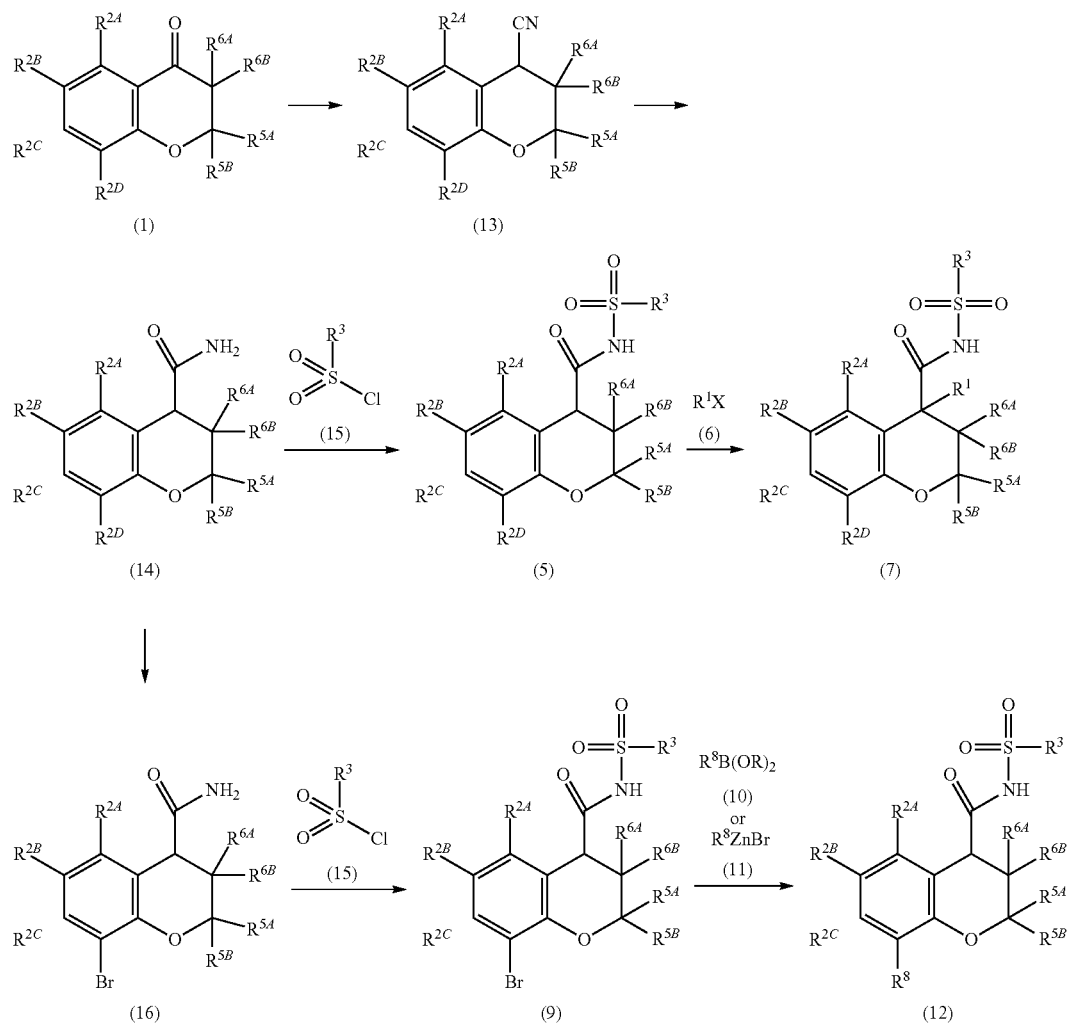

As shown in Scheme 2, compounds of formula (12) can be prepared from compounds of formula (1) in an alternative sequence. A mixture of chromanones of formula (1) and toluenesulfonylmethyl isocyanide can be treated with a base such as, but not limited to, potassium tert-butoxide under nitrogen to provide nitriles of formula (13). The addition is typically performed at low temperature in a solvent such as but not limited to 1,2-dimethoxyethane before warming to ambient temperature. Compounds of formula (14) can be prepared by treating compounds of formula (13) with sodium hydroxide. The reaction is typically performed at ambient temperature in a solvent such as but not limited to ethanol. Compounds of formula (14) can be reacted with acid chlorides of formula (15), wherein $R^3$ is as described herein, in the presence of a base such as sodium hydride in a solvent such as, but not limited to, N,N-dimethylformamide to provide compounds of formula (5). As previously described in Scheme 1, compounds of formula (7), which are representative of compounds of Formula (I), can be prepared from compounds of formula (5) by treating the former with a base such as a potassium tert-butoxide, followed by compounds of formula (6), wherein $R^1$ is as described herein. The additions are typically performed in a solvent such as, but not limited to, N,N-dimethylformamide at a low temperature, such as about −60° C. for the potassium tert-butoxide addition and about 0° C. for the addition of compounds of formula (6).

Compounds of formula (14), wherein one or more of $R^{2A}$, $R^{2B}$, $R^{2C}$, $R^{2D}$ is hydrogen, can be treated with bromine in carbon disulfide to provide compounds of formula (16), wherein one or more of $R^{2A}$, $R^{2B}$, $R^{2C}$, $R^{2D}$, is bromine. The reaction is typically performed at ambient temperature. Compounds of formula (16) can be reacted with acid chlorides of formula (15), wherein $R^3$ is as described herein, in the presence of a base such as sodium hydride in a solvent such as, but not limited to, N,N-dimethylformamide to provide compounds of formula (9). As described in Scheme 1, compounds of formula (9) can be reacted with boronic acids of formula (10) or zinc halides of formula (11) wherein $R^8$ is as described herein and X is X is I, Br, Cl or triflate, to provide compounds of formula (12), which are representative of compounds of Formula (I).

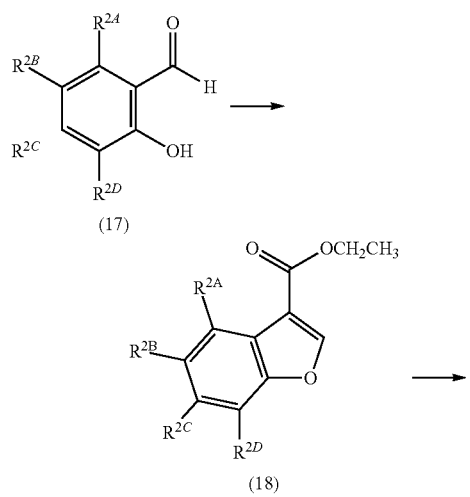

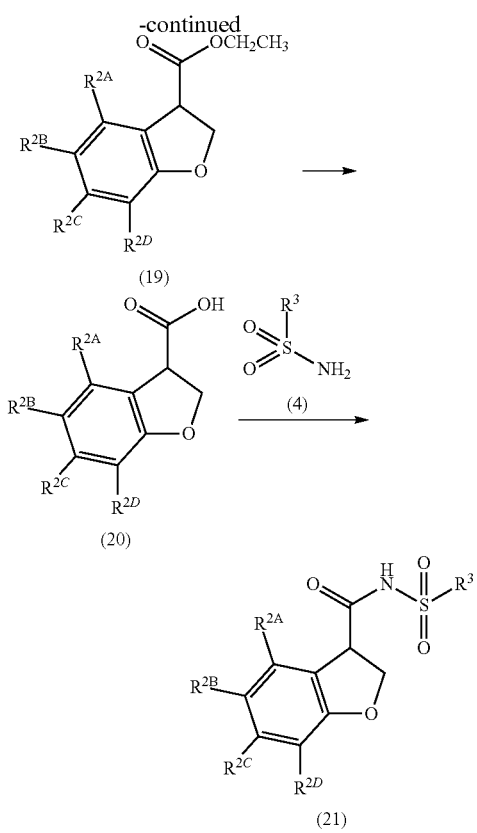

As described in Scheme 3, compounds of formula (21), can be prepared from compounds of formula (17). Compounds of formula (17), wherein $R^{2A}$, $R^{2B}$, $R^{2C}$, and $R^{2D}$ are as described herein, can be reacted with ethyl diazoacetate in the presence of tetrafluoroboric acid diethyl ether complex, followed by sulfuric acid to provide compounds of formula (18). The reaction is typically performed at ambient temperature in a solvent such as, but not limited to, dichloromethane. Compounds of formula (18) can be treated with magnesium to provide compounds of formula (19). The reaction is typically performed at ambient temperature in a solvent such as, but not limited to, methanol. Compounds of formula (20) can be prepared by treating compounds of formula (19) with aqueous sodium hydroxide. The reaction is typically performed at ambient temperature in a solvent such as, but not limited to, tetrahydrofuran, methanol, or mixtures thereof.

Carboxylic acids of formula (20), can be coupled with sulfonamides of formula (4), wherein $R^3$ is as described herein, to provide compounds of formula (21), which are representative of compounds of Formula (I), under coupling conditions described in Scheme 1.

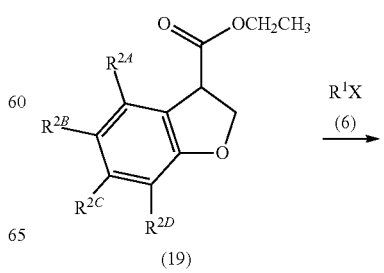

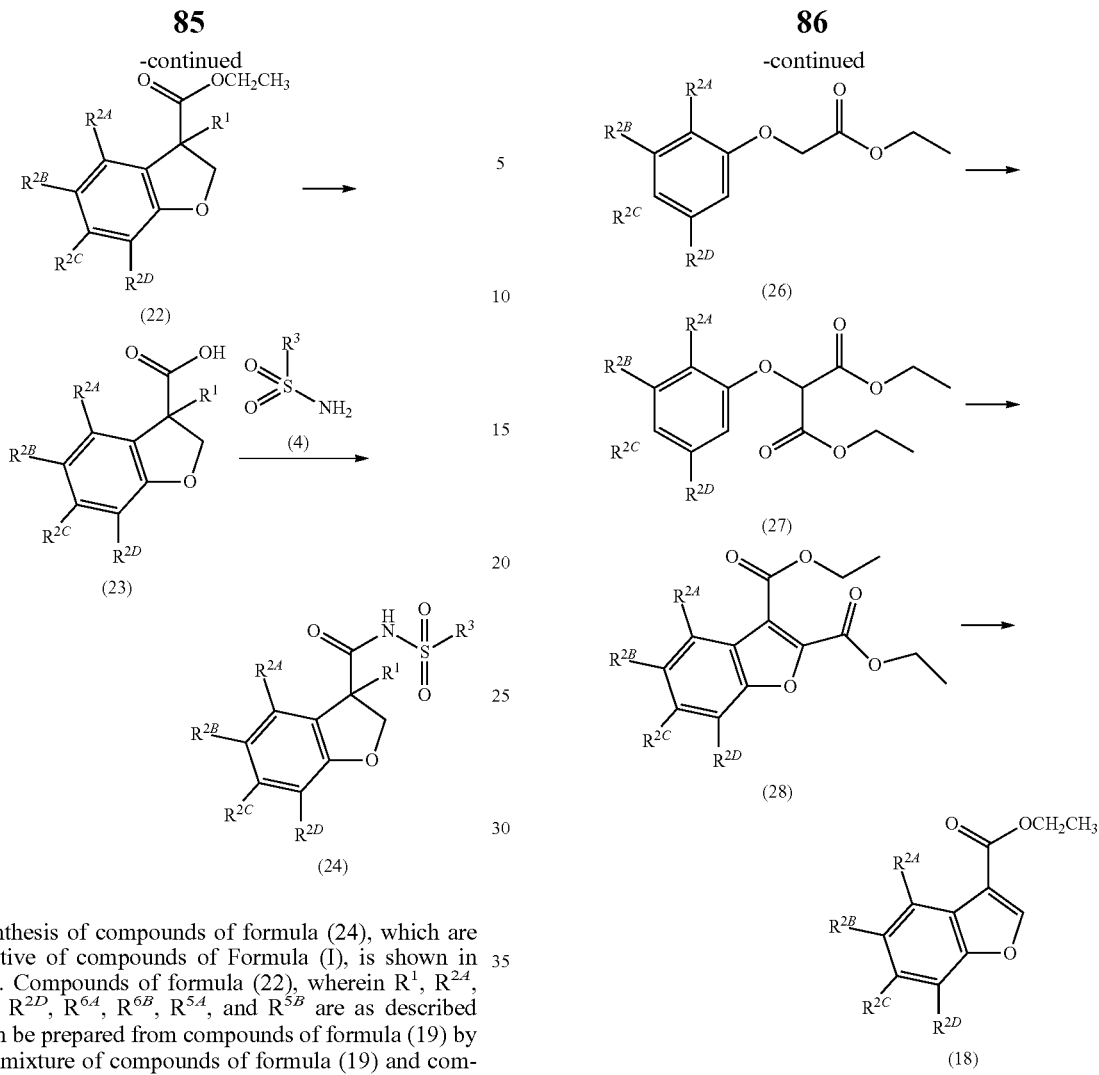

The synthesis of compounds of formula (24), which are representative of compounds of Formula (I), is shown in Scheme 4. Compounds of formula (22), wherein $R^1$, $R^{2A}$, $R^{2B}$, $R^{2C}$, $R^{2D}$, $R^{6A}$, $R^{6B}$, $R^{5A}$, and $R^{5B}$ are as described herein, can be prepared from compounds of formula (19) by treating a mixture of compounds of formula (19) and compounds of formula (6), wherein $R^1$ is as described herein, with a base such as sodium hydride or potassium tert-butoxide. The additions are typically performed in a solvent such as, but not limited to, N,N-dimethylformamide at a low temperature, such as about 0° C. Compounds of formula (23) can be prepared by treating compounds of formula (22) with aqueous sodium hydroxide. The reaction is typically performed at ambient temperature in a solvent such as, but not limited to, tetrahydrofuran, methanol, or mixtures thereof.

Carboxylic acids of formula (23), can be coupled with sulfonamides of formula (4), wherein $R^3$ is as described herein, to provide compounds of formula (24), which are representative of compounds of Formula (I), under coupling conditions described in Scheme 1.

Scheme 5

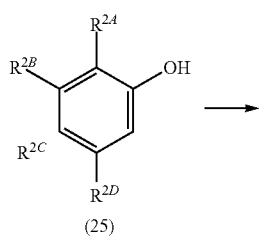

As shown in Scheme 5, compounds of formula (18) can be prepared in an alternative to the synthesis described in Scheme 3. Compounds of formula (25), wherein $R^{2A}$, $R^{2B}$, $R^{2C}$, and $R^{2D}$ are as described herein, can be reacted with ethyl 2-bromoacetate in the presence of a base such as but not limited to potassium carbonate, to provide compounds of formula (26). The reaction is typically performed at ambient temperature under a nitrogen atmosphere in a solvent, such as, but not limited to, acetone. Diethyl oxalate can be reacted with a mixture of sodium hydride in tetrahydrofuran and ethanol, followed by reaction with compounds of formula (26), to provide compounds of formula (27). The reaction is typically performed at an elevated temperature, such as under reflux. Compounds of formula (28) can be prepared by treating compounds of formula (27) with concentrated sulfuric acid. The addition is typically performed at a low temperature such as about −15° C., before slowly warming up to about 15° C. Compounds of formula (18) can be prepared by treating compounds of formula (28) with sodium chloride in a mixture of dimethyl sulfoxide and water. The reaction is typically performed under nitrogen at an elevated temperature such as 160° C.

EXAMPLES

Example 1

6-bromo-N-(naphthalene-1-sulfonyl)-4-phenyl-3,4-dihydro-2H-1-benzopyran-4-carboxamide 6-Bromo-4-phenyl-chroman-4-carboxylic acid (33.7 mg, 0.1 mmol, 1.0 equivalent) was weighed into a 4 mL vial. A stock solution of 1-(3-dimethylaminopropyl)-3-ethylcarbodiimide hydrochloride and 4-dimethylaminopyridine in $CH_2Cl_2$ (0.67 M and 0.37 M respectively, 300 µL, 0.20 mmol 1-(3-dimethylaminopropyl)-3-ethylcarbodiimide hydrochloride and 0.11 mmol 4-dimethylaminopyridine, 2.0 equivalents 1-(3-dimethylaminopropyl)-3-ethylcarbodiimide hydrochloride and 1.1 equivalents 4-dimethylaminopyridine) was added. A slurry of naphthalene-1-sulfonamide in $CH_2Cl_2$ (0.33 M, 300 µL, 0.10 mmol 1.0 equivalent) was added via pipette and the reaction was stirred overnight at ambient temperature. The solvent was removed under a stream of nitrogen and the residue was reconstituted in acetonitrile. The material was purified via preparative reverse phase HPLC MS method TFA8 to provide the title compound. $^1$H NMR (400 MHz, dimethylsulfoxide-$d_6$:$D_2O$=9:1 (v/v)) δ ppm 8.64-8.57 (m, 1H), 8.28 (dd, J=7.4, 1.3 Hz, 1H), 8.24-8.16 (m, 1H), 8.09-8.02 (m, 1H), 7.68-7.56 (m, 3H), 7.28-7.14 (m, 4H), 6.93-6.82 (m, 3H), 6.68 (d, J=8.8 Hz, 1H), 3.90-3.74 (m, 2H), 2.80 (ddd, J=14.3, 6.1, 3.1 Hz, 1H), 2.26 (ddd, J=14.3, 8.6, 3.8 Hz, 1H). MS (APCI+) m/z 521.8 (M+H)$^+$.

Example 2

(2R,4R)-2-[(ethylsulfanyl)methyl]-N-(naphthalene-1-sulfonyl)-4-phenyl-3,4-dihydro-2H-1-benzopyran-4-carboxamide (2R,4R)-2-Ethylsulfanylmethyl-4-phenyl-chroman-4-carboxylic acid (32.8 mg, 0.1 mmol, 1.0 equivalent) was weighed into a 4 mL vial. A stock solution of 1-(3-dimethylaminopropyl)-3-ethylcarbodiimide hydrochloride and 4-dimethylaminopyridine in $CH_2Cl_2$ (0.67 M and 0.37 M respectively, 300 µL, 0.20 mmol 1-(3-dimethylaminopropyl)-3-ethylcarbodiimide hydrochloride and 0.11 mmol 4-dimethylaminopyridine, 2.0 equivalents 1-(3-dimethylaminopropyl)-3-ethylcarbodiimide hydrochloride and 1.1 equivalents 4-dimethylaminopyridine) was added. A slurry of naphthalene-1-sulfonamide in $CH_2Cl_2$ (0.33 M, 300 µL, 0.10 mmol 1.0 equivalent) was added via pipette and the reaction was stirred overnight at ambient temperature. The solvent was removed under a stream of nitrogen and the residue was reconstituted in acetonitrile. The material was purified via preparative reverse phase HPLC MS method TFA8 to provide the title compound. $^1$H NMR (400 MHz, dimethylsulfoxide-$d_6$:$D_2O$=9:1 (v/v)) δ ppm 8.60 (d, J=8.3 Hz, 1H), 8.26 (dd, J=7.4, 1.3 Hz, 1H), 8.16 (d, J=8.2 Hz, 1H), 8.06-7.99 (m, 1H), 7.66-7.52 (m, 3H), 7.24-7.09 (m, 3H), 7.09-7.01 (m, 1H), 6.99-6.91 (m, 2H), 6.75 (dd, J=7.8, 1.8 Hz, 1H), 6.71-6.62 (m, 2H), 3.94-3.86 (m, 1H), 2.80 (dd, J=13.9, 2.0 Hz, 1H), 2.72-2.57 (m, 2H), 2.49-2.45 (m, 2H), 2.06 (dd, J=13.8, 11.5 Hz, 1H), 1.17 (t, J=7.3 Hz, 3H). MS (APCI+) m/z 517.9 (M+H)$^+$.

Example 3

6-methoxy-2,2-dimethyl-N-(naphthalene-1-sulfonyl)-4-phenyl-3,4-dihydro-2H-1-benzopyran-4-carboxamide 6-Methoxy-2,2-dimethyl-4-phenyl-chroman-4-carboxylic acid (31.2 mg, 0.1 mmol, 1.0 equivalent) was weighed into a 4 mL vial. A stock solution of 1-(3-dimethylaminopropyl)-3-ethylcarbodiimide hydrochloride and 4-dimethylaminopyridine in $CH_2Cl_2$ (0.67 M and 0.37 M respectively, 300 µL, 0.20 mmol 1-(3-dimethylaminopropyl)-3-ethylcarbodiimide hydrochloride and 0.11 mmol 4-dimethylaminopyridine, 2.0 equivalents 1-(3-dimethylaminopropyl)-3-ethylcarbodiimide hydrochloride and 1.1 equivalents 4-dimethylaminopyridine) was added. A slurry of naphthalene-1-sulfonamide in $CH_2Cl_2$ (0.33 M, 300 µL, 0.10 mmol, 1.0 equivalent) was added via pipette and the reaction was stirred overnight at ambient temperature. The solvent was removed under a stream of nitrogen and the residue was reconstituted in acetonitrile. The material was purified via preparative reverse phase HPLC MS method TFA8 to provide the title compound. $^1$H NMR (400 MHz, dimethylsulfoxide-$d_6$:$D_2O$=9:1 (v/v)) δ ppm 8.63-8.56 (m, 1H), 8.31 (dd, J=7.4, 1.3 Hz, 1H), 8.26-8.18 (m, 1H), 8.10-8.02 (m, 1H), 7.69-7.55 (m, 3H), 7.19-7.05 (m, 3H), 6.95-6.86 (m, 2H), 6.73 (dd, J=8.9, 3.0 Hz, 1H), 6.68-6.64 (m, 1H), 6.25 (t, J=2.4 Hz, 1H), 3.46 (s, 3H), 2.89 (d, J=14.5 Hz, 1H), 2.25 (d, J=14.5 Hz, 1H), 1.01 (s, 3H), 0.92 (s, 3H). MS (APCI+) m/z 502.0 (M+H)$^+$.

Example 4

6-methoxy-N-(naphthalene-1-sulfonyl)-4-phenyl-3,4-dihydro-2H-1-benzopyran-4-carboxamide 6-Methoxy-4-phenyl-chroman-4-carboxylic acid (28.4 mg, 0.1 mmol, 1.0 equivalent) was weighed into a 4 mL vial. A stock solution of 1-(3-dimethylaminopropyl)-3-ethylcarbodiimide hydrochloride and 4-dimethylaminopyridine in $CH_2Cl_2$ (0.67 M and 0.37 M respectively, 300 µL, 0.20 1-(3-dimethylaminopropyl)-3-ethylcarbodiimide hydrochloride and 0.11 mmol 4-dimethylaminopyridine, 2.0 equivalents 1-(3-dimethylaminopropyl)-3-ethylcarbodiimide hydrochloride and 1.1 equivalents 4-dimethylaminopyridine) was added. A slurry of naphthalene-1-sulfonamide in $CH_2Cl_2$ (0.33 M, 300 µL, 0.10 mmol 1.0 equivalent) was added via pipette and the reaction was stirred overnight at ambient temperature. The solvent was removed under a stream of nitrogen and the residue was reconstituted in acetonitrile. The material was purified via preparative reverse phase HPLC MS method TFA8 to provide the title compound. $^1$H NMR (400 MHz, dimethylsulfoxide-$d_6$:$D_2O$=9:1 (v/v)) δ ppm 8.59 (d, J=8.5 Hz, 1H), 8.28 (dd, J=7.4, 1.3 Hz, 1H), 8.25-8.15 (m, 1H), 8.13-7.97 (m, 1H), 7.68-7.54 (m, 3H), 7.26-7.13 (m, 3H), 6.93-6.84 (m, 2H), 6.72 (dd, J=8.9, 2.9 Hz, 1H), 6.66 (d, J=8.9 Hz, 1H), 6.40-6.32 (m, 1H), 3.84-3.67 (m, 2H), 3.45 (s, 3H), 2.86-2.73 (m, 1H), 2.28-2.10 (m, 1H). MS (APCI+) m/z 473.9 (M+H)$^+$.

Example 5

6-benzoyl-5,7-dimethyl-N-(naphthalene-1-sulfonyl)-3,4-dihydro-2H-1-benzopyran-4-carboxamide 6-Benzoyl-5,7-dimethyl-chroman-4-carboxylic acid (31.0 mg, 0.1 mmol, 1.0 equivalent) was weighed into a 4 mL vial. A stock solution of 1-(3-dimethylaminopropyl)-3-ethylcarbodiimide hydrochloride and 4-dimethylaminopyridine in $CH_2Cl_2$ (0.67 M and 0.37 M respectively, 300 µL, 0.20 mmol 1-(3-dimethylaminopropyl)-3-ethylcarbodiimide hydrochloride and 0.11 mmol 4-dimethylaminopyridine, 2.0 equivalents 1-(3-dimethylaminopropyl)-3-ethylcarbodiimide hydrochloride and 1.1 equivalents 4-dimethylaminopyridine) was added. A slurry of naphthalene-1-sulfonamide in CH$_2$Cl$_2$ (0.33 M, 300 µL, 0.10 mmol, 1.0 equivalent) was added via pipette and the reaction was stirred overnight at ambient temperature. The solvent was removed under a stream of nitrogen and the residue was reconstituted in acetonitrile. The material was purified via preparative reverse phase HPLC MS method TFA8 to provide the title compound. $^1$H NMR (400 MHz, dimethylsulfoxide-d$_6$: D$_2$O=9:1 (v/v)) δ ppm 8.66 (d, J=8.6 Hz, 1H), 8.31-8.24 (m, 1H), 8.20-8.13 (m, 1H), 8.00-7.93 (m, 1H), 7.69-7.54 (m, 4H), 7.54-7.48 (m, 2H), 7.48-7.40 (m, 2H), 6.49 (s, 1H), 3.98 (dt, J=11.1, 3.7 Hz, 1H), 3.77 (dd, J=6.7, 3.2 Hz, 1H), 3.73-3.61 (m, 1H), 2.18-2.04 (m, 1H), 1.99-1.89 (m, 1H), 1.87 (s, 3H), 1.28 (s, 3H). MS (APCI+) m/z 499.9 (M+H)$^+$.

Example 6

N-(naphthalene-1-sulfonyl)-3-phenyl-2,3-dihydro-1-benzofuran-3-carboxamide

3-Phenyl-2,3-dihydro-benzofuran-3-carboxylic acid (19.1 mg, 0.08 mmol, 1.0 equivalent) was weighed into a 4 mL vial. A stock solution of 1-(3-dimethylaminopropyl)-3-ethylcarbodiimide hydrochloride and 4-dimethylaminopyridine in CH$_2$Cl$_2$ (0.40 M and 0.22 M respectively, 400 µL, 0.16 mmol 1-(3-dimethylaminopropyl)-3-ethylcarbodiimide hydrochloride and 0.09 mmol 4-dimethylaminopyridine, 2.0 equivalents 1-(3-dimethylaminopropyl)-3-ethylcarbodiimide hydrochloride and 1.1 equivalents 4-dimethylaminopyridine) was added. A slurry of naphthalene-1-sulfonamide in CH$_2$Cl$_2$ (0.20 M, 400 µL, 0.08 mmol 1.0 equivalent) was added via pipette and the reaction was stirred overnight at ambient temperature. The solvent was removed under a stream of nitrogen and the residue was reconstituted in acetonitrile. The material was purified via preparative reverse phase HPLC MS method TFA8 to provide the title compound. $^1$H NMR (400 MHz, dimethylsulfoxide-d$_6$: D$_2$O=9:1 (v/v)) δ ppm 8.50-8.41 (m, 1H), 8.33-8.25 (m, 2H), 8.10 (dd, J=7.3, 1.9 Hz, 1H), 7.74-7.61 (m, 3H), 7.58-7.51 (m, 1H), 7.37-7.22 (m, 3H), 7.16 (td, J=7.8, 1.4 Hz, 1H), 6.97-6.91 (m, 2H), 6.89-6.81 (m, 1H), 6.76 (d, J=8.1 Hz, 1H), 4.99 (d, J=9.5 Hz, 1H), 4.36 (d, J=9.6 Hz, 1H). MS (APCI+) m/z 430.0 (M+H)$^+$.

Example 7

8-chloro-N-(naphthalene-1-sulfonyl)-3,4-dihydro-2H-1-benzopyran-4-carboxamide

Example 7A 8-chlorochroman-4-carbonitrile

In a 50 mL round bottom flask, 8-chlorochroman-4-one (0.891 g, 4.88 mmol) and toluenesulfonylmethyl isocyanide (1.209 g, 6.19 mmol) were dissolved in 1,2-dimethoxyethane (24 mL) to give a colorless solution. The reaction was cooled to −8° C. (internal temperature) with ice/acetone/dry ice under nitrogen. Solid potassium tert-butoxide (1.259 g, 11.22 mmol) was added in portions, keeping the internal temperature <−5° C. over about an hour. The reaction was allowed to slowly warm to room temperature overnight. The solvent was removed in vacuo and the crude material was quenched with water (30 mL). The aqueous layer was extracted with diethyl ether (4×50 mL) and the organics were washed with brine, dried (Na$_2$SO$_4$), and filtered. The solvent was removed in vacuo and the crude oil was chromatographed using a 40 g silica gel cartridge with 1-40% ethyl acetate/hexanes to give 8-chlorochroman-4-carbonitrile. $^1$H NMR (400 MHz, Chloroform-d) δ ppm 7.34 (ddt, J=7.9, 1.6, 0.8 Hz, 1H), 7.23 (ddd, J=7.8, 1.6, 1.0 Hz, 1H), 6.91 (td, J=7.8, 1.0 Hz, 1H), 4.47 (dddd, J=11.9, 6.1, 4.6, 1.0 Hz, 1H), 4.42-4.35 (m, 1H), 4.09-4.02 (m, 1H), 2.38 (tdt, J=5.3, 4.3, 0.9 Hz, 2H).

Example 7B 8-chlorochroman-4-carboxylic Acid

Example 7A (0.376 g, 1.942 mmol) was dissolved in ethanol (6.47 mL). A solution of sodium hydroxide (0.777 g, 19.42 mmol) in 6 mL of water was added, and the resulting mixture was heated at 80° C. for 16 hours. The reaction was cooled in an ice bath and was acidified with aqueous 6 M HCl (5 mL). The solvent was reduced in volume and the resulting precipitate was filtered and washed with water to give 8-chlorochroman-4-carboxylic acid. $^1$H NMR (501 MHz, Chloroform-d) δ ppm 7.31 (ddd, J=7.9, 1.6, 0.6 Hz, 1H), 7.22 (ddd, J=7.8, 1.6, 0.8 Hz, 1H), 6.86 (t, J=7.7 Hz, 1H), 4.44 (dtd, J=11.2, 4.1, 1.1 Hz, 1H), 4.38 (td, J=11.0, 2.6 Hz, 1H), 3.87 (dd, J=6.0, 3.8 Hz, 1H), 2.44-2.36 (m, 1H), 2.20 (dddd, J=14.3, 10.5, 6.0, 4.0 Hz, 1H). MS (ESI+) m/z 213 (M+H)$^+$.

Example 7C 8-chloro-N-(naphthalen-1-ylsulfonyl)chroman-4-carboxamide

Example 7B (50 mg, 0.235 mmol) was combined with a mixture of N$^1$-((ethylimino)methylene)-N$^3$,N$^3$-dimethylpropane-1,3-diamine hydrochloride (90 mg, 0.470 mmol) and N,N-dimethylpyridin-4-amine (31.6 mg, 0.259 mmol) in dichloromethane (2.5 mL). After 30 minutes, naphthalene-1-sulfonamide (48.7 mg, 0.235 mmol) was added. After 2 hours, the reaction was quenched with 1.0 mL of 2 N aqueous HCl. The organics were removed and the crude material was purified by reverse-phase preparative HPLC on a Phenomenex® Luna® C8(2) 5 µm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to give 8-chloro-N-(naphthalen-1-ylsulfonyl)chroman-4-carboxamide. $^1$H NMR (400 MHz, Chloroform-d) δ ppm 8.53 (dd, J=7.5, 1.2 Hz, 1H), 8.33-8.24 (m, 2H), 8.18 (d, J=8.2 Hz, 1H), 8.04-7.98 (m, 1H), 7.69-7.62 (m, 3H), 7.37 (dd, J=7.6, 1.8 Hz, 1H), 6.85-6.80 (m, 1H), 6.78 (ddd, J=7.6, 1.8, 0.8 Hz, 1H), 4.18-4.11 (m, 1H), 3.69 (td, J=11.1, 2.7 Hz, 1H), 3.61 (t, J=5.2 Hz, 1H), 2.25-2.16 (m, 1H), 2.03 (tdd, J=12.7, 5.9, 3.7 Hz, 1H). MS (APCI+) m/z 402 (M+H)$^+$.

Example 8

3-ethyl-4-methoxy-N-(naphthalene-1-sulfonyl)-2,3-dihydro-1-benzofuran-3-carboxamide Example 8A Ethyl 4-oxo-4,5,6,7-tetrahydrobenzofuran-3-carboxylate A solution of 4-oxo-4,5,6,7-tetrahydrobenzo[b]furan-3-carboxylic acid (CAS#56671-28-4) (4 g, 22.20 mmol) in ethanol (200 mL) was treated with concentrated $H_2SO_4$ (4 drops). The mixture was heated to reflux overnight, cooled to room temperature, treated with excess $NaHCO_3$ (solid, ~2 g), stirred at room temperature for 15 minutes, and concentrated to remove the majority of the ethanol. The residue was partitioned between ethyl acetate (75 mL) and water (50 mL). The layers were separated, and the aqueous layer was extracted with ethyl acetate (2×50 mL). The combined ethyl acetate layers were washed with brine, dried ($MgSO_4$), filtered and concentrated to provide the title compound. $^1$H NMR (501 MHz, $CDCl_3$) δ ppm 7.86 (s, 1H), 4.32 (q, J=7.1 Hz, 2H), 2.89 (t, J=6.3 Hz, 2H), 2.56-2.52 (m, 2H), 2.17 (p, J=6.4 Hz, 2H), 1.35 (t, J=7.1 Hz, 3H). LC/MS (APCI+) m/z 209 (M+H)$^+$.

Example 8B

Ethyl 4-hydroxybenzofuran-3-carboxylate

A solution of Example 8A (4.41 g, 21.18 mmol) in $CCl_4$ (85 m) was treated with 6 drops of water, and heated to reflux. The mixture was treated with N-bromosuccinimide (3.77 g, 21.18 mmol) and 2,2'-azobis(2-methylpropionitrile) (0.174 g, 1.059 mmol), heated to reflux for 2 hours, cooled, and partitioned between water (50 mL) and $CH_2Cl_2$ (~50 mL). The layers were separated and the aqueous layer was extracted with $CH_2Cl_2$ (30 mL). The combined organic layers were dried ($MgSO_4$), filtered, concentrated and chromatographed on silica gel, eluting with a gradient of 15% to 100% $CH_2Cl_2$ in heptanes to provide the title compound (contaminated with 2 minor compounds wherein the benzene ring of the title compound was brominated). $^1$H NMR (501 MHz, $CDCl_3$) δ ppm 10.07 (s, 1H), 8.11 (s, 1H), 7.25 (t, J=8.2 Hz, 1H), 7.03 (dd, J=8.3, 0.7 Hz, 1H), 6.80 (dd, J=8.0, 0.7 Hz, 1H), 4.44 (q, J=7.1 Hz, 2H), 1.43 (t, J=7.1 Hz, 3H).

Example 8C

Ethyl 4-methoxybenzofuran-3-carboxylate

A solution of Example 8B (2 g, 9.70 mmol) and methyl iodide (1.819 mL, 29.1 mmol) in acetonitrile (20 mL) was treated with cesium carbonate (6.32 g, 19.40 mmol), and stirred at room temperature for 30 minutes. The mixture was diluted with methyl tert-butyl ether (~100 mL) and filtered to remove the solids. The filtrate was washed with brine, dried ($MgSO_4$), filtered, and concentrated. The residue was chromatographed on silica gel, eluting with a gradient of 5% to 15% ethyl acetate in heptanes to provide the title compound. $^1$H NMR (400 MHz, $CDCl_3$) δ ppm 8.14 (s, 1H), 7.28 (t, J=8.2 Hz, 1H), 7.14 (d, J=8.3 Hz, 1H), 6.76 (d, J=8.1 Hz, 1H), 4.37 (q, J=7.1 Hz, 2H), 3.97 (s, 3H), 1.39 (t, J=7.1 Hz, 3H). LC/MS (APCI+) m/z 221 (M+H)$^+$.

Example 8D methyl 4-methoxy-2,3-dihydrobenzofuran-3-carboxylate

A solution of Example 8C (1.58 g, 7.17 mmol) in methanol (20 mL) was treated in portions with magnesium turnings (0.523 g, 21.52 mmol) over 20 minutes. The mixture was stirred at room temperature for 3.5 hours, treated with more magnesium turnings (3 turnings), and stirred at room temperature for 1 hour. The mixture was partitioned between methyl tert-butyl ether (100 mL) and 0.5 M aqueous HCl (100 mL). The layers were separated, and the aqueous layer was extracted with methyl tert-butyl ether (30 mL). The combined methyl tert-butyl ether layers were washed with brine, dried ($MgSO_4$), filtered, and concentrated to provide the title compound. $^1$H NMR (400 MHz, $CDCl_3$) δ ppm 7.18-7.13 (m, 1H), 6.49 (d, J=8.1 Hz, 1H), 6.43 (d, J=8.3 Hz, 1H), 4.75-4.68 (m, 2H), 4.31 (dd, J=8.7, 7.0 Hz, 1H), 3.82 (s, 3H), 3.74 (s, 3H).

Example 8E 3-ethyl-4-methoxy-2,3-dihydrobenzofuran-3-carboxylic acid

A solution of Example 8D (0.1 g, 0.480 mmol) and ethyl iodide (0.388 mL, 4.80 mmol) in N,N-dimethylformamide (2 mL) under $N_2$ at 0° C. was treated all at once with a 60% dispersion of sodium hydride in mineral oil (0.038 g, 0.961 mmol). The mixture was stirred at 0° C. for 20 minutes. The mixture was partitioned between methyl tert-butyl ether (~30 mL) and 1 M aqueous HCl (~15 mL). The layers were separated, and the methyl tert-butyl ether layer was washed with 0.1 M aqueous HCl (~15 mL), washed with brine, dried ($MgSO_4$), filtered, and concentrated. The residue was dissolved in tetrahydrofuran (1.5 mL), diluted with methanol (1.5 mL), treated with 1 M aqueous NaOH (1.5 mL) and stirred at room temperature for 15 minutes. The mixture was partitioned between 1 M aqueous NaOH (15 mL) and methyl tert-butyl ether (30 mL). The methyl tert-butyl ether layer was discarded. The aqueous layer was acidified with 3 M aqueous HCl and was extracted with methyl tert-butyl ether. The methyl tert-butyl ether layer was washed with brine, dried ($MgSO_4$), filtered, and concentrated. The residue was chromatographed on silica gel eluting with a gradient of 15% to 100% 200:1:1 ethyl acetate:HCOOH:$H_2O$ in heptanes to provide the title compound. $^1$H NMR (501 MHz, $CDCl_3$) δ ppm 7.19 (t, J=8.2 Hz, 1H), 6.52 (dd, J=8.1, 0.6 Hz, 1H), 6.49 (d, J=8.3 Hz, 1H), 5.03 (d, J=9.4 Hz, 1H), 4.39 (d, J=9.4 Hz, 1H), 3.94 (s, 3H), 2.20-2.12 (m, 1H), 2.09-2.02 (m, 1H), 0.86 (t, J=7.5 Hz, 3H).

Example 8F 3-ethyl-4-methoxy-N-(naphthalene-1-sulfonyl)-2,3-dihydro-1-benzofuran-3-carboxamide A solution of Example 8E (9 mg, 0.040 mmol), 1-(3-dimethylaminopropyl)-3-ethylcarbodiimide hydrochloride (15.53 mg, 0.081 mmol) and 4-dimethylaminopyridine (5.44 mg, 0.045 mmol) in $CH_2Cl_2$ (0.3 mL) was treated with naphthalene-1-sulfonamide (9.23 mg, 0.045 mmol). The mixture was stirred at room temperature for 1 hour. The mixture was concentrated with a stream of $N_2$, diluted with N,N-dimethylformamide (~1 mL) and was purified by reverse-phase HPLC (Waters XBridge™ RP18 column, 5 µm, 30×100 mm, flow rate 40 mL/minute, 5% to 40% (over 15 minutes) gradient of acetonitrile in 0.1% TFA) to provide the title compound. $^1$H NMR (400 MHz, dimethylsulfoxide-$d_6$) δ ppm 11.93 (s, 1H), 8.54-8.49 (m, 1H), 8.32-8.28 (m, 2H), 8.13-8.08 (m, 1H), 7.73-7.64 (m, 3H), 7.15 (t, J=8.2 Hz, 1H), 6.47 (d, J=8.1 Hz, 1H), 6.39 (dd, J=8.0, 0.6 Hz, 1H), 4.50 (d, J=9.5 Hz, 1H), 4.25 (d, J=9.5 Hz, 1H), 3.46 (s, 3H), 1.88 (dq, J=14.7, 7.4 Hz, 1H), 1.75 (dq, J=14.8, 7.4 Hz, 1H), 0.49 (t, J=7.4 Hz, 3H). LC/MS (APCI+) m/z 412 (M+H)$^+$.

Example 9

5-methoxy-N-(naphthalene-1-sulfonyl)-3,4-dihydro-2H-1-benzopyran-4-carboxamide

Example 9A 5-methoxychroman-4-carbonitrile

In a 50 mL round bottom flask, 5-methoxychroman-4-one (0.998 g, 5.60 mmol) (CAS#863309-86-8) and toluenesulfonylmethyl isocyanide (1.422 g, 7.28 mmol) were dissolved in 1,2-dimethoxyethane (24 mL) to give a colorless solution. The reaction was cooled to −8° C. (internal temperature) with ice/acetone/dry ice under nitrogen. Solid potassium tert-butoxide (1.446 g, 12.88 mmol) was added in portions keeping the internal temperature <−5° C. over about an hour. The reaction was allowed to slowly warm to room temperature overnight. The solvent was removed in vacuo and the crude material was quenched with water (30 mL). The aqueous layer was extracted with ether (4×50 mL). The solvent was removed in vacuo and the crude oil was chromatographed using a 40 g silica gel cartridge with 1-40% ethyl acetate/hexanes to give 5-methoxychroman-4-carbonitrile. $^1$H NMR (501 MHz, Chloroform-d) δ ppm 7.20 (t, J=8.3 Hz, 1H), 6.53 (dd, J=8.4, 1.0 Hz, 1H), 6.50 (dd, J=8.2, 1.0 Hz, 1H), 4.39 (dtd, J=11.6, 3.4, 1.5 Hz, 1H), 4.26 (td, J=11.6, 2.2 Hz, 1H), 4.04 (dt, J=6.0, 2.0 Hz, 1H), 3.92 (s, 3H), 2.33 (ddt, J=14.2, 3.3, 2.3 Hz, 1H), 2.23 (dddd, J=14.2, 11.8, 5.9, 3.6 Hz, 1H). MS (APCI+) m/z 190 (M+H)$^+$.

Example 9B 5-methoxychroman-4-carboxylic Acid

Example 9A (0.491 g, 2.59 mmol) was dissolved in ethanol (8.65 mL). A solution of sodium hydroxide (1.038 g, 25.9 mmol) in water (8 mL) was added, and the resulting mixture was heated at 80° C. for 16 hours. The reaction was heated further at 90° C. overnight, cooled in an ice bath and acidified with 6 M aqueous HCl (5 mL). The solvent volume was reduced and the resulting precipitate was filtered and washed with water to give 5-methoxychroman-4-carboxylic acid. $^1$H NMR (400 MHz, Chloroform-d) δ ppm 9.47 (s, 1H), 7.18 (t, J=8.3 Hz, 1H), 6.58 (d, J=8.3 Hz, 1H), 6.51 (d, J=8.3 Hz, 1H), 4.29 (dt, J=11.4, 4.0 Hz, 1H), 4.21 (td, J=11.3, 2.2 Hz, 1H), 3.93 (s, 4H), 2.37 (dq, J=14.1, 2.9 Hz, 1H), 2.11-2.00 (m, 1H). MS (APCI+) m/z 209 (M+H)$^+$.

Example 9C 5-methoxy-N-(naphthalene-1-sulfonyl)-3,4-dihydro-2H-1-benzopyran-4-carboxamide Example 9B (200 mg, 0.961 mmol) was combined with a mixture of N$^1$-((ethylimino)methylene)-N$^3$,N$^3$-dimethylpropane-1,3-diamine hydrochloride (368 mg, 1.921 mmol) and N,N-dimethylpyridin-4-amine (129 mg, 1.057 mmol) in dichloromethane (2.5 mL). After 30 minutes, naphthalene-1-sulfonamide (199 mg, 0.961 mmol) was added. The reaction was stirred at room temperature for 4 hours, quenched with 2.0 mL of 1 N aqueous HCl and was put through an aqueous/organic extractor tube with dichloromethane. The solvent was removed in vacuo. The crude material was purified by reverse-phase preparative HPLC on a Phenomenex® Luna® C8(2) 5 μm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to give 5-methoxy-N-(naphthalen-1-ylsulfonyl)chroman-4-carboxamide. $^1$H NMR (400 MHz, Chloroform-d) δ ppm 9.60 (s, 1H), 8.51 (dd, J=7.4, 1.3 Hz, 1H), 8.43-8.32 (m, 1H), 8.13 (dt, J=8.2, 1.1 Hz, 1H), 7.98-7.91 (m, 1H), 7.64-7.49 (m, 3H), 7.19 (t, J=8.3 Hz, 1H), 6.51 (d, J=8.3 Hz, 2H), 4.12 (dddd, J=11.3, 4.2, 3.1, 1.5 Hz, 1H), 3.89 (ddd, J=12.0, 11.3, 2.3 Hz, 1H), 3.81 (s, 3H), 3.71 (dt, J=5.5, 2.1 Hz, 1H), 2.22 (dq, J=14.1, 2.6 Hz, 1H), 1.77 (dddd, J=14.0, 12.1, 5.7, 4.0 Hz, 1H). MS (APCI+) m/z 402 (M+H)$^+$.

Example 10

4-ethyl-5-methoxy-N-(naphthalene-1-sulfonyl)-3,4-dihydro-2H-1-benzopyran-4-carboxamide To a cooled (ice bath) solution of Example 9C (50 mg, 0.126 mmol), 1,3-dimethyl-3,4,5,6-tetrahydro-2-pyrimidinone (0.029 mL) and iodoethane (0.022 mL, 0.277 mmol) in tetrahydrofuran (0.5 mL), was added a solution of 1 M lithium bis(trimethylsilyl)amide (0.377 mL, 0.377 mmol) in tetrahydrofuran dropwise. The reaction mixture was stirred cold five minutes before the ice bath was removed and stirring was continued at room temperature for 40 minutes. Additional iodoethane (0.022 mL, 0.277 mmol) was added and additional 1 M lithium bis(trimethylsilyl)amide (0.377 mL, 0.377 mmol) in tetrahydrofuran was added. The reaction was stirred at room temperature overnight. Additional iodoethane (0.022 mL, 0.277 mmol) was added followed by dropwise addition of 1 M lithium bis(trimethylsilyl)amide in tetrahydrofuran (0.377 mL, 0.377 mmol). The reaction mixture was stirred another 4 hours, and was heated at 60° C. for 4 hours. The reaction was quenched with 1 M aqueous HCl (1 mL) and put through an aqueous/organic extractor tube with dichloromethane. The organics were dried with sodium sulfate, filtered, and the crude material was purified by reverse-phase preparative HPLC on a Phenomenex® Luna® C8(2) 5 μm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to give 4-ethyl-5-methoxy-N-(naphthalen-1-ylsulfonyl)chroman-4-carboxamide. $^1$H NMR (400 MHz, Chloroform-d) δ ppm 8.99 (s, 1H), 8.55 (dd, J=7.4, 1.2 Hz, 1H), 8.39-8.30 (m, 1H), 8.13 (d, J=8.2 Hz, 1H), 7.99-7.92 (m, 1H), 7.64 (t, J=7.8 Hz, 1H), 7.62-7.54 (m, 2H), 7.19 (t, J=8.2 Hz, 1H), 6.56 (dd, J=8.3, 1.1 Hz, 1H), 6.39 (dd, J=8.1, 1.1 Hz, 1H), 4.07 (ddd, J=11.3, 6.1, 3.4 Hz, 1H), 3.90 (ddd, J=11.5, 9.1, 2.9 Hz, 1H), 3.35 (s, 3H), 2.11 (ddd, J=14.3, 6.0, 2.8 Hz, 1H), 2.06-1.94 (m, 1H), 1.94-1.84 (m, 2H), 0.56 (t, J=7.5 Hz, 3H). MS (ESI+) m/z 426 (M+H)$^+$.

Example 11

8-bromo-5-methoxy-N-(naphthalene-1-sulfonyl)-3,4-dihydro-2H-1-benzopyran-4-carboxamide

Example 11A 5-methoxychroman-4-carboxylic Acid

To a solution of 5-methoxychroman-4-one [CAS#863309-86-8] (2.7 g, 15.15 mmol) and zinc(II) iodide (0.193 g, 0.606 mmol) in dichloromethane (25 mL) cooled in an ice-bath was added trimethylsilanecarbonitrile (5.69 mL, 45.5 mmol) slowly. The mixture was stirred at ambient temperature for 3 hours. LC/MS showed a new peak at 0.90 minute and the starting material peak at room temperature 0.57 minute nearly disappeared. The solvent was removed under pressure and the residue was purified via chromatography on a 40 g silica gel cartridge, eluting with ethyl acetate in heptane at 0-40% gradient to give the intermediate, 5-methoxy-4-((trimethylsilyl)oxy)chroman-4-carbonitrile (3.2 g). The intermediate was dissolved in acetic acid (40 mL) and aqueous 6 M HCl (6 mL), and tin(II) chloride hydrate (12.58 g, 60.6 mmol) was added. The mixture was heated at 130° C. overnight. LC/MS indicated the conversion was finished. The mixture was concentrated to half its volume and was extracted with dichloromethane (60 mL×3). The combined extracts were washed with water, saturated aqueous NaHCO$_3$ and brine, dried over MgSO$_4$, filtered and concentrated. The residue was purified via chromatography on an 80 g cartridge, eluting with ethyl acetate/methanol in heptane at 5-80% eluent to provide 5-methoxychroman-4-carboxylic acid. $^1$H NMR (501 MHz, dimethylsulfoxide-d$_6$) δ ppm 12.25 (s, 1H), 7.09 (t, J=8.2 Hz, 1H), 6.50 (dd, J=8.2, 1.0 Hz, 1H), 6.41 (dd, J=8.3, 1.0 Hz, 1H), 4.14 (dddd, J=11.1, 4.5, 3.6, 1.0 Hz, 1H), 3.98 (ddd, J=11.0, 10.2, 2.9 Hz, 1H), 3.72 (s, 3H), 3.64 (dd, J=6.6, 3.9 Hz, 1H), 2.14-2.02 (m, 2H).

Example 11B 8-bromo-5-methoxychroman-4-carboxylic Acid

To Example 11A (200 mg, 0.961 mmol) in carbon disulfide (2.5 mL) at 0° C. was added bromine (0.054 mL, 1.06 mmol) in 0.5 mL carbon disulfide dropwise. The mixture was stirred for 30 minutes at room temperature, and LC/MS indicated the conversion was complete and about 5% dibromo-compound also was detected. The solvent was removed and the residue was purified via chromatography on a 12 g silica gel cartridge, eluting with ethyl acetate/methanol (9:1) in heptane at 0-60% gradient to provide the title compound. $^1$H NMR (400 MHz, Chloroform-d) δ ppm 7.40 (d, J=8.7 Hz, 1H), 6.39 (d, J=8.8 Hz, 1H), 4.38 (dtd, J=11.3, 3.9, 1.1 Hz, 1H), 4.24 (td, J=11.1, 2.5 Hz, 1H), 3.91-3.86 (m, 1H), 3.83 (s, 3H), 2.31 (dtd, J=14.3, 3.8, 2.6 Hz, 1H), 2.18 (dtd, J=14.1, 6.8, 3.3 Hz, 1H). MS (ESI+) m/z 286.9 (M+H)$^+$.

Example 11C 8-bromo-5-methoxy-N-(naphthalen-1-ylsulfonyl)chroman-4-carboxamide

A mixture of 8-bromo-5-methoxychroman-4-carboxylic acid (60 mg, 0.209 mmol), N$^1$-((ethylimino)methylene)-N$^3$,N$^3$-dimethylpropane-1,3-diamine hydrochloride (80 mg, 0.418 mmol) and N,N-dimethylpyridin-4-amine (28.1 mg, 0.230 mmol) in dichloromethane (5 mL) was stirred at room temperature for 30 minutes, and naphthalene-1-sulfonamide (43.3 mg, 0.209 mmol) was added. The mixture was stirred at room temperature overnight. LC/MS showed a new product peak at 0.93 minutes and the starting material peak at 0.73 minutes disappeared. The mixture was purified by HPLC on a Phenomenex® Luna® C8(2) 5 um 100 Å AXIA™ column (30 mm×75 mm), with a gradient of acetonitrile (A) and 0.1% trifluoroacetic acid in water (B) was used, at a flow rate of 50 mL/minute (0-1.0 minute 5% A, 1.0-8.5 minute linear gradient 5-100% A, 8.5-11.5 minute 100% A, 11.5-12.0 minute linear gradient 95-5% A) to provide the title compound. $^1$H NMR (501 MHz, Chloroform-d) δ ppm 9.41 (s, 1H), 8.49 (dd, J=7.4, 1.2 Hz, 1H), 8.39-8.30 (m, 1H), 8.12 (dt, J=8.3, 1.1 Hz, 1H), 7.99-7.91 (m, 1H), 7.64-7.49 (m, 3H), 7.43 (d, J=8.8 Hz, 1H), 6.41 (d, J=8.8 Hz, 1H), 4.25 (dddd, J=11.3, 4.3, 3.0, 1.5 Hz, 1H), 3.96-3.89 (m, 1H), 3.78 (s, 3H), 3.72 (dt, J=5.5, 2.0 Hz, 1H), 2.22 (dq, J=14.1, 2.6 Hz, 1H), 1.80-1.73 (m, 1H). MS (ESI+) m/z 477.9 (M+H)$^+$.

Example 12

6,8-dibromo-5-methoxy-N-(naphthalene-1-sulfonyl)-3,4-dihydro-2H-1-benzopyran-4-carboxamide Example 12 was obtained as a by-product during the synthesis of Example 11. $^1$H NMR (400 MHz, Chloroform-d) δ ppm 10.12 (s, 1H), 8.47 (dd, J=7.4, 1.3 Hz, 1H), 8.33 (dd, J=8.6, 1.0 Hz, 1H), 7.91 (dd, J=8.1, 1.4 Hz, 1H), 7.71-7.50 (m, 4H), 4.34-4.22 (m, 1H), 4.00-3.85 (m, 4H), 3.71 (dt, J=5.3, 1.8 Hz, 1H), 2.27 (dq, J=14.2, 2.3 Hz, 1H), 1.76 (dd, J=5.4, 4.3 Hz, 1H). MS (ESI+) m/z 555.8 (M+H)$^+$.

Example 13

8-cyclobutyl-5-methoxy-N-(naphthalene-1-sulfonyl)-3,4-dihydro-2H-1-benzopyran-4-carboxamide Example 11 (31 mg, 0.07 mmol, 1.0 equivalent) was dissolved in tetrahydrofuran (0.5 mL). Dichloro[1,3-bis(2,6-di-3-pentylphenyl)imidazol-2-ylidene](3-chloropyridyl)palladium(II) (PEPPSI IPentCl, 23.4 mg, 0.03 mmol, 0.10 equivalents) in tetrahydrofuran (0.5 mL) was added and the vial was flushed with N$_2$. Cyclobutylzinc(II) bromide (0.5 M in tetrahydrofuran, 0.52 mL, 0.26 mmol, 4.0 equivalents) was added and the reaction mixture was stirred overnight at room temperature. The material was purified directly via reverse phase preparative HPLC/MS method TFA8 to provide the title compound. $^1$H NMR (400 MHz, dimethylsulfoxide-d$_6$:D$_2$O=9:1 (v/v)) δ ppm 8.66 (dd, J=8.6, 1.0 Hz, 1H), 8.32-8.21 (m, 2H), 8.17-8.10 (m, 1H), 7.86-7.77 (m, 1H), 7.76-7.62 (m, 2H), 6.92 (d, J=8.5 Hz, 1H), 6.23 (d, J=8.5 Hz, 1H), 3.99-3.89 (m, 1H), 3.67-3.59 (m, 2H), 3.51-3.37 (m, 1H), 2.89 (s, 3H), 2.18-1.64 (m, 8H). MS (APCI+) m/z 452.0 (M+H)$^+$.

Example 14

8-cyclopentyl-5-methoxy-N-(naphthalene-1-sulfonyl)-3,4-dihydro-2H-1-benzopyran-4-carboxamide Example 11 (31 mg, 0.07 mmol, 1.0 equivalent) was dissolved in tetrahydrofuran (0.5 mL). Dichloro[1,3-bis(2,6-di-3-pentylphenyl)imidazol-2-ylidene](3-chloropyridyl)palladium(II) (PEPPSI IPentCl, 23.4 mg, 0.03 mmol, 0.10 equivalents) dissolved in tetrahydrofuran (0.5 mL) was added and the vial was flushed with N$_2$. Cyclopentylzinc(II) bromide (0.5 M in tetrahydrofuran, 0.52 mL, 0.26 mmol, 4.0 equivalents) was added and the reaction was stirred overnight at room temperature. The material was purified directly via reverse phase preparative HPLC/MS method TFA8 to provide the title compound. $^1$H NMR (400 MHz, dimethylsulfoxide-d$_6$:D$_2$O=9:1 (v/v)) δ ppm 8.69 (d, J=8.7 Hz, 1H), 8.29-8.20 (m, 2H), 8.12 (d, J=8.1 Hz, 1H), 7.79 (t, J=7.9 Hz, 1H), 7.75-7.61 (m, 2H), 6.90 (d, J=8.5 Hz, 1H), 6.22 (d, J=8.5 Hz, 1H), 4.08-3.90 (m, 1H), 3.64 (s, 2H), 3.09-2.97 (m, 1H), 2.94 (s, 3H), 2.03-1.96 (m, 1H), 1.84-1.76 (m, 3H), 1.71-1.62 (m, 2H), 1.62-1.50 (m, 2H), 1.40-1.35 (m, 2H). MS (APCI+) m/z 466.0 (M+H)+.

Example 15

3-ethyl-7-methoxy-N-(naphthalene-1-sulfonyl)-2,3-dihydro-1-benzofuran-3-carboxamide Example 15A Ethyl 7-methoxybenzofuran-3-carboxylate A solution of 2-hydroxy-3-methoxybenzaldehyde (CAS #148-53-8) (3.10 g, 20.4 mmol) in $CH_2Cl_2$ (40 mL) at room temperature was treated with tetrafluoroboric acid-diethyl ether complex (0.560 mL, 4.08 mmol) followed by a solution of ethyl diazoacetate (8.58 mL, 82 mmol) in $CH_2Cl_2$ (30 mL) dropwise over 30 minutes (gas evolution occurred during addition). The mixture was stirred at room temperature for 10 more minutes and was concentrated on a rotavap using a room temperature water bath to remove the solvents. The residue was treated with concentrated $H_2SO_4$ (~3 mL), dropwise at first (exothermic with gas release). The mixture was stirred for 25 minutes, and was diluted with methyl tert-butyl ether (~150 mL). The mixture was cooled to 0° C. and was poured into cold water (150 mL). The layers were separated and the aqueous layer was extracted with methyl tert-butyl ether (75 mL). The combined methyl tert-butyl ether layers were washed with saturated aqueous $NaHCO_3$ solution (30 mL) and brine, dried ($MgSO_4$), filtered, and concentrated. The residue was chromatographed on silica gel, eluting with a gradient of 5% to 30% ethyl acetate in heptane to provide the title compound. $^1$H NMR (400 MHz, $CDCl_3$) δ ppm 8.25 (s, 1H), 7.64 (d, J=7.9 Hz, 1H), 7.27 (t, J=7.9 Hz, 1H), 6.86 (d, J=8.0 Hz, 1H), 4.40 (q, J=7.1 Hz, 2H), 4.01 (s, 3H), 1.42 (t, J=7.1 Hz, 3H).

Example 15B methyl 7-methoxy-2,3-dihydrobenzofuran-3-carboxylate

A solution of Example 15A (ethyl 7-methoxybenzofuran-3-carboxylate) (1.8 g, 8.17 mmol) in methanol (30 mL) was treated in portions with magnesium turnings (0.596 g, 24.52 mmol) over a period of 30 minutes. The mixture was stirred at room temperature for 2 days. The mixture was partitioned between methyl tert-butyl ether (150 mL) and aqueous 1 M HCl (50 mL). The layers were separated and the aqueous layer was extracted with methyl tert-butyl ether (50 mL). The combined methyl tert-butyl ether layers were washed with brine, dried ($MgSO_4$), filtered, concentrated and chromatographed on silica gel, eluting with a gradient of 10% to 50% to provide the title compound. $^1$H NMR (400 MHz, $CDCl_3$) δ ppm 6.99 (dt, J=7.4, 1.0 Hz, 1H), 6.87-6.78 (m, 1H), 4.98 (dd, J=9.3, 6.8 Hz, 1H), 4.72 (t, J=9.5 Hz, 1H), 4.36 (dd, J=9.8, 6.8 Hz, 1H), 3.87 (s, 3H), 3.77 (s, 3H).

Example 15C methyl 3-ethyl-7-methoxy-2,3-dihydrobenzofuran-3-carboxylate

A solution of Example 15B (methyl 7-methoxy-2,3-dihydrobenzofuran-3-carboxylate) (140 mg, 0.672 mmol) and ethyl iodide (543 μl, 6.72 mmol) in N,N-dimethylformamide (2 mL) under $N_2$ at 0° C. was treated dropwise with 1 M potassium tert-butoxide in tetrahydrofuran (1009 μl, 1.009 mmol). The mixture was stirred at 0° C. for 15 minutes and was partitioned between methyl tert-butyl ether (~50 mL) and aqueous 1 M HCl (~10 mL). The methyl tert-butyl ether layer was washed with aqueous 0.2 M HCl (~15 mL) and brine, dried ($MgSO_4$), filtered, concentrated, and chromatographed on silica gel, eluting with a gradient of 5% to 15% ethyl acetate in heptane provided the title compound. $^1$H NMR (400 MHz, $CDCl_3$) δ ppm 6.98 (dd, J=7.5, 1.2 Hz, 1H), 6.85 (t, J=7.8 Hz, 1H), 6.79 (dd, J=8.1, 1.1 Hz, 1H), 5.09 (d, J=9.3 Hz, 1H), 4.42 (d, J=9.3 Hz, 1H), 3.86 (s, 3H), 3.74 (s, 3H), 2.12 (dq, J=14.8, 7.4 Hz, 1H), 1.94-1.84 (m, 1H), 0.87 (t, J=7.4 Hz, 3H).

Example 15D 3-ethyl-7-methoxy-2,3-dihydrobenzofuran-3-carboxylic Acid

A solution of Example 15C (methyl 3-ethyl-7-methoxy-2,3-dihydrobenzofuran-3-carboxylate) (0.103 g, 0.436 mmol) in tetrahydrofuran (3 mL) was diluted with methanol (3 mL), treated with 1 M aqueous NaOH (2 mL), stirred at room temperature for 15 minutes, heated to 45° C. for 20 minutes, cooled, and partitioned between aqueous 1 M HCl (15 mL) and methyl tert-butyl ether (50 mL). The methyl tert-butyl ether layer was washed with brine, dried ($MgSO_4$), filtered, and concentrated to provide the title compound. $^1$H NMR (501 MHz, $CDCl_3$) δ ppm 7.01 (dd, J=7.6, 1.2 Hz, 1H), 6.87 (t, J=7.8 Hz, 1H), 6.81 (dd, J=8.1, 1.1 Hz, 1H), 5.09 (d, J=9.4 Hz, 1H), 4.43 (d, J=9.4 Hz, 1H), 3.87 (s, 3H), 2.16 (dq, J=14.8, 7.4 Hz, 1H), 1.93 (dq, J=14.9, 7.5 Hz, 1H), 0.91 (t, J=7.4 Hz, 3H).

Example 15E 3-ethyl-7-methoxy-N-(naphthalene-1-sulfonyl)-2,3-dihydro-1-benzofuran-3-carboxamide To a solution of Example 15D (3-ethyl-7-methoxy-2,3-dihydrobenzofuran-3-carboxylic acid) (32 mg, 0.144 mmol), 1-(3-dimethylaminopropyl)-3-ethylcarbodiimide hydrochloride (55.2 mg, 0.288 mmol) and 4-dimethylaminopyridine (19.35 mg, 0.158 mmol) in $CH_2Cl_2$ (0.3 mL) was added naphthalene-1-sulfonamide (32.8 mg, 0.158 mmol). The mixture was stirred for 1 hour, diluted with $CH_2Cl_2$ (2 mL), diluted further with methyl tert-butyl ether (~30 mL), washed with aqueous 1 M HCl (~15 mL), washed with brine, dried ($MgSO_4$), filtered, and concentrated to dryness. The residue was diluted with N,N-dimethylformamide (1.5 mL) and was purified by reverse-phase HPLC [Waters XBridge™ RP18 column, m, 30×100 mm, flow rate 40 mL/minute, 5-40% (over 15 minutes) gradient of acetonitrile in 0.1% TFA] to provide the title compound. $^1$H NMR (400 MHz, dimethylsulfoxide-$d_6$) δ ppm 12.36 (s, 1H), 8.61 (d, J=8.5 Hz, 1H), 8.30-8.26 (m, 2H), 8.09 (d, J=7.5 Hz, 1H), 7.75-7.64 (m, 3H), 7.03 (dd, J=7.4, 1.3 Hz, 1H), 6.82 (dd, J=8.1, 1.2 Hz, 1H), 6.79-6.75 (m, 1H), 4.72 (d, J=9.4 Hz, 1H), 4.22 (d, J=9.4 Hz, 1H), 3.69 (s, 3H), 2.19 (dq, J=14.6, 7.3 Hz, 1H), 1.73 (dq, J=14.7, 7.3 Hz, 1H), 0.45 (t, J=7.4 Hz, 3H). LC/MS (APCI+) m/z 382 (M+H)+.

Example 16

2-methyl-N-(2-methylbenzene-1-sulfonyl)-2,3-dihydro-1-benzofuran-2-carboxamide

2-Methyl-2,3-dihydrobenzofuran-2-carboxylic acid (CAS: 93885-44-0, 80 mg, 0.45 mmol) and 1,1'-carbonyldiimidazole (CAS: 530-62-1, 120 mg, 0.74 mmol) were combined in anhydrous tetrahydrofuran (2 mL), and the mixture was heated at 50° C. and stirred for 30 minutes. The mixture was cooled to room temperature and 2-methylbenzenesulfonamide (CAS: 88-19-7, 80 mg, 0.47 mmol) and DBU (2,3,4,6,7,8,9,10-octahydropyrimido[1,2-a]azepine, CAS: 6674-22-2, 76 µL, 0.51 mmol) were added. The resultant mixture was stirred at room temperature for 24 hours. The reaction mixture was diluted with water and the mixture was extracted with ethyl acetate (3 times). The combined organic layers were dried (MgSO$_4$), filtered and concentrated under reduced pressure. The resultant residue was taken up in acetonitrile and filtered. The crude material was purified by reversed-phase HPLC (Waters Sunfire C18 150×19 mm id 10 um, flow rate 20 mL/minute, 5-20% (0 to 1 minute), 20% (1 to 3.5 minute), 20-80% (3.5 to 16 minute), 80% (16-23.5 minute) gradient of acetonitrile in 0.1% formic acid) to provide the title compound. $^1$H NMR (400 MHz, dimethylsulfoxide-d$_6$) δ ppm 12.55 (m, 1H), 7.95-7.92 (m, 1H), 7.58-7.54 (m, 1H), 7.44-7.35 (m, 2H), 7.16 (dd, J=7.5, 15.1 Hz, 2H), 6.89-6.84 (m, 2H), 3.43 (d, J=16.1 Hz, 1H), 3.06 (d, J=16.2 Hz, 1H), 2.50-2.49 (m, 3H obs), 1.54 (s, 3H). MS (ESI) m/z 332 (M+H)$^+$.

Example 17

N-(2-methylbenzene-1-sulfonyl)-2,3-dihydro-1-benzofuran-2-carboxamide

The title compound was prepared and purified as described in Example 1, substituting 2,3-dihydrobenzofuran-2-carboxylic acid for 6-bromo-4-phenyl-chroman-4-carboxylic acid, and 2-methylbenzene-1-sulfonyl chloride for naphthalene-1-sulfonamide. $^1$H NMR (400 MHz, dimethylsulfoxide-d$_6$:D$_2$O=9:1 (v/v)) δ ppm 7.95 (dd, J=8.2, 1.4 Hz, 1H), 7.88-7.69 (m, 1H), 7.63-7.50 (m, 1H), 7.48-7.35 (m, 2H), 7.24-7.17 (m, 1H), 7.17-7.07 (m, 1H), 6.93-6.78 (m, 2H), 5.24-5.13 (m, 1H), 3.54-3.42 (m, 1H), 3.16-3.03 (m, 1H), 2.59 (s, 3H). MS (APCI+) m/z 318.1 (M+H)$^+$.

Example 18

6-methyl-N-(naphthalene-1-sulfonyl)-4-phenyl-3,4-dihydro-2H-1-benzopyran-4-carboxamide The title compound was prepared and purified as described in Example 1, substituting 6-methyl-4-phenyl-chroman-4-carboxylic acid for 6-bromo-4-phenyl-chroman-4-carboxylic acid. $^1$H NMR (400 MHz, dimethylsulfoxide-d$_6$:D$_2$O=9:1 (v/v)) δ ppm 8.62-8.54 (m, 1H), 8.30 (dd, J=7.4, 1.3 Hz, 1H), 8.26-8.19 (m, 1H), 8.10-8.03 (m, 1H), 7.69-7.56 (m, 3H), 7.26-7.13 (m, 3H), 6.93-6.82 (m, 3H), 6.62 (d, J=8.3 Hz, 1H), 6.47 (d, J=2.1 Hz, 1H), 3.87-3.76 (m, 1H), 3.76-3.65 (m, 1H), 2.87-2.75 (m, 1H), 2.28-2.16 (m, 1H), 1.91 (s, 3H). MS (APCI+) m/z 458.0 (M+H)$^+$.

Example 19

6-chloro-N-(naphthalene-1-sulfonyl)-4-phenyl-3,4-dihydro-2H-1-benzopyran-4-carboxamide The title compound was prepared and purified as described in Example 1, substituting 6-chloro-4-phenylchroman-4-carboxylic acid for 6-bromo-4-phenyl-chroman-4-carboxylic acid. $^1$H NMR (400 MHz, dimethylsulfoxide-d$_6$: D$_2$O=9:1 (v/v)) δ ppm 8.64-8.56 (m, 1H), 8.28 (dd, J=7.4, 1.3 Hz, 1H), 8.24-8.16 (m, 1H), 8.09-8.01 (m, 1H), 7.68-7.55 (m, 3H), 7.27-7.14 (m, 3H), 7.08 (dd, J=8.8, 2.6 Hz, 1H), 6.93-6.85 (m, 2H), 6.76-6.68 (m, 2H), 3.90-3.74 (m, 2H), 2.86-2.75 (m, 1H), 2.32-2.20 (m, 1H). MS (APCI+) m/z 477.9 (M+H)$^+$.

Example 20

4-methoxy-N-(naphthalene-1-sulfonyl)-2,3-dihydro-1-benzofuran-3-carboxamide

Example 20A 4-methoxy-2,3-dihydrobenzofuran-3-carboxylic acid

A solution of Example 8D (methyl 4-methoxy-2,3-dihydrobenzofuran-3-carboxylate) (0.51 g, 2.449 mmol) in tetrahydrofuran (6 mL) and methanol (6 mL) was treated with 1 M aqueous NaOH (5 mL, 5.00 mmol) and was stirred at room temperature overnight. The mixture was concentrated to remove the majority of tetrahydrofuran and methanol. The residue was partitioned between aqueous 1 M HCl (15 mL) and methyl tert-butyl ether (50 mL). The methyl tert-butyl ether layer was washed with brine, dried (MgSO$_4$), filtered, and concentrated to provide the title compound. $^1$H NMR (501 MHz, CDCl$_3$) δ ppm 7.19 (d, J=13.2 Hz, 1H), 6.52 (d, J=8.1 Hz, 1H), 6.48 (d, J=8.3 Hz, 1H), 4.94 (dd, J=9.3, 5.3 Hz, 1H), 4.70 (dd, J=9.9, 9.5 Hz, 1H), 4.35 (dd, J=9.9, 5.3 Hz, 1H), 3.90 (s, 3H).

Example 20B 4-methoxy-N-(naphthalene-1-sulfonyl)-2,3-dihydro-1-benzofuran-3-carboxamide To a solution of Example 20A (4-methoxy-2,3-dihydrobenzofuran-3-carboxylic acid) (25 mg, 0.129 mmol), 1-(3-dimethylaminopropyl)-3-ethylcarbodiimide hydrochloride (49.4 mg, 0.257 mmol) and 4-dimethylaminopyridine (17.30 mg, 0.142 mmol) in CH$_2$Cl$_2$ (0.3 mL) was added naphthalene-1-sulfonamide (29.4 mg, 0.142 mmol). The mixture was stirred at room temperature for 3 hours, concentrated with a stream of N$_2$, dissolved in N,N-dimethylformamide (1 mL) and directly purified by reverse-phase HPLC [Waters XBridge™ RP18 column, 5 µm, 30×100 mm, flow rate 40 mL/minute, 5-40% (over 15 minutes) gradient of acetonitrile in 0.1% TFA] to provide the title compound. $^1$H NMR (400 MHz, dimethylsulfoxide-d$_6$) δ ppm 12.72 (s, 1H), 8.65 (d, J=8.5 Hz, 1H), 8.33-8.27 (m, 2H), 8.14 (d, J=8.0 Hz, 1H), 7.81 (ddd, J=8.5, 6.9, 1.3 Hz, 1H), 7.74-7.67 (m, 2H), 7.04 (t, J=8.2 Hz, 1H), 6.35-6.32 (m, 2H), 4.62 (t, J=9.3 Hz, 1H), 4.29 (dd, J=9.5, 6.0 Hz, 1H), 4.21 (dd, J=8.9, 6.0 Hz, 1H), 3.25 (s, 3H). LC/MS (APCI+) m/z 384 (M+H)$^+$.

Example 21

7-bromo-N-(naphthalene-1-sulfonyl)-2,3-dihydro-1-benzofuran-3-carboxamide

Example 21A

Ethyl 2-(2-bromophenoxy)acetate

A solution of 2-bromophenol (6.13 mL, 57.8 mmol) in acetone (30 mL) was treated with ethyl bromoacetate (9.01 mL, 81 mmol) and was heated to reflux for 2 hours. The mixture was cooled and filtered to remove the solids. The solids were washed with ethyl acetate. The combined filtrates were concentrated and dried under vacuum at ~50° C. for 1 hour to provide the title compound. $^1$H NMR (501 MHz, CDCl$_3$) δ ppm 7.56 (dd, J=7.9, 1.6 Hz, 1H), 7.24 (ddd, J=8.2, 7.5, 1.6 Hz, 1H), 6.88 (td, J=7.7, 1.3 Hz, 1H), 6.82 (dd, J=8.2, 1.3 Hz, 1H), 4.69 (s, 2H), 4.27 (q, J=7.1 Hz, 2H), 1.29 (t, J=7.1 Hz, 3H).

Example 21B

Diethyl 2-(2-bromophenoxy)-3-oxosuccinate

A suspension of 60% dispersion of sodium hydride in mineral oil (2.427 g, 60.7 mmol) in diethyl ether (anhydrous, 150 mL) was treated dropwise with ethanol (3.37 mL, 57.8 mmol) over 5 minutes, treated with diethyl oxalate (9.16 mL, 67.0 mmol), heated to reflux, treated dropwise with a solution of Example 21A (ethyl 2-(2-bromophenoxy)acetate) (14.98 g, 57.8 mmol) in diethyl ether (anhydrous, 30 mL) and heated to reflux for 2 more hours. The mixture was cooled and poured into a swirled mixture of aqueous 2 M HCl (100 mL) and ice (100 g). The layers were separated and the aqueous layer was extracted with methyl tert-butyl ether (200 mL). The combined organic layers were washed with brine, dried (MgSO$_4$), filtered, and concentrated to provide the title compound.

Example 21C

Diethyl 7-bromobenzofuran-2,3-dicarboxylate

A flask containing concentrated H$_2$SO$_4$ (180 mL) was cooled to −15° C. and was treated portionwise with Example 21B (diethyl 2-(2-bromophenoxy)-3-oxosuccinate) (20.76 g, 57.8 mmol). The mixture was allowed to slowly warm up to 15° C. over about 5 hours. The mixture was slowly poured into a stirred mixture of 1 L ice water and methyl tert-butyl ether (300 mL). More ice was added during the addition to bring the final volume of the aqueous layer to 1.5 L. The methyl tert-butyl ether layer was isolated and the aqueous layer was extracted with methyl tert-butyl ether (300 mL). The combined methyl tert-butyl ether layers were washed with brine, dried (MgSO$_4$), filtered, and concentrated. The residue was chromatographed on silica gel, eluting with a gradient of 10% to 20% ethyl acetate in heptanes to provide the title compound. $^1$H NMR (400 MHz, CDCl$_3$) δ ppm 7.88 (dd, J=8.0, 1.0 Hz, 1H), 7.63 (dd, J=7.8, 1.0 Hz, 1H), 7.26 (t, J=7.9 Hz, 1H), 4.47 (dq, J=9.3, 7.1 Hz, 4H), 1.46-1.41 (m, 6H).

Example 21D

Ethyl 7-bromobenzofuran-3-carboxylate

A solution of Example 21C (diethyl 7-bromobenzofuran-2,3-dicarboxylate) (9.4 g, 27.6 mmol) in dimethylsulfoxide (65 mL) was treated with sodium chloride (3.22 g, 55.1 mmol), treated with water (0.993 mL, 55.1 mmol), heated to 160° C. under N$_2$ for 8 hours and was allowed to stir at room temperature overnight. The mixture was cooled in an ice bath and was added to 150 g of ice. The mixture was diluted with water (100 mL) and extracted with methyl tert-butyl ether four times, using 100 mL for each extraction. The combined methyl tert-butyl ether extractions were washed with brine, dried (MgSO$_4$), filtered, and concentrated. The residue was chromatographed on silica gel, eluting with a gradient of 5% to 15% ethyl acetate in heptanes to provide the title compound. $^1$H NMR (501 MHz, CDCl$_3$) δ ppm 8.30 (s, 1H), 8.01 (dd, J=7.9, 1.1 Hz, 1H), 7.53 (dd, J=7.8, 1.0 Hz, 1H), 7.24 (t, J=7.8 Hz, 1H), 4.41 (q, J=7.1 Hz, 2H), 1.43 (t, J=7.1 Hz, 3H).

Example 21E

Methyl 7-bromo-2,3-dihydrobenzofuran-3-carboxylate

A solution of Example 21D (ethyl 7-bromobenzofuran-3-carboxylate) (2.58 g, 9.59 mmol) in methanol (30 mL) was treated in portions with magnesium turnings (0.699 g, 28.8 mmol) over a period of 30 minutes. After stirring at room temperature for about 1 hour, the magnesium started to react. The reaction was stirred for approximately 30 minutes at room temperature, while cooling intermittently with an ice bath to keep the temperature of the reaction at about room temperature. The mixture was stored overnight at 0° C. The mixture was partitioned between methyl tert-butyl ether (200 mL) and aqueous 1 M HCl (~100 mL). The layers were separated and the aqueous layer was extracted with additional methyl tert-butyl ether. The combined organic layers were washed with brine, dried (MgSO$_4$), filtered, concentrated and chromatographed on silica gel, eluting with a gradient of 5% to 20% ethyl acetate in heptane to provide the title compound. $^1$H NMR (400 MHz, CDCl$_3$) δ ppm 7.34 (d, J=8.0 Hz, 1H), 7.31 (dt, J=7.5, 1.1 Hz, 1H), 6.77 (t, J=7.7 Hz, 1H), 5.01 (dd, J=9.4, 6.8 Hz, 1H), 4.76 (t, J=9.6 Hz, 1H), 4.43 (dd, J=9.8, 6.8 Hz, 1H), 3.78 (s, 3H).

Example 21F 7-bromo-2,3-dihydrobenzofuran-3-carboxylic Acid

A solution of Example 21E (methyl 7-bromo-2,3-dihydrobenzofuran-3-carboxylate) (85 mg, 0.331 mmol) in tetrahydrofuran (2 mL) and methanol (2 mL) was treated with 1 M aqueous NaOH (1500 μl, 1.500 mmol) and was stirred at room temperature for 30 minutes. The mixture was partitioned between methyl tert-butyl ether (50 mL) and aqueous 0.2 M HCl (~25 mL). The methyl tert-butyl ether layer was washed with brine, dried (MgSO$_4$), filtered, and concentrated to provide the title compound. $^1$H NMR (501 MHz, CDCl$_3$) δ ppm 7.36 (ddd, J=7.3, 5.4, 0.9 Hz, 2H), 6.80 (t, J=7.8 Hz, 1H), 5.01 (dd, J=9.5, 6.5 Hz, 1H), 4.77 (t, J=9.6 Hz, 1H), 4.47 (dd, J=9.8, 6.6 Hz, 1H).

Example 21G 7-bromo-N-(naphthalene-1-sulfonyl)-2,3-dihydro-1-benzofuran-3-carboxamide A solution of Example 21F (7-bromo-2,3-dihydrobenzofuran-3-carboxylic acid) (25 mg, 0.103 mmol), 1-(3-dimethylaminopropyl)-3-ethylcarbodiimide hydrochloride (39.4 mg, 0.206 mmol) and 4-dimethylaminopyridine (13.82 mg, 0.113 mmol) in CH$_2$Cl$_2$ (0.3 mL) was added naphthalene-1-sulfonamide (23.45 mg, 0.113 mmol). The mixture was stirred at room temperature for 25 minutes, concentrated with a stream of nitrogen, dissolved in N,N-dimethylformamide (~1 mL) and directly purified by reverse-phase HPLC [Waters XBridge™ RP18 column, 5 μm, 30×100 mm, flow rate 40 mL/minute, 5-40% (over 15 minutes) gradient of acetonitrile in 0.1% TFA] to provide the title compound. $^1$H NMR (501 MHz, dimethylsulfoxide-d$_6$) δ ppm 13.02 (s, 1H), 8.66 (dd, J=8.6, 0.7 Hz, 1H), 8.31-8.24 (m, 2H), 8.10 (d, J=8.2 Hz, 1H), 7.84 (ddd, J=8.5, 6.9, 1.3 Hz, 1H), 7.71

(ddd, J=8.1, 6.9, 1.0 Hz, 1H), 7.67 (dd, J=8.1, 7.5 Hz, 1H), 7.25-7.23 (m, 1H), 7.11 (dt, J=7.5, 1.0 Hz, 1H), 6.55-6.52 (m, 1H), 4.63-4.57 (m, 2H), 4.45 (t, J=7.4 Hz, 1H). LC/MS (APCI+) m/z 432, 434 (M+H)+.

Example 22

7-bromo-3-ethyl-N-(naphthalene-1-sulfonyl)-2,3-dihydro-1-benzofuran-3-carboxamide Example 22A methyl 7-bromo-3-ethyl-2,3-dihydrobenzofuran-3-carboxylate A solution of Example 21E (methyl 7-bromo-2,3-dihydrobenzofuran-3-carboxylate) (250 mg, 0.972 mmol) and ethyl iodide (393 μl, 4.86 mmol) in N,N-dimethylformamide (2 mL) under $N_2$ at 0° C. was treated dropwise with 1 M potassium tert-butoxide in tetrahydrofuran (1459 μl, 1.459 mmol), stirred at 0° C. for 15 minutes, and partitioned between methyl tert-butyl ether (~50 mL) and aqueous 0.5 M HCl (~20 mL). The methyl tert-butyl ether layer was washed with water, washed with brine, dried ($MgSO_4$), filtered, concentrated, and chromatographed on silica gel, eluting with a gradient of 5% to 15% ethyl acetate in heptane to provide the impure title compound. $^1$H NMR (400 MHz, $CDCl_3$) δ ppm 7.34 (dd, J=8.0, 1.2 Hz, 1H), 7.30 (dd, J=7.5, 1.2 Hz, 1H), 6.81-6.77 (m, 1H), 5.13 (d, J=9.4 Hz, 1H), 4.46 (d, J=9.4 Hz, 1H), 3.76 (s, 3H), 2.17-2.07 (m, 1H), 1.96-1.85 (m, 1H), 0.88 (t, J=7.4 Hz, 3H)).

Example 22B 7-bromo-3-ethyl-2,3-dihydrobenzofuran-3-carboxylic Acid

A solution of Example 22A (methyl 7-bromo-3-ethyl-2,3-dihydrobenzofuran-3-carboxylate) (0.277 g, 0.972 mmol) in tetrahydrofuran (3 mL) and methanol (3 mL) was treated with 1 M aqueous NaOH (2 mL), stirred at room temperature for 30 minutes, and partitioned between methyl tert-butyl ether (~30 mL) and saturated aqueous $NaHCO_3$ solution (~30 mL). The methyl tert-butyl ether layer was discarded. The $NaHCO_3$ layer was acidified with aqueous 6 M HCl and was extracted with methyl tert-butyl ether (50 mL). The methyl tert-butyl ether layer was washed with brine, dried ($MgSO_4$), filtered, and concentrated to provide the title compound which contained an impurity. $^1$H NMR (501 MHz, $CDCl_3$) δ ppm 7.36 (dd, J=8.0, 1.1 Hz, 1H), 7.33 (dd, J=7.5, 1.1 Hz, 1H), 6.80 (t, J=7.8 Hz, 1H), 5.12 (d, J=9.5 Hz, 1H), 4.46 (d, J=9.5 Hz, 1H), 2.16 (dq, J=14.8, 7.4 Hz, 1H), 1.94 (dq, J=14.8, 7.5 Hz, 1H), 0.92 (t, J=7.4 Hz, 3H).

Example 22C 7-bromo-3-ethyl-N-(naphthalene-1-sulfonyl)-2,3-dihydro-1-benzofuran-3-carboxamide To a solution of Example 22B (7-bromo-3-ethyl-2,3-dihydrobenzofuran-3-carboxylic acid) (34 mg, 0.125 mmol), 1-(3-dimethylaminopropyl)-3-ethylcarbodiimide hydrochloride (48.1 mg, 0.251 mmol) and 4-dimethylaminopyridine (16.85 mg, 0.138 mmol) in $CH_2Cl_2$ (0.3 mL) was added naphthalene-1-sulfonamide (28.6 mg, 0.138 mmol). The mixture was stirred at room temperature overnight. The mixture was diluted with methyl tert-butyl ether (~30 mL), washed with aqueous 1 M HCl (15 mL), washed with brine, dried ($MgSO_4$), filtered, concentrated and chromatographed on silica gel, eluting with a gradient of 50% to 100% ethyl acetate in heptane to provide the title compound. $^1$H NMR (400 MHz, dimethylsulfoxide-$d_6$) δ ppm 8.58 (d, J=8.4 Hz, 1H), 8.19 (s, 2H), 8.02 (d, J=7.1 Hz, 1H), 7.68-7.55 (m, 3H), 7.35 (d, J=7.5 Hz, 1H), 7.28 (d, J=7.9 Hz, 1H), 6.73 (t, J=7.7 Hz, 1H), 4.80 (d, J=9.3 Hz, 1H), 4.29 (d, J=9.3 Hz, 1H), 2.16-2.01 (m, 1H), 1.78-1.65 (m, 1H), 0.43 (t, J=7.3 Hz, 3H). LC/MS (APCI+) m/z 460.462 (M+H)+.

Example 23

3-ethyl-N-(naphthalene-1-sulfonyl)-2,3-dihydro-1-benzofuran-3-carboxamide

Example 23A methyl 3-ethyl-2,3-dihydrobenzofuran-3-carboxylate

A solution of methyl 2,3-dihydrobenzofuran-3-carboxylate (CAS #39891-56-0) (76 mg, 0.427 mmol) and ethyl iodide (345 μl, 4.27 mmol) in N,N-dimethylformamide (2 mL) under $N_2$ at 0° C. was treated dropwise with 1 M potassium tert-butoxide in tetrahydrofuran (640 μl, 0.640 mmol). The mixture was stirred at 0° C. for 15 minutes and was partitioned between methyl tert-butyl ether (~50 mL) and aqueous 1 M HCl (~10 mL). The methyl tert-butyl ether layer was washed with brine, dried ($MgSO_4$), filtered, and concentrated. The residue was chromatographed on silica gel, eluting with a gradient of 5% to 15% ethyl acetate in heptane to provide the title compound. $^1$H NMR (501 MHz, $CDCl_3$) δ ppm 7.36 (ddd, J=7.6, 1.4, 0.5 Hz, 1H), 7.18 (ddd, J=8.1, 7.5, 1.4 Hz, 1H), 6.90 (td, J=7.5, 1.0 Hz, 1H), 6.80 (ddd, J=8.1, 0.9, 0.5 Hz, 1H), 5.04 (d, J=9.3 Hz, 1H), 4.36 (d, J=9.2 Hz, 1H), 3.75 (s, 3H), 2.18-2.10 (m, 1H), 1.93-1.85 (m, 1H), 0.88 (t, J=7.4 Hz, 3H).

Example 23B 3-ethyl-2,3-dihydrobenzofuran-3-carboxylic Acid

A solution of Example 23A (methyl 3-ethyl-2,3-dihydrobenzofuran-3-carboxylate) (53 mg, 0.257 mmol) in tetrahydrofuran (1.5 mL) was diluted with methanol (1.5 mL), treated with 1 M aqueous NaOH (1 mL, 1 mmol), stirred at room temperature for 30 minutes, acidified with aqueous 1 M HCl (~3 mL) and extracted with methyl tert-butyl ether (50 mL). The methyl tert-butyl ether layer was washed with brine, dried ($MgSO_4$), filtered, and concentrated to provide the title compound. $^1$H NMR (400 MHz, $CDCl_3$) δ ppm 7.41-7.37 (m, 1H), 7.22-7.17 (m, 1H), 6.91 (td, J=7.5, 1.0 Hz, 1H), 6.81 (d, J=7.8 Hz, 1H), 5.03 (d, J=9.3 Hz, 1H), 4.36 (d, J=9.3 Hz, 1H), 2.18 (dq, J=14.7, 7.4 Hz, 1H), 1.93 (dq, J=14.8, 7.4 Hz, 1H), 0.92 (t, J=7.4 Hz, 3H).

Example 23C 3-ethyl-N-(naphthalene-1-sulfonyl)-2,3-dihydro-1-benzofuran-3-carboxamide A solution of 3-ethyl-2,3-dihydrobenzofuran-3-carboxylic acid (25 mg, 0.130 mmol), 1-(3-dimethylaminopropyl)-3-ethylcarbodiimide hydrochloride (49.9 mg, 0.260 mmol) and 4-dimethylaminopyridine (17.48 mg, 0.143 mmol) in $CH_2Cl_2$ (0.3 mL) was treated with naphthalene-1-sulfonamide (29.7 mg, 0.143 mmol), stirred at room temperature overnight, concentrated with a stream of N$_2$, diluted with N,N-dimethylformamide (~1 mL) and directly purified by reverse-phase HPLC [Waters XBridge™ RP18 column, 5 µm, 30×100 mm, flow rate 40 mL/minute, 5-40% (over 15 minutes) gradient of acetonitrile in 0.1% TFA] to provide the title compound. $^1$H NMR (500 MHz, dimethylsulfoxide-d$_6$) δ ppm 12.43 (bs, 1H), 8.62 (d, J=8.7 Hz, 1H), 8.31-8.27 (m, 2H), 8.10 (d, J=8.0 Hz, 1H), 7.74 (ddd, J=8.5, 6.9, 1.3 Hz, 1H), 7.71-7.65 (m, 2H), 7.46 (dd, J=7.6, 1.1 Hz, 1H), 7.12 (td, J=8.0, 1.4 Hz, 1H), 6.83 (td, J=7.5, 0.9 Hz, 1H), 6.70 (d, J=7.8 Hz, 1H), 4.71 (d, J=9.4 Hz, 1H), 4.23 (d, J=9.4 Hz, 1H), 2.20 (dq, J=14.6, 7.3 Hz, 1H), 1.76 (dq, J=14.7, 7.3 Hz, 1H), 0.45 (t, J=7.4 Hz, 3H). LC/MS (APCI+) m/z 382 (M+H)$^+$.

Example 24

N-(naphthalene-1-sulfonyl)-3,4-dihydro-2H-1-benzopyran-4-carboxamide

A mixture of chroman-4-carboxylic acid (30 mg, 0.168 mmol) [20426-80-6], N$^1$-((ethylimino)methylene)-N$^3$,N$^3$-dimethylpropane-1,3-diamine hydrochloride (64.6 mg, 0.337 mmol) and N,N-dimethylpyridin-4-amine (22.63 mg, 0.185 mmol) in dichloromethane (5 mL) was stirred at ambient temperature for 30 minutes, and naphthalene-1-sulfonamide (34.9 mg, 0.168 mmol) was added. The mixture was stirred for another 4 hours, and dichloromethane (20 mL) was added. The mixture was washed with saturated aqueous NaHCO$_3$ and brine, and concentrated. Purification via HPLC on a Phenomenex® Luna® C8(2) 5 um 100 Å AXIA™ column (30 mm×75 mm), with a gradient of acetonitrile (A) and 0.1% trifluoroacetic acid in water (B) was used, at a flow rate of 50 mL/minute (0-1.0 minute 5% A, 1.0-8.5 minute linear gradient 5-100% A, 8.5-11.5 minute 100% A, 11.5-12.0 minute linear gradient 95-5% A) provided the title compound. $^1$H NMR (500 MHz, Chloroform-d) δ ppm 8.52 (dd, J=7.4, 1.3 Hz, 1H), 8.40 (s, 1H), 8.33-8.28 (m, 1H), 8.18-8.13 (m, 1H), 8.02-7.97 (m, 1H), 7.68-7.60 (m, 3H), 7.25 (dddd, J=8.2, 7.1, 1.8, 0.5 Hz, 1H), 6.91-6.80 (m, 3H), 4.01 (dddd, J=11.5, 4.7, 3.6, 1.1 Hz, 1H), 3.68 (ddd, J=11.4, 10.5, 2.7 Hz, 1H), 3.57 (t, J=5.2 Hz, 1H), 2.17 (dtd, J=14.1, 4.6, 2.7 Hz, 1H), 2.07-2.00 (m, 1H). MS (ESI+) m/z 368 (M+H)$^+$.

Example 25

7-methoxy-N-(naphthalene-1-sulfonyl)-2,3-dihydro-1-benzofuran-3-carboxamide

Example 25A

Ethyl 7-methoxybenzofuran-3-carboxylate

A solution of 2-hydroxy-3-methoxybenzaldehyde (3.10 g, 20.4 mmol) in CH$_2$Cl$_2$ (40 mL) at room temperature was treated with tetrafluoroboric acid-diethyl ether complex (0.560 mL, 4.08 mmol) followed by a solution of ethyl diazoacetate (8.58 mL, 82 mmol) in CH$_2$Cl$_2$ (30 mL) dropwise over 30 minutes (gas evolution occurred during addition). The mixture was stirred at room temperature for 10 more minutes and was concentrated on a rotavap using a room temperature water bath. The residue was treated with concentrated H$_2$SO$_4$ (~3 mL), dropwise at first (exothermic with gas release). The mixture was stirred for 25 minutes, diluted with methyl tert-butyl ether (~150 mL), cooled to 0° C. and poured into cold water (150 mL). The layers were separated and the aqueous layer was extracted with methyl tert-butyl ether (75 mL). The combined methyl tert-butyl ether layers was washed with saturated aqueous NaHCO$_3$ solution (30 mL), washed with brine, dried (MgSO$_4$), filtered, and concentrated. The residue was chromatographed on silica gel, eluting with a gradient of 5% to 30% ethyl acetate in heptane to provide the title compound. $^1$H NMR (400 MHz, CDCl$_3$) δ ppm 8.25 (s, 1H), 7.64 (d, J=7.9 Hz, 1H), 7.27 (t, J=7.9 Hz, 1H), 6.86 (d, J=8.0 Hz, 1H), 4.40 (q, J=7.1 Hz, 2H), 4.01 (s, 3H), 1.42 (t, J=7.1 Hz, 3H).

Example 25B

Methyl 7-methoxy-2,3-dihydrobenzofuran-3-carboxylate

A solution of Example 25A (ethyl 7-methoxybenzofuran-3-carboxylate) (1.8 g, 8.17 mmol) in methanol (30 mL) was treated in portions with magnesium turnings (0.596 g, 24.52 mmol) over a period of 30 minutes. The mixture was stirred at room temperature for 2 days, and partitioned between methyl tert-butyl ether (150 mL) and aqueous 1 M HCl (50 mL). The layers were separated and the aqueous layer was extracted with methyl tert-butyl ether (50 mL). The combined methyl tert-butyl ether layers were washed with brine, dried (MgSO$_4$), filtered, concentrated and chromatographed on silica gel, eluting with a gradient of 10% to 50% to provide the title compound. $^1$H NMR (400 MHz, CDCl$_3$) δ ppm 6.99 (dt, J=7.4, 1.0 Hz, 1H), 6.87-6.78 (m, 1H), 4.98 (dd, J=9.3, 6.8 Hz, 1H), 4.72 (t, J=9.5 Hz, 1H), 4.36 (dd, J=9.8, 6.8 Hz, 1H), 3.87 (s, 3H), 3.77 (s, 3H).

Example 25C 7-methoxy-2,3-dihydrobenzofuran-3-carboxylic Acid

A solution of Example 25B (methyl 7-methoxy-2,3-dihydrobenzofuran-3-carboxylate) (0.29 g, 1.393 mmol) in tetrahydrofuran (4 mL) was diluted with methanol (4 mL), treated with 1 M aqueous NaOH (3 mL), stirred at room temperature for 15 minutes, and partitioned between aqueous 1 M HCl (15 mL) and methyl tert-butyl ether (50 mL). The methyl tert-butyl ether layer was washed with brine, dried (MgSO$_4$), filtered, and concentrated to provide the title compound. $^1$H NMR (400 MHz, CDCl$_3$) δ ppm 7.02 (dt, J=7.4, 1.0 Hz, 1H), 6.89-6.79 (m, 2H), 4.97 (dd, J=9.4, 6.5 Hz, 1H), 4.72 (t, J=9.6 Hz, 1H), 4.39 (dd, J=9.7, 6.5 Hz, 1H), 3.87 (s, 3H).

Example 25D 7-methoxy-N-(naphthalene-1-sulfonyl)-2,3-dihydro-1-benzofuran-3-carboxamide To a solution of Example 25C (7-methoxy-2,3-dihydrobenzofuran-3-carboxylic acid) (33 mg, 0.170 mmol), 1-(3-dimethylaminopropyl)-3-ethylcarbodiimide hydrochloride (65.2 mg, 0.340 mmol) and 4-dimethylaminopyridine (22.84 mg, 0.187 mmol) in CH$_2$Cl$_2$ (0.3 mL) was added naphthalene-1-sulfonamide (38.7 mg, 0.187 mmol). The mixture was stirred for 1 hour, diluted with CH$_2$Cl$_2$ (2 mL), diluted further with methyl tert-butyl ether (~30 mL), washed with aqueous 1 M HCl (~15 mL), washed with brine, dried (MgSO$_4$), filtered, concentrated, diluted with N,N-dimethylformamide (1.5 mL) and directly purified by reverse-phase HPLC [Waters XBridge™ RP18 column, 5 µm, 30×100 mm, flow rate 40 mL/minute, 5-40% (over 15 minutes) gradient of acetonitrile in 0.1% TFA] to provide the title compound. $^1$H NMR (400 MHz, dimethylsulfoxide-d$_6$) δ ppm 12.94 (s, 1H), 8.67 (d, J=8.6 Hz, 1H), 8.30 8.25 (m, 2H), 8.11 (d, J=8.1 Hz, 1H), 7.84 (ddd, J=8.5, 6.9, 1.3 Hz, 1H), 7.71 (ddd, J=8.0, 7.0, 1.0 Hz, 1H), 7.66 (dd, J=8.1, 7.6 Hz, 1H), 6.73 (d, J=8.0 Hz, 1H), 6.69 (d, J=7.6 Hz, 1H), 6.53 (t, J=7.8 Hz, 1H), 4.55-4.47 (m, 2H), 4.32 (dd, J=8.4, 6.6 Hz, 1H), 3.66 (s, 3H). LC/MS (APCI+) m/z 384 (M+H)$^+$.

Example 26

2-methyl-N-[4-(propan-2-yl)benzene-1-sulfonyl]-2,3-dihydro-1-benzofuran-2-carboxamide The title compound was prepared as described in Example 16, substituting 4-isopropylbenzenesulfonamide for 2-methylbenzenesulfonamide (CAS: 6335-39-3). The crude material was purified by reversed-phase HPLC (Waters Sunfire C18 150×19 mm id 10 um, flow rate 20 mL/minute, 5-20% (0 to 1 minute), 20% (1 to 3.5 minute), 20-80% (3.5 to 16 minute), 5-20% (0 to 1 minute), 20% (1 to 3.5 minute), 20-80% (3.5 to 16 minute), 80% (16-23.5 minute) gradient of acetonitrile in 10 mM of ammonium carbonate in water) to provide the title compound. $^1$H NMR (400 MHz, dimethylsulfoxide-d$_6$) δ ppm 7.67 (d, J=8.3 Hz, 2H), 7.28 (d, J=8.3 Hz, 2H), 7.19 (s broad, 1H), 7.12 (d, J=7.3 Hz, 1H), 7.05 (dd, J=7.7, 7.7 Hz, 1H), 6.77 (dd, J=7.4, 7.4 Hz, 1H), 6.70 (d, J=7.9 Hz, 1H), 3.46 (d, J=16.1 Hz, 1H), 2.94-2.87 (m, 2H), 1.43 (s, 3H), 1.20 (d, J=7.0 Hz, 6H). MS (ESI+) m/z 360 (M+H)$^+$.

Example 27

5-chloro-N-(2-methylbenzene-1-sulfonyl)-2,3-dihydro-1-benzofuran-3-carboxamide

The title compound was prepared using the conditions described in Example 16 substituting 5-chloro-2,3-dihydrobenzofuran-3-carboxylic acid (CAS: 93670-12-3) for 2-methyl-2,3-dihydrobenzofuran-2-carboxylic acid. The crude material was purified by reverse-phase HPLC (Waters Sunfire C18 150×19 mm id 10 um, flow rate 20 mL/minute, 5-20% (0 to 1 minute), 20% (1 to 3.5 minute), 20-80% (3.5 to 16 minute), 80% (16-23.5 minute) gradient of acetonitrile in 0.1% formic acid) to provide the title compound. $^1$H NMR (400 MHz, dimethylsulfoxide-d$_6$) δ ppm 12.73-12.73 (m, 1H), 7.96-7.93 (m, 1H), 7.59-7.54 (m, 1H), 7.42-7.37 (m, 3H), 7.19 (dd, J=2.2, 8.7 Hz, 1H), 6.79 (d, J=8.5 Hz, 1H), 4.70-4.57 (m, 2H), 4.38 (dd, J=5.3, 9.2 Hz, 1H), 2.64 (s, 3H). MS (ESI−) m/z 350 (M−H)$^−$.

Example 28

5-chloro-N-(propane-1-sulfonyl)-2,3-dihydro-1-benzofuran-3-carboxamide

The title compound was prepared using the conditions described in Example 16 substituting 5-chloro-2,3-dihydrobenzofuran-3-carboxylic acid (CAS: 93670-12-3) for 2-methyl-2,3-dihydrobenzofuran-2-carboxylic acid and 1-propanesulfonamide (CAS: 24243-71-8) for 2-methylbenzenesulfonamide. The crude material was purified by reversed-phase HPLC (Waters Sunfire C18 150×19 mm id 10 um, flow rate 20 mL/minute, 5-20% (0 to 1 minute), 20% (1 to 3.5 minute), 20-80% (3.5 to 16 minute), 80% (16-23.5 minute) gradient of acetonitrile in 0.1% formic acid) to provide the title compound. $^1$H NMR (400 MHz, dimethylsulfoxide-d$_6$) δ ppm 12.18-12.13 (broad s, 1H), 7.40 (d, J=1.8 Hz, 1H), 7.24 (dd, J=2.2, 8.7 Hz, 1H), 6.85 (d, J=8.5 Hz, 1H), 4.81 (dd, J=5.3, 9.3 Hz, 1H), 4.67 (dd, J=9.4, 9.4 Hz, 1H), 4.39 (dd, J=5.4, 9.4 Hz, 1H), 3.35 (t, J=8.1 Hz, 3H), 1.75-1.62 (m, 2H), 0.96 (t, J=7.4 Hz, 3H). MS (ESI−) m/z 302 (M−H)$^−$.

Example 29

N-(2-methylbenzene-1-sulfonyl)-2,3-dihydro-1-benzofuran-3-carboxamide

A solution of 2,3-dihydrobenzofuran-3-carboxylic acid (CAS: 39891-55-9, 52 mg, 0.32 mmol), 4-dimethylaminopyridine (CAS: 1122-58-3, 39 mg, 0.32 mmol) and 2-methylbenzenesulfonamide (CAS: 88-19-7, 60 mg, 0.35 mmol) was prepared in dichloromethane (2 mL). N-Ethyl-N'-(3-dimethylaminopropyl)carbodiimide hydrochloride (CAS: 25952-53-8, 67 mg, 0.35 mmol) was added. The reaction was stirred at room temperature for 18 hours, and the reaction mixture was diluted with dichloromethane and washed with aqueous 1N HCl. The aqueous phase was extracted with dichloromethane (twice). The combined organic layers were dried (MgSO$_4$), filtered and concentrated under reduced pressure. The resultant residue was taken up in acetonitrile, filtered, and the crude material was purified by reversed-phase HPLC (Waters Sunfire C18 150×19 mm id 10 um, flow rate 20 mL/minute, 5-20% (0 to 1 minute), 20% (1 to 3.5 minute), 20-80% (3.5 to 16 minute), 80% (16-23.5 minute) gradient of acetonitrile in 0.1% formic acid) to provide the title compound. $^1$H NMR (400 MHz, dimethylsulfoxide-d$_6$) δ ppm 12.81-12.77 (m, 1H), 8.01-7.97 (m, 1H), 7.64-7.58 (m, 1H), 7.48-7.38 (m, 3H), 7.20 (dd, J=7.5, 7.5 Hz, 1H), 6.94-6.89 (m, 1H), 6.81 (d, J=8.1 Hz, 1H), 4.70-4.57 (m, 2H), 4.41 (dd, J=5.6, 9.1 Hz, 1H), 2.69 (s, 3H). MS (ESI+) m/z 318 (M+H)$^+$.

Example 30

N-(2-methylbenzene-1-sulfonyl)-3,4-dihydro-2H-1-benzopyran-4-carboxamide

The title compound was prepared and purified as described in Example 1, substituting chroman-4-carboxylic acid for 6-bromo-4-phenyl-chroman-4-carboxylic acid, and 2-methylbenzene-1-sulfonyl chloride for naphthalene-1-sulfonamide. MS (APCI+) m/z 332.2 (M+H)$^+$.

Example 31

(2S)—N-(naphthalene-1-sulfonyl)-4-phenyl-2-[(pyrrolidin-1-yl)methyl]-3,4-dihydro-2H-1-benzopyran-4-carboxamide The title compound was prepared and purified as described in Example 1, substituting (2S)-4-phenyl-2-(pyrrolidin-1-ylmethyl)chroman-4-carboxylic acid for 6-bromo-4-phenyl-chroman-4-carboxylic acid. MS (APCI+) m/z 527.0 (M+H)$^+$.

Example 32

(7S)-2,2-difluoro-7-methyl-N-(naphthalene-1-sulfonyl)-6,7-dihydro-2H-furo[2,3-][1,3]benzodioxole-7-carboxamide

Example 32A 2,2-difluoro-2H-1,3-benzodioxol-5-ol

To a mixture of 5-bromo-2,2-difluorobenzo[d][1,3]dioxole (10 g, 42.2 mmol), 2-di-tert-butylphosphino-3,4,5,6-tetramethyl-2',4',6'-triisopropyl-1,1'-biphenyl (2.028 g, 4.22 mmol) and potassium hydroxide (4.74 g, 84 mmol) was added degassed water (10 mL). The reaction mixture was sparged with a nitrogen stream for 5 minutes. To the reaction mixture was added a degassed solution of tris(dibenzylideneacetone)dipalladium(0) (0.773 g, 0.844 mmol) in dioxane (10 mL). The combined reaction mixture was sparged with nitrogen for 5-7 minutes. The reaction vial was capped and was stirred at 100° C. overnight (16 hours). The reaction mixture was cooled to ambient temperature, and partitioned between ethyl acetate and aqueous 1 N HCl solution. The organic fractions were combined and washed with brine, dried over anhydrous sodium sulfate, filtered, and concentrated in vacuo, maintaining a bath temperature at or below 25° C. The residue was purified by flash chromatography using a 220 g silica gel cartridge, eluting with 25-75% dichloromethane/heptanes to provide the title compound. $^1$H NMR (400 MHz, CDCl$_3$) δ ppm 5.51 (s, 1H), 6.50 (dd, J=8.6, 2.5 Hz, 1H), 6.63 (d, J=2.4 Hz, 1H), 6.90 (dd, J=8.7, 1.4 Hz, 1H). MS (ESI−) m/z 173.1 (M−H)$^-$.

Example 32B 2,2-difluoro-6-iodo-2H-1,3-benzodioxol-5-ol

To a cold (−10° C.) solution of Example 32A (6.0215 g, 34.6 mmol) in 1-butyl-3-methylimidazolium hexafluorophosphate (14.00 mL, 67.6 mmol) was added N-iodosuccinimide (7.78 g, 34.6 mmol) in two portions over 5 minutes. The reaction was stirred for an additional 5 minutes at the same temperature, the ice bath was removed, and the reaction mixture was stirred at ambient temperature for 15 minutes. Then the reaction mixture was extracted twice with tert-butyl methyl ether. The combined extracts were washed with saturated aqueous Na$_2$S$_2$O$_3$ solution, dried over anhydrous sodium sulfate, and concentrated in vacuo. The resulting crude residue was purified by flash chromatography using a 220 g silica gel cartridge, eluting with 25-75% dichloromethane/hexanes to provide the title compound. $^1$H NMR (501 MHz, CDCl$_3$) δ ppm 5.27 (s, 1H), 6.84 (s, 1H), 7.34 (s, 1H). MS (ESI−) m/z 299.0 (M−H)$^-$.

Example 32C

Ethyl 2-{[(2,2-difluoro-6-iodo-2H-1,3-benzodioxol-5-yl)oxy]methyl}prop-2-enoate

To a stirred solution of Example 32B (4.6625 g, 15.54 mmol) in acetonitrile (42 mL) was added cesium carbonate (7.60 g, 23.31 mmol) at room temperature, and the resulting suspension was stirred for 5 minutes. Ethyl 2-(bromomethyl)acrylate (2.5 mL, 18.11 mmol) was added to the reaction mixture in one portion. The reaction mixture was stirred at ambient temperature for 30 minutes, and diluted with water. The resulting precipitate was collected by filtration and washed with water. The solid was dried in a vacuum oven at 70° C. for 3 hours to provide the title compound, which was used directly in the next step without further purification. $^1$H NMR (501 MHz, CDCl$_3$) δ ppm 1.37 (t, J=7.1 Hz, 3H), 4.31 (q, J=7.1 Hz, 2H), 4.78 (t, J=1.8 Hz, 2H), 6.23 (td, J=1.9, 1.1 Hz, 1H), 6.50 (q, J=1.5 Hz, 1H), 6.76 (s, 1H), 7.49 (s, 1H). LC/MS (ESI+) m/z 412.0 (M+H)$^+$.

Example 32D

Ethyl 2,2-difluoro-7-methyl-6,7-dihydro-2H-furo[2,3-f][1,3]benzodioxole-7-carboxylate To a solution of tributylamine (7.92 mL, 33.2 mmol) in acetonitrile (84 mL) was added formic acid (0.643 mL, 16.62 mmol) dropwise over 2 minutes, and the reaction mixture was stirred at ambient temperature for 10 minutes. Example 32C (6.2263 g, 15.11 mmol) was added to the reaction mixture, and the mixture was sparged with nitrogen for 5 minutes. Palladium(II) acetate (0.339 g, 1.511 mmol) was added to the reaction mixture, sparging was continued for 2-3 minutes more, and then the reaction flask was capped. The reaction mixture was stirred at 60° C. for 17 hours. The reaction mixture was filtered, and the collected solids were washed with tert-butyl methyl ether. Then the solids were partitioned between tert-butyl methyl ether and brine. The combined organic extracts were dried over anhydrous sodium sulfate, filtered, and concentrated in vacuo. The residue was purified via flash chromatography using a 120 g silica gel cartridge, and was eluted with 0-10% tert-butyl methyl ether/heptanes to provide the title compound. $^1$H NMR (501 MHz, CDCl$_3$) δ ppm 1.31 (t, J=7.1 Hz, 3H), 1.62 (s, 3H), 4.23 (q, J=7.1 Hz, 2H), 4.31 (d, J=9.1 Hz, 1H), 5.11 (d, J=9.1 Hz, 1H), 6.59 (s, 1H), 7.05 (s, 1H). LC/MS (ESI+) m/z 286.3 (M+H)$^+$.

Example 32E 2,2-difluoro-7-methyl-6,7-dihydro-2H-furo[2,3-f][1,3]benzodioxole-7-carboxylic acid To a solution of Example 32D (2.6849 g, 9.38 mmol) in tetrahydrofuran (36 mL) was added potassium trimethylsilanoate (1.444 g, 11.26 mmol), and the resultant reaction mixture was stirred at 50° C. for 70 minutes. The reaction mixture was diluted with water and washed with tert-butyl methyl ether. The aqueous layer was acidified with concentrated HCl solution, and the mixture was extracted with dichloromethane. The organic extracts were washed with brine, dried over anhydrous sodium sulfate, and then concentrated in vacuo to provide the title compound. $^1$H NMR (501 MHz, CDCl$_3$) δ ppm 1.67 (s, 3H), 4.32 (d, J=9.2 Hz, 1H), 5.11 (d, J=9.2 Hz, 1H), 6.60 (s, 1H), 7.07 (s, 1H). MS (ESI−) m/z 256.9 (M−H)$^-$.

Example 32F (7S)-2,2-difluoro-7-methyl-6,7-dihydro-2H-furo[2,3-f][1,3]benzodioxole-7-carboxylic Acid Example 32E (2.18 g) was chromatographed by preparative supercritical fluid chromatography using a CHIRALPAK® AD-H column, 21×250 mm, 5 micron, with the sample at a concentration of 100 mg/mL in methanol, and with a co-solvent of methanol to provide the title compound.

$[\alpha]_D^{23.5}$ +1.64° (c=1, CH$_3$OH), % ee=99.2%; retention time=1.158 minutes; stereochemistry was confirmed by X-ray analysis.

Example 32G (7R)-2,2-difluoro-7-methyl-6,7-dihydro-2H-furo[2,3-f][1,3]benzodioxole-7-carboxylic Acid The title compound was isolated as the second eluent during the separation described in Example 32F. $[\alpha]_D^{23.7}$ –2.43° (c=1, CH$_3$OH), % ee=94.7%; retention time=2.72 minutes; stereochemistry was confirmed by X-ray analysis.

Example 32H (7S)-2,2-difluoro-7-methyl-N-(naphthalene-1-sulfonyl)-6,7-dihydro-2H-furo[2,3-f][1,3]benzodioxole-7-carboxamide The title compound was prepared and purified as described in Example 1, substituting Example 32F for 6-bromo-4-phenyl-chroman-4-carboxylic acid. MS (APCI+) m/z 447.9 (M+H)$^+$.

Example 33

(7R)-2,2-difluoro-7-methyl-N-(naphthalene-1-sulfonyl)-6,7-dihydro-2H-furo[2,3-f][1,3]benzodioxole-7-carboxamide The title compound was prepared and purified as described in Example 1, substituting Example 32G for 6-bromo-4-phenyl-chroman-4-carboxylic acid. MS (APCI+) m/z 447.8 (M+H)$^+$.

Example 34

N-(naphthalene-1-sulfonyl)-2,3-dihydro-1-benzofuran-3-carboxamide

Example 34A 2,3-dihydrobenzofuran-3-carboxylic Acid

A solution of methyl 2,3-dihydrobenzofuran-3-carboxylate (CAS #39891-56-0) (67 mg, 0.376 mmol) in tetrahydrofuran (1.5 mL) and methanol (1.5 mL) was treated with 1 M aqueous NaOH (1 mL, 1.000 mmol), stirred at room temperature for 30 minutes, and partitioned between methyl tert-butyl ether (50 mL) and aqueous 1 M HCl (10 mL). The methyl tert-butyl ether layer was washed with brine, dried (MgSO$_4$), filtered, and concentrated to provide the title compound. $^1$H NMR (400 MHz, CDCl$_3$) δ ppm 7.41 (d, J=7.5 Hz, 1H), 7.23-7.18 (m, 1H), 6.91 (t, J=7.5 Hz, 1H), 6.84 (d, J=8.1 Hz, 1H), 4.92 (dd, J=9.3, 6.4 Hz, 1H), 4.67 (t, J=9.5 Hz, 1H), 4.37 (dd, J=9.6, 6.4 Hz, 1H).

Example 34B

N-(naphthalene-1-sulfonyl)-2,3-dihydro-1-benzofuran-3-carboxamide

A solution of Example 34A (2,3-dihydrobenzofuran-3-carboxylic acid) (25 mg, 0.152 mmol), 1-(3-dimethylaminopropyl)-3-ethylcarbodiimide hydrochloride (58.4 mg, 0.305 mmol) and 4-dimethylaminopyridine (20.47 mg, 0.168 mmol) in CH$_2$Cl$_2$ (0.3 mL) was treated with naphthalene-1-sulfonamide (34.7 mg, 0.168 mmol). The mixture was stirred at room temperature for 25 minutes, concentrated with a stream of nitrogen, dissolved in N,N-dimethylformamide (1 mL) and directly purified by reverse-phase HPLC [Waters XBridge™ RP18 column, 5 μm, 30×100 mm, flow rate 40 mL/minute, 5-40% (over 15 minutes) gradient of acetonitrile in 0.1% TFA] to provide the title compound. $^1$H NMR (400 MHz, dimethylsulfoxide-d$_6$) δ ppm 12.97 (s, 1H), 8.69 (d, J=8.4 Hz, 1H), 8.29-8.25 (m, 2H), 8.10 (d, J=8.1 Hz, 1H), 7.84 (ddd, J=8.4, 6.9, 1.2 Hz, 1H), 7.73-7.69 (m, 1H), 7.68-7.64 (m, 1H), 7.11 (d, J=7.5 Hz, 1H), 7.02 (t, J=7.8 Hz, 1H), 6.65 (d, J=8.0 Hz, 1H), 6.59 (td, J=7.5, 0.8 Hz, 1H), 4.54-4.47 (m, 2H), 4.32 (t, J=7.5 Hz, 1H). LC/MS (APCI+) m/z 354 (M+H)$^+$.

Example 35

(4S)-8-bromo-5-methoxy-N-(naphthalene-1-sulfonyl)-3,4-dihydro-2H-1-benzopyran-4-carboxamide Example 11C was separated via chiral SFC using the instrument Aurora-2 with column of ChiralPak ADC and method of 5-50% methanol, 10 minutes, 150 bar. The first eluent at 5.698 minutes was the title compound. $^1$H NMR (501 MHz, Chloroform-d) δ ppm 9.47 (s, 1H), 8.49 (d, J=7.4 Hz, 1H), 8.40 (d, J=8.4 Hz, 1H), 8.12 (d, J=8.2 Hz, 1H), 7.99-7.93 (m, 1H), 7.64-7.53 (m, 3H), 7.44 (d, J=8.8 Hz, 1H), 6.41 (d, J=8.8 Hz, 1H), 4.24 (s, 1H), 3.94 (t, J=11.6 Hz, 1H), 3.79 (s, 3H), 3.73 (d, J=6.6 Hz, 1H), 2.23 (d, J=13.7 Hz, 1H), 1.87-1.74 (m, 1H). MS (ESI+) m/z 475.8 (M+H)$^+$.

Example 36

(4R)-8-bromo-5-methoxy-N-(naphthalene-1-sulfonyl)-3,4-dihydro-2H-1-benzopyran-4-carboxamide The title compound was isolated as the second eluent at 6.77 minute during the SFC separation described in Example 35. $^1$H NMR (400 MHz, Chloroform-d) δ ppm 9.43 (s, 1H), 8.51 (dd, J=7.4, 1.2 Hz, 1H), 8.36 (dd, J=7.9, 1.6 Hz, 1H), 8.13 (d, J=8.2 Hz, 1H), 7.96 (dd, J=7.9, 1.6 Hz, 1H), 7.67-7.52 (m, 3H), 7.45 (d, J=8.6 Hz, 1H), 6.43 (d, J=8.8 Hz, 1H), 4.31-4.22 (m, 1H), 3.95 (td, J=11.9, 2.4 Hz, 1H), 3.79 (s, 3H), 3.73 (dd, J=5.2, 2.3 Hz, 1H), 2.23 (dq, J=14.1, 2.8 Hz, 1H), 1.77 (tt, J=14.0, 4.9 Hz, 1H). MS (ESI+) m/z 476 (M+H)$^+$.

Example 37

4-bromo-7-methoxy-N-(naphthalene-1-sulfonyl)-2,3-dihydro-1-benzofuran-3-carboxamide Example 37A Ethyl 4-bromo-7-methoxybenzofuran-3-carboxylate A room temperature solution of 6-bromo-2-hydroxy-3-methoxybenzaldehyde (CAS #20035-41-0) (1 g, 4.33 mmol) in CH$_2$Cl$_2$ (8 mL) was treated with tetrafluoroboric acid-diethyl ether complex (0.059 mL, 0.433 mmol), and was treated dropwise with a solution of ethyl diazoacetate (0.910 mL, 8.66 mmol) in CH$_2$Cl$_2$ (8 mL) over 15 minutes. The mixture was stirred at room temperature for 10 more minutes and concentrated on a rotovap using a room temperature water bath. The residue was treated with concentrated H$_2$SO$_4$ (~0.5 mL), dropwise at first (exothermic with gas release). The mixture was stirred for 10 minutes, diluted with methyl tert-butyl ether (~50 mL), washed with saturated aqueous NaHCO$_3$ solution, washed with brine, dried (MgSO$_4$), filtered, and concentrated. The residue was chromatographed on silica gel, eluting with a gradient of 5% to 15% ethyl acetate in heptane to provide the title compound. $^1$H NMR (400 MHz, CDCl$_3$) δ ppm 8.19 (s, 1H), 7.44 (d, J=8.5 Hz, 1H), 6.74 (d, J=8.6 Hz, 1H), 4.40 (q, J=7.1 Hz, 2H), 3.99 (s, 3H), 1.41 (t, J=7.1 Hz, 3H). LC/MS (APCI+) m/z 299, 301 (M+H)$^+$.

Example 37B

Ethyl 4-bromo-7-methoxy-2,3-dihydrobenzofuran-3-carboxylate

A solution of Example 37A (ethyl 4-bromo-7-methoxybenzofuran-3-carboxylate) (174 mg, 0.582 mmol) in methanol (2 mL) was treated with magnesium turnings (42.4 mg, 1.745 mmol), stirred at room temperature for 1 hour, and partitioned between methyl tert-butyl ether (50 mL) and aqueous 1 M HCl (10 mL). The methyl tert-butyl ether layer was washed with brine, dried (MgSO$_4$), filtered, concentrated and chromatographed on silica gel, eluting with a gradient of 5% to 20% ethyl acetate in heptanes to provide the title compound. $^1$H NMR (400 MHz, CDCl$_3$) δ ppm 6.97 (d, J=8.6 Hz, 1H), 6.70 (d, J=8.6 Hz, 1H), 4.81-4.78 (m, 2H), 4.32-4.28 (m, 1H), 4.22 (q, J=7.1 Hz, 2H), 3.85 (s, 3H), 1.28 (t, J=7.1 Hz, 3H).

Example 37C 4-bromo-7-methoxy-2,3-dihydrobenzofuran-3-carboxylic Acid

A solution of Example 37B (ethyl 4-bromo-7-methoxy-2,3-dihydrobenzofuran-3-carboxylate) (0.12 g, 0.398 mmol) in tetrahydrofuran (3 mL) was diluted with methanol (3 mL), treated with 1 M aqueous NaOH (2 mL), stirred at room temperature for 20 minutes, and partitioned between methyl tert-butyl ether (~50 mL) and aqueous 1 M HCl (~10 mL). The methyl tert-butyl ether layer was washed with brine, dried (MgSO$_4$), filtered, and concentrated to provide the title compound. $^1$H NMR (400 MHz, CDCl$_3$) δ ppm 7.00 (d, J=8.6 Hz, 1H), 6.72 (d, J=8.6 Hz, 1H), 4.87 (dd, J=9.4, 4.9 Hz, 1H), 4.81 (t, J=9.5 Hz, 1H), 4.32 (dd, J=9.7, 4.9 Hz, 1H), 3.86 (s, 3H).

Example 37D 4-bromo-7-methoxy-N-(naphthalene-1-sulfonyl)-2,3-dihydro-1-benzofuran-3-carboxamide To a solution of Example 37C (4-bromo-7-methoxy-2,3-dihydrobenzofuran-3-carboxylic acid) (20 mg, 0.073 mmol), 1-(3-dimethylaminopropyl)-3-ethylcarbodiimide hydrochloride (28.1 mg, 0.146 mmol) and 4-dimethylaminopyridine (9.84 mg, 0.081 mmol) in N,N-dimethylformamide (0.3 mL) was added naphthalene-1-sulfonamide (16.70 mg, 0.081 mmol). The mixture was stirred overnight, diluted with N,N-dimethylformamide and directly purified by reverse-phase HPLC [Waters XBridge™ RP18 column, 5 µm, 30×100 mm, flow rate 40 mL/minute, 5-40% (over 15 minutes) gradient of acetonitrile in 0.1% TFA] to provide the title compound. $^1$H NMR (400 MHz, dimethylsulfoxide-d$_6$) δ ppm 12.92 (s, 1H), 8.65 (d, J=8.3 Hz, 1H), 8.33-8.27 (m, 2H), 8.13 (d, J=8.0 Hz, 1H), 7.77 (ddd, J=8.5, 6.9, 1.4 Hz, 1H), 7.72-7.66 (m, 2H), 6.77 (s, 2H), 4.76-4.67 (m, 1H), 4.31-4.23 (m, 2H), 3.68 (s, 3H). LC/MS (APCI+) m/z 462, 464 (M+H)$^+$.

Example 38

5-methoxy-N-(naphthalene-1-sulfonyl)-3,4-dihydrospiro[1-benzopyran-2,1'-cyclohexane]-4-carboxamide Example 38A 5-methoxyspiro[chroman-2,1'-cyclohexan]-4-one A mixture of 5-hydroxyspiro[chroman-2,1'-cyclohexan]-4-one (1.0 g, 4.31 mmol) [CAS#81107-97-3] and potassium carbonate (1.190 g, 8.61 mmol) in N,N-dimethylformamide (6 mL) was stirred at ambient temperature for 30 minutes and iodomethane (0.402 mL, 6.46 mmol) was added. The reaction was stirred for 4 hours, and LC/MS indicated the reaction was complete. The mixture was filtered and the filter cake was washed with dichloromethane (20 mL×3). The combined filtrates were washed with brine, dried over MgSO$_4$, filtered, and concentrated. The residue was purified via chromatography, eluting with ethyl acetate in heptane at 0-50% gradient to provide the title compound. (TFA/APCI+) m/z 247.24 (M+1)$^+$.

Example 38B 5-methoxy-N-(naphthalen-1-ylsulfonyl)spiro[chroman-2,1'-cyclohexane]-4-carboxamide To a mixture of Example 38A (1.0 g, 4.06 mmol) and zinc(II) iodide (0.039 g, 0.122 mmol) in dichloromethane (10 mL) cooled in an ice bath was added trimethylsilanecarbonitrile (1.016 mL, 8.12 mmol) slowly. The reaction mixture was stirred at ambient temperature overnight. LC/MS indicated the starting material had disappeared. The solvent was removed and the residue was dissolved in acetic acid (40 mL) with aqueous 6 M HCl (4 mL). Tin (II) chloride hydrate (2612 mg, 11.58 mmol) was added. The mixture was refluxed at 100° C. overnight. LC/MS showed the starting material peak at room temperature 1.05 minutes had disappeared and a new peak appeared at 0.71 minutes. The mixture was concentrated and the residue was extracted with dichloromethane (30 mL×3). The organic layer was washed with brine, dried over MgSO$_4$, filtered, and concentrated under pressure. The residue was purified via chromatography, eluting with ethyl acetate/methanol (5:1) in heptane at 0-60% to provide the title compound. $^1$H NMR (400 MHz, Chloroform-d) δ ppm 7.15 (t, J=8.2 Hz, 1H), 6.54 (dd, J=8.3, 0.9 Hz, 1H), 6.50-6.39 (m, 1H), 5.49 (s, 1H), 5.19 (s, 1H), 3.81 (s, 3H), 3.64 (t, J=8.0 Hz, 1H), 2.25-2.08 (m, 2H), 1.88-1.66 (m, 3H), 1.59-1.21 (m, 7H). MS (ESI+) m/z 276 (M+H)$^+$.

Example 38C 5-methoxy-N-(naphthalen-1-ylsulfonyl)spiro[chroman-2,1'-cyclohexane]-4-carboxamide A mixture of Example 38B (60 mg, 0.218 mmol) and sodium hydride (34.9 mg, 0.872 mmol) in N,N-dimethylformamide (2 mL) was stirred at ambient temperature for 30 minutes. Naphthalene-1-sulfonyl chloride (49.4 mg, 0.218 mmol) was added slowly. The mixture was stirred at room temperature overnight. LC/MS showed a new product peak at 0.93 minutes and the starting material peak at 0.73 minutes had disappeared. The reaction mixture was purified via HPLC on a Phenomenex® Luna® C8(2) 5 um 100 Å AXIA™ column (30 mm×75 mm), with a gradient of acetonitrile (A) and 0.1% trifluoroacetic acid in water (B) was used, at a flow rate of 50 mL/minute (0-1.0 minute 5% A, 1.0-8.5 minute linear gradient 5-100% A, 8.5-11.5 minute 100% A, 11.5-12.0 minute linear gradient 95-5% A) to provide the title compound. $^1$H NMR (501 MHz, Chloroform-d) δ ppm 8.54 (dd, J=7.4, 1.2 Hz, 1H), 8.44-8.36 (m, 1H), 8.26 (s, 1H), 8.13 (dd, J=8.3, 1.1 Hz, 1H), 7.99-7.94 (m, 1H), 7.65-7.57 (m, 3H), 7.18 (td, J=8.2, 0.7 Hz, 1H), 6.54 (dd, J=8.3, 1.0 Hz, 1H), 6.28 (dd, J=8.1, 1.0 Hz, 1H), 3.53 (t, J=8.3 Hz, 1H), 3.15 (s, 3H), 1.93 (dd, J=8.2, 1.7 Hz, 2H), 1.64-1.49 (m, 6H), 1.35 (ddp, J=13.1, 8.6, 4.9 Hz, 2H), 1.25 (ddt, J=10.6, 7.3, 3.0 Hz, 2H). MS (ESI+) m/z 466.1 (M+H)$^+$.

Example 39

7-bromo-4-methoxy-N-(naphthalene-1-sulfonyl)-2,3-dihydro-1-benzofuran-3-carboxamide Example 39A 3-bromo-2-hydroxy-6-methoxybenzaldehyde A solution of 3-bromo-2,6-dimethoxybenzaldehyde (CAS #29866-51-1) (2 g, 8.16 mmol) in toluene (40 mL) was treated with portions with of aluminum chloride (1.088 g, 8.16 mmol) over 15 minutes, stirred at room temperature for 15 minutes, heated to 80° C. for 10 minutes, and cooled. The mixture consisted of a toluene solvent layer and a thick oil. The toluene layer of the reaction was decanted off. The toluene layer was treated 1 M aqueous HCl (100 mL) and was extracted with CH$_2$Cl$_2$ (2×50 mL). The CH$_2$Cl$_2$ layers were combined, dried (MgSO$_4$), filtered and concentrated. The thick oil portion of the reaction was treated with water (100 mL) and stirred vigorously, resulting in a solid. The mixture was partitioned between aqueous 1 M HCl and CH$_2$Cl$_2$. The layers were separated and the aqueous layer was extracted further with CH$_2$Cl$_2$. The combined CH$_2$Cl$_2$ layers were dried (MgSO$_4$), filtered and concentrated. The two crude products were combined to provide the title compound. $^1$H NMR (400 MHz, CDCl$_3$) δ ppm 12.61 (s, 1H), 10.28 (s, 1H), 7.65 (d, J=8.9 Hz, 1H), 6.35 (d, J=8.9 Hz, 1H), 3.90 (s, 3H).

Example 39B

Ethyl 7-bromo-4-methoxybenzofuran-3-carboxylate

A room temperature solution of Example 39A (3-bromo-2-hydroxy-6-methoxybenzaldehyde) (0.94 g, 4.07 mmol) in CH$_2$Cl$_2$ (8 mL) was treated with tetrafluoroboric acid-diethyl ether complex (0.056 mL, 0.407 mmol), treated dropwise with a solution of ethyl diazoacetate (0.856 mL, 8.14 mmol) in CH$_2$Cl$_2$ (8 mL), stirred at room temperature for 10 minutes and concentrated to ~2 mL volume. Concentrated H$_2$SO$_4$ was added and the mixture was stirred at room temperature for 10 minutes. The mixture was diluted with CH$_2$Cl$_2$ (~10 mL) and methyl tert-butyl ether (~50 mL), and was treated with water (~30 mL). The layers were separated and the organic layer was washed with saturated aqueous NaHCO$_3$ solution and brine, dried (MgSO$_4$), filtered, concentrated and chromatographed on silica gel, eluting with a gradient of 5% to 30% ethyl acetate in heptane to provide the title compound. $^1$H NMR (400 MHz, CDCl$_3$) δ ppm 8.18 (s, 1H), 7.43 (d, J=8.6 Hz, 1H), 6.67 (d, J=8.6 Hz, 1H), 4.37 (q, J=7.1 Hz, 2H), 3.95 (s, 3H), 1.39 (t, J=7.1 Hz, 3H).

Example 39C

Ethyl 7-bromo-4-methoxy-2,3-dihydrobenzofuran-3-carboxylate

A solution of Example 39B (ethyl 7-bromo-4-methoxybenzofuran-3-carboxylate) (0.3 g, 1.003 mmol) in methanol (5 mL) was treated with magnesium turnings (0.073 g, 3.01 mmol), stirred at room temperature for 90 minutes, and partitioned between methyl tert-butyl ether (~50 mL) and aqueous 1 M HCl (~15 mL). The methyl tert-butyl ether layer was washed with brine, dried (MgSO$_4$), filtered, concentrated and chromatographed on silica gel, eluting with a gradient of 5% to 15% ethyl acetate in heptane to provide the title compound. $^1$H NMR (400 MHz, CDCl$_3$) δ ppm 7.28 (dd, J=8.8, 0.6 Hz, 1H), 6.35 (d, J=8.8 Hz, 1H), 4.83-4.79 (m, 2H), 4.40-4.35 (m, 1H), 4.21 (qd, J=7.1, 4.1 Hz, 2H), 3.80 (s, 3H), 1.26 (t, J=7.1 Hz, 3H).

Example 39D 7-bromo-4-methoxy-2,3-dihydrobenzofuran-3-carboxylic Acid

A solution of Example 39C (ethyl 7-bromo-4-methoxy-2,3-dihydrobenzofuran-3-carboxylate) (87 mg, 0.289 mmol) in tetrahydrofuran (3 mL) was diluted with methanol (3 mL), treated with 1 M aqueous NaOH (2 mL), stirred at room temperature for 20 minutes, and partitioned between methyl tert-butyl ether (~50 mL) and aqueous 1 M HCl (~10 mL). The methyl tert-butyl ether layer was washed with brine, dried (MgSO$_4$), filtered, and concentrated to provide the title compound. $^1$H NMR (501 MHz, CDCl$_3$) δ ppm 7.34-7.30 (m, 1H), 6.39 (d, J=8.8 Hz, 1H), 4.98 (dd, J=9.4, 5.4 Hz, 1H), 4.80 (t, J=9.7 Hz, 1H), 4.43 (dd, J=9.9, 5.4 Hz, 1H), 3.87 (s, 3H).

Example 39E 7-bromo-4-methoxy-N-(naphthalene-1-sulfonyl)-2,3-dihydro-1-benzofuran-3-carboxamide To a solution of Example 39D (7-bromo-4-methoxy-2,3-dihydrobenzofuran-3-carboxylic acid) (26.5 mg, 0.097 mmol), 1-(3-dimethylaminopropyl)-3-ethylcarbodiimide hydrochloride (37.2 mg, 0.194 mmol) and 4-dimethylaminopyridine (13.04 mg, 0.107 mmol) in CH$_2$Cl$_2$ (0.3 mL) was added naphthalene-1-sulfonamide (22.12 mg, 0.107 mmol). The mixture was stirred for 4 hours, concentrated with a stream of N$_2$, diluted with N,N-dimethylformamide and directly purified by reverse-phase HPLC [Waters XBridge™ RP18 column, 5 μm, 30×100 mm, flow rate 40 mL/minute, 5-95% gradient of acetonitrile in 0.1% TFA] to provide the title compound. $^1$H NMR (400 MHz, dimethylsulfoxide-d$_6$) δ ppm 12.79 (s, 1H), 8.63 (d, J=8.5 Hz, 1H), 8.31 (d, J=8.3 Hz, 1H), 8.28 (dd, J=7.4, 1.1 Hz, 1H), 8.15 (d, J=8.0 Hz, 1H), 7.80 (ddd, J=8.5, 6.9, 1.3 Hz, 1H), 7.74-7.67 (m, 2H), 7.25 (d, J=8.8 Hz, 1H), 6.34 (d, J=8.9 Hz, 1H), 4.73 (t, J=9.4 Hz, 1H), 4.38 (dd, J=9.6, 5.9 Hz, 1H), 4.31 (dd, J=9.1, 5.9 Hz, 1H), 3.24 (s, 3H). LC/MS (APCI+) m/z 462, 464 (M+H)$^+$.

Example 40

4-methoxy-N-(naphthalene-1-sulfonyl)-5-(trifluoromethyl)-2,3-dihydro-1-benzofuran-3-carboxamide and 4-methoxy-N-(naphthalene-1-sulfonyl)-7-(trifluoromethyl)-2,3-dihydro-1-benzofuran-3-carboxamide

Example 40A

Methyl 4-methoxy-7-(trifluoromethyl)-2,3-dihydrobenzofuran-3-carboxylate and Methyl 4-methoxy-5-(trifluoromethyl)-2,3-dihydrobenzofuran-3-carboxylate A mixture of Example 8D (methyl 4-methoxy-2,3-dihydrobenzofuran-3-carboxylate) (50 mg, 0.240 mmol), trimethyl(trifluoromethyl)silane (0.071 mL, 0.480 mmol), silver (I) fluoride (7.62 mg, 0.060 mmol) and (diacetoxyiodo)benzene (155 mg, 0.480 mmol) in dimethylsulfoxide (0.2 mL) was stirred at room temperature overnight. The mixture was partitioned between water and $CH_2Cl_2$. The $CH_2Cl_2$ layer was dried ($MgSO_4$), filtered, concentrated, and chromatographed on silica gel, eluting with a gradient of 5% to 15% ethyl acetate in heptanes to provide the title compounds as a 9:2 mixture of isomers. Major isomer, methyl 4-methoxy-7-(trifluoromethyl)-2,3-dihydrobenzofuran-3-carboxylate: $^1$H NMR (400 MHz, $CDCl_3$) δ ppm 7.40 (d, J=8.7 Hz, 1H), 6.47 (d, J=8.7 Hz, 1H), 4.87-4.83 (m, 2H), 4.33 (dd, J=9.2, 7.0 Hz, 1H), 3.86 (s, 3H), 3.75 (s, 3H); Minor isomer, methyl 4-methoxy-5-(trifluoromethyl)-2,3-dihydrobenzofuran-3-carboxylate: $^1$H NMR (400 MHz, $CDCl_3$) δ ppm 7.44 (d, J=8.5 Hz, 1H), 6.62 (d, J=8.5 Hz, 1H), 4.90-4.84 (m, 1H), 4.77 (t, J=9.4 Hz, 1H), 4.45 (dd, J=9.5, 5.5 Hz, 1H), 3.91 (s, 3H), 3.78 (s, 3H).

Example 40B 4-methoxy-7-(trifluoromethyl)-2,3-dihydrobenzofuran-3-carboxylic Acid and 4-methoxy-5-(trifluoromethyl)-2,3-dihydrobenzofuran-3-carboxylic Acid A solution of Example 40A (16.3 mg, 0.059 mmol) in tetrahydrofuran (2 mL) and methanol (2 mL) was treated with 1 M aqueous NaOH (~1.5 mL), stirred at room temperature for 15 minutes, and partitioned between aqueous 1 M HCl (10 mL) and methyl tert-butyl ether (~50 mL). The methyl tert-butyl ether layer was washed with brine, dried ($MgSO_4$), filtered, and concentrated to provide the title compound as a mixture of isomers in a 4:1 ratio. Major isomer, 4-methoxy-7-(trifluoromethyl)-2,3-dihydrobenzofuran-3-carboxylic acid: $^1$H NMR (400 MHz, $CDCl_3$) δ ppm 7.43 (d, J=8.7 Hz, 1H), 6.51 (d, J=8.7 Hz, 1H), 4.99 (dd, J=9.4, 5.6 Hz, 1H), 4.86 (t, J=9.7 Hz, 1H), 4.36 (dd, J=10.0, 5.5 Hz, 1H), 3.91 (s, 3H); Minor isomer, 4-methoxy-5-(trifluoromethyl)-2,3-dihydrobenzofuran-3-carboxylic acid: $^1$H NMR (400 MHz, $CDCl_3$) δ ppm 7.47 (d, J=8.5 Hz, 1H), 6.64 (d, J=8.5 Hz, 1H), 4.94 (dd, J=9.4, 5.1 Hz, 1H), 4.79 (t, J=9.5 Hz, 1H), 4.47 (dd, J=9.5, 5.1 Hz, 1H), 3.95 (s, 3H).

Example 40C 4-methoxy-N-(naphthalene-1-sulfonyl)-5-(trifluoromethyl)-2,3-dihydro-1-benzofuran-3-carboxamide and 4-methoxy-N-(naphthalene-1-sulfonyl)-7-(trifluoromethyl)-2,3-dihydro-1-benzofuran-3-carboxamide To a solution of Example 40B (13.5 mg, 0.051 mmol), 1-(3-dimethylaminopropyl)-3-ethylcarbodiimide hydrochloride (19.74 mg, 0.103 mmol) and 4-dimethylaminopyridine (6.92 mg, 0.057 mmol) in $CH_2Cl_2$ (0.3 mL) was added naphthalene-1-sulfonamide (11.74 mg, 0.057 mmol). The mixture was stirred overnight, concentrated with a stream of $N_2$, diluted with N,N-dimethylformamide and directly purified by reverse-phase HPLC [Waters XBridge™ RP18 column, 5 μm, 30×100 mm, flow rate 40 mL/minute, 5-95% gradient of acetonitrile in 0.1% TFA] to provide the title compound as a 4:1 mixture of isomers. Major component, 4-methoxy-N-(naphthalen-1-ylsulfonyl)-7-(trifluoromethyl)-2,3-dihydrobenzofuran-3-carboxamide: $^1$H NMR (400 MHz, dimethylsulfoxide-$d_6$) δ ppm 12.88 (s, 1H), 8.64 (d, J=8.6 Hz, 1H), 8.32 (d, J=7.9 Hz, 1H), 8.28 (dd, J=7.4, 1.1 Hz, 1H), 8.15 (d, J=7.8 Hz, 1H), 7.81 (ddd, J=8.6, 7.0, 1.3 Hz, 1H), 7.75-7.67 (m, 2H), 7.37 (d, J=8.7 Hz, 1H), 6.50 (d, J=8.8 Hz, 1H), 4.82 (t, J=9.2 Hz, 1H), 4.41-4.30 (m, 2H), 3.29 (s, 3H). LC/MS (APCI+) m/z 452 (M+H)$^+$.

Example 41

8-bromo-5-methoxy-N-(naphthalene-1-sulfonyl)-3,4-dihydrospiro[1-benzopyran-2,1'-cyclohexane]-4-carboxamide

Example 41A 8-bromo-5-methoxyspiro[chroman-2,1'-cyclohexane]-4-carboxamide

To Example 38B (200 mg, 0.726 mmol) in $CS_2$ (5 mL) in an ice-bath was added bromine (0.037 mL, 0.726 mmol) in $CS_2$ (1 mL) slowly. The mixture was stirred at room temperature for 30 minutes, and LC/MS indicated the conversion was complete. The solvent was removed under pressure and the residue was purified via chromatography, eluting with ethyl acetate/methanol (9:1) in heptane at 0-60% to provide the title compound. $^1$H NMR (501 MHz, Chloroform-d) δ ppm 7.41 (dd, J=8.7, 0.7 Hz, 1H), 6.38 (d, J=8.7 Hz, 1H), 5.42 (s, 1H), 5.14 (s, 1H), 3.80 (s, 3H), 3.67 (t, J=8.3 Hz, 1H), 2.20-2.08 (m, 2H), 1.93-1.83 (m, 2H), 1.77-1.58 (m, 4H), 1.53-1.41 (m, 2H), 1.36-1.28 (m, 2H). MS (ESI+) m/z 354 (M+H)$^+$.

Example 41B 5-methoxy-N-(naphthalen-1-ylsulfonyl)chroman-4-carboxamide

A mixture of Example 41A (100 mg, 0.282 mmol) and sodium hydride (45.2 mg, 1.129 mmol) in N,N-dimethylformamide (2.5 mL) was stirred at ambient temperature for 30 minutes. Naphthalene-1-sulfonyl chloride (70.4 mg, 0.311 mmol) was added slowly, and stirring was continued overnight. LC/MS showed a new product peak at 0.82 minutes and starting material at 0.43 minutes disappeared. The mixture was dissolved in dichloromethane (20 mL), washed with brine, dried over $MgSO_4$, filtered, and concentrated. The residue was purified on a 25 g silica gel cartridge, eluting with ethyl acetate/methanol (9:1) in heptane at 0-60% gradient to provide the title compound. $^1$H NMR (400 MHz, Chloroform-d) δ ppm 8.53 (dd, J=7.5, 1.3 Hz, 1H), 8.43-8.35 (m, 1H), 8.32-8.18 (m, 1H), 8.13 (d, J=8.2 Hz, 1H), 7.96 (dt, J=7.8, 2.7 Hz, 1H), 7.69-7.56 (m, 3H), 7.41 (d, J=8.8 Hz, 1H), 6.19 (d, J=8.8 Hz, 1H), 3.56 (t, J=8.5 Hz, 1H), 3.10 (s, 3H), 2.00 (s, 2H), 1.94-1.91 (m, 1H), 1.67-1.56 (m, 4H), 1.39 (td, J=8.4, 4.1 Hz, 2H), 1.28-1.11 (m, 3H). MS (ESI+) m/z 546 (M+H)+.

Example 42

8-bromo-5-methoxy-N-(quinoline-8-sulfonyl)-3,4-dihydro-2H-1-benzopyran-4-carboxamide Example 42A 5-methoxychroman-4-carboxamide To a solution of 5-methoxychroman-4-one (1 g, 5.61 mmol) and zinc(II) iodide (0.054 g, 0.168 mmol) in dichloromethane (10 mL) cooled in an ice bath was added trimethylsilanecarbonitrile (1.114 g, 11.22 mmol) slowly. The mixture was stirred at room temperature overnight. Zinc(II) iodide (0.039 g, 0.122 mmol) and additional trimethylsilanecarbonitrile (1.016 mL, 8.12 mmol) were added, and the mixture was stirred for 30 minutes. The reaction mixture was filtered through a syringe filter and the filtrate was concentrated. The residue was dissolved in acetic acid (10 mL) and concentrated HCl (1 mL), followed by addition of tin (II) chloride hydrate (4.66 g, 22.45 mmol). The mixture was refluxed at 90° C. overnight. The mixture was concentrated and the residue was dissolved in dichloromethane (50 mL), and washed with brine. The organic layer was dried over MgSO$_4$, filtered, and concentrated. Purification via chromatography eluting with ethyl acetate/methanol (9:1) in heptane at a 0-80% gradient provided two fractions. The first fraction was 5-methoxychroman-4-carboxylic acid, MS (APCI+) m/z 208 (M+H)+. The second fraction was 5-methoxychroman-4-carboxamide. $^1$H NMR (501 MHz, Chloroform-d) δ ppm 7.15 (t, J=8.2 Hz, 1H), 6.53 (dd, J=8.4, 1.0 Hz, 1H), 6.48 (dd, J=8.2, 1.0 Hz, 1H), 6.06 (s, 1H), 5.51 (s, 1H), 4.29 (dddd, J=11.2, 4.3, 2.8, 1.5 Hz, 1H), 4.22-4.16 (m, 1H), 3.86 (s, 3H), 3.78 (dt, J=5.8, 2.0 Hz, 1H), 2.41 (dq, J=13.9, 2.5 Hz, 1H), 1.96 (dddd, J=13.9, 12.3, 6.0, 4.0 Hz, 1H). MS (ESI+) m/z 208 (M+H)+.

Example 42B 8-bromo-5-methoxychroman-4-carboxamide

To a mixture of Example 42A (210 mg, 1.013 mmol) in CS$_2$ (10 mL) cooled in an ice-bath, dibromine (0.052 mL, 1.013 mmol) in CS$_2$ (0.5 mL) was added slowly. The solvent was removed under pressure and the residue was dissolved in dichloromethane (30 mL). The mixture was washed with saturated aqueous NaS$_2$O$_3$ and brine, dried over MgSO$_4$, filtered, and concentrated. The residue was purified via HPLC with TFA method on a Phenomenex® Luna® C8(2) 5 um 100 Å AXIA™ column (30 mm×75 mm), with a gradient of acetonitrile (A) and 0.1% trifluoroacetic acid in water (B) was used, at a flow rate of 50 mL/minute (0-1.0 minute 5% A, 1.0-8.5 minute linear gradient 5-100% A, 8.5-11.5 minute 100% A, 11.5-12.0 minute linear gradient 95-5% A) to provide the title compound. $^1$H NMR (400 MHz, Chloroform-d) δ ppm 7.43 (d, J=8.7 Hz, 1H), 6.42 (d, J=8.8 Hz, 1H), 5.98 (s, 1H), 5.56 (s, 1H), 4.46 (dddd, J=11.2, 4.2, 2.8, 1.5 Hz, 1H), 4.29 (ddd, J=12.3, 11.2, 2.3 Hz, 1H), 3.87 (s, 3H), 3.81 (dt, J=6.0, 2.0 Hz, 1H), 2.44 (dq, J=14.1, 2.5 Hz, 1H), 1.97 (dddd, J=14.0, 12.4, 5.9, 4.1 Hz, 1H). MS (ESI+) m/z 286 (M+H)+.

Example 42C 8-bromo-5-methoxy-N-(quinolin-8-ylsulfonyl)chroman-4-carboxamide

A mixture of Example 42B (40 mg, 0.140 mmol) and sodium hydride (22.37 mg, 0.559 mmol) in N,N-dimethylformamide (2 mL) was stirred at ambient temperature for 30 minutes. Quinoline-8-sulfonyl chloride (47.7 mg, 0.210 mmol) was added slowly. The mixture was stirred overnight. Water (20 mL) and dichloromethane (20 mL) were added. The organic layer was washed with brine, dried over MgSO$_4$, filtered, and concentrated. The residue was purified using a 25 g silica gel cartridge, eluting with ethyl acetate/methanol (9:1) in heptane at a 0-60% gradient to provide the title compound. $^1$H NMR (400 MHz, Chloroform-d) δ ppm 8.76 (dd, J=4.3, 1.8 Hz, 1H), 8.61 (dd, J=7.3, 1.5 Hz, 1H), 8.27 (dd, J=8.3, 1.8 Hz, 1H), 8.10 (dd, J=8.2, 1.4 Hz, 1H), 7.70 (dd, J=8.2, 7.4 Hz, 1H), 7.53 (dd, J=8.3, 4.3 Hz, 1H), 7.45 (d, J=8.7 Hz, 1H), 7.30 (s, 1H), 6.38 (d, J=8.8 Hz, 1H), 4.22-4.14 (m, 1H), 3.86-3.80 (m, 1H), 3.76 (d, J=2.4 Hz, 1H), 3.72 (s, 3H), 2.22 (dq, J=13.9, 2.7 Hz, 1H), 1.88-1.76 (m, 1H). MS (ESI+) m/z 479.1 (M+H)+.

Example 43

7-chloro-N-(naphthalene-1-sulfonyl)-2,3-dihydro-1-benzofuran-3-carboxamide

Example 43A

Ethyl 7-chlorobenzofuran-3-carboxylate

HBF$_4$.OEt$_2$ (tetrafluoroboric acid diethyl ether complex) was added to 3-chloro-2-hydroxybenzaldehyde (6 g, 38.3 mmol) in CH$_2$Cl$_2$ (60 mL). A solution of ethyl diazoacetate (80 mL, 61.3 mmol) in CH$_2$Cl$_2$ (30 mL) was introduced into the reaction mixture as the evolution of N$_2$ gas permitted (ca. 3-6 minute addition time) and the reaction was not allowed to go above 38° C. Once gas evolution ceased, the reaction mixture was concentrated by rotary evaporator and concentrated H$_2$SO$_4$ (0.3 to 0.5 mL) was added to the mixture while stirring. After 5 to 10 minutes, the mixture was diluted with CH$_2$Cl$_2$ (100 mL) and the H$_2$SO$_4$ was quenched with solid NaHCO$_3$. The mixture was filtered through silica gel (100 g) and concentrated by rotary evaporation to provide the title compound. $^1$H NMR (400 MHz, CDCl$_3$) δ ppm 8.30 (s, 1H), 7.97 (d, J=7.7 Hz, 1H), 7.50-7.23 (m, 2H), 4.42 (dd, J=14.2, 7.1 Hz, 2H), 1.43 (t, J=7.1 Hz, 3H). MS (ESI+) m/z 225 (M+H)+.

Example 43B

Ethyl 7-chloro-2,3-dihydrobenzofuran-3-carboxylate

A solution of Example 43A (2.5 g, 11.13 mmol) in methanol (20 mL) was treated in portions with Mg (0.811 g, 33.4 mmol) over a period of 30 minutes. The mixture was stirred at room temperature and was monitored by LC/MS until the reaction was complete. The mixture was partitioned between tert-butyl methyl ether (200 mL) and aqueous 1 M HCl (~100 mL). The layers were separated and the aqueous layer was extracted with additional tert-butyl methyl ether. The combined organic layers were washed with brine, dried (Na$_2$SO$_4$), filtered, concentrated and purified directly by chromatography over silica gel eluting with (petroleum ether:ethyl acetate=10:1) to give title compound. $^1$H NMR (400 MHz, CDCl$_3$) δ ppm 7.36-7.25 (m, 1H), 7.20 (d, J=8.0 Hz, 1H), 6.85 (d, J=7.7 Hz, 1H), 5.12-4.93 (m, 1H), 4.79 (d, J=9.7 Hz, 1H), 4.40 (s, 1H), 4.24 (dd, J=7.1, 3.3 Hz, 2H), 1.31 (t, J=7.1 Hz, 3H). MS (ESI+) m/z 227 (M+H)$^+$.

Example 43C 7-chloro-2,3-dihydrobenzofuran-3-carboxylic acid

A solution Example 43B (1.6 g, 7.06 mmol) in tetrahydrofuran (30 mL) and methanol (30 mL) was treated with 1M aqueous NaOH (35.3 mL, 35.3 mmol) and the mixture was stirred at room temperature for 30 minutes. The mixture was partitioned between tert-butyl methyl ether (500 mL) and aqueous 0.2 M HCl (~200 mL). The tert-butyl methyl ether layer was washed with brine, dried (Na$_2$SO$_4$), filtered and concentrated to give the title compound. $^1$H NMR (400 MHz, CDCl$_3$) δ ppm 7.32 (d, J=7.5 Hz, 1H), 7.22 (d, J=8.0 Hz, 1H), 6.86 (t, J=7.8 Hz, 1H), 5.02 (dd, J=9.4, 6.5 Hz, 1H), 4.78 (t, J=9.6 Hz, 1H), 4.45 (dd, J=9.7, 6.6 Hz, 1H).

Example 43D 7-chloro-N-(naphthalene-1-sulfonyl)-2,3-dihydro-1-benzofuran-3-carboxamide To a solution of 7-chloro-2,3-dihydrobenzofuran-3-carboxylic acid (40 mg, 0.20 mmol), EDAC (1-ethyl-3-[3-(dimethylamino)propyl]-carbodiimide hydrochloride, 77 mg, 0.40 mmol) and 4-dimethylaminopyridine (27 mg, 0.22 mmol) in anhydrous dichloromethane (500 µL) was added naphthalene-1-sulfonamide (50 mg, 0.24 mmol). The solution was stirred overnight at room temperature. TFA (20 µL) was added and the reaction mixture was placed directly on silica for chromatography (5 to 20% methyl tert-butylether/CH$_2$Cl$_2$) to give the impure title compound which was repurified by reverse-phase HPLC [Waters XBridge™ C18 5 µm OBD column, 30×100 mm, flow rate 40 mL/minute, 20 to 60% gradient of acetonitrile in 0.1% aqueous TFA] to give the title compound. $^1$H NMR (400 MHz, dimethylsulfoxide-d$_6$) δ ppm 8.67 (dd, J=8.6, 1.0 Hz, 1H), 8.30-8.25 (m, 2H), 8.12-8.08 (m, 1H), 7.84 (ddd, J=8.5, 6.9, 1.4 Hz, 1H), 7.73-7.64 (m, 2H), 7.12 (d, J=8.0 Hz, 1H), 7.10-7.06 (m, 1H), 6.60 (dd, J=8.0, 7.5 Hz, 1H), 4.64-4.58 (m, 2H), 4.45-4.40 (m, 1H). MS (ESI) m/z 388 (M+H)$^+$.

Example 44

7-chloro-3-ethyl-N-(naphthalene-1-sulfonyl)-2,3-dihydro-1-benzofuran-3-carboxamide Example 44A Ethyl 7-chloro-3-ethyl-2,3-dihydrobenzofuran-3-carboxylate To a solution of Example 43B (600 mg, 2.65 mmol) in N,N-dimethylformamide (6 mL) cooled to 0° C. was added 1 M potassium tert-butoxide (3.97 mL, 3.97 mmol) in tetrahydrofuran dropwise. The solution went dark and was stirred for a further 5 minutes at −60° C., after which the acetone-dry ice bath was swapped for an ice bath at 0° C. and ethyliodide (2.139 mL, 26.5 mmol) was added. The resulting solution turned clearer and was left to warm up to room temperature over 30 minutes. Aqueous 1 N hydrochloric acid was added, and the mixture was extracted with diethyl ether (2×30 mL). The combined organic layers were dried (Na$_2$SO$_4$), filtered, concentrated under reduced pressure, and purified directly by chromatography over silica gel eluting with (petroleum ether:ethyl acetate=10:1) to provide the title compound. MS (ESI) m/z 255 (M+H)$^+$.

Example 44B 7-chloro-3-ethyl-2,3-dihydrobenzofuran-3-carboxylic Acid

A solution of Example 44A (523 mg, 2.053 mmol) in tetrahydrofuran (10 mL) and methanol (10 mL) was treated with 1 M aqueous NaOH (10.27 mL, 10.27 mmol) and was stirred at room temperature and was monitored by LC/MS until the reaction was complete. The mixture was partitioned between tert-butyl methyl ether (300 mL) and aqueous 0.2 M HCl (150 mL). The tert-butyl methyl ether layer was washed with brine, dried over Na$_2$SO$_4$, filtered, and concentrated to provide title compound. $^1$H NMR (400 MHz, CDCl$_3$) δ ppm 7.27 (d, J=7.4 Hz, 1H), 7.21 (dd, J=8.0, 1.0 Hz, 1H), 6.85 (t, J=7.8 Hz, 1H), 5.11 (d, J=9.5 Hz, 1H), 4.45 (d, J=9.5 Hz, 1H), 2.15 (m, 1H), 1.93 (m, 1H), 0.91 (t, J=7.4 Hz, 3H).

Example 44C 7-chloro-3-ethyl-N-(naphthalene-1-sulfonyl)-2,3-dihydro-1-benzofuran-3-carboxamide To a solution of the acid Example 44B (47 mg, 0.21 mmol), 1-(3-dimethylaminopropyl)-3-ethylcarbodiimide hydrochloride (81 mg, 0.42 mmol) and 4-dimethylaminopyridine (28 mg, 0.23 mmol) in anhydrous dichloromethane (500 µL) was added naphthalene-1-sulfonamide (52 mg, 0.25 mmol). The solution was stirred overnight at room temperature. The reaction solution was concentrated and was purified by reverse-phase HPLC [Waters XBridge™ C18 5 µm OBD column, 30×100 mm, flow rate 40 mL/minute, 20 to 70% gradient of acetonitrile in 0.1% aqueous TFA] to give the title compound. $^1$H NMR (400 MHz, dimethylsulfoxide-d$_6$) δ ppm 8.59 (d, J=8.6 Hz, 1H), 8.32-8.25 (m, 2H), 8.09 (d, J=8.1 Hz, 1H), 7.76-7.63 (m, 3H), 7.36 (d, J=7.5 Hz, 1H), 7.21 (d, J=8.0 Hz, 1H), 6.84 (dd, J=8.0, 7.5 Hz, 1H), 4.81 (d, J=9.6 Hz, 1H), 4.37 (d, J=9.6 Hz, 1H), 2.17 (dq, J=14.5, 7.3 Hz, 1H), 1.78 (dq, J=14.5, 7.3 Hz, 1H), 0.45 (t, J=7.3 Hz, 3H). MS (ESI) m/z 416 (M+H)$^+$.

Example 45

N-(naphthalene-1-sulfonyl)-7-(trifluoromethyl)-2,3-dihydro-1-benzofuran-3-carboxamide Example 45A Ethyl 2-(2-(trifluoromethyl)phenoxy)acetate To a stirred solution of 2-(trifluoromethyl)phenol (15.00 g, 93 mmol) in acetone (150 mL) under nitrogen at ambient temperature were added K$_2$CO$_3$ (14.07 g, 102 mmol) and ethyl 2-bromoacetate (10.30 mL, 93 mmol). The reaction mixture was heated to reflux and was stirred under nitrogen for 16 hours. After cooling to ambient temperature, the reaction mixture was filtered to remove insoluble material. The filtrate was concentrated under reduced pressure to give crude title compound.

Example 45B

Diethyl 2-oxo-3-(2-(trifluoromethyl)phenoxy)succinate

A suspension of NaH (2.482 g, 62.0 mmol) in tetrahydrofuran (100 mL) was treated dropwise with ethanol (3.25 mL, 56.4 mmol)) over 5 minutes, treated with diethyl oxalate (8.86 mL, 64.9 mmol), heated to reflux, treated dropwise with a solution of ethyl 2-(2-(trifluoromethyl) phenoxy)acetate (Example 45A, 14.00 g, 56.4 mmol) in tetrahydrofuran (anhydrous, 20 mL) and heated to reflux for 2 more hours. The mixture was cooled and poured into a swirled mixture of aqueous 2 M HCl (200 mL) and ice (200 g). The layers were separated and the aqueous layer was extracted with ethyl acetate (200 mL). The combined organic layers were washed with brine, dried ($MgSO_4$), filtered, and concentrated to provide the crude title compound which was carried onto the next step without purification.

Example 45C 3-ethyl 2-methyl 7-(trifluoromethyl)benzofuran-2,3-dicarboxylate A flask containing concentrated $H_2SO_4$ (50 mL, 938 mmol) was cooled to –15° C. in an acetone/dry ice bath and was treated dropwise/portionwise with diethyl 2-oxo-3-(2-(trifluoromethyl)phenoxy)succinate (Example 45B, 19.00 g, 54.6 mmol). The mixture was allowed to slowly warm up to 15° C. and was stirred for about 16 hours. The mixture was slowly poured into a stirred mixture of 400 mL ice water and ethyl acetate (600 mL). Additional ice was added during the addition. The aqueous layer was extracted with ethyl acetate (300 mL). The combined organic layers were washed with brine, dried ($MgSO_4$), filtered, and concentrated to provide the title compound. MS (ESI) m/z 331.2 $(M+H)^+$.

Example 45D

Ethyl 7-(trifluoromethyl)benzofuran-3-carboxylate

A solution of diethyl 7-(trifluoromethyl)benzofuran-2,3-dicarboxylate (Example 45C, 5 g, 13.47 mmol) in dimethyl sulfoxide (60 mL) was treated with sodium chloride (1.575 g, 26.9 mmol), treated with water (0.485 mL, 26.9 mmol), heated to 160° C. under $N_2$ for 5 hours, and allowed to stir at room temperature overnight. The mixture was cooled in ice bath and was added to 150 g of ice. The mixture was diluted with water (100 mL) and extracted with ethyl acetate (4 times, ~100 mL each extraction). The combined ethyl acetate extractions were washed with brine, dried ($Na_2SO_4$), filtered, and concentrated. Chromatography on an 80 g silica gel column (eluting with 5% (15 minutes), 5 to 15% (over 25 minutes) ethyl acetate in heptanes) provided the title compound. MS (ESI) m/z 259.1 $(M+H)^+$.

Example 45E

Ethyl 7-(trifluoromethyl)-2,3-dihydrobenzofuran-3-carboxylate

A solution of ethyl 7-(trifluoromethyl)benzofuran-3-carboxylate (Example 45D, 2.000 g, 7.75 mmol) in methanol (methanol) (24 mL) was treated in portions with magnesium (0.941 g, 38.7 mmol) over a period of 30 minutes. The mixture was stirred at 15° C. After stirring for about 3 hours, the mixture was extracted with ethyl acetate (100 mL×2), washed with NaCl solution (50 mL), dried over $Na_2SO_4$, filtered, and concentrated to give the title compound. MS (ESI) m/z 247.1 $(M+H)^+$.

Example 45F 7-(trifluoromethyl)-2,3-dihydrobenzofuran-3-carboxylic Acid

To a stirred solution of ethyl 7-(trifluoromethyl)-2,3-dihydrobenzofuran-3-carboxylate (Example 45E, 1.6 g, 5.53 mmol) in 1,4-dioxane (Ratio: 1.000, Volume: 10 mL) and water (Ratio: 1.000, Volume: 10 mL) was added NaOH (0.443 g, 11.07 mmol). The resultant reaction mixture was stirred at 25° C. for 3 hours. The organics were acidified to pH=1~2 with aqueous 3 M hydrochloric acid solution and the title compound was extracted with ethyl acetate (2×100 mL). The combined organic layers were passed through a hydrophobic frit and the filtrate was concentrated under reduced pressure. The crude solid was washed with 5% ethyl acetate in hexane (10 mL×2) to provide the title compound. $^1$H NMR (400 MHz, $CDCl_3$) δ ppm 7.60 (d, J=7.5 Hz, 1H), 7.44 (d, J=7.8 Hz, 1H), 6.98 (t, J=7.7 Hz, 1H), 5.07 (dd, J=9.5, 6.6 Hz, 1H), 4.83 (t, J=9.7 Hz, 1H), 4.42 (dd, J=9.8, 6.6 Hz, 1H).

Example 45G

N-(naphthalene-1-sulfonyl)-7-(trifluoromethyl)-2,3-dihydro-1-benzofuran-3-carboxamide To a solution of Example 45F (49 mg, 0.21 mmol), EDAC (1-ethyl-3-[3-(dimethylamino)propyl]-carbodiimide hydrochloride, 81 mg, 0.42 mmol) and 4-dimethylaminopyridine (28 mg, 0.23 mmol) in anhydrous dichloromethane (500 µL) was added naphthalene-1-sulfonamide (52 mg, 0.25 mmol). The solution was stirred overnight at room temperature. TFA (20 µL) was added and the reaction mixture was placed directly on silica for chromatography (5 to 20% methyl tert-butyl ether/$CH_2Cl_2$) to give crude material which was repurified by reverse-phase HPLC [Waters XBridge™ C18 5 µm OBD column, 30×100 mm, flow rate 40 mL/minute, 20 to 70% gradient of acetonitrile in 0.1% aqueous TFA] to provide the title compound. $^1$H NMR (400 MHz, dimethylsulfoxide-$d_6$) δ ppm 8.70-8.66 (m, 1H), 8.31-8.26 (m, 2H), 8.12-8.09 (m, 1H), 7.86 (ddd, J=8.4, 6.9, 1.3 Hz, 1H), 7.72 (ddd, J=8.2, 6.9, 1.1 Hz, 1H), 7.67 (dd, J=8.1, 7.5 Hz, 1H), 7.39 (d, J=7.5 Hz, 1H), 7.33 (d, J=7.9 Hz, 1H), 6.79-6.74 (m, 1H), 4.72-4.66 (m, 2H), 4.46-4.40 (m, 1H). MS (ESI) m/z 439 $(M+NH_4)^+$.

Example 46

8-bromo-5-methoxy-2,2-dimethyl-N-(quinoline-5-sulfonyl)-3,4-dihydro-2H-1-benzopyran-4-carboxamide

Example 46A 5-methoxy-2,2-dimethylchroman-4-one

To a mixture of 5-hydroxy-2,2-dimethylchroman-4-one [CAS#4236-32-2] (2.5 g, 13.01 mmol) and potassium carbonate (3.60 g, 26.0 mmol) in N,N-dimethylformamide (10 mL) was added iodomethane (1.215 mL, 19.51 mmol) at ambient temperature. The reaction mixture was stirred overnight, and LC/MS showed the reaction was complete. The mixture was filtered and the filter cake was washed with dichloromethane (10 mL×3). The combined filtrates were washed with brine, dried over MgSO$_4$, filtered, and concentrated. The residue was purified via chromatography, eluting with ethyl acetate in heptane at 0-50% gradient to provide the title compound. MS (APCI+) m/z 207.1 (M+1)$^+$.

Example 46B 5-methoxy-2,2-dimethylchroman-4-carboxamide

To a solution of Example 46A (2.25 g, 10.91 mmol) and zinc(II) iodide (0.139 g, 0.436 mmol) in dichloromethane (25 mL) cooled in an ice-bath was added trimethylsilanecarbonitrile (4.09 mL, 32.7 mmol) slowly. The mixture was stirred at room temperature overnight. LC/MS showed a new peak at 97 minutes, and the starting material peak at 0.71 minutes nearly disappeared. The solvent was removed under pressure and the residue was purified via chromatography, eluting ethyl acetate in heptane at 0-60% gradient to afford a crude material which was dissolved in ethyl acetate (30 mL) and aqueous 6 M HCl (3 mL). Tin(II) chloride hydrate (9.06 g, 43.6 mmol) was added. The mixture was heated at 90° C. and was stirred overnight and cooled down to ambient temperature. The solvent was removed under pressure and dichloromethane (30 mL) was added. The mixture was washed with brine, dried over MgSO$_4$, filtered, and concentrated. Purification via chromatography on a 40 g silica gel cartridge, eluting with ethyl acetate/methanol (9:1) in heptane at 0-80% gradient provided the title compound. $^1$H NMR (400 MHz, dimethylsulfoxide-d$_6$) δ ppm 7.26 (s, 1H), 7.05 (td, J=8.2, 0.7 Hz, 1H), 6.73 (s, 1H), 6.46 (dd, J=8.2, 1.0 Hz, 1H), 6.35 (dd, J=8.3, 1.0 Hz, 1H), 3.67 (s, 3H), 3.54 (dd, J=10.1, 7.1 Hz, 1H), 2.00 (dd, J=13.4, 7.2 Hz, 1H), 1.83 (dd, J=13.4, 10.1 Hz, 1H), 1.33 (s, 3H), 1.14 (s, 3H). MS (ESI+) m/z 236.1 (M+H)$^+$.

Example 46C 8-bromo-5-methoxy-2,2-dimethylchroman-4-carboxamide

To the mixture of 5-methoxy-2,2-dimethylchroman-4-carboxamide (300 mg, 1.28 mmol) in CS$_2$ (10 mL) cooled in an ice-bath, was added bromine (0.072 mL, 1.4 mmol) in CS$_2$ (1 mL) slowly. After addition, LC/MS showed a new product peak at 0.93 minutes and the starting material at 0.73 minutes disappeared. Na$_2$S$_2$O$_3$ (10 mL, 15%) was added. The mixture was washed with brine, dried over MgSO$_4$, filtered, and concentrated. The residue was purified via HPLC on a Phenomenex® Luna® C8(2) 5 um 100 Å AXIA™ column (30 mm×75 mm), with a gradient of acetonitrile (A) and 0.1% trifluoroacetic acid in water (B) was used, at a flow rate of 50 mL/minute (0-1.0 minute 5% A, 1.0-8.5 minute linear gradient 5-100% A, 8.5-11.5 minute 100% A, 11.5-12.0 minute linear gradient 95-5% A), to provide the title compound. MS (APCI+) m/z 341.12 (M+1)$^+$.

Example 46D 8-bromo-5-methoxy-2,2-dimethyl-N-(quinolin-5-ylsulfonyl)chroman-4-carboxamide A mixture of Example 46C (100 mg, 0.318 mmol) and sodium hydride (50.9 mg, 1.273 mmol) in N,N-dimethylformamide (2 mL) was stirred at room temperature for 30 minutes. Quinoline-5-sulfonyl chloride (94 mg, 0.414 mmol) was added slowly. After continued stirring overnight, LC/MS indicated the reaction was complete. Water (10 mL) and dichloromethane (30 mL) were added, and the organic layer washed with brine, dried over MgSO$_4$, filtered, and concentrated. The residue was purified via a 25 g silica gel cartridge, eluting with ethyl acetate/methanol (9:1) in heptane at 0-60% gradient to provide the title compound. $^1$H NMR (500 MHz, dimethylsulfoxide-d$_6$) δ ppm 12.69 (s, 1H), 9.11 (dd, J=4.2, 1.6 Hz, 1H), 9.06 (dt, J=8.7, 1.3 Hz, 1H), 8.38 (ddd, J=8.8, 7.4, 1.1 Hz, 2H), 8.00-7.92 (m, 1H), 7.85 (dd, J=8.8, 4.2 Hz, 1H), 7.31 (d, J=8.8 Hz, 1H), 6.27 (d, J=8.9 Hz, 1H), 3.70-3.61 (m, 1H), 2.76 (s, 3H), 2.08 (s, 1H), 1.58 (dd, J=13.5, 10.5 Hz, 1H), 1.25 (s, 3H), 1.09 (s, 3H). MS (ESI+) m/z 505.0 (M+H)$^+$.

Example 47

5-methoxy-2,2-dimethyl-N-(quinoline-8-sulfonyl)-3,4-dihydro-2H-1-benzopyran-4-carboxamide The title compound was prepared and purified as described in Example 46D, substituting Example 46B for Example 46C, and quinoline-8-sulfonyl chloride [CAS#18704-37-5] for quinoline-5-sulfonyl chloride. $^1$H NMR (501 MHz, dimethylsulfoxide-d$_6$) δ ppm 12.28 (s, 1H), 9.07 (dd, J=4.2, 1.8 Hz, 1H), 8.49 (dd, J=8.4, 1.8 Hz, 1H), 8.35 (dd, J=7.4, 1.4 Hz, 1H), 8.26 (dd, J=8.2, 1.5 Hz, 1H), 7.74-7.60 (m, 2H), 6.88 (t, J=8.2 Hz, 1H), 6.18 (dd, J=12.7, 8.2 Hz, 2H), 3.63 (dd, J=9.4, 7.3 Hz, 1H), 2.94 (s, 3H), 1.86 (dd, J=13.5, 7.3 Hz, 1H), 1.34 (dd, J=13.5, 9.5 Hz, 1H), 0.96 (s, 3H), 0.89 (s, 3H). MS (ESI+) m/z 427.2 (M+H)$^+$.

Example 48

5-methoxy-2,2-dimethyl-N-(quinoline-5-sulfonyl)-3,4-dihydro-2H-1-benzopyran-4-carboxamide The title compound was prepared and purified as described in Example 46D, substituting Example 46B for Example 46C. $^1$H NMR (501 MHz, dimethylsulfoxide-d$_6$) δ ppm 12.63 (s, 1H), 9.20-9.00 (m, 2H), 8.38 (td, J=7.9, 7.4, 1.2 Hz, 2H), 7.96 (dd, J=8.4, 7.5 Hz, 1H), 7.85 (dd, J=8.7, 4.2 Hz, 1H), 6.99 (t, J=8.2 Hz, 1H), 6.35-6.20 (m, 2H), 3.63-3.57 (m, 1H), 2.77 (s, 3H), 2.01 (dd, J=13.4, 7.1 Hz, 1H), 1.54 (dd, J=13.4, 10.5 Hz, 1H), 1.19 (s, 3H), 1.08 (s, 3H). MS (ESI+) m/z 427.1 (M+H)$^+$.

Example 49

5-methoxy-2,2-dimethyl-N-(naphthalene-1-sulfonyl)-3,4-dihydro-2H-1-benzopyran-4-carboxamide A mixture of Example 46B (50 mg, 0.213 mmol) and sodium hydride (34.0 mg, 0.850 mmol) in N,N-dimethylformamide (2 mL) was stirred at ambient temperature for 30 minutes. Naphthalene-1-sulfonyl chloride (72.3 mg, 0.319 mmol) was added slowly, and the mixture continued stirring overnight. LC/MS showed a new product peak at 0.79 minutes. Water (10 mL) and dichloromethane (20 mL) were added. The organic layer was washed with brine, dried over MgSO$_4$, filtered, and concentrated. The residue was purified via a 25 g silica gel cartridge, eluting with ethyl acetate/methanol (9:1) in heptane at 0-60% gradient to provide the title compound. $^1$H NMR (400 MHz, dimethylsulfoxide-d$_6$)

δ ppm 12.51 (s, 1H), 8.70 (dd, J=8.6, 1.1 Hz, 1H), 8.30 (td, J=7.5, 1.1 Hz, 2H), 8.20-8.11 (m, 1H), 7.82 (ddd, J=8.5, 6.9, 1.4 Hz, 1H), 7.76-7.66 (m, 2H), 6.97 (t, J=8.2 Hz, 1H), 6.26 (ddd, J=18.1, 8.3, 1.0 Hz, 2H), 3.64 (dd, J=10.3, 7.1 Hz, 1H), 2.74 (s, 3H), 1.99 (dd, J=13.4, 7.1 Hz, 1H), 1.53 (dd, J=13.4, 10.3 Hz, 1H), 1.14 (s, 3H), 1.07 (s, 3H). MS (ESI+) m/z 426.1 (M+H)$^+$.

Example 50

8-cyano-5-methoxy-2,2-dimethyl-N-(naphthalene-1-sulfonyl)-3,4-dihydro-2H-1-benzopyran-4-carboxamide Example 50A 8-cyano-5-methoxy-2,2-dimethylchroman-4-carboxamide A mixture of Example 46C (120 mg, 0.382 mmol) and cyanocopper (103 mg, 1.146 mmol) in N,N-dimethylformamide (6 mL) was heated at 120° C. overnight. LC/MS indicated the conversion was complete. The solvent was removed under pressure and the residue was dissolved in dichloromethane (20 mL). The mixture was washed with brine, dried over MgSO$_4$, filtered, and concentrated. Purification via chromatography on a 24 g silica gel cartridge, eluting with a methanol/ethyl acetate 0-10% gradient provided the title compound.

Example 50B 8-cyano-5-methoxy-2,2-dimethyl-N-(naphthalen-1-ylsulfonyl)chroman-4-carboxamide A mixture of Example 50A (50 mg, 0.192 mmol) and sodium hydride (30.7 mg, 0.768 mmol) in N,N-dimethylformamide (2 mL) was stirred at ambient temperature for 30 minutes. Naphthalene-1-sulfonyl chloride (65.3 mg, 0.288 mmol) was added slowly, and the mixture was stirred overnight. Water (10 mL) and dichloromethane (20 mL) were added. The organic layer was washed with brine, dried over MgSO$_4$, filtered, and concentrated. The residue was purified via a 25 g silica gel cartridge, eluting with ethyl acetate/methanol (9:1) in heptane at 0-60% gradient to provide the title compound. $^1$H NMR (501 MHz, dimethylsulfoxide-d$_6$) δ ppm 8.67 (dd, J=8.6, 1.0 Hz, 1H), 8.36-8.27 (m, 2H), 8.16 (dd, J=8.3, 1.4 Hz, 1H), 7.81 (ddd, J=8.5, 6.9, 1.4 Hz, 1H), 7.77-7.67 (m, 2H), 7.52 (d, J=8.7 Hz, 1H), 6.44 (d, J=8.8 Hz, 1H), 3.64 (dd, J=9.9, 7.2 Hz, 1H), 2.83 (s, 3H), 2.10 (dd, J=13.6, 7.2 Hz, 1H), 1.63 (dd, J=13.7, 10.0 Hz, 1H), 1.20 (s, 3H), 1.13 (s, 3H). MS (ESI+) m/z 451.0 (M+H)$^+$.

Example 51

8-chloro-5-methoxy-2,2-dimethyl-N-(naphthalene-1-sulfonyl)-3,4-dihydro-2H-1-benzopyran-4-carboxamide A mixture of Example 52 (50 mg, 0.099 mmol), copper(I) chloride (147 mg, 1.487 mmol) and N,N-dimethylacetamide (0.5 mL) was sealed in a high pressure tube was refluxed at 150° C. overnight. LC/MS indicated the conversion was complete. Dichloromethane (2 mL) was added and the mixture was loaded on a 24 g silica gel cartridge. Chromatography with methanol in ethyl acetate at a 0-10% gradient provided the title compound. $^1$H NMR (400 MHz, dimethylsulfoxide-d$_6$) δ ppm 12.57 (s, 1H), 8.68 (dd, J=8.6, 1.0 Hz, 1H), 8.30 (ddd, J=8.8, 7.3, 1.1 Hz, 2H), 8.16 (dt, J=8.1, 0.8 Hz, 1H), 7.82 (ddd, J=8.5, 6.9, 1.4 Hz, 1H), 7.79-7.63 (m, 2H), 7.15 (d, J=8.8 Hz, 1H), 6.28 (d, J=8.9 Hz, 1H), 3.67 (dd, J=10.2, 7.2 Hz, 1H), 2.74 (s, 3H), 2.05 (dd, J=13.5, 7.2 Hz, 1H), 1.57 (dd, J=13.6, 10.3 Hz, 1H), 1.20 (s, 3H), 1.09 (s, 3H). MS (ESI+) m/z 460.2 (M+H)$^+$.

Example 52

8-bromo-5-methoxy-2,2-dimethyl-N-(naphthalene-1-sulfonyl)-3,4-dihydro-2H-1-benzopyran-4-carboxamide A mixture of Example 46C (175 mg, 0.557 mmol) and sodium hydride (89 mg, 2.228 mmol) in N,N-dimethylformamide (4 mL) was stirred at ambient temperature for 30 minutes. Naphthalene-1-sulfonyl chloride (189 mg, 0.836 mmol) was added slowly, and the mixture was stirred overnight. Water (15 mL) and dichloromethane (30 mL) were added. The organic layer was washed with brine, dried over MgSO$_4$, filtered, and concentrated. The residue was purified using a 25 g silica gel cartridge, eluting with ethyl acetate/methanol (9:1) in heptane at 0-60% gradient to provide the title compound. $^1$H NMR (501 MHz, dimethylsulfoxide-d$_6$) δ ppm 12.57 (s, 1H), 8.68 (dd, J=8.6, 1.0 Hz, 1H), 8.36-8.23 (m, 2H), 8.20-8.08 (m, 1H), 7.81 (ddd, J=8.5, 6.9, 1.4 Hz, 1H), 7.75-7.66 (m, 2H), 7.29 (dd, J=8.8, 0.7 Hz, 1H), 6.25 (d, J=8.9 Hz, 1H), 3.66 (dd, J=10.5, 7.4 Hz, 1H), 2.74 (s, 3H), 2.05 (dd, J=13.5, 7.2 Hz, 1H), 1.56 (dd, J=13.5, 10.3 Hz, 1H), 1.20 (s, 3H), 1.08 (s, 3H). MS (ESI+) m/z 504 (M+H)$^+$.

Example 53

5-methoxy-N-(naphthalene-1-sulfonyl)-8-(trifluoromethyl)-3,4-dihydro-2H-1-benzopyran-4-carboxamide Example 53A 5-methoxy-8-(trifluoromethyl)chroman-4-one A mixture of 5-methoxychroman-4-one [CAS#863309-86-8] (896 mg, 5.03 mmol), trimethyl(trifluoromethyl)silane (1430 mg, 10.06 mmol), silver(I) fluoride (159 mg, 1.257 mmol) and PhI(OAc)$_2$ ((diacetoxyiodo)benzene, 3239 mg, 10.06 mmol) in dimethylsulfoxide (10 mL) was stirred at 45° C. overnight. The mixture was cooled to ambient temperature, and dichloromethane (50 mL) was added into the reaction mixture. The mixture was washed with saturated aqueous NaHCO$_3$ and brine, dried over MgSO$_4$, filtered, and concentrated. The residue was purified via chromatography, eluting with an ethyl acetate/methanol (9:1) in heptane at 0-60% gradient. $^1$H NMR (400 MHz, Chloroform-d) δ ppm 7.66 (d, J=8.9 Hz, 1H), 6.82 (d, J=8.9 Hz, 1H), 4.56 (t, J=6.4 Hz, 2H), 3.96 (s, 3H), 2.86-2.77 (m, 2H). MS (ESI+) m/z 247 (M+H). The second fraction was the title compound, 5-methoxy-8-(trifluoromethyl)chroman-4-one. $^1$H NMR (400 MHz, Chloroform-d) δ ppm 7.67 (dd, J=8.9, 0.7 Hz, 1H), 6.57 (d, J=8.9 Hz, 1H), 4.60 (dd, J=6.9, 6.1 Hz, 2H), 3.96 (s, 3H), 2.92-2.76 (m, 2H). MS (ESI+) m/z 247 (M+H)$^+$.

Example 53B

5-methoxy-8-(trifluoromethyl)chroman-4-carbonitrile

Example 53A (0.586 g, 2.380 mmol) and toluenesulfonylmethyl isocyanide (0.604 g, 3.09 mmol) was dissolved in 1,2-dimethoxyethane (24 mL) in a 50 mL round bottom flask. The mixture was cooled to −8° C. (internal temperature) with ice/acetone/dry ice under nitrogen. Solid potassium tert-butoxide (0.614 g, 5.47 mmol) was added in portions, keeping the internal temperature <−5° C. for about 30 minutes. The reaction was allowed to slowly warm to room temperature and was stirred overnight. The solvent was removed under vacuum and the crude residue was quenched with water (30 mL). The aqueous layer was extracted with ether (4×50 mL). The combined extracts were removed under vacuum and the residue was chromatographed using a 40 g silica gel cartridge, eluting with ethyl acetate in hexanes at 0-50% gradient to provide the title compound. $^1$H NMR (400 MHz, Chloroform-d) δ ppm 7.52 (d, J=8.7 Hz, 1H), 6.52 (d, J=8.7 Hz, 1H), 4.56-4.46 (m, 1H), 4.38-4.24 (m, 1H), 4.04 (dt, J=5.8, 2.0 Hz, 1H), 3.96 (d, J=0.6 Hz, 3H), 2.36 (dq, J=14.3, 2.6 Hz, 1H), 2.31-2.18 (m, 1H). MS (APCI+) m/z 258 (M+H)$^+$.

Example 53C

5-methoxy-8-(trifluoromethyl)chroman-4-carboxamide

A mixture of Example 53B (200 mg, 0.778 mmol) and sodium hydroxide (311 mg, 7.78 mmol) in ethanol (6 mL) was stirred at 90° C. overnight. LC/MS indicated the conversion was complete. The solvent was removed under pressure and the residue was dissolved in dichloromethane (20 mL). The mixture was washed with aqueous 1M HCl and brine, dried over MgSO$_4$, filtered, and concentrated. The residue was purified via chromatography on a 12 g cartridge, eluting with ethyl acetate/methanol (9:1) in heptane at 0-70% gradient to provide the title compound. $^1$H NMR (400 MHz, Chloroform-d) δ ppm 7.48 (d, J=8.7 Hz, 1H), 6.50 (d, J=8.7 Hz, 1H), 5.90 (s, 1H), 5.56 (s, 1H), 4.42 (dddd, J=11.3, 4.2, 2.8, 1.5 Hz, 1H), 4.28 (ddd, J=12.3, 11.2, 2.4 Hz, 1H), 3.91 (s, 3H), 3.79 (dt, J=6.1, 1.9 Hz, 1H), 2.41 (dq, J=14.1, 2.6 Hz, 1H), 2.06-1.93 (m, 1H). MS (ESI+) m/z 276 (M+H)$^+$.

Example 53D

5-methoxy-N-(naphthalen-1-ylsulfonyl)-8-(trifluoromethyl)chroman-4-carboxamide A mixture of Example 53C (170 mg, 0.618 mmol) and sodium hydride (99 mg, 2.471 mmol) in N,N-dimethylformamide (2 mL) was stirred at room temperature for 30 minutes. Naphthalene-1-sulfonyl chloride (210 mg, 0.927 mmol) was added slowly and the mixture was stirred overnight. LC/MS showed a new product peak at 0.79 minutes and that starting material still existed. Water (10 mL) and dichloromethane (30 mL) were added into the mixture. The organic layer was washed with brine, dried over MgSO$_4$, filtered, and concentrated. The residue was purified via a 25 g silica gel cartridge, eluting with ethyl acetate/methanol (9:1) in heptane at a 0-60% gradient to provide the title compound. $^1$H NMR (500 MHz, dimethylsulfoxide-d$_6$) δ ppm 12.77 (s, 1H), 8.68 (dd, J=8.7, 1.0 Hz, 1H), 8.31 (dt, J=8.3, 1.1 Hz, 1H), 8.26 (dd, J=7.4, 1.3 Hz, 1H), 8.19-8.13 (m, 1H), 7.83 (ddd, J=8.5, 6.9, 1.4 Hz, 1H), 7.77-7.64 (m, 2H), 7.37 (d, J=8.8 Hz, 1H), 7.25-7.00 (m, 1H), 6.41 (d, J=8.8 Hz, 1H), 4.09 (dt, J=11.0, 4.1 Hz, 1H), 3.80-3.69 (m, 2H), 3.00 (s, 3H), 2.17-2.05 (m, 1H), 1.85 (dtd, J=14.4, 4.6, 2.7 Hz, 1H). MS (ESI+) m/z 466.2 (M+H)$^+$.

Example 54

8-cyclobutyl-5-methoxy-N-(quinoline-5-sulfonyl)-3,4-dihydro-2H-1-benzopyran-4-carboxamide

Example 54A

8-bromo-5-methoxy-N-(quinolin-5-ylsulfonyl)chroman-4-carboxamide

Example 11B (100 mg, 0.35 mmol, 1.0 equivalent), 1-(3-dimethylaminopropyl)-3-ethylcarbodiimide hydrochloride (132.3 mg, 0.70 mmol, 2.0 equivalents) and 4-dimethylaminopyridine (46.81 mg, 0.38 mmol, 1.1 equivalents) were dissolved in dichloromethane (1 mL). The solution was added to a vial containing 5-quinoline-1-sulfonamide (124.9 mg, 0.060 mmol, 1.2 equivalents) and the mixture was stirred overnight at room temperature. The solvent was removed under N$_2$ and the residue was reconstituted in 1:1 v/v dimethylsulfoxide/methanol, and was purified via preparative reverse phase HPLC/MS method 7 to provide the title compound. $^1$H NMR (501 MHz, dimethylsulfoxide-d$_6$:D$_2$O=9:1 (v/v)) δ ppm 9.10 (dd, J=4.2, 1.6 Hz, 1H), 9.06 (ddd, J=8.8, 1.6, 0.9 Hz, 1H), 8.39 (dt, J=8.5, 1.1 Hz, 1H), 8.36 (dd, J=7.5, 1.2 Hz, 1H), 7.97 (dd, J=8.5, 7.5 Hz, 1H), 7.87 (dd, J=8.8, 4.2 Hz, 1H), 7.31 (d, J=8.8 Hz, 1H), 6.30 (d, J=8.9 Hz, 1H), 4.11 (dt, J=11.0, 4.0 Hz, 1H), 3.82-3.77 (m, 1H), 3.71-3.63 (m, 1H), 2.96 (s, 3H), 2.14-2.03 (m, 1H), 1.88-1.80 (m, 1H). MS (APCI+) m/z 476.9 (M+H)$^+$.

Example 54B

8-cyclobutyl-5-methoxy-N-(quinoline-5-sulfonyl)-3,4-dihydro-2H-1-benzopyran-4-carboxamide Example 54A (130 mg, 0.27 mmol, 1.0 equivalent) was dissolved in tetrahydrofuran (1 mL). Dichloro[1,3-bis(2,6-di-3-pentylphenyl)imidazol-2-ylidene](3-chloropyridyl)palladium(II) (PEPPSI IPentCl, 23.4 mg, 0.03 mmol, 0.10 equivalents) was added and the vial was flushed with N$_2$. Cyclobutylzinc(II) bromide (0.5 M in tetrahydrofuran, 1.63 mL, 0.82 mmol, 3.0 equivalents) was added and the reaction was stirred overnight at room temperature. The material was purified directly via reverse phase preparative HPLC/MS method TFA 7 to provide the title compound. $^1$H NMR (501 MHz, dimethylsulfoxide-d$_6$:D$_2$O=9:1 (v/v)) δ ppm 9.13-9.05 (m, 2H), 8.39 (dt, J=8.4, 1.1 Hz, 1H), 8.35 (dd, J=7.5, 1.2 Hz, 1H), 7.96 (dd, J=8.4, 7.5 Hz, 1H), 7.86 (dd, J=8.8, 4.2 Hz, 1H), 6.95 (d, J=8.4 Hz, 1H), 6.25 (d, J=8.5 Hz, 1H), 4.03-3.95 (m, 1H), 3.79-3.75 (m, 1H), 3.64 (dd, J=7.1, 4.3 Hz, 1H), 3.52-3.41 (m, 1H), 2.92 (s, 3H), 2.17-2.07 (m, 2H), 2.07-1.97 (m, 1H), 1.97-1.80 (m, 3H), 1.80-1.66 (m, 2H). MS (APCI+) m/z 453.0 (M+H)$^+$.

Example 55

(4S)-8-cyclobutyl-5-methoxy-N-(naphthalene-1-sulfonyl)-3,4-dihydro-2H-1-benzopyran-4-carboxamide The racemic compound of Example 13 (50 mg, 0.1 μmmol) was separated via chiral SFC using instrument:

Aurora-2 and column: ChiralPak AD-H and Column Size: 21×250 mm, 5 micron; concentration: 15 mg/mL in methanol; co-Solvent: methanol. The first eluent at 2.64 minutes was the title compound; ee %>99. $^1$H NMR (500 MHz, dimethylsulfoxide-d$_6$) δ ppm 12.61 (s, 1H), 8.69 (dd, J=8.7, 1.0 Hz, 1H), 8.34-8.22 (m, 2H), 8.13 (d, J=8.2 Hz, 1H), 7.80 (ddd, J=8.4, 6.9, 1.4 Hz, 1H), 7.78-7.65 (m, 2H), 6.92 (d, J=8.4 Hz, 1H), 6.23 (d, J=8.5 Hz, 1H), 3.94 (dt, J=11.1, 4.0 Hz, 1H), 3.72-3.60 (m, 2H), 3.56-3.40 (m, 1H), 2.93 (s, 3H), 2.19-2.05 (m, 2H), 2.05-1.66 (m, 6H). MS (ESI+) m/z 452.0 (M+H)$^+$. The stereochemistry was confirmed by X-ray analysis.

Example 56

(4R)-8-cyclobutyl-5-methoxy-N-(naphthalene-1-sulfonyl)-3,4-dihydro-2H-1-benzopyran-4-carboxamide The title compound was isolated during the chiral separation described in Example 55. It was the second eluent at 4.75 minutes; ee %>99. $^1$H NMR (500 MHz, dimethylsulfoxide-d$_6$) δ ppm 12.60 (s, 1H), 8.69 (dd, J=8.5, 1.1 Hz, 1H), 8.36-8.23 (m, 2H), 8.14 (d, J=8.4 Hz, 1H), 7.81 (ddd, J=8.5, 6.9, 1.4 Hz, 1H), 7.75-7.61 (m, 2H), 6.92 (d, J=8.4 Hz, 1H), 6.23 (d, J=8.5 Hz, 1H), 3.94 (dt, J=11.0, 4.0 Hz, 1H), 3.67 (ddd, J=16.3, 8.9, 3.4 Hz, 2H), 3.52-3.40 (m, 1H), 2.92 (s, 3H), 2.19-2.04 (m, 2H), 2.04-1.66 (m, 6H). MS (ESI+) m/z 451.9 (M+H)$^+$.

Example 57

(4S)-5-methoxy-N-(naphthalene-1-sulfonyl)-8-(trifluoromethyl)-3,4-dihydro-2H-1-benzopyran-4-carboxamide 5-Methoxy-N-(naphthalen-1-ylsulfonyl)-8-(trifluoromethyl)chroman-4-carboxamide (Example 53, 76 mg, 0.163 mmol) was separated via chiral SFC using instrument: Aurora-2 and column: ChiralPak AD-H, column size 21×250 mm, 5 micron and concentration: 15 mg/mL in methanol; co-solvent: methanol. The first eluent was the title compound, ee %>99. $^1$H NMR (400 MHz, dimethylsulfoxide-d$_6$) δ ppm 12.74 (s, 1H), 8.70 (d, J=8.6 Hz, 1H), 8.23 (dd, J=10.9, 7.7 Hz, 2H), 8.11 (d, J=8.0 Hz, 1H), 7.78 (ddd, J=8.5, 6.8, 1.4 Hz, 1H), 7.67 (dt, J=17.7, 7.7 Hz, 2H), 7.36 (d, J=8.8 Hz, 1H), 6.42 (d, J=8.7 Hz, 1H), 4.08 (dt, J=11.0, 3.9 Hz, 1H), 3.74 (td, J=10.8, 2.6 Hz, 1H), 3.67 (d, J=6.8, 3.7 Hz, 1H), 3.08 (s, 3H), 2.06 (dddd, J=14.3, 10.5, 6.9, 3.6 Hz, 1H), 1.95-1.83 (m, 1H). MS (ESI+) m/z 466 (M+H)$^+$.

Example 58

(4R)-5-methoxy-N-(naphthalene-1-sulfonyl)-8-(trifluoromethyl)-3,4-dihydro-2H-1-benzopyran-4-carboxamide The title compound was obtained as the second eluent from the chiral separation described in Example 57, ee %>99. $^1$H NMR (501 MHz, dimethylsulfoxide-d$_6$) δ ppm 12.76 (s, 1H), 8.69 (d, J=8.8 Hz, 1H), 8.34-8.20 (m, 2H), 8.13 (dd, J=8.2, 1.2 Hz, 1H), 7.80 (ddd, J=8.5, 6.8, 1.4 Hz, 1H), 7.75-7.61 (m, 2H), 7.36 (d, J=8.8 Hz, 1H), 6.42 (d, J=8.8 Hz, 1H), 4.08 (dt, J=10.9, 4.0 Hz, 1H), 3.84-3.67 (m, 2H), 3.05 (s, 3H), 2.08 (dddd, J=14.1, 10.4, 6.9, 3.5 Hz, 1H), 1.87 (ddt, J=12.3, 4.1, 2.2 Hz, 1H). MS (ESI+) m/z 466 (M+H)$^+$.

Example 59

(4S)-8-cyclobutyl-5-methoxy-N-(quinoline-5-sulfonyl)-3,4-dihydro-2H-1-benzopyran-4-carboxamide The racemic material from Example 54 (34.0 mg) was separated by chiral preparative SFC chromatography using a CHIRALPAK AD-H, column size 21×250 mm, 5 micron, serial Number: ADHSAMA003-810291, using a concentration of 12 mg/mL in methanol at a flow rate of 52 g/minutes CO$_2$ and UV monitoring at 220 nm to provide (4S)-8-cyclobutyl-5-methoxy-N-(quinoline-5-sulfonyl)-3,4-dihydro-2H-1-benzopyran-4-carboxamide as the first eluent with retention time of about 2.05 minutes. $^1$H NMR (501 MHz, dimethylsulfoxide-d$_6$:D$_2$O=9:1 (v/v)) δ ppm 9.14-8.98 (m, 2H), 8.44-8.24 (m, 2H), 7.94 (dd, J=8.4, 7.5 Hz, 1H), 7.84 (dd, J=8.6, 4.3 Hz, 1H), 6.94 (d, J=8.4 Hz, 1H), 6.25 (d, J=8.5 Hz, 1H), 4.05-3.94 (m, 1H), 3.78-3.74 (m, 1H), 3.63 (dd, J=7.0, 4.1 Hz, 1H), 3.53-3.40 (m, 1H), 2.94 (s, 3H), 2.18-1.61 (m, 8H). MS (APCI+) m/z 453.0 (M+H)$^+$. Stereochemistry was confirmed by X-ray analysis.

Example 60

(4R)-8-cyclobutyl-5-methoxy-N-(quinoline-5-sulfonyl)-3,4-dihydro-2H-1-benzopyran-4-carboxamide The title compound was isolated as the second eluent during the separation described in Example 59 with a retention time around 2.60 minutes. $^1$H NMR (501 MHz, dimethylsulfoxide-d$_6$:D$_2$O=9:1 (v/v)) δ ppm 9.12-9.04 (m, 2H), 8.41-8.32 (m, 2H), 7.95 (dd, J=8.5, 7.4 Hz, 1H), 7.86 (dd, J=8.7, 4.2 Hz, 1H), 6.94 (d, J=8.4 Hz, 1H), 6.25 (d, J=8.5 Hz, 1H), 3.99 (ddd, J=11.0, 5.3, 3.5 Hz, 1H), 3.78-3.73 (m, 1H), 3.64 (dd, J=7.1, 4.2 Hz, 1H), 3.52-3.41 (m, 1H), 2.92 (s, 3H), 2.17-1.98 (m, 3H), 1.96-1.66 (m, 5H). MS (APCI+) m/z 453.0 (M+H)$^+$. Stereochemistry was confirmed by X-ray analysis.

Example 61

3-ethyl-N-(naphthalene-1-sulfonyl)-7-(trifluoromethyl)-2,3-dihydro-1-benzofuran-3-carboxamide Example 61A methyl 3-ethyl-7-(trifluoromethyl)-2,3-dihydrobenzofuran-3-carboxylate To a solution of crude methyl 7-(trifluoromethyl)-2,3-dihydrobenzofuran-3-carboxylate (Example 45E, 0.880 g, 3.57 mmol) and iodoethane (5.78 mL, 71.5 mmol) in N,N-dimethylformamide (8 mL) was cooled to −60° C. with an acetone-dry ice bath, was added a solution of potassium 2-methylpropan-2-olate (5.36 mL, 5.36 mmol). After 5 minutes the solution was swapped for an ice bath at 0° C. The resulting solution turned clearer and was left to warm up to room temperature over 4 hours. Aqueous 1N hydrochloric acid was added, and the mixture was extracted with diethyl ether (2×50 mL). The combined organic layers were dried (Na$_2$SO$_4$), filtered, and concentrated under reduced pressure to provide the crude title compound methyl 3-ethyl-7-(trifluoromethyl)-2,3-dihydrobenzofuran-3-carboxylate.

Example 61B 3-ethyl-7-(trifluoromethyl)-2,3-dihydrobenzofuran-3-carboxylic Acid To a stirred solution of methyl 3-ethyl-7-(trifluoromethyl)-2,3-dihydrobenzofuran-3-carboxylate (Example 61A, 950 mg, 1.386 mmol) in 1,4-dioxane (10 mL) and water (10 mL) was added NaOH (554 mg, 13.86 mmol). The resultant reaction mixture was stirred at 25° C. for 3 hours. The organics were acidified to pH=1~2 with aqueous 3M hydrochloric acid solution and extracted with ethyl acetate (2×100 mL). The combined organic layers were passed through a hydrophobic frit and the filtrate was concentrated under reduced pressure to provide the crude material. The solid was purified with silica gel chromatography, using 10-20% ethyl acetate in hexane. The crude solid was washed with 5% ethyl acetate in petroleum (2×5 mL) to provide the title compound. $^1$H NMR (400 MHz, CDCl$_3$) δ ppm 7.57 (d, J=7.5 Hz, 1H), 7.42 (d, J=7.5 Hz, 1H), 6.98 (t, J=7.7 Hz, 1H), 5.17 (d, J=9.5 Hz, 1H), 4.51 (d, J=9.5 Hz, 1H), 2.19 (dq, J=14.7, 7.4 Hz, 1H), 1.96 (dq, J=14.5, 7.4 Hz, 1H), 0.93 (t, J=7.4 Hz, 3H).

Example 61C 3-ethyl-N-(naphthalene-1-sulfonyl)-7-(trifluoromethyl)-2,3-dihydro-1-benzofuran-3-carboxamide To a solution of Example 61B (53 mg, 0.20 mmol), 1-(3-dimethylaminopropyl)-3-ethylcarbodiimide hydrochloride (80 mg, 0.42 mmol) and 4-dimethylaminopyridine (28 mg, 0.23 mmol) in anhydrous dichloromethane (500 µL) was added naphthalene-1-sulfonamide (51 mg, 0.25 mmol). The mixture was stirred overnight at room temperature, concentrated and purified by reverse-phase HPLC [Waters XBridge™ C18 5 µm OBD column, 30×100 mm, flow rate 40 mL/minute, 20 to 70% gradient of acetonitrile in 0.1% aqueous TFA] to provide the title compound. $^1$H NMR (400 MHz, dimethylsulfoxide-d$_6$) δ ppm 8.59 (dd, J=8.6, 1.1 Hz, 1H), 8.30-8.26 (m, 2H), 8.09 (dd, J=8.2, 1.3 Hz, 1H), 7.76-7.63 (m, 4H), 7.42 (d, J=7.8 Hz, 1H), 7.02-6.97 (m, 1H), 4.86 (d, J=9.6 Hz, 1H), 4.45 (d, J=9.6 Hz, 1H), 2.15 (dq, J=14.5, 7.3 Hz, 1H), 1.79 (dq, J=14.5, 7.3 Hz, 1H), 0.44 (t, J=7.3 Hz, 3H). MS (ESI) m/z 467 (M+NH$_4$)$^+$.

Example 62

4,7-dimethoxy-N-(naphthalene-1-sulfonyl)-2,3-dihydro-1-benzofuran-3-carboxamide

Example 62A

Ethyl 4,7-dimethoxybenzofuran-3-carboxylate

A room temperature solution of 2-hydroxy-3,6-dimethoxybenzaldehyde (CAS #64466-51-9) (0.25 g, 1.372 mmol) in CH$_2$Cl$_2$ (2 mL) was treated with tetrafluoroboric acid-diethyl ether complex (0.019 mL, 0.137 mmol), treated dropwise with a solution of ethyl diazoacetate (0.289 mL, 2.74 mmol) in CH$_2$Cl$_2$ (2 mL), stirred at room temperature for 10 minutes, concentrated to ~4 mL volume, treated with concentrated H$_2$SO$_4$ (0.658 mL, 12.35 mmol), stirred thoroughly at room temperature for 10 minutes, diluted with CH$_2$Cl$_2$ (~2 mL), diluted further with methyl tert-butyl ether (~10 mL), cooled to 0° C., and partitioned between cold water (~30 mL) and methyl tert-butyl ether (~30 mL). The layers were separated and the aqueous layer was extracted with methyl tert-butyl ether (~25 mL). The combined methyl tert-butyl ether layers were washed with brine, dried (MgSO$_4$), filtered, concentrated and chromatographed on silica gel, eluting with a gradient of 5% to 30% ethyl acetate in heptanes to provide the title compound. $^1$H NMR (501 MHz, CDCl$_3$) δ ppm 8.16 (s, 1H), 6.78 (d, J=8.6 Hz, 1H), 6.66 (d, J=8.7 Hz, 1H), 4.37 (q, J=7.1 Hz, 2H), 3.96 (s, 3H), 3.92 (s, 3H), 1.39 (t, J=7.1 Hz, 3H). LC/MS (ESI+) m/z 251 (M+H)$^+$.

Example 62B

Ethyl 4,7-dimethoxy-2,3-dihydrobenzofuran-3-carboxylate and Methyl 4,7-dimethoxy-2,3-dihydrobenzofuran-3-carboxylate A solution of Example 62A (ethyl 4,7-dimethoxybenzofuran-3-carboxylate) (25 mg, 0.100 mmol) in methanol (3 mL) was treated with a magnesium turnings (~12 mg), stirred at room temperature for 100 minutes, treated with more magnesium turnings (~50 mg), stirred at room temperature for 3 hours, diluted with methyl tert-butyl ether (~15 mL), treated with aqueous 1 M HCl (~20 mL), stirred for 5 minutes and extracted with additional methyl tert-butyl ether (50 mL). The layers were separated and the aqueous layer was extracted with methyl tert-butyl ether (~25 mL). The combined methyl tert-butyl ether layers were washed with brine, dried (MgSO$_4$), filtered, and concentrated to provide the title compound as a mixture of ethyl and methyl esters in approximately a 2:1 ratio respectively. NMR of major ethyl ester: $^1$H NMR (400 MHz, CDCl$_3$) δ ppm 6.75 (d, J=8.7 Hz, 1H), 6.33 (d, J=8.8 Hz, 1H), 4.78 (dd, J=1.4, 8.3 Hz, 2H), 4.38-4.29 (m, 1H), 4.26-4.14 (m, 2H), 3.83 (s, 3H), 3.77 (s, 3H), 1.26 (t, J=7.1 Hz, 3H). LC/MS (ESI+) m/z 253 (M+H)$^+$ and m/z 239 (M+H)$^+$.

Example 62C 4,7-dimethoxy-2,3-dihydrobenzofuran-3-carboxylic Acid

A solution of Example 62B (ethyl 4,7-dimethoxy-2,3-dihydrobenzofuran-3-carboxylate and methyl 4,7-dimethoxy-2,3-dihydrobenzofuran-3-carboxylate) in tetrahydrofuran (~1.5 mL) and methanol (~1.5 mL) was treated with 1 M aqueous NaOH (~1 mL), stirred at room temperature for 20 minutes and partitioned between methyl tert-butyl ether (~30 mL) and aqueous 1 M HCl (~10 mL). The layers were separated and the aqueous layer was extracted with methyl tert-butyl ether (~20 mL). The combined methyl tert-butyl ether layers were washed with brine, dried (MgSO$_4$), filtered and concentrated to provide the title compound. $^1$H NMR (501 MHz, CDCl$_3$) δ ppm 6.79 (d, J=8.8 Hz, 1H), 6.40 (d, J=8.8 Hz, 1H), 5.09 (dd, J=5.4, 9.4 Hz, 1H), 4.76 (dd, J=9.4, 10.0 Hz, 1H), 4.41 (dd, J=5.3, 9.9 Hz, 1H), 3.90 (s, 3H), 3.84 (s, 3H).

Example 62D 4,7-dimethoxy-N-(naphthalene-1-sulfonyl)-2,3-dihydro-1-benzofuran-3-carboxamide A solution of Example 62C (4,7-dimethoxy-2,3-dihydrobenzofuran-3-carboxylic acid) (21 mg, 0.094 mmol), 1-(3-dimethylaminopropyl)-3-ethylcarbodiimide hydrochloride (35.9 mg, 0.187 mmol), 4-dimethylaminopyridine (12.59 mg, 0.103 mmol) and naphthalene-1-sulfonamide (21.35 mg, 0.103 mmol) was treated with $CH_2Cl_2$ (0.3 mL). The mixture was stirred overnight at room temperature, concentrated with a stream of $N_2$, dissolved in N,N-dimethylformamide (~1 mL) and directly purified by reverse-phase HPLC [Waters XBridge™ RP18 column, 5 µm, 30×100 mm, flow rate 40 mL/minute, 5-95% gradient of acetonitrile in 0.1% TFA] to provide the title compound. $^1$H NMR (400 MHz, dimethylsulfoxide-$d_6$) δ ppm 12.70 (s, 1H), 8.65-8.62 (m, 1H), 8.31 (d, J=8.4 Hz, 1H), 8.28 (dd, J=1.3, 7.4 Hz, 1H), 8.14 (d, J=8.1 Hz, 1H), 7.80 (ddd, J=1.4, 6.9, 8.5 Hz, 1H), 7.74-7.67 (m, 2H), 6.73 (d, J=8.8 Hz, 1H), 6.23 (d, J=8.8 Hz, 1H), 4.63 (t, J=9.1 Hz, 1H), 4.32-4.21 (m, 2H), 3.63 (s, 3H), 3.20 (s, 3H). LC/MS (ESI+) m/z 414 (M+H)$^+$.

Example 63

7-chloro-4-methoxy-N-(naphthalene-1-sulfonyl)-2,3-dihydro-1-benzofuran-3-carboxamide Example 63A Ethyl 7-chloro-4-methoxybenzofuran-3-carboxylate A mixture of Example 39B (ethyl 7-bromo-4-methoxybenzofuran-3-carboxylate) (42 mg, 0.140 mmol), copper(I) chloride (278 mg, 2.81 mmol), and dimethylacetamide (0.5 mL) was heated at 120° C. for 1 hour, heated at 150° C. for 3 hours, cooled to room temperature, and partitioned between methyl tert-butyl ether (~30 mL) and aqueous 1 M HCl (~15 mL). The layers were separated and the aqueous layer was extracted with methyl tert-butyl ether (~15 mL). The combined methyl tert-butyl ether layers were washed with brine, dried ($MgSO_4$), filtered, concentrated and chromatographed on silica gel to provide the title compound. $^1$H NMR (501 MHz, $CDCl_3$) δ ppm 8.18 (s, 1H), 7.29 (d, J=8.7 Hz, 1H), 6.71 (d, J=8.6 Hz, 1H), 4.38 (q, J=7.1 Hz, 2H), 3.96 (s, 3H), 1.40 (t, J=7.1 Hz, 3H).

Example 63B

Ethyl 7-chloro-4-methoxy-2,3-dihydrobenzofuran-3-carboxylate and Methyl 7-chloro-4-methoxy-2,3-dihydrobenzofuran-3-carboxylate A solution of Example 63A (ethyl 7-chloro-4-methoxybenzofuran-3-carboxylate) (23 mg, 0.090 mmol) in methanol (3 mL) was treated with a magnesium turning (~12 mg), stirred at room temperature for ~100 minutes, treated with 4 more turnings (~50 mg), stirred at room temperature for 3 hours, diluted with methyl tert-butyl ether (~15 mL), treated with aqueous 1 M HCl (~20 mL), stirred for 5 minutes, and extracted with additional methyl tert-butyl ether (50 mL). The layers were separated and the aqueous layer was extracted with methyl tert-butyl ether (~25 mL). The combined methyl tert-butyl ether layers were washed with brine, dried ($MgSO_4$), filtered, and concentrated to provide the title compound as a mixture of isomers in approximately a 2:1 ratio respectively. NMR of major isomer, ethyl 7-chloro-4-methoxy-2,3-dihydrobenzofuran-3-carboxylate: $^1$H NMR (400 MHz, $CDCl_3$) δ ppm 7.14 (d, J=8.8 Hz, 1H), 6.38 (d, J=8.8 Hz, 1H), 4.83-4.80 (m, 2H), 4.35 (t, J=8.1 Hz, 1H), 4.21 (qd, J=4.5, 7.1 Hz, 2H), 3.80 (s, 3H), 1.27 (t, J=7.1 Hz, 3H).

Example 63C 7-chloro-4-methoxy-2,3-dihydrobenzofuran-3-carboxylic Acid

A mixture of Example 63B in tetrahydrofuran (~1.5 mL) and methanol (~1.5 mL) was treated with 1 M aqueous NaOH (~1 mL), stirred at room temperature for 20 minutes and partitioned between methyl tert-butyl ether (~30 mL) and aqueous 1 M HCl (~10 mL). The layers were separated and the aqueous layer was extracted with methyl tert-butyl ether (~20 mL). The combined methyl tert-butyl ether layers were washed with brine, dried ($MgSO_4$), filtered and concentrated to provide the title compound. $^1$H NMR (400 MHz, $CDCl_3$) δ ppm 7.19 (d, J=8.8 Hz, 1H), 6.43 (d, J=8.8 Hz, 1H), 5.03 (dd, J=5.3, 9.4 Hz, 1H), 4.81 (t, J=9.7 Hz, 1H), 4.42 (dd, J=5.4, 10.0 Hz, 1H), 3.89 (s, 3H)).

Example 63D 7-chloro-4-methoxy-N-(naphthalene-1-sulfonyl)-2,3-dihydro-1-benzofuran-3-carboxamide To a mixture of Example 63C (7-chloro-4-methoxy-2,3-dihydrobenzofuran-3-carboxylic acid) (25 mg, 0.109 mmol), 1-(3-dimethylaminopropyl)-3-ethylcarbodiimide hydrochloride (41.9 mg, 0.219 mmol), 4-dimethylaminopyridine (14.69 mg, 0.120 mmol) and naphthalene-1-sulfonamide (24.93 mg, 0.120 mmol) was added $CH_2Cl_2$ (0.3 mL). The reaction mixture was stirred overnight at room temperature, concentrated with a stream of $N_2$, dissolved in N,N-dimethylformamide (~1 mL) and directly purified by reverse-phase HPLC [Waters XBridge™ RP18 column, 5 µm, 30×100 mm, flow rate 40 mL/minute, 5-95% gradient of acetonitrile in 0.1% TFA] to provide the title compound. $^1$H NMR (400 MHz, dimethylsulfoxide-$d_6$) δ ppm 12.79 (s, 1H), 8.63 (d, J=8.6 Hz, 1H), 8.31 (d, J=8.3 Hz, 1H), 8.28 (dd, J=1.2, 7.4 Hz, 1H), 8.14 (d, J=8.1 Hz, 1H), 7.80 (ddd, J=1.4, 6.9, 8.6 Hz, 1H), 7.74-7.67 (m, 2H), 7.13 (d, J=8.8 Hz, 1H), 6.38 (d, J=8.9 Hz, 1H), 4.74 (t, J=8.5 Hz, 1H), 4.39-4.30 (m, 2H), 3.24 (s, 3H). LC/MS (ESI+) m/z 418 (M+H)$^+$.

Example 64

8-cyclopropyl-5-methoxy-N-(naphthalene-1-sulfonyl)-3,4-dihydro-2H-1-benzopyran-4-carboxamide Into a 4 mL vial was added 8-bromo-5-methoxy-N-(naphthalen-1-ylsulfonyl)chroman-4-carboxamide (Example 11C, 20 mg, 0.042 mmol) and dichloro[1,3-bis(2,6-di-3-pentylphenyl)imidazol-2-ylidene](3-chloropyridyl)palladium(II) (PEPPSI IPentCl, 3.61 mg, 4.20 µmol) in tetrahydrofuran (0.5 mL). Cyclopropylzinc(II) bromide (0.420 mL, 0.210 mmol) was added and the reaction was stirred overnight at room temperature. The sample was directly injected onto a preparative HPLC/MS and was purified using TFA method 8 to provide the title compound. $^1$H NMR (400 MHz, dimethylsulfoxide-$d_6$:$D_2O$=9:1 (v/v)) δ ppm 8.66 (dd, J=8.7, 1.1 Hz, 1H), 8.37-8.21 (m, 2H), 8.19-8.07 (m, 1H), 7.87-7.77 (m, 1H), 7.76-7.63 (m, 2H), 6.56 (d, J=8.5 Hz, 1H), 6.16 (d, J=8.5 Hz, 1H), 3.99 (dt, J=11.2, 3.9 Hz, 1H), 3.76-3.74 (m, 1H), 3.66 (dd, J=7.1, 4.2 Hz, 1H), 2.88 (s, 3H), 2.10-1.93 (m, 1H), 1.89-1.72 (m, 2H), 0.83-0.63 (m, 2H), 0.49-0.33 (m, 2H). MS (APCI+) m/z 438.0 (M+H)$^+$.

Example 65

(3S)-7-cyclobutyl-4-methoxy-N-(naphthalene-1-sulfonyl)-2,3-dihydro-1-benzofuran-3-carboxamide Into a 4 mL vial was added Example 39 (80 mg, 0.173 mmol) and dichloro[1,3-bis(2,6-di-3-pentylphenyl)imidazol-2-ylidene](3-chloropyridyl)palladium(II) (Pd PEPPSI IPentCl, 14.13 mg, 0.017 mmol) in tetrahydrofuran (0.5 mL). Cyclobutylzinc(II) bromide (1.5 mL, 0.750 mmol) was added. The reaction was stirred overnight at room temperature. The material was directly injected onto prep HPLC MS and was purified via preparative reverse phase chromatography TFA method 8 to provide the title compound as a racemate. The racemic material was separated by chiral preparative SFC chromatography using a CHIRALPAK AD-H, column size 21×250 mm, 5 micron, serial Number: ADHSAMA003-810291, using a concentration of 4.7 mg/mL in methanol at a flow rate of 48 g/minutes $CO_2$ and UV monitoring at 220 nm to provide (3S)-7-cyclobutyl-4-methoxy-N-(naphthalene-1-sulfonyl)-2,3-dihydro-1-benzofuran-3-carboxamide. $^1$H NMR (400 MHz, dimethylsulfoxide-$d_6$:$D_2O$=9:1 (v/v)) δ ppm 8.62 (d, J=8.7 Hz, 1H), 8.30-8.21 (m, 2H), 8.11 (d, J=8.3 Hz, 1H), 7.78 (ddd, J=8.5, 6.9, 1.4 Hz, 1H), 7.73-7.62 (m, 2H), 6.96 (d, J=8.4 Hz, 1H), 6.30 (d, J=8.4 Hz, 1H), 4.64-4.53 (m, 1H), 4.26-4.16 (m, 2H), 3.34 (p, J=8.6 Hz, 1H), 3.24 (s, 3H), 2.15-1.79 (m, 5H), 1.77-1.64 (m, 1H). MS (APCI+) m/z 438.0 (M+H)$^+$.

Example 66

(3R)-7-cyclobutyl-4-methoxy-N-(naphthalene-1-sulfonyl)-2,3-dihydro-1-benzofuran-3-carboxamide Example 66 was isolated as the second enantiomer during the chiral separation described in Example 65. $^1$H NMR (400 MHz, dimethylsulfoxide-$d_6$:$D_2O$=9:1 (v/v)) δ ppm 8.63 (d, J=8.6 Hz, 1H), 8.35-8.21 (m, 2H), 8.18-8.11 (m, 1H), 7.81 (ddd, J=8.5, 6.9, 1.4 Hz, 1H), 7.77-7.63 (m, 2H), 6.98 (d, J=8.4 Hz, 1H), 6.32 (d, J=8.4 Hz, 1H), 4.61 (t, J=8.7 Hz, 1H), 4.32-4.14 (m, 2H), 3.43-3.29 (m, 1H), 3.24 (s, 3H), 2.18-1.80 (m, 5H), 1.79-1.65 (m, 1H). MS (APCI+) m/z 438.0 (M+H)$^+$.

Example 67

(3R)-7-chloro-4-methoxy-N-(naphthalene-1-sulfonyl)-2,3-dihydro-1-benzofuran-3-carboxamide The enantiomers of Example 63 were separated by Supercritical Fluid Chromatography (SFC) using a 21×250 mm Whelk-O (S,S) chiral column eluting with 30% methanol in liquid $CO_2$ using a flow rate of 80 mL/minute to provide the title compound as the first peak to elute from the column. $^1$H NMR (400 MHz, dimethylsulfoxide-$d_6$) δ ppm 12.79 (s, 1H), 8.63 (d, J=8.6 Hz, 1H), 8.31 (d, J=8.3 Hz, 1H), 8.28 (dd, J=1.2, 7.4 Hz, 1H), 8.14 (d, J=8.1 Hz, 1H), 7.80 (ddd, J=1.4, 6.9, 8.6 Hz, 1H), 7.74-7.67 (m, 2H), 7.13 (d, J=8.8 Hz, 1H), 6.38 (d, J=8.9 Hz, 1H), 4.74 (t, J=8.5 Hz, 1H), 4.39-4.30 (m, 2H), 3.24 (s, 3H). LC/MS (ESI+) m/z 418 (M+H)$^+$.

Example 68

(3S)-7-chloro-4-methoxy-N-(naphthalene-1-sulfonyl)-2,3-dihydro-1-benzofuran-3-carboxamide The enantiomers of Example 63 were separated by Supercritical Fluid Chromatography (SFC) using a 21×250 mm Whelk-O (S,S) chiral column eluting with 30% methanol in liquid $CO_2$ using a flow rate of 80 mL/minute to provide the title compound as the second peak to elute from the column. $^1$H NMR (400 MHz, dimethylsulfoxide-$d_6$) δ ppm 12.79 (s, 1H), 8.63 (d, J=8.6 Hz, 1H), 8.31 (d, J=8.3 Hz, 1H), 8.28 (dd, J=1.2, 7.4 Hz, 1H), 8.14 (d, J=8.1 Hz, 1H), 7.80 (ddd, J=1.4, 6.9, 8.6 Hz, 1H), 7.74-7.67 (m, 2H), 7.13 (d, J=8.8 Hz, 1H), 6.38 (d, J=8.9 Hz, 1H), 4.74 (t, J=8.5 Hz, 1H), 4.39-4.30 (m, 2H), 3.24 (s, 3H). LC/MS (ESI+) m/z 418 (M+H)$^+$.

Example 69

(4S)-8-bromo-5-methoxy-N-(1-methyl-1H-indazole-7-sulfonyl)-3,4-dihydro-2H-1-benzopyran-4-carboxamide

Example 69A 1-methyl-1H-indazole-7-sulfonamide n-Butyllithium (2.5 M in tetrahydrofuran, 0.758 mL, 1.895 mmol) and n-$Bu_2$Mg (di-n-butylmagnesium, 1.0 M in heptane, 5.69 mL, 5.69 mmol) were charged into a nitrogen filled three-necked flask at room temperature. The reaction mixture turned turbid white. A solution of 7-bromo-1-methyl-1H-indazole (1.000 g, 4.74 mmol) in tetrahydrofuran (15 mL) was added dropwise to the n-$Bu_3$MgLi (tri-n-butyl lithium magnesate complex) solution at −25° C. and the mixture was stirred at −10° C. for 1 hour. LC/MS indicated the consumption of the reaction substrates. The resulting mixture was added to a solution of $SO_2Cl_2$ (0.959 mL, 11.85 mmol) in toluene (10 mL) at −10° C. and the mixture was stirred for 20 minutes at −10° C. The LC/MS indicated completion of the reaction. The organic solvents were removed using a rotary evaporator. Ammonium hydroxide (15 mL) was added to the crude solid at room temperature, and the mixture was stirred for 15 minutes. The reaction mixture was concentrated by rotary evaporation. The residue was diluted with ethyl acetate (200 mL), washed with saturated NaCl solution (50 mL), dried over $Na_2SO_4$, filtered, and concentrated to give crude title product. The crude material was purified by Combi-Flash chromatography ($H_2O$ (0.01% TFA) (A)/methanol (B), gradient from 20-50% of B at 10-20 minutes to provide the title compound. $^1$H NMR (400 MHz, dimethylsulfoxide-$d_6$) δ ppm 8.27 (s, 1H), 8.05 (dd, J=8.0, 0.9 Hz, 1H), 7.93 (dd, J=8.0, 0.9 Hz, 1H), 7.92 (s, 2H), 7.28 (t, J=7.7 Hz, 1H), 4.37 (s, 3H). LC/MS (ESI+) m/z 212.1 (M+H)$^+$.

Example 69B 8-bromo-5-methoxy-N-((1-methyl-1H-indazol-7-yl)sulfonyl)chroman-4-carboxamide A mixture of Example 11B (8-bromo-5-methoxychroman-4-carboxylic acid, 45 mg, 0.157 mmol) and $N^1$-((ethylimino)methylene)-$N^3$,$N^3$-dimethylpropane-1,3-diamine hydrochloride (60.1 mg, 0.313 mmol) and N,N-dimethylpyridin-4-amine (21.06 mg, 0.172 mmol) in dichloromethane (2 mL) was stirred at ambient temperature for 30 minutes. 1-Methyl-1H-indazole-7-sulfonamide (Example 69A, 36.4 mg, 0.172 mmol) was added. The mixture was stirred at room temperature for 2 hours. LC/MS indicated conversion was finished. The solvent was removed and the residue was purified via HTP with a Phenomenex® Luna® C8(2) 5 um 100 Å AXIA™ column (30 mm×75 mm), with a gradient of acetonitrile (A) and 0.1% trifluoroacetic acid in water (B) was used, at a flow rate of 50 mL/minute (0-1.0 minute 5% A, 1.0-8.5 minute linear gradient 5-100% A, 8.5-11.5 minute 100% A, 11.5-12.0 minute linear gradient 95-5% A), to provide the title compound. MS (APCI+) m/z 482.3 (M+1)$^+$.

Example 69C (4S)-8-bromo-5-methoxy-N-(1-methylindazol-7-yl)sulfonyl-chromane-4-carboxamide Example 69B (54 mg) was separated via chiral SFC using Instrument: Aurora-2, Column: ChiralPak AD-H, Column Size: 21×250 mm ID, 5 micron and Concentration: 10 mg/mL in methanol; co-solvent: methanol. The first eluent was the title compound at 4.83 minutes. $^1$H NMR (400 MHz, dimethylsulfoxide-d$_6$) δ ppm 12.75 (s, 1H), 8.29 (s, 1H), 8.12 (dd, J=8.1, 1.1 Hz, 1H), 8.02 (dd, J=7.5, 1.1 Hz, 1H), 7.31-7.22 (m, 2H), 6.31 (d, J=8.8 Hz, 1H), 4.42 (s, 3H), 4.16 (dt, J=11.1, 3.9 Hz, 1H), 3.90 (td, J=10.7, 2.6 Hz, 1H), 3.74 (dd, J=7.0, 4.0 Hz, 1H), 3.14 (s, 3H). MS (ESI+) m/z 482 (M+H)$^+$.

Example 70

(4R)-8-bromo-5-methoxy-N-(1-methyl-1H-indazole-7-sulfonyl)-3,4-dihydro-2H-1-benzopyran-4-carboxamide The title compound was isolated during the chiral separation described in Example 69 as the second eluent at 6.87 minutes, ee %>99. $^1$H NMR (400 MHz, dimethylsulfoxide-d$_6$) δ ppm 12.76 (s, 1H), 8.29 (s, 1H), 8.12 (dd, J=8.0, 1.1 Hz, 1H), 8.02 (dd, J=7.5, 1.1 Hz, 1H), 7.39-7.22 (m, 2H), 6.31 (d, J=8.9 Hz, 1H), 4.42 (s, 3H), 4.23-4.10 (m, 1H), 3.90 (td, J=10.7, 2.6 Hz, 1H), 3.74 (dd, J=7.0, 4.0 Hz, 1H), 3.14 (s, 3H), 2.17-2.07 (m, 1H), 1.94 (dtd, J=14.4, 4.6, 2.7 Hz, 1H). MS (ESI+) m/z 482 (M+H)$^+$.

Example 71

(4S)-8-bromo-5-methoxy-2,2-dimethyl-N-(quinoline-5-sulfonyl)-3,4-dihydro-2H-1-benzopyran-4-carboxamide Example 46 (195 mg, 0.386 mmol) was separated via chiral SFC using Instrument: Aurora-2, Column: Chiralpak IC, Column Size: 21×250 mm, 5 micron; Concentration: 20 mg/mL in methanol; Co-Solvent: methanol. The first eluent was the title compound at 1.73 minutes. $^1$H NMR (400 MHz, dimethylsulfoxide-d$_6$) δ ppm 12.67 (s, 1H), 9.17-9.03 (m, 2H), 8.45-8.33 (m, 2H), 8.02-7.79 (m, 2H), 7.30 (d, J=8.8 Hz, 1H), 6.27 (d, J=8.9 Hz, 1H), 3.65 (dd, J=10.4, 7.1 Hz, 1H), 2.77 (s, 3H), 2.07 (dd, J=13.5, 7.2 Hz, 1H), 1.58 (dd, J=13.5, 10.5 Hz, 1H), 1.25 (s, 3H), 1.09 (s, 3H). MS (ESI+) m/z 507 (M+H)$^+$.

Example 72

(4R)-8-bromo-5-methoxy-2,2-dimethyl-N-(quinoline-5-sulfonyl)-3,4-dihydro-2H-1-benzopyran-4-carboxamide The title compound was isolated as the second eluent at 2.8 minutes during the chiral separation of Example 71. $^1$H NMR (400 MHz, dimethylsulfoxide-d$_6$) δ ppm 12.67 (s, 1H), 9.23-8.98 (m, 2H), 8.47-8.27 (m, 2H), 7.97 (d, J=8.0 Hz, 1H), 7.84 (dd, J=8.8, 4.2 Hz, 1H), 7.30 (d, J=8.7 Hz, 1H), 6.27 (d, J=8.9 Hz, 1H), 3.74-3.63 (m, 1H), 2.77 (s, 3H), 2.07 (dd, J=13.5, 7.2 Hz, 1H), 1.58 (dd, J=13.5, 10.5 Hz, 1H), 1.25 (s, 3H), 1.09 (s, 3H). MS (ESI+) m/z 507 (M+H)$^+$.

Example 73

(3R)-7-bromo-4-methoxy-N-(1-naphthylsulfonyl)-2,3-dihydrobenzofuran-3-carboxamide The enantiomers of Example 39 were separated by Supercritical Fluid Chromatography (SFC) using a 21×250 mm Whelk-O (S,S) chiral column eluting with 40% methanol in liquid CO$_2$ using a flow rate of 80 mL/minute to provide the titled compound as the first peak to elute from the column. $^1$H NMR (400 MHz, dimethylsulfoxide-d$_6$) δ ppm 12.79 (s, 1H), 8.65-8.62 (m, 1H), 8.31 (d, J=8.5 Hz, 1H), 8.28 (dd, J=1.2, 7.4 Hz, 1H), 8.14 (d, J=7.9 Hz, 1H), 7.80 (ddd, J=1.4, 6.9, 8.5 Hz, 1H), 7.74-7.67 (m, 2H), 7.25 (d, J=8.8 Hz, 1H), 6.34 (d, J=8.8 Hz, 1H), 4.73 (t, J=9.4 Hz, 1H), 4.38 (dd, J=5.9, 9.7 Hz, 1H), 4.31 (dd, J=5.9, 9.1 Hz, 1H), 3.24 (s, 3H). LC/MS (ESI+) m/z 462, 464 (M+H)$^+$. Stereochemistry was confirmed by X-ray analysis.

Example 74

(3S)-7-bromo-4-methoxy-N-(1-naphthylsulfonyl)-2,3-dihydrobenzofuran-3-carboxamide The enantiomers of Example 39 were separated by Supercritical Fluid Chromatography (SFC) using a 21×250 mm Whelk-O (S,S) chiral column eluting with 40% methanol in liquid CO$_2$ using a flow rate of 80 mL/minute to provide the title compound as the second peak to elute from the column. $^1$H NMR (400 MHz, dimethylsulfoxide-d$_6$) δ ppm 12.79 (s, 1H), 8.65-8.62 (m, 1H), 8.31 (d, J=8.5 Hz, 1H), 8.28 (dd, J=1.2, 7.4 Hz, 1H), 8.14 (d, J=7.9 Hz, 1H), 7.80 (ddd, J=1.4, 6.9, 8.5 Hz, 1H), 7.74-7.67 (m, 2H), 7.25 (d, J=8.8 Hz, 1H), 6.34 (d, J=8.8 Hz, 1H), 4.73 (t, J=9.4 Hz, 1H), 4.38 (dd, J=5.9, 9.7 Hz, 1H), 4.31 (dd, J=5.9, 9.1 Hz, 1H), 3.24 (s, 3H). LC/MS (ESI+) m/z 462, 464 (M+H)$^+$. Stereochemistry is confirmed by X-ray analysis.

Example 75

8-cyclobutyl-5-methoxy-N-(2-methylquinoline-5-sulfonyl)-3,4-dihydro-2H-1-benzopyran-4-carboxamide Example 75A 8-bromo-5-methoxychroman-4-one To a solution of 5-methoxychroman-4-one (30 g, 168 mmol) in acetic acid (30 mL) was added sodium bromide (17.32 g, 168 mmol) and hydrogen peroxide (51.6 mL, 505 mmol). The mixture was stirred at 25° C. for 18 hours. The mixture was filtered. The solid was triturated with ethanol (25 mL) and filtered to provide the title compound. $^1$H NMR (400 MHz, Chloroform-d) δ ppm 7.61 (d, J=9.2 Hz, 1H), 6.46 (d, J=8.8 Hz, 1H), 4.59 (br t, J=6.4 Hz, 2H), 3.91 (s, 3H), 2.82 (br t, J=6.4 Hz, 2H).

Example 75B 8-bromo-5-methoxychroman-4-carbonitrile

Into a 500 mL round bottom flask was added 8-bromo-5-methoxychroman-4-one (Example 75A, 19.8 g, 75 mmol)

and toluenesulfonylmethyl isocyanide (15 g, 75 mmol), followed by dimethoxy ethane (250 mL) and methanol (3.3 mL). The reaction mixture was cooled to 0° C. in an ice bath under nitrogen. Potassium tert-butoxide (127 mL, 1 M in tetrahydrofuran) was added slowly over 0.5 hours. The reaction mixture was allowed to warm to room temperature and was stirred for 2 hours. The solvent was removed in vacuo and the crude residue was quenched with water (100 mL). The aqueous layer was extracted with ethyl acetate (3×100 mL). The combined organic layer was washed with brine, dried over $Na_2SO_4$, filtered, and concentrated to give a crude residue. The residue was chromatographed using a 150 g silica gel cartridge, eluting with ethyl acetate in heptane (0 to 30%) to provide the title compound. $^1$H NMR (501 MHz, Chloroform-d) δ ppm 7.46 (d, J=8.8 Hz, 1H), 6.43 (d, J=8.8 Hz, 1H), 4.56 (dtd, J=11.6, 3.3, 1.5 Hz, 1H), 4.33 (td, J=11.8, 2.1 Hz, 1H), 4.07-4.01 (m, 1H), 3.91 (s, 3H), 2.36 (ddt, J=14.3, 3.2, 2.2 Hz, 1H), 2.23 (dddd, J=14.4, 12.1, 5.8, 3.6 Hz, 1H). MS (DCI+) m/z 284.9 $(M+NH_4)^+$.

Example 75C 8-cyclobutyl-5-methoxychroman-4-carbonitrile

A solution of Example 75B (11 g, 41.0 mmol) and [1,1'-bis(diphenylphosphino)ferrocene]dichloropalladium (II) (3.42 g, 4.18 mmol) in tetrahydrofuran (205 mL) (degassed by bubbling a stream of nitrogen through the suspension) was treated with cyclobutylzinc bromide (123 mL, 61.5 mmol, 0.5 M in tetrahydrofuran) and the reaction was stirred at room temperature under nitrogen overnight. The reaction was quenched with saturated aqueous ammonium chloride, and the organic layer was washed with saturated aqueous ammonium chloride and brine, dried over sodium sulfate, filtered and concentrated. The residue was chromatographed using a 220 g silica gel cartridge, eluting with 0-20% ethyl acetate/heptane column to give the title compound. $^1$H NMR (400 MHz, Chloroform-d) δ ppm 7.12 (d, J=8.4 Hz, 1H), 6.46 (d, J=8.3 Hz, 1H), 4.40 (dtd, J=11.5, 3.4, 1.5 Hz, 1H), 4.28-4.16 (m, 1H), 4.01 (dt, J=5.9, 1.9 Hz, 1H), 3.88 (d, J=0.7 Hz, 3H), 3.66-3.55 (m, 1H), 2.36-2.24 (m, 3H), 2.24-2.12 (m, 1H), 2.12-1.94 (m, 3H), 1.90-1.74 (m, 1H). MS (ESI+) m/z 244 $(M+H)^+$.

Example 75D 8-cyclobutyl-5-methoxychroman-4-carboxamide

To Example 75C (9.3 g, 38.2 mmol) in ethanol (127 mL) was added a mixture of sodium hydroxide (15.29 g, 382 mmol) in 122 mL of water, and the resulting mixture was heated at 83° C. for 16 hours. The reaction was cooled in an ice bath and was acidified with 6 M aqueous HCl (66 mL) to pH-2. The resulting precipitate was filtered and washed with water and dried in oven to provide the title compound.

Example 75E 8-cyclobutyl-5-methoxychroman-4-carboxylic Acid

A mixture of Example 75D (500 mg, 1.913 mmol) and sodium hydroxide (765 mg, 19.13 mmol) in ethanol (10 mL) was refluxed at 120° C. for 12 hours. The solvent was concentrated to half the volume and the mixture was poured slowly into 1N aqueous HCl (30 mL) with stirring. The mixture was extracted with dichloromethane (30 mL×3). The combined organics were washed with brine, dried over $MgSO_4$, filtered, and concentrated to provide the title compound, which was used in next step without purification. $^1$H NMR (501 MHz, Chloroform-d) δ ppm 7.09 (d, J=8.4 Hz, 1H), 6.46 (d, J=8.3 Hz, 1H), 4.26 (dtd, J=11.1, 3.8, 1.2 Hz, 1H), 4.15 (td, J=11.2, 2.3 Hz, 1H), 3.87 (d, J=3.2 Hz, 1H), 3.85 (s, 3H), 3.62 (p, J=8.7 Hz, 1H), 2.28 (dddd, J=15.1, 11.7, 5.4, 2.3 Hz, 3H), 2.13-1.91 (m, 4H), 1.85-1.74 (m, 1H). MS (ESI+) m/z 263 $(M+H)^+$.

Example 75F 8-cyclobutyl-5-methoxy-N-(2-methylquinoline-5-sulfonyl)-3,4-dihydro-2H-1-benzopyran-4-carboxamide A mixture of Example 75E (100 mg, 0.381 mmol), $N^1$-((ethylimino)methylene)-$N^3$,$N^3$-dimethylpropane-1,3-diamine, hydrochloric acid (146 mg, 0.762 mmol), and N,N-dimethylpyridin-4-amine (93 mg, 0.762 mmol) in dichloromethane (2 mL) was stirred at room temperature for 30 minutes. 2-Methylquinoline-5-sulfonamide (93 mg, 0.419 mmol) was added. The mixture was stirred at room temperature for 2 hours. The solvent was removed under reduced pressure and the residue was purified via HPLC with the TFA method on a Phenomenex® Luna® C8(2) 5 um 100 Å AXIA™ column (30 mm×75 mm), with a gradient of acetonitrile (A) and 0.1% trifluoroacetic acid in water (B) was used, at a flow rate of 50 mL/minute (0-1.0 minute 5% A, 1.0-8.5 minute linear gradient 5-100% A, 8.5-11.5 minute 100% A, 11.5-12.0 minute linear gradient 95-5% A), to yield a racemate of 8-cyclobutyl-5-methoxy-N-(2-methylquinoline-5-sulfonyl)-3,4-dihydro-2H-1-benzopyran-4-carboxamide. $^1$H NMR (501 MHz, Chloroform-d) δ ppm 9.72 (s, 1H), 8.62 (dd, J=8.9, 0.9 Hz, 1H), 8.42 (dd, J=7.5, 1.2 Hz, 1H), 8.26 (dt, J=8.5, 1.1 Hz, 1H), 7.77 (dd, J=8.5, pm 12.66 (s, 1H), 8.95 (dd, J=8.8, 0.8 Hz, 1H), 8.31-8.16 (m, 2H), 7.86 (dd, J=8.4, 7.5 Hz, 1H), 7.72 (d, J=8.9 Hz, 1H), 6.93 (d, J=8.4 Hz, 1H), 6.25 (d, J=8.5 Hz, 1H), 3.98 (ddd, J=10.9, 4.9, 3.4 Hz, 1H), 3.72 (td, J=10.7, 2.5 Hz, 1H), 3.62 (dd, J=7.0, 4.0 Hz, 1H), 3.52-3.43 (m, 1H), 2.99 (s, 3H), 2.72 (s, 3H), 2.18-2.05 (m, 2H), 2.00 (dddd, J=14.6, 11.1, 7.5, 3.7 Hz, 1H), 1.95-1.81 (m, 3H), 1.81-1.66 (m, 2H). MS (ESI+) m/z 467 $(M+H)^+$.

Example 76

(4S)-8-cyclobutyl-5-methoxy-N-(2-methylquinoline-5-sulfonyl)-3,4-dihydro-2H-1-benzopyran-4-carboxamide Example 76A 8-bromo-5-methoxychroman-4-one To a solution of 5-methoxychroman-4-one (30 g, 168 mmol) in acetic acid (30 mL) was added sodium bromide (17.32 g, 168 mmol) and hydrogen peroxide (51.6 mL, 505 mmol). The mixture was stirred at 25° C. for 18 hours. The mixture was filtered. The solid was triturated with ethanol (25 mL) and filtered to provide the title compound. $^1$H NMR (400 MHz, Chloroform-d) δ ppm 7.61 (d, J=9.2 Hz, 1H), 6.46 (d, J=8.8 Hz, 1H), 4.59 (br t, J=6.4 Hz, 2H), 3.91 (s, 3H), 2.82 (br t, J=6.4 Hz, 2H).

Example 76B 8-bromo-5-methoxychroman-4-carbonitrile

Into a 500 mL round bottom flask was added 8-bromo-5-methoxychroman-4-one (Example 76A, 19.8 g, 75 mmol)

and toluenesulfonylmethyl isocyanide (15 g, 75 mmol), followed by dimethoxy ethane (250 mL) and methanol (3.3 mL). The reaction mixture was cooled to 0° C. in an ice bath under nitrogen. Potassium tert-butoxide (127 mL, 1 M in tetrahydrofuran) was added slowly over 0.5 hours. The reaction mixture was allowed to warm to room temperature and was stirred for 2 hours. The solvent was removed in vacuo and the crude residue was quenched with water (100 mL). The aqueous layer was extracted with ethyl acetate (3×100 mL). The combined organic layer was washed with brine, dried over $Na_2SO_4$, filtered, and concentrated to give a crude residue. The residue was chromatographed using a 150 g silica gel cartridge, eluting with ethyl acetate in heptane (0 to 30%) to provide the title compound. $^1$H NMR (501 MHz, Chloroform-d) δ ppm 7.46 (d, J=8.8 Hz, 1H), 6.43 (d, J=8.8 Hz, 1H), 4.56 (dtd, J=11.6, 3.3, 1.5 Hz, 1H), 4.33 (td, J=11.8, 2.1 Hz, 1H), 4.07-4.01 (m, 1H), 3.91 (s, 3H), 2.36 (ddt, J=14.3, 3.2, 2.2 Hz, 1H), 2.23 (dddd, J=14.4, 12.1, 5.8, 3.6 Hz, 1H). MS (DCI+) m/z 284.9 $(M+NH_4)^+$.

Example 76C 8-cyclobutyl-5-methoxychroman-4-carbonitrile

A solution of Example 76B (11 g, 41.0 mmol) and [1,1'-bis(diphenylphosphino)ferrocene]dichloropalladium (II) (3.42 g, 4.18 mmol) in tetrahydrofuran (205 mL) (degassed by bubbling a stream of nitrogen through the suspension) was treated with cyclobutylzinc bromide (123 mL, 61.5 mmol, 0.5 M in tetrahydrofuran) and the reaction was stirred at room temperature under nitrogen overnight. The reaction was quenched with saturated aqueous ammonium chloride, and the organic layer was washed with saturated aqueous ammonium chloride and brine, dried over sodium sulfate, filtered and concentrated. The residue was chromatographed using a 220 g silica gel cartridge, eluting with 0-20% ethyl acetate/heptane column to give the title compound). $^1$H NMR (400 MHz, Chloroform-d) δ ppm 7.12 (d, J=8.4 Hz, 1H), 6.46 (d, J=8.3 Hz, 1H), 4.40 (dtd, J=11.5, 3.4, 1.5 Hz, 1H), 4.28-4.16 (m, 1H), 4.01 (dt, J=5.9, 1.9 Hz, 1H), 3.88 (d, J=0.7 Hz, 3H), 3.66-3.55 (m, 1H), 2.36-2.24 (m, 3H), 2.24-2.12 (m, 1H), 2.12-1.94 (m, 3H), 1.90-1.74 (m, 1H). MS (ESI+) m/z 244 $(M+H)^+$.

Example 76D 8-cyclobutyl-5-methoxychroman-4-carboxamide

To Example 76C (9.3 g, 38.2 mmol) in ethanol (127 mL) was added a mixture of sodium hydroxide (15.29 g, 382 mmol) in 122 mL of water, and the resulting mixture was heated at 83° C. for 16 hours. The reaction was cooled in an ice bath and was acidified with 6 M aqueous HCl (66 mL) to pH-2. The resulting precipitate was filtered and washed with water and dried in oven to provide the title compound.

Example 76E 8-cyclobutyl-5-methoxychroman-4-carboxylic Acid

A mixture of Example 76D (500 mg, 1.913 mmol) and sodium hydroxide (765 mg, 19.13 mmol) in ethanol (10 mL) was refluxed at 120° C. for 12 hours. The solvent was concentrated to half the volume and the mixture was poured slowly into 1 N aqueous HCl (30 mL) with stirring. The mixture was extracted with dichloromethane (30 mL×3). The combined organics were washed with brine, dried over $MgSO_4$, filtered, and concentrated to provide the title compound, which was used in next step without purification. $^1$H NMR (501 MHz, Chloroform-d) δ ppm 7.09 (d, J=8.4 Hz, 1H), 6.46 (d, J=8.3 Hz, 1H), 4.26 (dtd, J=11.1, 3.8, 1.2 Hz, 1H), 4.15 (td, J=11.2, 2.3 Hz, 1H), 3.87 (d, J=3.2 Hz, 1H), 3.85 (s, 3H), 3.62 (p, J=8.7 Hz, 1H), 2.28 (dddd, J=15.1, 11.7, 5.4, 2.3 Hz, 3H), 2.13-1.91 (m, 4H), 1.85-1.74 (m, 1H). MS (ESI+) m/z 263 $(M+H)^+$.

Example 76F 8-cyclobutyl-5-methoxy-N-(2-methylquinoline-5-sulfonyl)-3,4-dihydro-2H-1-benzopyran-4-carboxamide A mixture of Example 76E (100 mg, 0.381 mmol), $N^1$-((ethylimino)methylene)-$N^3$,$N^3$-dimethylpropane-1,3-diamine, hydrochloric acid (146 mg, 0.762 mmol), and N,N-dimethylpyridin-4-amine (93 mg, 0.762 mmol) in dichloromethane (2 mL) was stirred at room temperature for 30 minutes. 2-Methylquinoline-5-sulfonamide (93 mg, 0.419 mmol) was added. The mixture was stirred at room temperature for 2 hours. The solvent was removed under reduced pressure and the residue was purified via HPLC with the TFA method on a Phenomenex® Luna® C8(2) 5 um 100 Å AXIA™ column (30 mm×75 mm), with a gradient of acetonitrile (A) and 0.1% trifluoroacetic acid in water (B) was used, at a flow rate of 50 mL/minute (0-1.0 minute 5% A, 1.0-8.5 minute linear gradient 5-100% A, 8.5-11.5 minute 100% A, 11.5-12.0 minute linear gradient 95-5% A), to yield a racemate of 8-cyclobutyl-5-methoxy-N-(2-methylquinoline-5-sulfonyl)-3,4-dihydro-2H-1-benzopyran-4-carboxamide. $^1$H NMR (501 MHz, Chloroform-d) δ ppm 9.72 (s, 1H), 8.62 (dd, J=8.9, 0.9 Hz, 1H), 8.42 (dd, J=7.5, 1.2 Hz, 1H), 8.26 (dt, J=8.5, 1.1 Hz, 1H), 7.77 (dd, J=8.5, pm 12.66 (s, 1H), 8.95 (dd, J=8.8, 0.8 Hz, 1H), 8.31-8.16 (m, 2H), 7.86 (dd, J=8.4, 7.5 Hz, 1H), 7.72 (d, J=8.9 Hz, 1H), 6.93 (d, J=8.4 Hz, 1H), 6.25 (d, J=8.5 Hz, 1H), 3.98 (ddd, J=10.9, 4.9, 3.4 Hz, 1H), 3.72 (td, J=10.7, 2.5 Hz, 1H), 3.62 (dd, J=7.0, 4.0 Hz, 1H), 3.52-3.43 (m, 1H), 2.99 (s, 3H), 2.72 (s, 3H), 2.18-2.05 (m, 2H), 2.00 (dddd, J=14.6, 11.1, 7.5, 3.7 Hz, 1H), 1.95-1.81 (m, 3H), 1.81-1.66 (m, 2H). MS (ESI+) m/z 467 $(M+H)^+$.

Example 76G (4S)-8-cyclobutyl-5-methoxy-N-(2-methylquinoline-5-sulfonyl)-3,4-dihydro-2H-1-benzopyran-4-carboxamide The racemic material from Example 76F (45 mg, 0.096 mmol) was separated by chiral preparative SFC chromatography using a ChiralPak IC column, size 21×250 mm, 5 micron, serial number: ICOSALK014-812151, using a concentration of 15 mg/mL in methanol at a flow rate of 49 g/minute $CO_2$ and UV monitoring at 220 nm. The first compound to elute was the title compound. $^1$H NMR (500 MHz, DMSO-$d_6$) δ ppm 12.66 (s, 1H), 8.95 (dd, J=8.8, 0.8 Hz, 1H), 8.31-8.16 (m, 2H), 7.86 (dd, J=8.4, 7.5 Hz, 1H), 7.72 (d, J=8.9 Hz, 1H), 6.93 (d, J=8.4 Hz, 1H), 6.25 (d, J=8.5 Hz, 1H), 3.98 (ddd, J=10.9, 4.9, 3.4 Hz, 1H), 3.72 (td, J=10.7, 2.5 Hz, 1H), 3.62 (dd, J=7.0, 4.0 Hz, 1H), 3.52-3.43 (m, 1H), 2.99 (s, 3H), 2.72 (s, 3H), 2.18-2.05 (m, 2H), 2.00 (dddd, J=14.6, 11.1, 7.5, 3.7 Hz, 1H), 1.95-1.81 (m, 3H), 1.81-1.66 (m, 2H). MS (ESI+) m/z 467 $(M+H)^+$.

Example 77

(4R)-8-cyclobutyl-5-methoxy-N-(2-methylquinoline-5-sulfonyl)-3,4-dihydro-2H-1-benzopyran-4-carboxamide

Example 77A 8-bromo-5-methoxychroman-4-one

To a solution of 5-methoxychroman-4-one (30 g, 168 mmol) in acetic acid (30 mL) was added sodium bromide (17.32 g, 168 mmol) and hydrogen peroxide (51.6 mL, 505 mmol). The mixture was stirred at 25° C. for 18 hours. The mixture was filtered. The solid was triturated with ethanol (25 mL) and filtered to provide the title compound. $^1$H NMR (400 MHz, Chloroform-d) δ ppm 7.61 (d, J=9.2 Hz, 1H), 6.46 (d, J=8.8 Hz, 1H), 4.59 (br t, J=6.4 Hz, 2H), 3.91 (s, 3H), 2.82 (br t, J=6.4 Hz, 2H).

Example 77B 8-bromo-5-methoxychroman-4-carbonitrile

Into a 500 mL round bottom flask was added 8-bromo-5-methoxychroman-4-one (Example 77A, 19.8 g, 75 mmol) and toluenesulfonylmethyl isocyanide (15 g, 75 mmol), followed by dimethoxy ethane (250 mL) and methanol (3.3 mL). The reaction mixture was cooled to 0° C. in an ice bath under nitrogen. Potassium tert-butoxide (127 mL, 1 M in tetrahydrofuran) was added slowly over 0.5 hours. The reaction mixture was allowed to warm to room temperature and was stirred for 2 hours. The solvent was removed in vacuo and the crude residue was quenched with water (100 mL). The aqueous layer was extracted with ethyl acetate (3×100 mL). The combined organic layer was washed with brine, dried over $Na_2SO_4$, filtered, and concentrated to give a crude residue. The residue was chromatographed using a 150 g silica gel cartridge, eluting with ethyl acetate in heptane (0 to 30%) to provide the title compound. $^1$H NMR (501 MHz, Chloroform-d) δ ppm 7.46 (d, J=8.8 Hz, 1H), 6.43 (d, J=8.8 Hz, 1H), 4.56 (dtd, J=11.6, 3.3, 1.5 Hz, 1H), 4.33 (td, J=11.8, 2.1 Hz, 1H), 4.07-4.01 (m, 1H), 3.91 (s, 3H), 2.36 (ddt, J=14.3, 3.2, 2.2 Hz, 1H), 2.23 (dddd, J=14.4, 12.1, 5.8, 3.6 Hz, 1H). MS (DCI+) m/z 284.9 (M+NH$_4$)$^+$.

Example 77C 8-cyclobutyl-5-methoxychroman-4-carbonitrile

A solution of Example 77B (11 g, 41.0 mmol) and [1,1'-bis(diphenylphosphino)ferrocene]dichloropalladium (II) (3.42 g, 4.18 mmol) in tetrahydrofuran (205 mL) (degassed by bubbling a stream of nitrogen through the suspension) was treated with cyclobutylzinc bromide (123 mL, 61.5 mmol, 0.5 M in tetrahydrofuran) and the reaction was stirred at room temperature under nitrogen overnight. The reaction was quenched with saturated aqueous ammonium chloride, and the organic layer was washed with saturated aqueous ammonium chloride and brine, dried over sodium sulfate, filtered and concentrated. The residue was chromatographed using a 220 g silica gel cartridge, eluting with 0-20% ethyl acetate/heptane column to give the title compound. $^1$H NMR (400 MHz, Chloroform-d) δ ppm 7.12 (d, J=8.4 Hz, 1H), 6.46 (d, J=8.3 Hz, 1H), 4.40 (dtd, J=11.5, 3.4, 1.5 Hz, 1H), 4.28-4.16 (m, 1H), 4.01 (dt, J=5.9, 1.9 Hz, 1H), 3.88 (d, J=0.7 Hz, 3H), 3.66-3.55 (m, 1H), 2.36-2.24 (m, 3H), 2.24-2.12 (m, 1H), 2.12-1.94 (m, 3H), 1.90-1.74 (m, 1H). MS (ESI+) m/z 244 (M+H)$^+$.

Example 77D 8-cyclobutyl-5-methoxychroman-4-carboxamide

To Example 77C (9.3 g, 38.2 mmol) in ethanol (127 mL) was added a mixture of sodium hydroxide (15.29 g, 382 mmol) in 122 mL of water, and the resulting mixture was heated at 83° C. for 16 hours. The reaction was cooled in an ice bath and was acidified with 6 M aqueous HCl (66 mL) to pH-2. The resulting precipitate was filtered and washed with water and dried in oven to provide the title compound.

Example 77E 8-cyclobutyl-5-methoxychroman-4-carboxylic acid

A mixture of Example 77D (500 mg, 1.913 mmol) and sodium hydroxide (765 mg, 19.13 mmol) in ethanol (10 mL) was refluxed at 120° C. for 12 hours. The solvent was concentrated to half the volume and the mixture was poured slowly into 1N aqueous HCl (30 mL) with stirring. The mixture was extracted with dichloromethane (30 mL×3). The combined organics were washed with brine, dried over MgSO$_4$, filtered, and concentrated to provide the title compound, which was used in next step without purification. $^1$H NMR (501 MHz, Chloroform-d) δ ppm 7.09 (d, J=8.4 Hz, 1H), 6.46 (d, J=8.3 Hz, 1H), 4.26 (dtd, J=11.1, 3.8, 1.2 Hz, 1H), 4.15 (td, J=11.2, 2.3 Hz, 1H), 3.87 (d, J=3.2 Hz, 1H), 3.85 (s, 3H), 3.62 (p, J=8.7 Hz, 1H), 2.28 (dddd, J=15.1, 11.7, 5.4, 2.3 Hz, 3H), 2.13-1.91 (m, 4H), 1.85-1.74 (m, 1H). MS (ESI+) m/z 263 (M+H)$^+$.

Example 77F 8-cyclobutyl-5-methoxy-N-(2-methylquinoline-5-sulfonyl)-3,4-dihydro-2H-1-benzopyran-4-carboxamide A mixture of Example 77E (100 mg, 0.381 mmol), $N^1$-((ethylimino)methylene)-$N^3$,$N^3$-dimethylpropane-1,3-diamine, hydrochloric acid (146 mg, 0.762 mmol), and N,N-dimethylpyridin-4-amine (93 mg, 0.762 mmol) in dichloromethane (2 mL) was stirred at room temperature for 30 minutes. 2-Methylquinoline-5-sulfonamide (93 mg, 0.419 mmol) was added. The mixture was stirred at room temperature for 2 hours. The solvent was removed under reduced pressure and the residue was purified via HPLC with the TFA method on a Phenomenex® Luna® C8(2) 5 um 100 Å AXIA™ column (30 mm×75 mm), with a gradient of acetonitrile (A) and 0.1% trifluoroacetic acid in water (B) was used, at a flow rate of 50 mL/minute (0-1.0 minute 5% A, 1.0-8.5 minute linear gradient 5-100% A, 8.5-11.5 minute 100% A, 11.5-12.0 minute linear gradient 95-5% A), to yield a racemate of 8-cyclobutyl-5-methoxy-N-(2-methylquinoline-5-sulfonyl)-3,4-dihydro-2H-1-benzopyran-4-carboxamide. $^1$H NMR (501 MHz, Chloroform-d) δ ppm 9.72 (s, 1H), 8.62 (dd, J=8.9, 0.9 Hz, 1H), 8.42 (dd, J=7.5, 1.2 Hz, 1H), 8.26 (dt, J=8.5, 1.1 Hz, 1H), 7.77 (dd, J=8.5, pm 12.66 (s, 1H), 8.95 (dd, J=8.8, 0.8 Hz, 1H), 8.31-8.16 (m, 2H), 7.86 (dd, J=8.4, 7.5 Hz, 1H), 7.72 (d, J=8.9 Hz, 1H), 6.93 (d, J=8.4 Hz, 1H), 6.25 (d, J=8.5 Hz, 1H), 3.98 (ddd, J=10.9, 4.9, 3.4 Hz, 1H), 3.72 (td, J=10.7, 2.5 Hz, 1H), 3.62 (dd, J=7.0, 4.0 Hz, 1H), 3.52-3.43 (m, 1H), 2.99 (s, 3H), 2.72 (s, 3H), 2.18-2.05 (m, 2H), 2.00 (dddd, J=14.6, 11.1, 7.5, 3.7 Hz, 1H), 1.95-1.81 (m, 3H), 1.81-1.66 (m, 2H). MS (ESI+) m/z 467 (M+H)$^+$.

Example 77G (4R)-8-cyclobutyl-5-methoxy-N-(2-methylquinoline-5-sulfonyl)-3,4-dihydro-2H-1-benzopyran-4-carboxamide The racemic material from Example 77F (45 mg, 0.096 mmol) was separated by chiral preparative SFC chromatography using a ChiralPak IC column, size 21×250 mm, 5 micron, serial number: ICOSALK014-812151, using a concentration of 15 mg/mL in methanol at a flow rate of 49 g/minute CO$_2$ and UV monitoring at 220 nm. The title compound was the second compound to elute. $^1$H NMR (501 MHz, DMSO-d$_6$) δ ppm 12.67 (s, 1H), 8.95 (d, J=8.8 Hz, 1H), 8.29-8.20 (m, 2H), 7.90-7.82 (m, 1H), 7.72 (d, J=8.9 Hz, 1H), 6.93 (d, J=8.4 Hz, 1H), 6.25 (d, J=8.5 Hz, 1H), 3.98 (ddd, J=10.9, 5.0, 3.4 Hz, 1H), 3.72 (td, J=10.6, 2.5 Hz, 1H), 3.63 (dd, J=7.0, 4.1 Hz, 1H), 3.47 (s, 1H), 2.99 (s, 3H), 2.72 (s, 3H), 2.13 (dddd, J=12.3, 7.2, 4.4, 2.2 Hz, 2H), 1.99 (dtd, J=14.3, 7.3, 3.8 Hz, 1H), 1.96-1.81 (m, 3H), 1.81-1.64 (m, 2H). MS (ESI+) m/z 467 (M+H)$^+$.

Example 78

5-bromo-8-methoxy-N-(naphthalene-1-sulfonyl)-3,4-dihydro-1H-2-benzopyran-1-carboxamide Example 78A Ethyl 2-acetoxy-2-(2-bromo-5-methoxyphenethoxy)acetate A mixture of 2-(2-bromo-5-methoxyphenyl)ethanol (CAS #75534-35-9) (0.586 mL, 2.73 mmol) and ethyl glyoxalate (0.482 mL, 2.478 mmol) was stirred at room temperature for 1 hour, diluted with pyridine (2.005 mL, 24.78 mmol), treated with 4-dimethylaminopyridine (0.030 g, 0.248 mmol), cooled to 0° C., and treated dropwise with acetyl chloride (0.529 mL, 7.44 mmol). The reaction was stirred at 0° C. for a few minutes and then warmed to room temperature. An exotherm occurred upon warming. The mixture was stirred for 1 hour, diluted with tert-butyl methyl ether (100 mL), cooled to 0° C. and washed with cold 1 M aqueous HCl (50 mL). The aqueous layer was extracted with tert-butyl methyl ether (50 mL). The combined organic layers were washed with brine, dried (MgSO$_4$), filtered, concentrated and chromatographed on silica gel, eluting with a gradient of 10% to 20% ethyl acetate in heptanes to provide the title compound. $^1$H NMR (400 MHz, CDCl$_3$) δ ppm 7.40 (d, J=8.8 Hz, 1H), 6.84 (d, J=3.0 Hz, 1H), 6.66 (dd, J=3.1, 8.7 Hz, 1H), 5.96 (s, 1H), 4.25 (q, J=7.1 Hz, 2H), 3.97 (dt, J=7.0, 9.6 Hz, 1H), 3.89 (dt, J=7.1, 9.7 Hz, 1H), 3.77 (s, 3H), 3.05 (t, J=7.1 Hz, 2H), 2.13 (s, 3H), 1.30 (t, J=7.2 Hz, 3H).

Example 78B

Ethyl 5-bromo-8-methoxyisochromane-1-carboxylate

A solution of Example 78A (ethyl 2-acetoxy-2-(2-bromo-5-methoxyphenethoxy)acetate) (0.68 g, 1.812 mmol) in CH$_2$Cl$_2$ (18 mL) under N$_2$ was cooled to −20% C, treated with aluminum chloride (0.242 g, 1.812 mmol), stirred for 1 hour at −20° C., treated with additional aluminum chloride (0.242 g, 1.812 mmol), stirred for 3 hours, diluted with tert-butyl methyl ether (~100 mL) and washed with cold 1 M aqueous HCl (50 mL). The layers were separated and the aqueous layer was extracted with tert-butyl methyl ether (50 mL). The combined organic layers were washed with brine, dried (MgSO$_4$), filtered, concentrated and chromatographed on silica gel, eluting with a gradient of 5% to 10% ethyl acetate in heptanes to provide the title compound. $^1$H NMR (400 MHz, CDCl$_3$) δ ppm 7.45 (d, J=8.7 Hz, 1H), 6.64 (d, J=8.7 Hz, 1H), 5.27 (s, 1H), 4.24 (qd, J=2.6, 7.2 Hz, 2H), 4.04-4.02 (m, 1H), 4.01 (d, J=4.5 Hz, 1H), 3.77 (s, 3H), 2.87-2.73 (m, 2H), 1.30 (t, J=7.1 Hz, 3H).

Example 78C 5-bromo-8-methoxyisochroman-1-carboxylic acid

A solution of Example 78B (ethyl 5-bromo-8-methoxyisochromane-1-carboxylate) (138 mg, 0.438 mmol) in tetrahydrofuran (3 mL) was diluted with methanol (3 mL), treated with 1 M aqueous NaOH (2 mL), stirred at room temperature for 15 minutes, stirred at 60° C. for 30 minutes, cooled and partitioned between tert-butyl methyl ether (30 mL) and 1 M aqueous HCl (10 mL). The layers were separated and the aqueous layer was extracted with tert-butyl methyl ether (20 mL). The combined organic layers were washed with brine, dried (MgSO$_4$), filtered, and concentrated to provide the title compound. $^1$H NMR (400 MHz, dimethylsulfoxide-d$_6$) δ ppm 7.52 (d, J=8.8 Hz, 1H), 6.87 (d, J=8.8 Hz, 1H), 5.09 (s, 1H), 3.98-3.84 (m, 2H), 3.74 (s, 3H), 2.74-2.59 (m, 2H).

Example 78D 5-bromo-8-methoxy-N-(naphthalene-1-sulfonyl)-3,4-dihydro-1H-2-benzopyran-1-carboxamide A solution of Example 78C (5-bromo-8-methoxyisochroman-1-carboxylic acid) (25 mg, 0.087 mmol) in CH$_2$Cl$_2$ (0.5 mL) was treated with oxalyl chloride (38.1 μl, 0.435 mmol), treated with a catalytic amount of N,N-dimethylformamide, stirred at room temperature for 1 hour and concentrated to dryness with a stream of nitrogen. The residue was dissolved in CH$_2$Cl$_2$ (0.5 mL) and a 0° C. solution of naphthalene-1-sulfonamide (23.46 mg, 0.113 mmol), 4-dimethylaminopyridine (1.064 mg, 8.71 μmol) and triethylamine (24.27 μl, 0.174 mmol) were added in CH$_2$Cl$_2$ (0.5 mL). The mixture was stirred at room temperature for 1 hour. The mixture was partitioned between tert-butyl methyl ether (30 mL) and 1 M aqueous HCl (10 mL). The layers were separated and the aqueous layer was extracted with tert-butyl methyl ether (20 mL). The combined organic layers were washed with brine, dried (MgSO$_4$), filtered, concentrated, and purified by reverse-phase HPLC [Waters XBridge™ RP18 column, 5 μm, 30×100 mm, flow rate 40 mL/minute, 5-95% gradient of acetonitrile in 0.1% TFA] to afford the title compound. $^1$H NMR (400 MHz, dimethylsulfoxide-d$_6$) δ ppm 12.90 (s, 1H), 8.67 (dd, J=1.1, 8.7 Hz, 1H), 8.31 (d, J=8.3 Hz, 1H), 8.27 (dd, J=1.2, 7.5 Hz, 1H), 8.14 (d, J=8.1 Hz, 1H), 7.80 (ddd, J=1.4, 6.9, 8.6 Hz, 1H), 7.74-7.66 (m, 2H), 7.42 (d, J=8.8 Hz, 1H), 6.61 (d, J=8.8 Hz, 1H), 5.07 (s, 1H), 3.75 (ddd, J=3.7, 5.5, 11.6 Hz, 1H), 3.53 (ddd, J=4.4, 8.9, 11.6 Hz, 1H), 2.92 (s, 3H), 2.62-2.46 (m, 2H). MS (ESI+) m/z 476, 478 (M+H)$^+$.

Example 79

5-cyclobutyl-8-methoxy-N-(naphthalene-1-sulfonyl)-3,4-dihydro-1H-2-benzopyran-1-carboxamide

Example 79A 5-cyclobutyl-8-methoxyisochromane-1-carboxylic acid

A solution of Example 78B (ethyl 5-bromo-8-methoxyisochromane-1-carboxylate) (50 mg, 0.159 mmol) and 1,1'-bis(diphenylphosphino)ferrocenedichloro palladium(II) dichloromethane complex (11.61 mg, 0.016 mmol) in tetrahydrofuran (0.3 mL) under $N_2$ was treated with 0.5 M cyclobutylzinc bromide in tetrahydrofuran (952 µl, 0.476 mmol), stirred at room temperature for 2 hours, and partitioned between tert-butyl methyl ether (50 mL) and 1 M aqueous HCl (15 mL). The layers were separated and the aqueous layer was extracted with tert-butyl methyl ether (50 mL). The combined organic layers were washed with brine, dried ($MgSO_4$), filtered, concentrated, and chromatographed on silica gel, eluting with a gradient of 5% to 10% tert-butyl methyl ether in heptanes to provide impure ethyl 5-cyclobutyl-8-methoxyisochromane-1-carboxylate. The material was dissolved in tetrahydrofuran (1.5 mL), diluted with methanol (1.5 mL), treated with 1 M aqueous NaOH (1.5 mL), stirred at room temperature for 10 minutes, heated to 55° C. for 20 minutes, cooled and partitioned between 1 M aqueous HCl (10 mL) and tert-butyl methyl ether (75 mL). The organic layer was washed with brine, dried ($MgSO_4$), filtered, concentrated, and purified by reverse-phase HPLC [Waters XBridge™ RP18 column, 5 µm, 30×100 mm, flow rate 40 mL/minute, 5%-40% gradient of acetonitrile in 0.1% TFA] to afford the title compound. $^1$H NMR (400 MHz, $CDCl_3$) δ ppm 7.20 (d, J=8.4 Hz, 1H), 6.80 (d, J=8.5 Hz, 1H), 5.43 (s, 1H), 4.17 (ddd, J=4.0, 10.1, 11.7 Hz, 1H), 4.08 (ddd, J=3.0, 6.1, 11.7 Hz, 1H), 3.88 (s, 3H), 3.58-3.49 (m, 1H), 2.78 (ddd, J=6.1, 10.2, 16.5 Hz, 1H), 2.61 (dt, J=3.5, 16.9 Hz, 1H), 2.36-2.26 (m, 2H), 2.20-1.95 (m, 3H), 1.89-1.78 (m, 1H). MS (APCI+) m/z 263 (M+H)$^+$.

Example 79B 5-cyclobutyl-8-methoxy-N-(naphthalene-1-sulfonyl)-3,4-dihydro-1H-2-benzopyran-1-carboxamide A solution of Example 79A (5-cyclobutyl-8-methoxyisochroman-1-carboxylic acid) (21 mg, 0.080 mmol) in $CH_2Cl_2$ (0.5 mL) was treated with oxalyl chloride (35.0 µl, 0.400 mmol), treated with catalytic amount of N,N-dimethylformamide, stirred at room temperature for 30 minutes and concentrated to dryness with a stream of nitrogen. The residue was dissolved in $CH_2Cl_2$ (0.5 mL), treated with naphthalene-1-sulfonamide (21.57 mg, 0.104 mmol), treated with triethylamine (22.32 µl, 0.160 mmol), treated with a catalytic amount of 4-dimethylaminopyridine (2 mg), and stirred at room temperature for 1 hour. The mixture was concentrated with a steam of $N_2$, and purified by reverse-phase HPLC [Waters XBridge™ RP18 column, 5 µm, 30×100 mm, flow rate 40 mL/minute, 5-95% gradient of acetonitrile in 0.1% TFA] to afford the title compound. $^1$H NMR (501 MHz, dimethylsulfoxide-$d_6$) δ ppm 12.79 (s, 1H), 8.69 (dd, J=1.0, 8.7 Hz, 1H), 8.30 (d, J=8.3 Hz, 1H), 8.26 (dd, J=1.3, 7.4 Hz, 1H), 8.14 (d, J=8.1 Hz, 1H), 7.80 (ddd, J=1.3, 6.8, 8.5 Hz, 1H), 7.71 (ddd, J=1.1, 6.9, 8.1 Hz, 1H), 7.69-7.65 (m, 1H), 7.02 (d, J=8.5 Hz, 1H), 6.56 (d, J=8.5 Hz, 1H), 5.06 (s, 1H), 3.70 (ddd, J=3.4, 5.6, 11.3 Hz, 1H), 3.53-3.47 (m, 1H), 3.46-3.40 (m, 1H), 2.90 (s, 3H), 2.56-2.47 (m, 1H), 2.40 (dt, J=3.7, 16.9 Hz, 1H), 2.24-2.13 (m, 2H), 2.01-1.85 (m, 3H), 1.76-1.67 (m, 1H). MS (APCI+) m/z 452 (M+H)$^+$.

Example 80

7-cyclobutyl-4-methoxy-N-(quinoline-5-sulfonyl)-2,3-dihydro-1-benzofuran-3-carboxamide

Example 80A

Ethyl 7-cyclobutyl-4-methoxybenzofuran-3-carboxylate

A solution of Example 39B (ethyl 7-bromo-4-methoxybenzofuran-3-carboxylate) (115 mg, 0.384 mmol) and 1,1'-bis(diphenylphosphino)ferrocenedichloro palladium(II) dichloromethane complex (28.1 mg, 0.038 mmol) in tetrahydrofuran (1 mL) was treated with 0.5 M cyclobutylzinc bromide in tetrahydrofuran (2307 µl, 1.153 mmol), stirred at room temperature for 1 hour, and partitioned between tert-butyl methyl ether (75 mL) and 1 M aqueous HCl (15 mL). The mixture was filtered through diatomaceous earth and the layers were separated. The aqueous layer was extracted with tert-butyl methyl ether (50 mL). The combined organic layers were washed with brine, dried ($MgSO_4$), filtered, concentrated, and chromatographed on silica gel, eluting with 5% tert-butyl methyl ether in heptanes to provide the title compound. $^1$H NMR (400 MHz, $CDCl_3$) δ ppm 8.14 (s, 1H), 7.13 (d, J=8.2 Hz, 1H), 6.73 (d, J=8.2 Hz, 1H), 4.37 (q, J=7.1 Hz, 2H), 3.95 (s, 3H), 3.92-3.82 (m, 1H), 2.45-2.36 (m, 2H), 2.32-2.21 (m, 2H), 2.15-2.02 (m, 1H), 1.96-1.86 (m, 1H), 1.39 (t, J=7.1 Hz, 3H). MS (APCI+) m/z 275 (M+H)$^+$.

Example 80B 7-cyclobutyl-4-methoxy-2,3-dihydrobenzofuran-3-carboxylic Acid

A solution of Example 80A (ethyl 7-cyclobutyl-4-methoxybenzofuran-3-carboxylate) (81.4 mg, 0.297 mmol) in methanol (3 mL) was treated with excess magnesium turnings (43.3 mg, 1.780 mmol), stirred at room temperature for 6 hours, and partitioned between tert-butyl methyl ether (50 mL) and 1 M aqueous HCl (15 mL). The layers were separated and the aqueous layer was extracted with tert-butyl methyl ether (25 mL). The combined organic layers were washed with brine, dried ($MgSO_4$), filtered, and concentrated to provide a 2:1 ratio of methyl 7-cyclobutyl-4-methoxy-2,3-dihydrobenzofuran-3-carboxylate and ethyl 7-cyclobutyl-4-methoxy-2,3-dihydrobenzofuran-3-carboxylate. The mixture was dissolved in tetrahydrofuran (2 mL), diluted with methanol (2 mL), treated with 1 M aqueous NaOH (2 mL) and stirred at room temperature for 15 minutes. The mixture was partitioned between tert-butyl methyl ether (75 mL) and 1 M aqueous HCl (5 mL). The layers were separated and the aqueous layer was extracted with tert-butyl methyl ether (15 mL). The combined organic layers were washed with brine, dried ($MgSO_4$), filtered, and concentrated to provide the title compound. $^1$H NMR (400 MHz, $CDCl_3$) δ ppm 7.09 (d, J=8.4 Hz, 1H), 6.45 (d, J=8.4 Hz, 1H), 4.97 (dd, J=5.4, 9.4 Hz, 1H), 4.68 (t, J=9.6 Hz, 1H), 4.35 (dd, J=5.3, 9.9 Hz, 1H), 3.89 (s, 3H), 3.60-3.50 (m, 1H), 2.32-2.22 (m, 2H), 2.20-2.07 (m, 2H), 2.04-1.92 (m, 1H), 1.88-1.78 (m, 1H). MS (APCI+) m/z 249 (M+H)$^+$.

Example 80C 7-cyclobutyl-4-methoxy-N-(quinoline-5-sulfonyl)-2,3-dihydro-1-benzofuran-3-carboxamide To a solution of Example 80B (7-cyclobutyl-4-methoxy-2,3-dihydrobenzofuran-3-carboxylic acid) (60 mg, 0.242 mmol), 1-(3-dimethylaminopropyl)-3-ethylcarbodiimide hydrochloride (93 mg, 0.483 mmol) and 4-dimethylaminopyridine (4-dimethylaminopyridine) (32.5 mg, 0.266 mmol) in $CH_2Cl_2$ (0.3 mL) was added quinoline-5-sulfonamide (55.4 mg, 0.266 mmol). The mixture was stirred for 2 hours and was partitioned between ethyl acetate (75 mL) and 1 M aqueous HCl (15 mL). The ethyl acetate layer was washed with brine, dried ($MgSO_4$), filtered, concentrated and chromatographed on silica gel, eluting with a gradient of 25% to 100% [200:1:1 ethyl acetate:$HCOOH:H_2O$] in heptanes to provide the title compound. $^1H$ NMR (400 MHz, dimethylsulfoxide-$d_6$) δ ppm 12.80 (s, 1H), 9.09 (dd, J=1.6, 4.2 Hz, 1H), 9.04 (ddd, J=1.0, 1.5, 8.7 Hz, 1H), 8.39-8.34 (m, 2H), 7.94 (dd, J=7.5, 8.4 Hz, 1H), 7.82 (dd, J=4.2, 8.8 Hz, 1H), 6.96 (d, J=8.4 Hz, 1H), 6.29 (d, J=8.4 Hz, 1H), 4.67-4.60 (m, 1H), 4.29-4.22 (m, 2H), 3.41-3.32 (m, 1H), 3.21 (s, 3H), 2.16-1.95 (m, 4H), 1.92-1.80 (m, 1H), 1.77-1.68 (m, 1H). MS (APCI+) m/z 439 (M+H)$^+$.

Example 81

5-cyclobutyl-8-methoxy-N-(quinoline-5-sulfonyl)-3,4-dihydro-1H-2-benzopyran-1-carboxamide Example 81A Ethyl 5-cyclobutyl-8-methoxyisochromane-1-carboxylate A solution of Example 78B (ethyl 5-bromo-8-methoxyisochromane-1-carboxylate) (100 mg, 0.317 mmol) and 1,1'-bis(diphenylphosphino)ferrocenedichloro palladium(II) dichloromethane complex (23.22 mg, 0.032 mmol) in tetrahydrofuran (0.3 mL) under $N_2$ was treated with 0.5 M cyclobutylzinc bromide in tetrahydrofuran (1904 μl, 0.952 mmol), stirred at room temperature for 4.5 hours, and partitioned between tert-butyl methyl ether (75 mL) and 1 M aqueous HCl (25 mL). An emulsion was present and the emulsion was removed by filtering the mixture through diatomaceous earth. The layers were separated and the aqueous layer was extracted with tert-butyl methyl ether (25 mL). The combined organic layers were washed with brine, dried ($MgSO_4$), filtered, concentrated and chromatographed on silica gel, eluting with 5% tert-butyl methyl ether in heptanes provided the title compound. $^1H$ NMR (501 MHz, $CDCl_3$) δ ppm 7.15 (d, J=8.5 Hz, 1H), 6.71 (d, J=8.4 Hz, 1H), 5.29 (s, 1H), 4.31-4.17 (m, 2H), 4.04 (ddd, J=4.1, 9.1, 11.4 Hz, 1H), 3.98 (ddd, J=3.9, 5.6, 11.3 Hz, 1H), 3.76 (s, 3H), 3.59-3.50 (m, 1H), 2.77-2.70 (m, 1H), 2.64 (dt, J=4.1, 16.7 Hz, 1H), 2.30 (tddd, J=2.6, 3.5, 8.1, 9.1 Hz, 2H), 2.21-2.12 (m, 1H), 2.10-1.95 (m, 2H), 1.87-1.79 (m, 1H), 1.30 (t, J=7.1 Hz, 3H).

Example 81B 5-cyclobutyl-8-methoxyisochromane-1-carboxylic Acid

A solution of Example 81A (ethyl 5-cyclobutyl-8-methoxyisochroman-1-carboxylate) (18.7 mg, 0.064 mmol) in tetrahydrofuran (1.5 mL) was diluted with methanol (1.5 mL), treated with 1 M aqueous NaOH (1.5 mL), heated to 60° C. for 30 minutes, cooled and partitioned between tert-butyl methyl ether (50 mL) and 1 M aqueous HCl (10 mL). The layers were separated and the aqueous layer was extracted with tert-butyl methyl ether (15 mL). The combined organic layers were washed with brine, dried ($MgSO_4$), filtered, and concentrated to provide the title compound. $^1H$ NMR (501 MHz, $CDCl_3$) δ ppm 7.20 (d, J=8.5 Hz, 1H), 6.80 (d, J=8.5 Hz, 1H), 5.43 (s, 1H), 4.17 (ddd, J=4.0, 10.3, 11.7 Hz, 1H), 4.09 (ddd, J=2.9, 6.1, 11.6 Hz, 1H), 3.89 (s, 3H), 3.53 (p, J=8.5 Hz, 1H), 2.78 (ddd, J=6.2, 10.3, 16.5 Hz, 1H), 2.61 (dt, J=3.4, 16.9 Hz, 1H), 2.35-2.28 (m, 2H), 2.19-1.97 (m, 3H), 1.86-1.79 (m, 1H).

Example 81C 5-cyclobutyl-8-methoxy-N-(quinoline-5-sulfonyl)-3,4-dihydro-1H-2-benzopyran-1-carboxamide A solution of Example 81B (5-cyclobutyl-8-methoxyisochroman-1-carboxylic acid) (16 mg, 0.061 mmol) in $CH_2Cl_2$ (0.5 mL) was treated with oxalyl chloride (26.7 μl, 0.305 mmol), treated with a catalytic amount of N,N-dimethylformamide, stirred at room temperature for 30 minutes and concentrated to dryness with a stream of nitrogen for 45 minutes. The residue was dissolved in $CH_2Cl_2$ (0.5 mL), treated with quinoline-5-sulfonamide (16.51 mg, 0.079 mmol), treated with triethylamine (17.00 μl, 0.122 mmol), treated with a catalytic amount of 4-dimethylaminopyridine, and stirred at room temperature overnight. The mixture was partitioned between ethyl acetate (75 mL) and 1 M aqueous HCl (15 mL). The ethyl acetate layer was washed with brine, dried ($MgSO_4$), filtered, concentrated and chromatographed on silica gel, eluting with a gradient of 15% to 50% [200:1:1 ethyl acetate:$HCOOH:H_2O$] in heptanes to provide the title compound. $^1H$ NMR (400 MHz, dimethylsulfoxide-$d_6$) δ ppm 12.91 (s, 1H), 9.11-9.05 (m, 2H), 8.38-8.31 (m, 2H), 7.93 (dd, J=7.6, 8.2 Hz, 1H), 7.83 (dd, J=4.2, 8.7 Hz, 1H), 7.03 (d, J=8.5 Hz, 1H), 6.58 (d, J=8.4 Hz, 1H), 5.04 (s, 1H), 3.73-3.66 (m, 1H), 3.52-3.39 (m, 2H), 2.97 (s, 3H), 2.58-2.46 (m, 1H), 2.40 (dt, J=3.7, 16.7 Hz, 1H), 2.24-2.14 (m, 2H), 2.03-1.86 (m, 3H), 1.77-1.67 (m, 1H). MS (ESI+) m/z 453 (M+H)$^+$.

Example 82

(3R)-7-cyclobutyl-4-methoxy-N-(quinoline-5-sulfonyl)-2,3-dihydro-1-benzofuran-3-carboxamide The enantiomers of Example 80 were separated by Supercritical Fluid Chromatography (SFC) using a 21×250 mm Whelk-O (S,S) chiral column eluting with 30% methanol in liquid $CO_2$ using a flow rate of 70 mL/minute to provide the title compound as the first peak to elute from the column. $^1H$ NMR (400 MHz, dimethylsulfoxide-$d_6$) δ ppm 12.80 (s, 1H), 9.09 (dd, J=1.6, 4.2 Hz, 1H), 9.04 (ddd, J=1.0, 1.5, 8.7 Hz, 1H), 8.39-8.34 (m, 2H), 7.94 (dd, J=7.5, 8.4 Hz, 1H), 7.82 (dd, J=4.2, 8.8 Hz, 1H), 6.96 (d, J=8.4 Hz, 1H), 6.29 (d, J=8.4 Hz, 1H), 4.67-4.60 (m, 1H), 4.29-4.22 (m, 2H), 3.41-3.32 (m, 1H), 3.21 (s, 3H), 2.16-1.95 (m, 4H), 1.92-1.80 (m, 1H), 1.77-1.68 (m, 1H). LC/MS (APCI+) m/z 439 (M+H)$^+$.

Example 83

(3S)-7-cyclobutyl-4-methoxy-N-(quinoline-5-sulfonyl)-2,3-dihydro-1-benzofuran-3-carboxamide The enantiomers of Example 80 were separated by Supercritical Fluid Chromatography (SFC) using a 21×250 mm Whelk-O (S,S) chiral column eluting with 30% methanol in liquid CO$_2$ using a flow rate of 70 mL/minute to provide the title compound as the second peak to elute from the column. $^1$H NMR (400 MHz, dimethylsulfoxide-d$_6$) δ ppm 12.80 (s, 1H), 9.09 (dd, J=1.6, 4.2 Hz, 1H), 9.04 (ddd, J=1.0, 1.5, 8.7 Hz, 1H), 8.39-8.34 (m, 2H), 7.94 (dd, J=7.5, 8.4 Hz, 1H), 7.82 (dd, J=4.2, 8.8 Hz, 1H), 6.96 (d, J=8.4 Hz, 1H), 6.29 (d, J=8.4 Hz, 1H), 4.67-4.60 (m, 1H), 4.29-4.22 (m, 2H), 3.41-3.32 (m, 1H), 3.21 (s, 3H), 2.16-1.95 (m, 4H), 1.92-1.80 (m, 1H), 1.77-1.68 (m, 1H). MS (APCI+) m/z 439 (M+H)$^+$.

Example 84

5-cyclobutyl-8-methoxy-1-methyl-N-(naphthalene-1-sulfonyl)-3,4-dihydro-1H-2-benzopyran-1-carboxamide Example 84A Ethyl 5-cyclobutyl-8-methoxy-1-methylisochromane-1-carboxylate A solution of Example 81A (ethyl 5-cyclobutyl-8-methoxyisochroman-1-carboxylate) (19.3 mg, 0.066 mmol) in tetrahydrofuran (0.5 mL) was treated with excess 60% dispersion of sodium hydride in mineral oil (25 mg) and excess iodomethane (5 drops), stirred at room temperature for 1 hour, diluted with N,N-dimethylformamide (1 mL), stirred at room temperature for 1 hour, heated to 60° C. for 75 minutes, then allowed to stir at room temperature overnight. The mixture was partitioned between tert-butyl methyl ether (7 mL) and 1 M aqueous HCl (15 mL). The tert-butyl methyl ether layer was washed with water (10 mL), washed with brine, dried (MgSO$_4$), filtered, and concentrated to provide a mixture of ethyl 5-cyclobutyl-8-methoxyisochroman-1-carboxylate and ethyl 5-cyclobutyl-8-methoxy-1-methylisochromane-1-carboxylate. The mixture was dissolved in tetrahydrofuran (1.5 mL), diluted with methanol (1.5 mL), treated with 1 M aqueous NaOH (1.5 mL), heated to 60° C. for 45 minutes, cooled, and partitioned between tert-butyl methyl ether (50 mL) and 1 M aqueous HCl (10 mL). The layers were separated and the aqueous layer was extracted with tert-butyl methyl ether (15 mL). The combined organic layers were washed with brine, dried (MgSO$_4$), filtered, concentrated and chromatographed on silica gel, eluting with a gradient of 5% to 15% ethyl acetate in heptanes to provide the title compound. $^1$H NMR (400 MHz, CDCl$_3$) δ ppm 7.12 (dd, J=0.9, 8.5 Hz, 1H), 6.72 (d, J=8.4 Hz, 1H), 4.18 (qd, J=2.7, 7.1 Hz, 2H), 4.04-3.94 (m, 2H), 3.73 (s, 3H), 3.60-3.50 (m, 1H), 2.70 (ddd, J=5.7, 8.2, 16.5 Hz, 1H), 2.62 (dt, J=4.1, 16.5 Hz, 1H), 2.38-2.25 (m, 2H), 2.22-1.94 (m, 3H), 1.89-1.78 (m, 1H), 1.68 (s, 3H), 1.22 (t, J=7.1 Hz, 3H).

Example 84B 5-cyclobutyl-8-methoxy-1-methylisochromane-1-carboxylic Acid

A mixture of Example 84A (ethyl 5-cyclobutyl-8-methoxy-1-methylisochroman-1-carboxylate) (10 mg, 0.033 mmol) in ethylene glycol (2 mL), was treated with 45% aqueous KOH (1 mL), heated to 160° C. for 45 minutes, cooled to room temperature and partitioned between tert-butyl methyl ether (50 mL) and 1 M aqueous HCl (25 mL). The layers were separated and the tert-butyl methyl ether layer was washed with 0.2 M aqueous HCl (15 mL), washed with brine, dried (MgSO$_4$), filtered, and concentrated to provide the title compound. $^1$H NMR (400 MHz, CDCl$_3$) δ ppm 7.15 (d, J=8.3 Hz, 1H), 6.76 (d, J=8.4 Hz, 1H), 4.07-3.95 (m, 2H), 3.78 (s, 3H), 3.59-3.50 (m, 1H), 2.72 (ddd, J=5.5, 8.6, 16.5 Hz, 1H), 2.63 (dt, J=3.9, 16.4 Hz, 1H), 2.37-2.27 (m, 2H), 2.20-1.95 (m, 3H), 1.88-1.79 (m, 1H), 1.71 (s, 3H).

Example 84C 5-cyclobutyl-8-methoxy-1-methyl-N-(naphthalene-1-sulfonyl)-3,4-dihydro-1H-2-benzopyran-1-carboxamide A solution of Example 84B (5-cyclobutyl-8-methoxy-1-methylisochroman-1-carboxylic acid) (10 mg, 0.036 mmol) in CH$_2$Cl$_2$ (0.3 mL) was cooled to 0° C., treated with excess oxalyl chloride (31.7 μl, 0.362 mmol), treated with catalytic N,N-dimethylformamide, stirred at room temperature for 45 minutes, and concentrated with a stream of N$_2$. The residue was dissolved in CH$_2$Cl$_2$ (0.5 mL), treated with naphthalene-1-sulfonamide (15.00 mg, 0.072 mmol), treated with triethylamine (10.09 μl, 0.072 mmol), treated with a catalytic amount of 4-dimethylaminopyridine and stirred at room temperature overnight. The mixture was partitioned between ethyl acetate (30 mL) and 1 M aqueous HCl (10 mL). The ethyl acetate layer was washed with brine, dried (MgSO$_4$), filtered, concentrated and chromatographed on silica gel, eluting with a gradient of 15% to 50% [200:1:1 ethyl acetate:HCOOH:H$_2$O] in heptanes to provide the title compound. $^1$H NMR (500 MHz, DMSO-d$_6$) δ 11.78 (s, 1H), 8.52 (d, J=8.6 Hz, 1H), 8.33-8.27 (m, 2H), 8.11 (d, J=8.3 Hz, 1H), 7.73-7.58 (m, 3H), 7.09 (d, J=8.3 Hz, 1H), 6.56 (d, J=8.4 Hz, 1H), 3.78-3.27 (m, 3H), 2.91 (s, 3H), 2.63-1.71 (m, 8H), 1.41 (s, 3H). MS (APCI+) m/z 466 (M+H)$^+$.

Example 85

8-cyclobutyl-5-methoxy-N-(1,2,3,4-tetrahydroquinoline-5-sulfonyl)-3,4-dihydro-2H-1-benzopyran-4-carboxamide A mixture of 8-cyclobutyl-5-methoxychroman-4-carboxylic acid (Example 75E, 100 mg, 0.381 mmol), N$^1$-((ethylimino)methylene)-N$^3$,N$^3$-dimethylpropane-1,3-diamine, hydrochloric acid (146 mg, 0.762 mmol) and N,N-dimethylpyridin-4-amine (93 mg, 0.762 mmol) in dichloromethane (2 mL) was stirred at room temperature for 30 minutes, followed by the addition of 1,2,3,4-tetrahydroquinoline-5-sulfonamide (89 mg, 0.419 mmol). The mixture was stirred at room temperature for 2 hours. The solvent was removed and the residue was purified by reverse-phase preparative HPLC on a Phenomenex® Luna® C8(2) 5 μm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound. $^1$H NMR (500 MHz, DMSO-d$_6$) δ ppm 7.07-6.94 (m, 3H), 6.67 (dd, J=8.0, 1.3 Hz, 1H), 6.41 (d, J=8.4 Hz, 1H), 6.12 (s, 1H), 4.09 (dt, J=11.0, 4.0 Hz, 1H), 3.88 (td, J=10.7, 2.5 Hz, 1H), 3.71 (dd, J=6.8, 3.8 Hz, 1H), 3.57 (s, 3H), 3.51 (q, J=8.9 Hz, 1H), 3.19 (d, J=4.6 Hz, 2H), 3.11-3.05 (m, 1H), 3.00 (ddd, J=17.2, 7.9, 5.4 Hz, 1H), 2.20-2.12 (m, 2H), 2.07-1.70 (m, 8H). MS (ESI+) m/z 457 (M+H)$^+$.

Example 86

(4R)-8-cyclobutyl-5-methoxy-2,2-dimethyl-N-(quinoline-5-sulfonyl)-3,4-dihydro-2H-1-benzopyran-4-carboxamide The title compound was prepared and isolated as described in Example 13, substituting Example 72 for Example 11. $^1$H NMR (501 MHz, DMSO-$d_6$:D$_2$O=9:1 (v/v)) δ ppm 9.13-9.05 (m, 2H), 8.39 (ddd, J=8.9, 7.4, 1.1 Hz, 2H), 7.98 (dd, J=8.5, 7.4 Hz, 1H), 7.85 (dd, J=8.8, 4.2 Hz, 1H), 6.89 (d, J=8.3 Hz, 1H), 6.23 (d, J=8.4 Hz, 1H), 3.61 (dd, J=10.4, 7.3 Hz, 1H), 3.42 (q, J=8.9 Hz, 1H), 2.76 (s, 3H), 2.19-2.09 (m, 2H), 2.03-1.95 (m, 1H), 1.95-1.83 (m, 3H), 1.73-1.68 (m, 1H), 1.48 (dd, J=13.3, 10.5 Hz, 1H), 1.19 (s, 3H), 1.05 (s, 3H). MS (APCI+) m/z 481.0 (M+H)$^+$.

Example 87

7-cyclobutyl-4-methoxy-N-(1-methyl-1H-benzimidazole-7-sulfonyl)-2,3-dihydro-1-benzofuran-3-carboxamide

Example 87A 2-bromo-N-methyl-6-nitroaniline

1-Bromo-2-fluoro-3-nitrobenzene (10.00 g, 45.5 mmol) was dissolved in a solution of methanamine (68.2 mL, 136 mmol) in tetrahydrofuran (2 M). The mixture was heated to 60° C. in a sealed flask for 18 hours. The reaction mixture was concentrated in vacuo. The resulting residue was dissolved in ethyl acetate (200 mL), washed sequentially with water (30 mL) and brine (30 mL), then dried over Na$_2$SO$_4$, filtered and concentrated to provide the title compound. MS (ESI+) m/z 231.1 (M+H)$^+$.

Example 87B 7-bromo-1-methyl-1H-benzo[d]imidazole

A suspension of iron (10.15 g, 182 mmol) in a solution of the 2-bromo-N-methyl-6-nitroaniline (7.00 g, 30.3 mmol) and ammonium chloride (9.72 g, 182 mmol) in isopropyl alcohol (60 mL) and formic acid (60 mL, 1564 mmol) was stirred at 90° C. under N$_2$ for 16 hours. The mixture was diluted with CH$_2$Cl$_2$ (200 mL) and filtered. The filtrate was concentrated to dryness and the resulting residue was partitioned between CH$_2$Cl$_2$ (100 mL) and saturated aqueous NaHCO$_3$ (100 mL). The aqueous layer was extracted with CH$_2$Cl$_2$ (3×100 mL). The combined organic layers were dried over Na$_2$SO$_4$, filtered, and concentrated to provide 7-bromo-1-methyl-1H-benzo[d]imidazole. The crude material was purified by silica gel chromatography (10% methanol in CH$_2$Cl$_2$) to provide the title compound. MS (ESI+) m/z 211.1 (M+H)$^+$.

Example 87C 1-methyl-1H-benzo[d]imidazole-7-sulfonyl fluoride

An 20 mL microwave vial was charged with DABSO (1,4-diazabicyclo[2.2.2]octane bis(sulfur dioxide) adduct, 569 mg, 2.369 mmol), PdCl$_2$(AmPhos)$_2$ (bis(di-tert-butyl(4-dimethylaminophenyl)phosphine)dichloropalladium(II), 84 mg, 0.118 mmol) and 7-bromo-1-methyl-1H-benzo[d]imidazole (500 mg, 2.369 mmol). A solution of N-cyclohexyl-N-methylcyclohexanamine (1.531 mL, 7.11 mmol) in anhydrous isopropyl alcohol (11 mL) was added. The vial was sealed with a Teflon cap, sparged for 5 minutes with N$_2$, and subjected to microwave conditions at 110° C. for 2.5 hours. After cooling to room temperature, N-fluoro-N-(phenylsulfonyl)benzenesulfonamide (1121 mg, 3.55 mmol) was added and the reaction mixture was stirred for 2 hours until completion. The reaction mixture was diluted with H$_2$O (30 mL), extracted with ethyl acetate (2×100 mL), dried over anhydrous Na$_2$SO$_4$, filtered and concentrated in vacuo to give the crude product. The crude product was purified by silica gel chromatography (50%-80% ethyl acetate in petroleum) to provide the title compound. MS (ESI+) m/z 215.1 (M+H)$^+$.

Example 87D 1-methyl-1H-benzo[d]imidazole-7-sulfonamide

Ammonium hydroxide (65 mL, 1669 mmol) in a round bottom flask was cooled to 0° C., and 1-methyl-1H-benzo[d]imidazole-7-sulfonyl fluoride (1.250 g, 5.84 mmol) was added to the solution. The mixture was stirred at 0° C. for 5 hours, and stirred at room temperature for 16 hours. The mixture was added dropwise into the 1 N aqueous HCl solution at 0° C., adjusting the pH within 4-5. The acidic solution was purified by combi-flash chromatography (mobile phase: 5% methanol (B) in H$_2$O (0.04% TFA) (A), time: 15-20 minutes). The mixture was concentrated to provide 1-methyl-1H-benzo[d]imidazole-7-sulfonamide. $^1$H NMR (400 MHz, DMSO-$d_6$) δ ppm 8.75 (s, 1H), 7.98 (s, 2H), 7.98 (d, J=7.6 Hz, 1H), 7.85 (d, J=7.6 Hz, 1H), 7.48 (t, J=7.8 Hz, 1H), 4.19 (s, 3H). MS (ESI+) m/z 212.1 (M+H)$^+$.

Example 87E 7-cyclobutyl-4-methoxy-N-(1-methyl-1H-benzimidazole-7-sulfonyl)-2,3-dihydro-1-benzofuran-3-carboxamide Into a 4 mL vial was weighed 7-cyclobutyl-4-methoxy-2,3-dihydrobenzofuran-3-carboxylic acid (Example 80B, 26.7 mg, 0.11 mmol). 1-Methyl-1H-benzo[d]imidazole-7-sulfonamide (25.0 mg, 0.12 mmol) in dichloromethane (0.5 mL) was added. N$^1$-((ethylimino)methylene)-N$^3$,N$^3$-dimethylpropane-1,3-diamine hydrochloride (40.9 mg, 0.22 mmol) and N,N-dimethylpyridin-4-amine (14.5 mg, 0.12 mmol) in dichloromethane (0.5 mL) were added and the reaction was stirred for 2 hours at room temperature. The reaction mixture was concentrated under a stream of nitrogen, dissolved in methanol and purified using preparative reverse phase HPLC/MS method TFA8 to provide the title compound. $^1$H NMR (501 MHz, DMSO-$d_6$:D$_2$O=9:1 (v/v)) δ ppm 8.45 (s, 1H), 8.05 (dd, J=8.1, 1.1 Hz, 1H), 7.93 (dd, J=7.8, 1.1 Hz, 1H), 7.44 (t, J=8.0 Hz, 1H), 7.02 (d, J=8.4 Hz, 1H), 6.39 (d, J=8.4 Hz, 1H), 4.69 (t, J=9.6 Hz, 1H), 4.44 (dd, J=9.3, 6.1 Hz, 1H), 4.34 (dd, J=9.8, 6.1 Hz, 1H), 4.20 (s, 3H), 3.45-3.35 (m, 4H), 2.20-2.09 (m, 2H), 2.10-1.97 (m, 2H), 1.96-1.83 (m, 1H), 1.80-1.69 (m, 1H). MS (APCI+) m/z 442.0 (M+H)$^+$.

Example 88

7-cyclobutyl-4-methoxy-N-(pyrazolo[1,5-a]pyridine-4-sulfonyl)-2,3-dihydro-1-benzofuran-3-carboxamide

Example 88A methyl 4-sulfamoylpyrazolo[1,5-a]pyridine-3-carboxylate n-Butyllithium (0.251 g, 3.92 mmol, 2.5 M in tetrahydrofuran) and dibutylmagnesium (1.629 g, 11.76 mmol, 1.0 M in heptane) were charged into a nitrogen filled three-necked flask at room temperature. A solution of methyl 4-bromopyrazolo[1,5-a]pyridine-3-carboxylate (2.000 g, 7.84 mmol) in tetrahydrofuran (25 mL) was added dropwise to the lithium tributylmagnesate complex (n-Bu$_3$MgLi) solution at −25° C. and the mixture was stirred at −10° C. for 1 hour. The resulting mixture was added to a solution of sulfuryl dichloride (1.587 mL, 19.60 mmol) in toluene (20 mL) at −10° C. and the mixture was stirred for 20 minutes at −10° C. The organic solvents were removed by rotary evaporation to give a crude solid. Ammonium hydroxide (15 mL, 7.84 mmol) was added to the crude solid at room temperature, and the mixture was stirred for 15 minutes. After completion, the reaction mixture was concentrated to give crude title product. The crude material was purified by silica gel chromatography (25%-40% ethyl acetated in petroleum) to give crude (75% purity) product. The material was then purified by Prep-HPLC on a Gilson 281(PHG013) with Boston pHlex ODS column (21.2×250 mm, 10 m), using a gradient of acetonitrile (B) and 0.05% trifluoroacetic acid in water (A) at 35-55% B in 10 minute with stop at 15 minute, at a flow rate of 25 mL/minute to provide the title compound. $^1$H NMR (400 MHz, CDCl$_3$) δ ppm 8.70 (dd, J=6.8, 1.0 Hz, 1H), 8.50 (s, 1H), 8.25 (dd, J=7.4, 1.0 Hz, 1H), 7.08 (t, J=7.1 Hz, 1H), 6.60 (s, 2H), 3.96 (s, 3H). MS (ESI+) m/z 256.1 (M+H)$^+$.

Example 88B pyrazolo[1,5-a]pyridine-4-sulfonamide

Methyl 4-sulfamoylpyrazolo[1,5-a]pyridine-3-carboxylate (0.535 g, 1.258 mmol) was heated in H$_2$SO$_4$ (12.33 g, 62.9 mmol) at 90° C. for 10 hours. After cooling, the reaction mixture was neutralized with 4 N aqueous NaOH to pH=5. The mixture was extracted with ethyl acetate (2×100 mL), and washed with brine (30 mL). The organic phase was dried over Na$_2$SO$_4$ (5 g), filtered, and concentrated to give the crude product. The residue was purified by Combi-Flash chromatography (H$_2$O (0.01% TFA) (A)/methanol (B), gradient from 5-25% of B at 10-25 minutes, and concentrated to provide the title compound. $^1$H NMR (400 MHz, DMSO-d$_6$) δ ppm 8.92 (d, J=7.2, 1H), 8.18 (s, 1H), 7.74 (s, 2H), 7.70 (d, J=6.8, 1H), 7.03 (t, J=7.0, 1H), 6.99 (s, 1H). MS (ESI+) m/z 198.7 (M+H)$^+$.

Example 88C 7-cyclobutyl-4-methoxy-N-(pyrazolo[1,5-a]pyridine-4-sulfonyl)-2,3-dihydro-1-benzofuran-3-carboxamide Example 88C was prepared and isolated as described in Example 87E, substituting pyrazolo[1,5-a]pyridine-4-sulfonamide (Example 88B) for 1-methyl-1H-benzo[d]imidazole-7-sulfonamide. $^1$H NMR (400 MHz, DMSO-d$_6$:D$_2$O=9:1 (v/v)) δ ppm 8.97 (dt, J=7.1, 1.1 Hz, 1H), 8.25 (d, J=2.3 Hz, 1H), 7.88 (dd, J=7.3, 1.0 Hz, 1H), 7.08 (t, J=7.1 Hz, 1H), 7.03-6.94 (m, 2H), 6.34 (d, J=8.5 Hz, 1H), 4.62 (t, J=8.9 Hz, 1H), 4.32-4.19 (m, 2H), 3.42-3.33 (m, 1H), 3.33 (s, 3H), 2.18-1.95 (m, 4H), 1.95-1.79 (m, 1H), 1.79-1.67 (m, 1H). MS (APCI+) m/z 428.1 (M+H)$^+$.

Example 89

7-cyclobutyl-4-methoxy-N-(1,2,3,4-tetrahydroquinoline-5-sulfonyl)-2,3-dihydro-1-benzofuran-3-carboxamide Into a 4 mL vial was added 7-cyclobutyl-4-methoxy-2,3-dihydrobenzofuran-3-carboxylic acid (Example 80B, 75 mg, 0.302 mmol), N$^1$-((ethylimino)methylene)-N$^3$,N$^3$-dimethylpropane-1,3-diamine hydrochloride (116 mg, 0.604 mmol), and N,N-dimethylpyridin-4-amine (40.6 mg, 0.332 mmol) in dichloromethane (2 mL). 1,2,3,4-Tetrahydroquinoline-5-sulfonamide (70.5 mg, 0.332 mmol) was added. The reaction was stirred overnight at room temperature. The reaction was dried down under a stream of nitrogen, dissolved in methanol and purified using preparative reverse phase HPLC/MS method TFA8 to yield the title compound. $^1$H NMR (501 MHz, DMSO-d$_6$:D$_2$O=9:1 (v/v)) δ ppm 7.10-6.97 (m, 3H), 6.71 (d, J=8.0 Hz, 1H), 6.47 (d, J=8.5 Hz, 1H), 4.64 (t, J=9.5 Hz, 1H), 4.42 (dd, J=9.3, 5.5 Hz, 1H), 4.35 4.24 (m, 1H), 3.69 (s, 3H), 3.42 (p, J=8.7 Hz, 1H), 3.24-3.08 (m, 2H), 3.08-2.85 (m, 2H), 2.16 (dtd, J=10.7, 8.2, 2.5 Hz, 2H), 2.11-1.98 (m, 2H), 1.98-1.85 (m, 1H), 1.85-1.67 (m, 3H). MS (APCI+) m/z 443.1 (M+H)$^+$.

Example 90

7-cyclobutyl-4-methoxy-N-(1,2,3,4-tetrahydroquinoline-8-sulfonyl)-2,3-dihydro-1-benzofuran-3-carboxamide Into a 4 mL vial was added 7-cyclobutyl-4-methoxy-2,3-dihydrobenzofuran-3-carboxylic acid (75 mg, 0.302 mmol), N$^1$-((ethylimino)methylene)-N$^3$,N$^3$-dimethylpropane-1,3-diamine hydrochloride (116 mg, 0.604 mmol), and N,N-dimethylpyridin-4-amine (40.6 mg, 0.332 mmol) in dichloromethane (2 mL). 1,2,3,4-Tetrahydroquinoline-8-sulfonamide (70.5 mg, 0.332 mmol) was added. The reaction was stirred overnight at room temperature. The reaction was dried down under a stream of nitrogen, dissolved in methanol, and purified using preparative reverse phase HPLC/MS method TFA8 to yield the title compound. $^1$H NMR (501 MHz, DMSO-d$_6$:D$_2$O=9:1 (v/v)) δ ppm 7.42 (d, J=7.2 Hz, 1H), 7.13 (d, J=7.0 Hz, 1H), 7.06 (d, J=8.4 Hz, 1H), 6.53 (dd, J=8.2, 7.2 Hz, 1H), 6.46 (d, J=8.4 Hz, 1H), 4.64 (t, J=9.6 Hz, 1H), 4.38 (dd, J=9.3, 5.7 Hz, 1H), 4.24 (dd, J=9.8, 5.8 Hz, 1H), 3.64 (s, 3H), 3.41 (q, J=8.8 Hz, 1H), 3.34 (t, J=5.6 Hz, 2H), 2.74 (t, J=6.3 Hz, 2H), 2.25-2.11 (m, 2H), 2.11-1.97 (m, 2H), 1.97-1.85 (m, 1H), 1.85-1.67 (m, 3H). MS (APCI+) m/z 443.1 (M+H)$^+$.

Example 91

(4S)-8-cyclobutyl-5-methoxy-N-(1,2,3,4-tetrahydroquinoline-5-sulfonyl)-3,4-dihydro-2H-1-benzopyran-4-carboxamide

Example 91A 7-methoxy-N-((2-methylquinolin-5-yl)sulfonyl)-4-(trifluoromethyl)-2,3-dihydro-1H-indene-1-carboxamide A mixture of 8-cyclobutyl-5-methoxychroman-4-carboxylic acid (Example 75E, 100 mg, 0.381 mmol), $N^1$-((ethylimino)methylene)-$N^3$,$N^3$-dimethylpropane-1,3-diamine, hydrochloric acid (146 mg, 0.762 mmol), and N,N-dimethylpyridin-4-amine (93 mg, 0.762 mmol) in dichloromethane (2 mL) was stirred at room temperature for 30 minutes, followed by addition of 1,2,3,4-tetrahydroquinoline-5-sulfonamide (89 mg, 0.419 mmol). The mixture was stirred at room temperature for 2 hours. The reaction mixture was concentrated in vacuo and the residue was purified by reverse-phase preparative HPLC on a Phenomenex® Luna® C8(2) 5 µm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound. $^1$H NMR (500 MHz, DMSO-$d_6$) δ ppm 7.07-6.94 (m, 3H), 6.67 (dd, J=8.0, 1.3 Hz, 1H), 6.41 (d, J=8.4 Hz, 1H), 6.12 (s, 1H), 4.09 (dt, J=11.0, 4.0 Hz, 1H), 3.88 (td, J=10.7, 2.5 Hz, 1H), 3.71 (dd, J=6.8, 3.8 Hz, 1H), 3.57 (s, 3H), 3.51 (q, J=8.9 Hz, 1H), 3.19 (d, J=4.6 Hz, 2H), 3.11-3.05 (m, 1H), 3.00 (ddd, J=17.2, 7.9, 5.4 Hz, 1H), 2.20-2.12 (m, 2H), 2.07-1.70 (m, 8H). MS (ESI+) m/z 457 (M+H)$^+$.

Example 91B (4S)-8-cyclobutyl-5-methoxy-N-(1,2,3,4-tetrahydroquinoline-5-sulfonyl)-3,4-dihydro-2H-1-benzopyran-4-carboxamide Racemic 8-cyclobutyl-5-methoxy-N-((1,2,3,4-tetrahydroquinolin-5-yl)sulfonyl)chroman-4-carboxamide (71.5 mg, 0.157 mmol) from Example 91A was subjected to chiral separation via SFC, column: Whelk-O (S,S), column size: 21×250 mm, 5 micron, concentration: 15 mg/mL in methanol, co-solvent: methanol. The first fraction at 5.62 minute was the title compound. $^1$H NMR (400 MHz, DMSO-$d_6$) δ ppm 12.11 (s, 1H), 7.08-6.95 (m, 3H), 6.69 (dd, J=8.1, 1.4 Hz, 1H), 6.42 (d, J=8.4 Hz, 1H), 6.14 (d, J=2.6 Hz, 1H), 4.09 (dt, J=11.0, 3.9 Hz, 1H), 3.88 (td, J=10.6, 2.5 Hz, 1H), 3.73 (dd, J=7.0, 3.9 Hz, 1H), 3.57 (s, 3H), 3.56-3.45 (m, 1H), 3.19 (tq, J=7.4, 4.6, 3.5 Hz, 2H), 3.14-2.95 (m, 2H), 2.22-2.11 (m, 2H), 2.10-1.67 (m, 8H). MS (ESI+) m/z 457 (M+H)$^+$.

Example 92

(4R)-8-cyclobutyl-5-methoxy-N-(1,2,3,4-tetrahydroquinoline-5-sulfonyl)-3,4-dihydro-2H-1-benzopyran-4-carboxamide Example 92 was the second fraction at 6.58 minutes from chiral separation described in Example 91B. $^1$H NMR (400 MHz, DMSO-$d_6$) δ ppm 12.11 (s, 1H), 7.10-6.92 (m, 3H), 6.67 (dd, J=8.0, 1.4 Hz, 1H), 6.41 (d, J=8.4 Hz, 1H), 6.11 (s, 1H), 4.09 (dt, J=11.0, 3.9 Hz, 1H), 3.88 (td, J=10.7, 2.5 Hz, 1H), 3.71 (dt, J=7.0, 3.6 Hz, 1H), 3.57 (s, 3H), 3.55-3.47 (m, 1H), 3.22-3.16 (m, 2H), 3.14-2.95 (m, 2H), 2.21-2.10 (m, 2H), 2.07-1.70 (m, 8H). MS (ESI+) m/z 457 (M+H)$^+$.

Example 93

8-cyclobutyl-5-methoxy-2,2-dimethyl-N-(1,2,3,4-tetrahydroquinoline-5-sulfonyl)-3,4-dihydro-2H-1-benzopyran-4-carboxamide

Example 93A

Ethyl 8-bromo-5-methoxy-2,2-dimethylchroman-4-carboxylate

To the mixture of 8-bromo-5-methoxy-2,2-dimethylchroman-4-carboxylic acid from Example 11B (1.0 g, 3.17 mmol) in ethanol (5 mL) was slowly added 10 drops of concentrated $H_2SO_4$. The mixture was stirred at 85° C. overnight. The solvent was removed under pressure, and dichloromethane (20 mL) was added. The mixture was washed with saturated aqueous $NaHCO_3$ and brine. The organic layer was dried over $MgSO_4$, filtered, and concentrated. The residue was purified via chromatography, eluting with ethyl acetate/methanol (9:1) in heptane at a 0-60% gradient to provide the title compound. MS (APCI+) m/z 344.9 (M+H)$^+$.

Example 93B

Ethyl 8-cyclobutyl-5-methoxy-2,2-dimethylchroman-4-carboxylate

A mixture of Example 93A (750 mg, 2.185 mmol) and Pd(dppf) ([1,1'-bis(diphenylphosphino)ferrocene]dichloropalladium(II), complex with dichloromethane, 238 mg) in tetrahydrofuran (3 mL) was degassed by bubbling a stream of nitrogen through the suspension. Cyclobutylzinc(II) bromide (876 mg, 4.37 mmol) (0.5 M in tetrahydrofuran, 12 mL) was added. The mixture was stirred at room temperature overnight. The solvent was removed under pressure and the residue was purified via chromatography, eluting with ethyl acetate/methanol (9:1) in heptane at a 0-50% gradient to provide the title compound. MS (APCI+) m/z 319.4 (M+H)$^+$.

Example 93C

To ethyl 8-cyclobutyl-5-methoxy-2,2-dimethylchroman-4-carboxylate from Example 93B (580 mg, 1.822 mmol) in methanol (6 mL) was added 6 N aqueous LiOH (2 mL). The mixture was stirred at 45° C. for overnight. The mixture was adjusted pH to ~2 by adding 2 N aqueous HCl. The solvent was removed under pressure and the residue was dissolved in dichloromethane (10 mL) and washed with brine, dried over $MgSO_4$ and concentrated to provide the title compound. $^1$H NMR (400 MHz, chloroform-d) δ ppm 7.08-6.98 (m, 1H), 6.40 (d, J=8.4 Hz, 1H), 3.77 (m, 1H), 3.81-3.73 (m, 1H), 3.60 (s, 3H), 2.34-2.20 (m, 2H), 2.16-1.91 (m, 5H), 1.83-1.74 (m, 1H), 1.40 (s, 3H), 1.22 (s, 3H). MS (ESI+) m/z 291 (M+H)$^+$.

Example 93D 8-cyclobutyl-5-methoxy-2,2-dimethyl-N-((1,2,3,4-tetrahydroquinolin-5-yl)sulfonyl)chroman-4-carboxamide A mixture of 8-cyclobutyl-5-methoxy-2,2-dimethylchroman-4-carboxylic acid (100 mg, 0.344 mmol) from Example 93C and N¹-((ethylimino)methylene)-N³,N³-dimethylpropane-1,3-diamine (107 mg, 0.689 mmol) and N,N-dimethylpyridin-4-amine (84 mg, 0.689 mmol) in dichloromethane (2 mL) was stirred at room temperature for 30 minutes, followed by addition of 1,2,3,4-tetrahydroisoquinoline-5-sulfonamide (80 mg, 0.379 mmol). The mixture was stirred at 50° C. for 3 hours. The solvent was removed under pressure and the residue was dissolved in methanol (3 mL) and filtered. Purification by reverse-phase HPLC [Waters XBridge™ RP18 column, 5 μm, 30×100 mm, flow rate 40 mL/minute, 5-95% gradient of acetonitrile in 0.1% TFA] provided the title compound. $^1$H NMR (500 MHz, DMSO-$d_6$) δ ppm 12.00 (s, 1H), 7.08 (dd, J=7.8, 1.3 Hz, 1H), 7.02 (t, J=7.9 Hz, 1H), 6.94 (d, J=8.4 Hz, 1H), 6.72 (dd, J=8.1, 1.4 Hz, 1H), 6.38 (d, J=8.4 Hz, 1H), 3.69 (dd, J=10.6, 7.2 Hz, 1H), 3.44 (s, 3H), 3.22 (d, J=5.6 Hz, 2H), 3.10-2.99 (m, 2H), 2.17 (qt, J=9.6, 3.9 Hz, 2H), 2.10-1.81 (m, 6H), 1.77-1.66 (m, 1H), 1.60 (dd, J=13.2, 10.6 Hz, 1H), 1.31 (s, 3H), 1.09 (s, 3H). MS (ESI+) m/z 485 (M+H)⁺.

Example 94

(3R)-7-cyclobutyl-4-methoxy-N-(1-methyl-1H-indazole-7-sulfonyl)-2,3-dihydro-1-benzofuran-3-carboxamide Into a 4 mL vial was added 7-cyclobutyl-4-methoxy-2,3-dihydrobenzofuran-3-carboxylic acid (80 mg, 0.323 mmol), N¹-((ethylimino)methylene)-N³,N³-dimethylpropane-1,3-diamine hydrochloride (124 mg, 0.646 mmol), and N,N-dimethylpyridin-4-amine (43.4 mg, 0.355 mmol) in dichloromethane (2 mL). 1-Methyl-1H-indazole-7-sulfonamide (Example 69A, 75 mg, 0.355 mmol) was added. The reaction was stirred overnight at room temperature. The reaction was concentrated under a stream of nitrogen, dissolved in methanol and purified using preparative reverse phase HPLC/MS method TFA8 to yield the racemate of the title compound. The material was separated by chiral preparative SFC chromatography using a WHELK-O (S,S), column size 21×250 mm, serial number 43170, 5 micron, using a concentration of 25 mg/mL in 3:1 methanol/dichloromethane at a flow rate of 49 g/minute $CO_2$ and UV monitoring at 220 nm to provide the title compound as the first eluting isomer. $^1$H NMR (400 MHz, DMSO-$d_6$:$D_2O$=9:1 (v/v)) δ ppm 8.31 (s, 1H), 8.19-8.12 (m, 1H), 8.07 (dd, J=7.5, 1.1 Hz, 1H), 7.30 (t, J=7.8 Hz, 1H), 6.99 (d, J=8.4 Hz, 1H), 6.34 (d, J=8.5 Hz, 1H), 4.69 (t, J=9.5 Hz, 1H), 4.43-4.38 (m, 4H), 4.30 (dd, J=9.8, 6.3 Hz, 1H), 3.44-3.33 (m, 1H), 3.32 (s, 3H), 2.19-2.08 (m, 2H), 2.08-1.96 (m, 2H), 1.94-1.80 (m, 1H), 1.80-1.67 (m, 1H). MS (APCI+) m/z 442.0 (M+H)⁺.

Example 95

(3S)-7-cyclobutyl-4-methoxy-N-(1-methyl-1H-indazole-7-sulfonyl)-2,3-dihydro-1-benzofuran-3-carboxamide Example 95 was isolated as the second enantiomer from the preparative SFC separation described in Example 94. $^1$H NMR (400 MHz, DMSO-$d_6$:$D_2O$=9:1 (v/v)) δ ppm 8.31 (s, 1H), 8.19-8.12 (m, 1H), 8.06 (dd, J=7.5, 1.2 Hz, 1H), 7.30 (t, J=7.8 Hz, 1H), 6.99 (d, J=8.4 Hz, 1H), 6.34 (d, J=8.5 Hz, 1H), 4.69 (t, J=9.5 Hz, 1H), 4.43-4.38 (m, 4H), 4.29 (dd, J=9.8, 6.3 Hz, 1H), 3.38 (p, J=8.8 Hz, 1H), 3.32 (s, 3H), 2.19-1.95 (m, 4H), 1.94-1.80 (m, 1H), 1.79-1.67 (m, 1H). MS (APCI+) m/z 442.0 (M+H)⁺.

Example 96

(4S)-8-cyclobutyl-5-methoxy-2,2-dimethyl-N-(1,2,3,4-tetrahydroquinoline-5-sulfonyl)-3,4-dihydro-2H-1-benzopyran-4-carboxamide 8-Cyclobutyl-5-methoxy-2,2-dimethyl-N-((1,2,3,4-tetrahydroquinolin-5-yl)sulfonyl)chroman-4-carboxamide (93 mg, 0.192 mmol) from Example 93D was subjected to chiral separation via SFC, using column: Whelk-O (S,S), column size: 21×250 mm, 5 micron, concentration: 14.25 mg/mL in dichloromethane/methanol, co-solvent: methanol, $CO_2$ flow rate: 56, co-solvent flow rate: 24 mL/minute, total flow rate: 80 mL/minute. The first fraction at 5.41 minute was (4S)-8-cyclobutyl-5-methoxy-2,2-dimethyl-N-((1,2,3,4-tetrahydroquinolin-5-yl)sulfonyl)chroman-4-carboxamide. $^1$H NMR (400 MHz, DMSO-$d_6$) δ ppm 11.97 (s, 1H), 7.08 (dd, J=7.8, 1.3 Hz, 1H), 7.00 (t, J=7.9 Hz, 1H), 6.93 (d, J=8.4 Hz, 1H), 6.71 (dd, J=8.0, 1.3 Hz, 1H), 6.37 (d, J=8.4 Hz, 1H), 6.15 (s, 1H), 3.68 (dd, J=10.4, 7.2 Hz, 1H), 3.48 (dd, J=9.6, 7.3 Hz, 1H), 3.43 (s, 3H), 3.21 (td, J=5.6, 2.5 Hz, 2H), 3.15-2.96 (m, 2H), 2.24-2.10 (m, 2H), 2.09-1.69 (m, 7H), 1.61 (dd, J=13.2, 10.6 Hz, 1H), 1.30 (s, 3H), 1.09 (s, 3H). MS (ESI+) m/z 485 (M+H)⁺.

Example 97

(4R)-8-cyclobutyl-5-methoxy-2,2-dimethyl-N-(1,2,3,4-tetrahydroquinoline-5-sulfonyl)-3,4-dihydro-2H-1-benzopyran-4-carboxamide The title compound was the second eluting isomer at 6.84 minutes from the chiral separation described in Example 96D. $^1$H NMR (400 MHz, DMSO-$d_6$) δ ppm 11.97 (s, 1H), 7.08 (dd, J=7.8, 1.3 Hz, 1H), 7.01 (t, J=7.9 Hz, 1H), 6.93 (d, J=8.4 Hz, 1H), 6.71 (dd, J=8.0, 1.4 Hz, 1H), 6.37 (d, J=8.4 Hz, 1H), 6.16 (s, 1H), 3.69 (dd, J=10.5, 7.2 Hz, 1H), 3.48 (dd, J=9.6, 7.3 Hz, 1H), 3.41 (s, 3H), 3.26-3.18 (m, 2H), 3.14-2.96 (m, 2H), 2.18 (tdd, J=8.2, 4.5, 2.4 Hz, 2H), 2.07-1.68 (m, 7H), 1.61 (dd, J=13.2, 10.6 Hz, 1H), 1.31 (s, 3H), 1.09 (s, 3H). MS (ESI+) m/z 485 (M+H)⁺.

Example 98

(3R)-7-cyclobutyl-4-methoxy-N-(1,2,3,4-tetrahydroquinoline-8-sulfonyl)-2,3-dihydro-1-benzofuran-3-carboxamide Example 90 (57 mg) was subjected to chiral preparative SFC chromatography using a WHELK-O (S,S), column size 21×250 mm, serial number 43170, 5 micron, using a concentration of 14.25 mg/mL in methanol at a flow rate of 56 g/minute $CO_2$ and UV monitoring at 220 nm to provide the title compound as the first eluting isomer. $^1$H NMR (501 MHz, DMSO-$d_6$:$D_2O$=9:1 (v/v)) δ ppm 7.42 (dd, J=8.1, 1.6 Hz, 1H), 7.12 (dd, J=7.2, 1.5 Hz, 1H), 7.05 (dd, J=8.4, 0.7 Hz, 1H), 6.53 (dd, J=8.1, 7.2 Hz, 1H), 6.46 (d, J=8.5 Hz, 1H), 4.64 (dd, J=9.9, 9.3 Hz, 1H), 4.38 (dd, J=9.3, 5.7 Hz, 1H), 4.22 (dd, J=9.8, 5.7 Hz, 1H), 3.64 (s, 3H), 3.47-3.36 (m, 1H), 3.33 (t, J=5.6 Hz, 2H), 2.73 (t, J=6.3 Hz, 2H), 2.21 2.11 (m, 2H), 2.11-1.98 (m, 2H), 1.97-1.85 (m, 1H), 1.84-1.72 (m, 3H). MS (APCI+) m/z 443.1 (M+H)⁺.

Example 99

(3S)-7-cyclobutyl-4-methoxy-N-(1,2,3,4-tetrahydroquinoline-8-sulfonyl)-2,3-dihydro-1-benzofuran-3-carboxamide Example 99 was isolated as the second enantiomer from the preparative SFC separation described in Example 98. $^1$H NMR (501 MHz, DMSO-d$_6$:D$_2$O=9:1 (v/v)) δ ppm 7.41 (dd, J=8.1, 1.6 Hz, 1H), 7.10 (d, J=7.2 Hz, 1H), 7.05 (d, J=8.4 Hz, 1H), 6.51 (dd, J=8.2, 7.2 Hz, 1H), 6.45 (d, J=8.5 Hz, 1H), 4.63 (dd, J=9.9, 9.2 Hz, 1H), 4.38 (dd, J=9.2, 5.7 Hz, 1H), 4.20 (dd, J=9.7, 5.8 Hz, 1H), 3.64 (s, 3H), 3.42 (p, J=8.8 Hz, 1H), 3.32 (t, J=5.6 Hz, 2H), 2.73 (t, J=6.3 Hz, 2H), 2.21-2.10 (m, 2H), 2.10-1.99 (m, 2H), 1.97-1.84 (m, 1H), 1.84-1.71 (m, 3H). MS (APCI+) m/z 443.1 (M+H)$^+$.

Example 100

(3R)-7-cyclobutyl-4-methoxy-N-(1,2,3,4-tetrahydro-quinoline-5-sulfonyl)-2,3-dihydro-1-benzofuran-3-carboxamide Example 89 (84 mg) was subjected to chiral preparative SFC chromatography using a WHELK-O (S,S), column size 21×250 mm, serial number 43170, 5 micron, using a concentration of 30 mg/mL in methanol at a flow rate of 64 g/minute CO$_2$ and UV monitoring at 220 nm to provide the title compound. $^1$H NMR (400 MHz, DMSO-d$_6$:D$_2$O=9:1 (v/v)) δ ppm 7.15-6.94 (m, 3H), 6.71 (d, J=7.8 Hz, 1H), 6.47 (d, J=8.4 Hz, 1H), 4.64 (t, J=9.6 Hz, 1H), 4.42 (dd, J=9.2, 5.4 Hz, 1H), 4.33-4.22 (m, 1H), 3.69 (s, 3H), 3.48-3.35 (m, 1H), 3.17 (dp, J=11.4, 5.8 Hz, 2H), 3.08-2.85 (m, 2H), 2.25-1.65 (m, 8H). MS (APCI+) m/z 443.1 (M+H)$^+$.

Example 101

(3S)-7-cyclobutyl-4-methoxy-N-(1,2,3,4-tetrahydro-quinoline-5-sulfonyl)-2,3-dihydro-1-benzofuran-3-carboxamide Example 101 was isolated as the second enantiomer from the preparative SFC separation described in Example 100. $^1$H NMR (400 MHz, DMSO-d$_6$:D$_2$O=9:1 (v/v)) δ ppm 7.10-6.96 (m, 3H), 6.70 (d, J=7.8 Hz, 1H), 6.47 (d, J=8.5 Hz, 1H), 4.64 (t, J=9.5 Hz, 1H), 4.42 (dd, J=9.2, 5.4 Hz, 1H), 4.29-4.24 (m, 1H), 3.69 (s, 3H), 3.47-3.35 (m, 1H), 3.24-3.11 (m, 2H), 3.06-2.90 (m, 2H), 2.22-1.98 (m, 4H), 1.99-1.84 (m, 1H), 1.84-1.72 (m, 3H). MS (APCI+) m/z 443.1 (M+H)$^+$.

Example 102

8-cyclobutyl-N-(1H-indole-4-sulfonyl)-5-methoxy-3,4-dihydro-2H-1-benzopyran-4-carboxamide Example 102A di(1H-indol-4-yl) 1,4-diazabicyclo[2.2.2]octane-1,4-diium-1,4-disulfinate 4-Bromo-1H-indole (6.00 g, 30.6 mmol), 1,4-diazabicyclo[2.2.2]octane-1,4-diium-1,4-disulfinate (4.41 g, 18.36 mmol), and PdCl$_2$(AmPhos)$_2$ (bis(di-tert-butyl(4-dimethylaminophenyl)phosphine)dichloropalladium(II), 1.084 g, 1.530 mmol) were added to isopropyl alcohol (140 mL). TEA (triethylamine, 12.80 mL, 92 mmol) was added to the solution. The reaction mixture was sparged for 5 minutes with N$_2$ and was stirred at 80° C. for 20 hours under nitrogen. After cooling to room temperature, the mixture was filtered and concentrated to give the crude title compound. MS (ESI+) m/z 182.2 (M+H)$^+$.

Example 102B 1H-indole-4-sulfonamide

To a solution of crude sulfinate (Example 102A, 11.04 g, 61.3 mmol) in 2-propanol (IPA) (ratio: 1.000, volume: 80 mL) and water (ratio: 2.500, volume: 200 mL) was added sodium acetate trihydrate (10.00 g, 73.5 mmol) and (aminooxy)sulfonic acid (8.31 g, 73.5 mmol). The mixture was stirred at room temperature for 2 hours. The mixture was concentrated under reduced pressure, filtered, and the solid was purified by Combi-Flash chromatography (used reverse phase silica gel column, RP-C18, 40-60 μm, 60 Å), (H$_2$O (0.01% TFA) (A)/methanol (B), gradient from 20-50% of B at 10 minutes-20 minutes), to provide the title compound. $^1$H NMR (400 MHz, DMSO-d$_6$) δ ppm 11.53 (s, 1H), 7.63 (d, J=8.0 Hz, 1H), 7.53 (s, 1H), 7.50 (d, J=7.4 Hz, 1H), 7.25 (s, 2H), 7.20 (t, J=7.8 Hz, 1H), 6.86 (s, 1H). MS (ESI+) m/z 219.1 (M+Na)$^+$.

Example 102C 8-cyclobutyl-N-(1H-indole-4-sulfonyl)-5-methoxy-3,4-dihydro-2H-1-benzopyran-4-carboxamide A mixture of 8-cyclobutyl-5-methoxychroman-4-carboxylic acid (120 mg, 0.457 mmol) from Example 75E and N$^1$-((ethylimino)methylene)-N$^3$,N$^3$-dimethylpropane-1,3-diamine, hydrochloric acid (175 mg, 0.915 mmol) and N,N-dimethylpyridin-4-amine (112 mg, 0.915 mmol) in dichloromethane (4 mL) was stirred at room temperature for 30 minutes. 1H-Indole-4-sulfonamide (91 mg, 0.457 mmol) was added. The mixture was stirred at 40° C. for 2 hours. The crude product was purified by reverse-phase HPLC [Waters XBridge™ RP18 column, 5 μm, 30×100 mm, flow rate 40 mL/minute, 5-95% gradient of acetonitrile in 0.1% TFA] to provide the title compound. $^1$H NMR (400 MHz, DMSO-d$_6$) δ ppm 12.19 (s, 1H), 11.66 (t, J=2.2 Hz, 1H), 7.73 (d, J=8.1 Hz, 1H), 7.64 (t, J=2.8 Hz, 1H), 7.60 (dd, J=7.5, 0.9 Hz, 1H), 7.23 (t, J=7.9 Hz, 1H), 6.94 (d, J=8.4 Hz, 1H), 6.92-6.86 (m, 1H), 6.29 (d, J=8.4 Hz, 1H), 3.95 (ddd, J=10.9, 5.1, 3.4 Hz, 1H), 3.69 (ddd, J=11.8, 8.7, 3.3 Hz, 2H), 3.47 (s, 1H), 3.13 (s, 3H), 2.19-2.07 (m, 2H), 2.02-1.82 (m, 4H), 1.80-1.61 (m, 2H). MS (ESI+) m/z 441 (M+H)$^+$.

Example 103

(4S)-8-cyclobutyl-N-(1H-indole-4-sulfonyl)-5-methoxy-3,4-dihydro-2H-1-benzopyran-4-carboxamide Example 103A di(1H-indol-4-yl) 1,4-diazabicyclo[2.2.2]octane-1,4-diium-1,4-disulfinate 4-Bromo-1H-indole (6.00 g, 30.6 mmol), 1,4-diazabicyclo[2.2.2]octane-1,4-diium-1,4-disulfinate (4.41 g, 18.36 mmol), and PdCl$_2$(AmPhos)$_2$ (bis(di-tert-butyl(4-dimethylaminophenyl)phosphine)dichloropalladium(II), 1.084 g, 1.530 mmol) were added to isopropyl alcohol (140 mL). TEA (triethylamine, 12.80 mL, 92 mmol) was added to the solution. The reaction mixture was sparged for 5 minutes with N$_2$ and was stirred at 80° C. for 20 hours under nitrogen. After cooling to room temperature, the mixture was filtered and concentrated to give the crude title compound. MS (ESI+) m/z 182.2 (M+H)+.

Example 103B 1H-indole-4-sulfonamide

To a solution of crude sulfinate (Example 103A, 11.04 g, 61.3 mmol) in 2-propanol (IPA) (ratio: 1.000, volume: 80 mL) and water (ratio: 2.500, volume: 200 mL) was added sodium acetate trihydrate (10.00 g, 73.5 mmol) and (aminooxy)sulfonic acid (8.31 g, 73.5 mmol). The mixture was stirred at room temperature for 2 hours. The mixture was concentrated under reduced pressure, filtered, and the solid was purified by Combi-Flash chromatography (used reverse phase silica gel column, RP-C18, 40-60 μm, 60 Å), ($H_2O$ (0.01% TFA) (A)/methanol (B), gradient from 20-50% of B at 10 minutes-20 minutes), to provide the title compound. $^1$H NMR (400 MHz, DMSO-$d_6$) δ ppm 11.53 (s, 1H), 7.63 (d, J=8.0 Hz, 1H), 7.53 (s, 1H), 7.50 (d, J=7.4 Hz, 1H), 7.25 (s, 2H), 7.20 (t, J=7.8 Hz, 1H), 6.86 (s, 1H). MS (ESI+) m/z 219.1 (M+Na)+.

Example 103C 8-cyclobutyl-N-(1H-indole-4-sulfonyl)-5-methoxy-3,4-dihydro-2H-1-benzopyran-4-carboxamide A mixture of 8-cyclobutyl-5-methoxychroman-4-carboxylic acid (120 mg, 0.457 mmol) from Example 75E and $N^1$-((ethylimino)methylene)-$N^3$,$N^3$-dimethylpropane-1,3-diamine, hydrochloric acid (175 mg, 0.915 mmol) and N,N-dimethylpyridin-4-amine (112 mg, 0.915 mmol) in dichloromethane (4 mL) was stirred at room temperature for 30 minutes. 1H-Indole-4-sulfonamide (91 mg, 0.457 mmol) was added. The mixture was stirred at 40° C. for 2 hours. The crude product was purified by reverse-phase HPLC [Waters XBridge™ RP18 column, 5 μm, 30×100 mm, flow rate 40 mL/minute, 5-95% gradient of acetonitrile in 0.1% TFA] to provide the title compound. $^1$H NMR (400 MHz, DMSO-$d_6$) δ ppm 12.19 (s, 1H), 11.66 (t, J=2.2 Hz, 1H), 7.73 (d, J=8.1 Hz, 1H), 7.64 (t, J=2.8 Hz, 1H), 7.60 (dd, J=7.5, 0.9 Hz, 1H), 7.23 (t, J=7.9 Hz, 1H), 6.94 (d, J=8.4 Hz, 1H), 6.92-6.86 (m, 1H), 6.29 (d, J=8.4 Hz, 1H), 3.95 (ddd, J=10.9, 5.1, 3.4 Hz, 1H), 3.69 (ddd, J=11.8, 8.7, 3.3 Hz, 2H), 3.47 (s, 1H), 3.13 (s, 3H), 2.19-2.07 (m, 2H), 2.02-1.82 (m, 4H), 1.80-1.61 (m, 2H). MS (ESI+) m/z 441 (M+H)+.

Example 103D (4S)-8-cyclobutyl-N-(1H-indole-4-sulfonyl)-5-methoxy-3,4-dihydro-2H-1-benzopyran-4-carboxamide Racemic N-((1H-indol-4-yl)sulfonyl)-8-cyclobutyl-5-methoxychroman-4-carboxamide (90 mg, 0.204 mmol) from Example 103C was separated via chiral SFC. Separation method: column: ChiralCel OJ-H, column size: 21×250 mm, 5 micron; concentration: 10 mg/mL in methanol, $CO_2$ flow rate: 49 mL/minute, co-solvent (methanol) flow rate: 21 mL/minute, total flow: 70. The first fraction at 2.21 minute was the title compound. $^1$H NMR (501 MHz, DMSO-$d_6$) δ ppm 12.18 (s, 1H), 11.65 (s, 1H), 7.72 (dt, J=8.0, 0.9 Hz, 1H), 7.63 (t, J=2.8 Hz, 1H), 7.59 (dd, J=7.5, 0.9 Hz, 1H), 7.22 (t, J=7.8 Hz, 1H), 6.94 (d, J=8.4 Hz, 1H), 6.90 (ddd, J=2.9, 1.9, 0.9 Hz, 1H), 6.28 (d, J=8.4 Hz, 1H), 3.94 (ddd, J=10.8, 5.0, 3.4 Hz, 1H), 3.74-3.64 (m, 2H), 3.54-3.43 (m, 1H), 3.17 (d, J=5.1 Hz, 1H), 3.14 (s, 3H), 2.13 (dddd, J=12.3, 8.4, 5.7, 2.2 Hz, 2H), 2.03-1.80 (m, 4H), 1.80-1.67 (m, 2H). MS (ESI+) m/z 441 (M+H)+.

Example 104

(4R)-8-cyclobutyl-N-(1H-indole-4-sulfonyl)-5-methoxy-3,4-dihydro-2H-1-benzopyran-4-carboxamide Example 104A di(1H-indol-4-yl) 1,4-diazabicyclo[2.2.2]octane-1,4-diium-1,4-disulfinate 4-Bromo-1H-indole (6.00 g, 30.6 mmol), 1,4-diazabicyclo[2.2.2]octane-1,4-diium-1,4-disulfinate (4.41 g, 18.36 mmol), and $PdCl_2(AmPhos)_2$ (bis(di-tert-butyl(4-dimethylaminophenyl)phosphine)dichloropalladium(II), 1.084 g, 1.530 mmol) were added to isopropyl alcohol (140 mL). TEA (triethylamine, 12.80 mL, 92 mmol) was added to the solution. The reaction mixture was sparged for 5 minutes with $N_2$ and was stirred at 80° C. for 20 hours under nitrogen. After cooling to room temperature, the mixture was filtered and concentrated to give the crude title compound. MS (ESI+) m/z 182.2 (M+H)+.

Example 104B 1H-indole-4-sulfonamide

To a solution of crude sulfinate (Example 104A, 11.04 g, 61.3 mmol) in 2-propanol (IPA) (ratio: 1.000, volume: 80 mL) and water (ratio: 2.500, volume: 200 mL) was added sodium acetate trihydrate (10.00 g, 73.5 mmol) and (aminooxy)sulfonic acid (8.31 g, 73.5 mmol). The mixture was stirred at room temperature for 2 hours. The mixture was concentrated under reduced pressure, filtered, and the solid was purified by Combi-Flash chromatography (used reverse phase silica gel column, RP-C18, 40-60 μm, 60 Å), ($H_2O$ (0.01% TFA) (A)/methanol (B), gradient from 20-50% of B at 10 minutes-20 minutes), to provide the title compound. $^1$H NMR (400 MHz, DMSO-$d_6$) δ ppm 11.53 (s, 1H), 7.63 (d, J=8.0 Hz, 1H), 7.53 (s, 1H), 7.50 (d, J=7.4 Hz, 1H), 7.25 (s, 2H), 7.20 (t, J=7.8 Hz, 1H), 6.86 (s, 1H). MS (ESI+) m/z 219.1 (M+Na)+.

Example 104C 8-cyclobutyl-N-(1H-indole-4-sulfonyl)-5-methoxy-3,4-dihydro-2H-1-benzopyran-4-carboxamide A mixture of 8-cyclobutyl-5-methoxychroman-4-carboxylic acid (120 mg, 0.457 mmol) from Example 75E and $N^1$-((ethylimino)methylene)-$N^3$,$N^3$-dimethylpropane-1,3-diamine, hydrochloric acid (175 mg, 0.915 mmol) and N,N-dimethylpyridin-4-amine (112 mg, 0.915 mmol) in dichloromethane (4 mL) was stirred at room temperature for 30 minutes. 1H-Indole-4-sulfonamide (91 mg, 0.457 mmol) was added. The mixture was stirred at 40° C. for 2 hours. The crude product was purified by reverse-phase HPLC [Waters XBridge™ RP18 column, 5 μm, 30×100 mm, flow rate 40 mL/minute, 5-95% gradient of acetonitrile in 0.1% TFA] to provide the title compound. $^1$H NMR (400 MHz, DMSO-$d_6$) δ ppm 12.19 (s, 1H), 11.66 (t, J=2.2 Hz, 1H), 7.73 (d, J=8.1 Hz, 1H), 7.64 (t, J=2.8 Hz, 1H), 7.60 (dd, J=7.5, 0.9 Hz, 1H), 7.23 (t, J=7.9 Hz, 1H), 6.94 (d, J=8.4 Hz, 1H), 6.92-6.86 (m, 1H), 6.29 (d, J=8.4 Hz, 1H), 3.95 (ddd, J=10.9, 5.1, 3.4 Hz, 1H), 3.69 (ddd, J=11.8, 8.7, 3.3 Hz, 2H), 3.47 (s, 1H), 3.13 (s, 3H), 2.19-2.07 (m, 2H), 2.02-1.82 (m, 4H), 1.80-1.61 (m, 2H). MS (ESI+) m/z 441 (M+H)$^+$.

Example 104D (4R)-8-cyclobutyl-N-(1H-indole-4-sulfonyl)-5-methoxy-3,4-dihydro-2H-1-benzopyran-4-carboxamide Racemic N-((1H-indol-4-yl)sulfonyl)-8-cyclobutyl-5-methoxychroman-4-carboxamide (90 mg, 0.204 mmol) from Example 104C was separated via chiral SFC. Separation method: column: ChiralCel OJ-H, column size: 21×250 mm, 5 micron; concentration: 10 mg/mL in methanol, CO$_2$ flow rate: 49 mL/minute, co-solvent (methanol) flow rate: 21 mL/minute, total flow: 70. The title compound was the second fraction with a retention time of 2.72 minutes. $^1$H NMR (501 MHz, DMSO-d$_6$) δ ppm 12.18 (s, 1H), 11.66 (t, J=2.3 Hz, 1H), 7.73 (dt, J=8.2, 0.9 Hz, 1H), 7.64 (t, J=2.8 Hz, 1H), 7.60 (dd, J=7.6, 0.9 Hz, 1H), 7.22 (t, J=7.8 Hz, 1H), 6.94 (d, J=8.4 Hz, 1H), 6.91 (ddd, J=2.9, 1.9, 0.9 Hz, 1H), 6.28 (d, J=8.5 Hz, 1H), 3.95 (ddd, J=10.9, 5.0, 3.4 Hz, 1H), 3.69 (ddd, J=14.0, 8.7, 3.3 Hz, 2H), 3.53-3.43 (m, 1H), 3.13 (s, 3H), 2.17-2.08 (m, 2H), 2.03-1.82 (m, 4H), 1.82-1.67 (m, 2H). MS (ESI+) m/z 441 (M+H)$^+$.

Example 105

5-cyclobutyl-8-methoxy-N-(quinoline-5-sulfonyl)-3,4-dihydro-2H-1-benzopyran-4-carboxamide Example 105A 8-methoxychroman-4-carbonitrile In a 25 mL round bottom flask 8-methoxychroman-4-one (0.320 g, 1.796 mmol) (CAS #20351-79-5) and TOSMIC ((toluenesulfonylmethyl isocyanide, 0.365 g, 1.870 mmol) were dissolved in dimethoxyethane (6 mL). The solution was cooled to −30° C. in an ice/acetone bath under nitrogen. Potassium tert-butoxide (1 M, 2.96 mL, 2.96 mmol) in tetrahydrofuran was added slowly over 30 minutes, keeping the temperature below −15° C. The reaction was allowed to warm to room temperature and was stirred overnight. The reaction was quenched with water (10 mL) and everything dissolved. The aqueous layer was extracted with methyl tert-butyl ether (2×100 mL). The organics were dried over Na$_2$SO$_4$, filtered, and concentrated to give a crude material which was chromatographed using an 40 g silica gel cartridge with ethyl acetate in heptanes (0 to 100% over 40 minutes) to provide the title compound. $^1$H NMR (400 MHz, chloroform-d) δ ppm 6.92 (d, J=5.8 Hz, 2H), 6.88-6.80 (m, 1H), 4.43 (ddd, J=11.2, 6.6, 4.4 Hz, 1H), 4.38-4.31 (m, 1H), 4.05 (t, J=6.0 Hz, 1H), 3.89 (s, 3H), 2.36 (tdd, J=5.8, 4.1, 1.6 Hz, 2H).

Example 105B 8-methoxychroman-4-carboxylic acid

8-Methoxychroman-4-carbonitrile (1.44 g, 7.61 mmol) was dissolved in ethanol (10 mL). A solution of sodium hydroxide (1.68 g, 42.0 mmol) in 10 mL of water was added, and the resulting mixture was heated at 100° C. After 16 hours, the ethanol was evaporated in vacuo. Water was added (30 mL), and the mixture was extracted with 20 mL ethyl acetate. The aqueous layer was cooled in an ice bath, and filtered. The filtrate was acidified with 6 M aqueous HCl (1.5 mL) to pH ~4. The resulting precipitate was filtered. The filtrate was acidified with 1 N aqueous HCl (15 mL) to pH ~2, and extracted with ethyl acetate (30 mL). The organic layer was concentrated in vacuo. The crude residue was purified by chromatography, eluting on 12 g silica gel cartridge with a gradient of 0-100% ethyl acetate/heptanes over a period of 8 minutes to provide the title compound. $^1$H NMR (400 MHz, DMSO-d$_6$) δ ppm 12.61 (s, 1H), 6.85-6.74 (m, 3H), 4.24-4.16 (m, 1H), 4.11 (ddd, J=10.9, 9.5, 2.9 Hz, 1H), 3.73 (t, J=5.7 Hz, 1H), 3.72 (s, 3H), 2.15 (dtd, J=14.1, 5.0, 2.9 Hz, 1H), 2.01 (dddd, J=13.8, 9.7, 6.1, 3.7 Hz, 1H). MS (APCI+) m/z 209 (M+H)$^+$.

Example 105C 5-bromo-8-methoxychroman-4-carboxylic Acid

To a solution of 8-methoxychroman-4-carboxylic acid (500 mg, 2.401 mmol) in dichloromethane (10 mL) at room temperature was added NBS (N-bromosuccinimide, 440 mg, 2.472 mmol) in 2 mL dichloromethane dropwise. The mixture stirred for 1 hour. The solvent was removed in vacuo and water (2 mL) was added. The mixture was extracted with dichloromethane, and the organic layer was concentrated in vacuo. The mixture was purified by chromatography, eluting on 24 g silica gel cartridge with a gradient of 0-100% ethyl acetate/heptanes over a period of 10 minutes to provide the title compound. $^1$H NMR (400 MHz, DMSO-d$_6$) δ ppm 12.73 (s, 1H), 7.05 (d, J=8.7 Hz, 1H), 6.80 (d, J=8.7 Hz, 1H), 4.27 (dt, J=11.0, 3.4 Hz, 1H), 3.86 (td, J=11.2, 3.4 Hz, 1H), 3.72 (m, 1H), 3.70 (s, 3H), 2.18-2.04 (m, 2H). MS (APCI+) m/z 241 (M-CO$_2$)$^+$.

Example 105D 5-cyclobutyl-8-methoxychroman-4-carboxylic Acid

Into a 4 mL vial was added 5-bromo-8-methoxychroman-4-carboxylic acid (70 mg, 0.244 mmol) in tetrahydrofuran (tetrahydrofuran, 1.5 mL). PEPPSI IPentCl (dichloro[1,3-bis(2,6-Di-3-pentylphenyl)imidazol-2-ylidene](3-chloropyridyl)palladium(II)), (21.01 mg, 0.024 mmol) was added. Cyclobutylzinc(II) bromide (0.5 M in tetrahydrofuran) (1.463 mL, 0.731 mmol) was added. The reaction mixture was stirred overnight at 50° C. Saturated aqueous NH$_4$Cl and 5 mL methyl tert-butyl ether were added. The aqueous layer was extracted with 5 mL methyl tert-butyl ether and dried. The crude material was used in the next step without further purification.

Example 105E 5-cyclobutyl-8-methoxy-N-(quinolin-5-ylsulfonyl)chroman-4-carboxamide Into a 4 mL vial was added crude 5-cyclobutyl-8-methoxychroman-4-carboxylic acid (110 mg, 0.419 mmol), N$^1$-((ethylimino)methylene)-N$^3$,N$^3$-dimethylpropane-1,3-diamine hydrochloride (161 mg, 0.839 mmol), and N,N-dimethylpyridin-4-amine (56.4 mg, 0.461 mmol) in dichloromethane (4 mL). Quinoline-5-sulfonamide (96 mg, 0.461 mmol) was added. The reaction was stirred overnight at room temperature. The solvent was removed under a stream of nitrogen, and the residue was reconstituted in dimethyl sulfoxide/CH₃OH and purified via preparative reverse phase HPLC method TFA7 to provide the title compound. $^1$H NMR (400 MHz, DMSO-$d_6$:D$_2$O=9:1 (v/v)) δ ppm 9.19-9.08 (m, 2H), 8.43-8.31 (m, 2H), 7.96 (dd, J=8.4, 7.5 Hz, 1H), 7.90 (dd, J=8.6, 4.4 Hz, 1H), 6.74 (d, J=8.4 Hz, 1H), 6.58 (d, J=8.4 Hz, 1H), 4.10 (dt, J=11.0, 3.4 Hz, 1H), 3.68 (d, J=2.6 Hz, 1H), 3.64 (s, 3H), 3.62-3.49 (m, 1H), 2.44 (p, J=8.7 Hz, 1H), 2.15-1.91 (m, 3H), 1.66 (p, J=9.7 Hz, 1H), 1.44 (p, J=9.5 Hz, 1H), 1.38-1.26 (m, 1H), 1.11-0.93 (m, 1H), 0.93-0.77 (m, 1H). MS (APCI+) m/z 453.0 (M+H)$^+$.

Example 106

(4R)-5-cyclobutyl-8-methoxy-N-(quinoline-5-sulfonyl)-3,4-dihydro-2H-1-benzopyran-4-carboxamide

Example 106A 8-methoxychroman-4-carbonitrile

In a 25 mL round bottom flask 8-methoxychroman-4-one (0.320 g, 1.796 mmol) (CAS #20351-79-5) and TOSMIC ((toluenesulfonylmethyl isocyanide, 0.365 g, 1.870 mmol) were dissolved in dimethoxyethane (6 mL). The solution was cooled to −30° C. in an ice/acetone bath under nitrogen. Potassium tert-butoxide (1 M, 2.96 mL, 2.96 mmol) in tetrahydrofuran was added slowly over 30 minutes, keeping the temperature below −15° C. The reaction was allowed to warm to room temperature and was stirred overnight. The reaction was quenched with water (10 mL) and everything dissolved. The aqueous layer was extracted with methyl tert-butyl ether (2×100 mL). The organics were dried over Na₂SO₄, filtered, and concentrated to give a crude material which was chromatographed using an 40 g silica gel cartridge with ethyl acetate in heptanes (0 to 100% over 40 minutes) to provide the title compound. $^1$H NMR (400 MHz, chloroform-d) δ ppm 6.92 (d, J=5.8 Hz, 2H), 6.88-6.80 (m, 1H), 4.43 (ddd, J=11.2, 6.6, 4.4 Hz, 1H), 4.38-4.31 (m, 1H), 4.05 (t, J=6.0 Hz, 1H), 3.89 (s, 3H), 2.36 (tdd, J=5.8, 4.1, 1.6 Hz, 2H).

Example 106B 8-methoxychroman-4-carboxylic Acid

8-Methoxychroman-4-carbonitrile (1.44 g, 7.61 mmol) was dissolved in ethanol (10 mL). A solution of sodium hydroxide (1.68 g, 42.0 mmol) in 10 mL of water was added, and the resulting mixture was heated at 100° C. After 16 hours, the ethanol was evaporated in vacuo. Water was added (30 mL), and the mixture was extracted with 20 mL ethyl acetate. The aqueous layer was cooled in an ice bath, and filtered. The filtrate was acidified with 6 M aqueous HCl (1.5 mL) to pH ~4. The resulting precipitate was filtered. The filtrate was acidified with 1 N aqueous HCl (15 mL) to pH ~2, and extracted with ethyl acetate (30 mL). The organic layer was concentrated in vacuo. The crude residue was purified by chromatography, eluting on 12 g silica gel cartridge with a gradient of 0-100% ethyl acetate/heptanes over a period of 8 minutes to provide the title compound. $^1$H NMR (400 MHz, DMSO-$d_6$) δ ppm 12.61 (s, 1H), 6.85-6.74 (m, 3H), 4.24-4.16 (m, 1H), 4.11 (ddd, J=10.9, 9.5, 2.9 Hz, 1H), 3.73 (t, J=5.7 Hz, 1H), 3.72 (s, 3H), 2.15 (dtd, J=14.1, 5.0, 2.9 Hz, 1H), 2.01 (dddd, J=13.8, 9.7, 6.1, 3.7 Hz, 1H). MS (APCI+) m/z 209 (M+H)$^+$.

Example 106C 5-bromo-8-methoxychroman-4-carboxylic Acid

To a solution of 8-methoxychroman-4-carboxylic acid (500 mg, 2.401 mmol) in dichloromethane (10 mL) at room temperature was added NBS (N-bromosuccinimide, 440 mg, 2.472 mmol) in 2 mL dichloromethane dropwise. The mixture stirred for 1 hour. The solvent was removed in vacuo and water (2 mL) was added. The mixture was extracted with dichloromethane, and the organic layer was concentrated in vacuo. The mixture was purified by chromatography, eluting on 24 g silica gel cartridge with a gradient of 0-100% ethyl acetate/heptanes over a period of 10 minutes to provide the title compound. $^1$H NMR (400 MHz, DMSO-$d_6$) δ ppm 12.73 (s, 1H), 7.05 (d, J=8.7 Hz, 1H), 6.80 (d, J=8.7 Hz, 1H), 4.27 (dt, J=11.0, 3.4 Hz, 1H), 3.86 (td, J=11.2, 3.4 Hz, 1H), 3.72 (m, 1H), 3.70 (s, 3H), 2.18-2.04 (m, 2H). MS (APCI+) m/z 241 (M-CO₂)$^+$.

Example 106D 5-cyclobutyl-8-methoxychroman-4-carboxylic Acid

Into a 4 mL vial was added 5-bromo-8-methoxychroman-4-carboxylic acid (70 mg, 0.244 mmol) in tetrahydrofuran (tetrahydrofuran, 1.5 mL). PEPPSI IPentCl (dichloro[1,3-bis(2,6-Di-3-pentylphenyl)imidazol-2-ylidene](3-chloropyridyl)palladium(II)), (21.01 mg, 0.024 mmol) was added. Cyclobutylzinc(II) bromide (0.5 M in tetrahydrofuran) (1.463 mL, 0.731 mmol) was added. The reaction mixture was stirred overnight at 50° C. Saturated aqueous NH₄Cl and 5 mL methyl tert-butyl ether were added. The aqueous layer was extracted with 5 mL methyl tert-butyl ether and dried. The crude material was used in the next step without further purification.

Example 106E 5-cyclobutyl-8-methoxy-N-(quinolin-5-ylsulfonyl)chroman-4-carboxamide Into a 4 mL vial was added crude 5-cyclobutyl-8-methoxychroman-4-carboxylic acid (110 mg, 0.419 mmol), N$^1$-((ethylimino)methylene)-N$^3$,N$^3$-dimethylpropane-1,3-diamine hydrochloride (161 mg, 0.839 mmol), and N,N-dimethylpyridin-4-amine (56.4 mg, 0.461 mmol) in dichloromethane (4 mL). Quinoline-5-sulfonamide (96 mg, 0.461 mmol) was added. The reaction was stirred overnight at room temperature. The solvent was removed under a stream of nitrogen, and the residue was reconstituted in dimethyl sulfoxide/CH₃OH and purified via preparative reverse phase HPLC method TFA7 to provide the title compound. $^1$H NMR (400 MHz, DMSO-$d_6$:D$_2$O=9:1 (v/v)) δ ppm 9.19-9.08 (m, 2H), 8.43-8.31 (m, 2H), 7.96 (dd, J=8.4, 7.5 Hz, 1H), 7.90 (dd, J=8.6, 4.4 Hz, 1H), 6.74 (d, J=8.4 Hz, 1H), 6.58 (d, J=8.4 Hz, 1H), 4.10 (dt, J=11.0, 3.4 Hz, 1H), 3.68 (d, J=2.6 Hz, 1H), 3.64 (s, 3H), 3.62-3.49 (m, 1H), 2.44 (p, J=8.7 Hz, 1H), 2.15-1.91 (m, 3H), 1.66 (p, J=9.7 Hz, 1H), 1.44 (p, J=9.5 Hz, 1H), 1.38-1.26 (m, 1H), 1.11-0.93 (m, 1H), 0.93-0.77 (m, 1H). MS (APCI+) m/z 453.0 (M+H)$^+$.

Example 106F (4R)-5-cyclobutyl-8-methoxy-N-(quinoline-5-sulfonyl)-3,4-dihydro-2H-1-benzopyran-4-carboxamide Example 106E (84 mg) was separated by chiral preparative SFC chromatography using a ChiralPak IC, column size 21×250 mm, serial number IC00SALK014-812151, 5 micron, using a concentration of 7.5 mg/mL in methanol at a flow rate of 49 g/minute $CO_2$ and UV monitoring at 220 nm to provide the title compound as the first eluting isomer. $^1$H NMR (400 MHz, DMSO-$d_6$:$D_2O$=9:1 (v/v)) δ ppm 9.13 (dd, J=8.7, 1.7 Hz, 1H), 9.09 (dd, J=4.3, 1.6 Hz, 1H), 8.38-8.26 (m, 2H), 7.92 (t, J=7.9 Hz, 1H), 7.85 (dd, J=8.7, 4.2 Hz, 1H), 6.73 (d, J=8.4 Hz, 1H), 6.57 (d, J=8.4 Hz, 1H), 4.15-4.03 (m, 1H), 3.68-3.53 (m, 5H), 2.52-2.42 (m, 1H), 2.12-1.90 (m, 3H), 1.65 (p, J=9.7 Hz, 1H), 1.49 (p, J=9.5 Hz, 1H), 1.41-1.28 (m, 1H), 1.13-0.84 (m, 2H). MS (APCI+) m/z 453.0 (M+H)$^+$.

Example 107

(4S)-5-cyclobutyl-8-methoxy-N-(quinoline-5-sulfonyl)-3,4-dihydro-2H-1-benzopyran-4-carboxamide 8-methoxychroman-4-carbonitrile

Example 107A 8-methoxychroman-4-carbonitrile

In a 25 mL round bottom flask 8-methoxychroman-4-one (0.320 g, 1.796 mmol) (CAS #20351-79-5) and TOSMIC ((toluenesulfonylmethyl isocyanide, 0.365 g, 1.870 mmol) were dissolved in dimethoxyethane (6 mL). The solution was cooled to −30° C. in an ice/acetone bath under nitrogen. Potassium tert-butoxide (1 M, 2.96 mL, 2.96 mmol) in tetrahydrofuran was added slowly over 30 minutes, keeping the temperature below −15° C. The reaction was allowed to warm to room temperature and was stirred overnight. The reaction was quenched with water (10 mL) and everything dissolved. The aqueous layer was extracted with methyl tert-butyl ether (2×100 mL). The organics were dried over $Na_2SO_4$, filtered, and concentrated to give a crude material which was chromatographed using an 40 g silica gel cartridge with ethyl acetate in heptanes (0 to 100% over 40 minutes) to provide the title compound. $^1$H NMR (400 MHz, chloroform-d) δ ppm 6.92 (d, J=5.8 Hz, 2H), 6.88-6.80 (m, 1H), 4.43 (ddd, J=11.2, 6.6, 4.4 Hz, 1H), 4.38-4.31 (m, 1H), 4.05 (t, J=6.0 Hz, 1H), 3.89 (s, 3H), 2.36 (tdd, J=5.8, 4.1, 1.6 Hz, 2H).

Example 107B 8-methoxychroman-4-carboxylic Acid

8-Methoxychroman-4-carbonitrile (1.44 g, 7.61 mmol) was dissolved in ethanol (10 mL). A solution of sodium hydroxide (1.68 g, 42.0 mmol) in 10 mL of water was added, and the resulting mixture was heated at 100° C. After 16 hours, the ethanol was evaporated in vacuo. Water was added (30 mL), and the mixture was extracted with 20 mL ethyl acetate. The aqueous layer was cooled in an ice bath, and filtered. The filtrate was acidified with 6 M aqueous HCl (1.5 mL) to pH ~4. The resulting precipitate was filtered. The filtrate was acidified with 1 N aqueous HCl (15 mL) to pH ~2, and extracted with ethyl acetate (30 mL). The organic layer was concentrated in vacuo. The crude residue was purified by chromatography, eluting on 12 g silica gel cartridge with a gradient of 0-100% ethyl acetate/heptanes over a period of 8 minutes to provide the title compound. $^1$H NMR (400 MHz, DMSO-$d_6$) δ ppm 12.61 (s, 1H), 6.85-6.74 (m, 3H), 4.24-4.16 (m, 1H), 4.11 (ddd, J=10.9, 9.5, 2.9 Hz, 1H), 3.73 (t, J=5.7 Hz, 1H), 3.72 (s, 3H), 2.15 (dtd, J=14.1, 5.0, 2.9 Hz, 1H), 2.01 (dddd, J=13.8, 9.7, 6.1, 3.7 Hz, 1H). MS (APCI+) m/z 209 (M+H)$^+$.

Example 107C 5-bromo-8-methoxychroman-4-carboxylic Acid

To a solution of 8-methoxychroman-4-carboxylic acid (500 mg, 2.401 mmol) in dichloromethane (10 mL) at room temperature was added NBS (N-bromosuccinimide, 440 mg, 2.472 mmol) in 2 mL dichloromethane dropwise. The mixture stirred for 1 hour. The solvent was removed in vacuo and water (2 mL) was added. The mixture was extracted with dichloromethane, and the organic layer was concentrated in vacuo. The mixture was purified by chromatography, eluting on 24 g silica gel cartridge with a gradient of 0-100% ethyl acetate/heptanes over a period of 10 minutes to provide the title compound. $^1$H NMR (400 MHz, DMSO-$d_6$) δ ppm 12.73 (s, 1H), 7.05 (d, J=8.7 Hz, 1H), 6.80 (d, J=8.7 Hz, 1H), 4.27 (dt, J=11.0, 3.4 Hz, 1H), 3.86 (td, J=11.2, 3.4 Hz, 1H), 3.72 (m, 1H), 3.70 (s, 3H), 2.18-2.04 (m, 2H). MS (APCI+) m/z 241 (M-$CO_2$)$^+$.

Example 107D 5-cyclobutyl-8-methoxychroman-4-carboxylic Acid

Into a 4 mL vial was added 5-bromo-8-methoxychroman-4-carboxylic acid (70 mg, 0.244 mmol) in tetrahydrofuran (tetrahydrofuran, 1.5 mL). PEPPSI IPentCl (dichloro[1,3-bis(2,6-Di-3-pentylphenyl)imidazol-2-ylidene](3-chloropyridyl)palladium(II)), (21.01 mg, 0.024 mmol) was added. Cyclobutylzinc(II) bromide (0.5 M in tetrahydrofuran) (1.463 mL, 0.731 mmol) was added. The reaction mixture was stirred overnight at 50° C. Saturated aqueous $NH_4Cl$ and 5 mL methyl tert-butyl ether were added. The aqueous layer was extracted with 5 mL methyl tert-butyl ether and dried. The crude material was used in the next step without further purification.

Example 107E 5-cyclobutyl-8-methoxy-N-(quinolin-5-ylsulfonyl)chroman-4-carboxamide Into a 4 mL vial was added crude 5-cyclobutyl-8-methoxychroman-4-carboxylic acid (110 mg, 0.419 mmol), $N^1$-((ethylimino)methylene)-$N^3$,$N^3$-dimethylpropane-1,3-diamine hydrochloride (161 mg, 0.839 mmol), and N,N-dimethylpyridin-4-amine (56.4 mg, 0.461 mmol) in dichloromethane (4 mL). Quinoline-5-sulfonamide (96 mg, 0.461 mmol) was added. The reaction was stirred overnight at room temperature. The solvent was removed under a stream of nitrogen, and the residue was reconstituted in dimethyl sulfoxide/$CH_3OH$ and purified via preparative reverse phase HPLC method TFA7 to provide the title compound. $^1$H NMR (400 MHz, DMSO-$d_6$:$D_2O$=9:1 (v/v)) δ ppm 9.19-9.08 (m, 2H), 8.43-8.31 (m, 2H), 7.96 (dd, J=8.4, 7.5 Hz, 1H), 7.90 (dd, J=8.6, 4.4 Hz, 1H), 6.74 (d, J=8.4 Hz, 1H), 6.58 (d, J=8.4 Hz, 1H), 4.10 (dt, J=11.0, 3.4 Hz, 1H), 3.68 (d, J=2.6 Hz, 1H), 3.64 (s, 3H), 3.62-3.49 (m, 1H), 2.44 (p, J=8.7 Hz, 1H), 2.15-1.91 (m, 3H), 1.66 (p, J=9.7 Hz, 1H), 1.44 (p, J=9.5 Hz, 1H), 1.38-1.26 (m, 1H), 1.11-0.93 (m, 1H), 0.93-0.77 (m, 1H). MS (APCI+) m/z 453.0 (M+H)$^+$.

Example 107F (4S)-5-cyclobutyl-8-methoxy-N-(quinoline-5-sulfonyl)-3,4-dihydro-2H-1-benzopyran-4-carboxamide 8-methoxychroman-4-carbonitrile Example 107E (84 mg) was separated by chiral preparative SFC chromatography using a ChiralPak IC, column size 21×250 mm, serial number IC00SALK014-812151, 5 micron, using a concentration of 7.5 mg/mL in methanol at a flow rate of 49 g/minute $CO_2$ and UV monitoring at 220 nm to provide the title compound as the second eluting enantiomer. $^1$H NMR (400 MHz, DMSO-$d_6$:$D_2O$=9:1 (v/v)) δ ppm 9.13 (dt, J=8.9, 1.2 Hz, 1H), 9.09 (dd, J=4.2, 1.6 Hz, 1H), 8.39-8.30 (m, 2H), 7.93 (dd, J=8.4, 7.5 Hz, 1H), 7.86 (dd, J=8.8, 4.2 Hz, 1H), 6.73 (d, J=8.4 Hz, 1H), 6.57 (d, J=8.4 Hz, 1H), 4.09 (dt, J=11.0, 3.4 Hz, 1H), 3.69-3.55 (m, 5H), 2.53-2.43 (m, 1H), 2.13-1.91 (m, 3H), 1.65 (p, J=9.7 Hz, 1H), 1.48 (p, J=9.6 Hz, 1H), 1.41-1.29 (m, 1H), 1.13-0.98 (m, 1H), 0.98-0.85 (m, 1H). MS (APCI+) m/z 453.0 (M+H)$^+$.

Example 108

8-bromo-5-methoxy-N-(naphthalene-1-sulfonyl)-3,4-dihydro-1H-2-benzopyran-1-carboxamide

Example 108A

Ethyl 2-acetoxy-2-(2-methoxyphenethoxy)acetate

A mixture of 2-(2-methoxyphenyl)ethanol (CAS #7417-18-7) (0.818 mL, 5.78 mmol) and 50% ethyl glyoxalate in toluene (0.750 mL, 3.85 mmol) was stirred at room temperature for 1 hour under $N_2$. The mixture was diluted with pyridine (3.12 mL, 38.5 mmol), treated with 4-dimethylaminopyridine (0.047 g, 0.385 mmol), cooled to 0° C. and treated dropwise with acetyl chloride (0.822 mL, 11.56 mmol). The mixture was stirred overnight at room temperature. The mixture was diluted with tert-butyl methyl ether (50 mL) and the solids were removed by filtration. The tert-butyl methyl ether layer was washed with saturated aqueous $NaHCO_3$ solution, washed with brine, dried ($MgSO_4$), filtered, and concentrated. The filtrate was dissolved in tert-butyl methyl ether (100 mL), cooled to 0° C., washed with cold 1 M aqueous HCl (50 mL), washed with brine, dried ($MgSO_4$), filtered, concentrated and chromatographed on silica gel, eluting with a gradient of 10% to 20% ethyl acetate in heptanes to provide the title compound. $^1$H NMR (500 MHz, CDCl$_3$) δ ppm 7.20 (td, J=1.7, 7.8 Hz, 1H), 7.16 (dd, J=1.8, 7.4 Hz, 1H), 6.88 (td, J=1.1, 7.4 Hz, 1H), 6.84 (dd, J=1.0, 8.2 Hz, 1H), 5.98 (s, 1H), 4.25 (q, J=7.1 Hz, 2H), 3.93 (dt, J=7.4, 9.5 Hz, 1H), 3.86 (dt, J=7.4, 9.5 Hz, 1H), 3.81 (s, 3H), 2.97 (t, J=7.4 Hz, 2H), 2.13 (s, 3H), 1.30 (t, J=7.1 Hz, 3H).

Example 108B

Ethyl 5-methoxyisochromane-1-carboxylate

A solution of Example 108A (ethyl 2-acetoxy-2-(2-methoxyphenethoxy)acetate) (0.65 g, 2.194 mmol) in $CH_2Cl_2$ (22 mL) under $N_2$ was cooled to −20° C., treated with aluminum chloride (0.292 g, 2.194 mmol), stirred for 1 hour at −20° C., treated with more aluminum chloride (0.292 g, 2.194 mmol), stirred for 3 hours, and partitioned between tert-butyl methyl ether (80 mL) and 1 M aqueous HCl (25 mL). The tert-butyl methyl ether layer was washed with brine, dried ($MgSO_4$), filtered, concentrated and chromatographed on silica gel, eluting with a gradient of 5% to 100% ethyl acetate in heptanes to provide the title compound. $^1$H NMR (400 MHz, CDCl$_3$) δ ppm 7.17 (t, J=8.0 Hz, 1H), 6.99 (d, J=7.8 Hz, 1H), 6.76 (d, J=8.1 Hz, 1H), 5.30 (s, 1H), 4.34-4.21 (m, 3H), 4.01 (dt, J=5.2, 11.7 Hz, 1H), 3.83 (s, 3H), 2.84-2.69 (m, 2H), 1.31 (t, J=7.1 Hz, 3H).

Example 108C

Ethyl 8-bromo-5-methoxyisochromane-1-carboxylate

A solution of Example 108B (ethyl 5-methoxyisochromane-1-carboxylate) (85.4 mg, 0.361 mmol) in acetonitrile (1 mL) was treated with N-bromosuccinimide (64.3 mg, 0.361 mmol) and was stirred at room temperature overnight. The mixture was concentrated and the residue was dissolved in $CH_2Cl_2$ (~1 mL) and diluted with heptanes (~3 mL), which resulted in the precipitation of a solid. The solid was removed by filtration and the filtrate was concentrated and chromatographed on silica gel, eluting with a gradient of 5% to 10% ethyl acetate in heptanes to provide the title compound. $^1$H NMR (400 MHz, CDCl$_3$) δ ppm 7.36 (d, J=8.7 Hz, 1H), 6.69 (d, J=8.7 Hz, 1H), 5.29 (s, 1H), 4.33-4.20 (m, 2H), 4.07 (ddd, J=2.8, 5.9, 11.6 Hz, 1H), 3.92 (ddd, J=4.8, 9.9, 11.6 Hz, 1H), 3.82 (s, 3H), 2.82-2.68 (m, 2H), 1.32 (t, J=7.1 Hz, 3H).

Example 108D 8-bromo-5-methoxyisochromane-1-carboxylic Acid

A solution of Example 108C (ethyl 8-bromo-5-methoxyisochroman-1-carboxylate) (84 mg, 0.267 mmol) in tetrahydrofuran (1.5 mL) was diluted with methanol (1.5 mL), treated with 1 M aqueous NaOH (1 mL), stirred at room temperature for 15 minutes, stirred at 60° C. for 20 minutes, cooled and partitioned between tert-butyl methyl ether (30 mL) and 1 M aqueous HCl (5 mL). The layers were separated and the aqueous layer was extracted with tert-butyl methyl ether (20 mL). The combined organic layers were washed with brine, dried ($MgSO_4$), filtered, and concentrated to provide the title compound. $^1$H NMR (400 MHz, CDCl$_3$) δ ppm 7.38 (d, J=8.8 Hz, 1H), 6.71 (d, J=8.8 Hz, 1H), 5.38 (s, 1H), 4.12 (ddd, J=2.8, 6.2, 11.6 Hz, 1H), 3.95 (ddd, J=4.6, 10.2, 11.7 Hz, 1H), 3.82 (s, 3H), 2.80 (ddd, J=6.2, 10.2, 16.4 Hz, 1H), 2.72 (ddd, J=2.7, 4.6, 17.3 Hz, 1H).

Example 108E 8-bromo-5-methoxy-N-(naphthalene-1-sulfonyl)-3,4-dihydro-1H-2-benzopyran-1-carboxamide A solution of Example 108D (8-bromo-5-methoxyisochroman-1-carboxylic acid) (22 mg, 0.077 mmol) in $CH_2Cl_2$ (0.5 mL) at room temperature was treated with oxalyl chloride (33.5 µl, 0.383 mmol), treated with a catalytic amount of N,N-dimethylformamide, stirred at room temperature for 1 hour and concentrated to dryness with a stream of nitrogen. The residue was dissolved in $CH_2Cl_2$ (0.5 mL) and was added to a 0° C. solution of naphthalene-1-sulfonamide (20.65 mg, 0.100 mmol), triethylamine (21.36 µl, 0.153 mmol) and 4-dimethylaminopyridine (0.936 mg, 7.66 µmol) in $CH_2Cl_2$ (0.5 mL). The mixture was stirred at room temperature for 1 hour. The mixture was partitioned between tert-butyl methyl ether (30 mL) and 1 M aqueous HCl (10 mL). The layers were separated and the aqueous layer was extracted with tert-butyl methyl ether (20 mL). The combined organic layers were washed with brine, dried (MgSO$_4$), filtered, concentrated, and purified by reverse-phase HPLC [Waters XBridge™ RP18 column, 5 μm, 30×100 mm, flow rate 40 mL/minute, 5-95% gradient of acetonitrile in 0.1% TFA] to afford the title compound. $^1$H NMR (501 MHz, dimethylsulfoxide-d$_6$) δ ppm 8.69 (d, J=8.3 Hz, 1H), 8.31-8.25 (m, 2H), 8.11 (d, J=8.2 Hz, 1H), 7.78-7.71 (m, 1H), 7.70-7.64 (m, 2H), 7.17 (d, J=8.8 Hz, 1H), 6.79 (d, J=8.9 Hz, 1H), 5.04 (s, 1H), 3.80-3.75 (m, 1H), 3.72 (s, 3H), 3.50-3.35 (m, 1H), 2.53-2.41 (m, 2H). MS (ESI+) m/z 476, 478 (M+H)$^+$.

Example 109

N-(naphthalene-1-sulfonyl)-7-(trifluoromethoxy)-3,4-dihydro-1H-2-benzopyran-1-carboxamide The title compound was prepared as described in Example 87, substituting naphthalene-1-sulfonamide for 1-methyl-1H-benzo[d]imidazole-7-sulfonamide and 7-(trifluoromethoxy)isochroman-1-carboxylic acid for 7-cyclobutyl-4-methoxy-2,3-dihydrobenzofuran-3-carboxylic acid. $^1$H NMR (400 MHz, DMSO-d$_6$:D$_2$O=9:1 (v/v)) δ ppm 8.63 (d, J=8.0 Hz, 1H), 8.28-8.20 (m, 2H), 8.07 (d, J=7.5 Hz, 1H), 7.72-7.60 (m, 3H), 7.21 (d, J=8.5 Hz, 1H), 7.14-7.07 (m, 1H), 6.90-6.85 (m, 1H), 5.16 (s, 1H), 3.88-3.83 (m, 1H), 3.79-3.73 (m, 1H), 2.74-2.69 (m, 2H). MS (APCI+) m/z 451.9 (M+H)$^+$.

Example 110

5-methoxy-N-(naphthalene-1-sulfonyl)-3,4-dihydro-1H-2-benzopyran-1-carboxamide

Example 110A 5-methoxyisochromane-1-carboxylic Acid

A solution of Example 108B (ethyl 5-methoxyisochromane-1-carboxylate) (49.7 mg, 0.210 mmol) in tetrahydrofuran (1.5 mL) was diluted with methanol (1.5 mL), treated with aqueous 1 M NaOH (1 mL) and stirred at room temperature for 15 minutes. The mixture was acidified with 1 M aqueous HCl (3 mL) and extracted with tert-butyl methyl ether (twice, 30 mL and 20 mL). The combined organic layers were washed with brine, dried (MgSO$_4$), filtered, and concentrated to provide the title compound. $^1$H NMR (400 MHz, CDCl$_3$) δ ppm 7.20 (t, J=7.9 Hz, 1H), 7.15 (d, J=7.8 Hz, 1H), 6.80 (d, J=1.2 Hz, 1H), 5.34 (s, 1H), 4.28 (dt, J=5.5, 11.2 Hz, 1H), 3.98 (dt, J=6.0, 11.7 Hz, 1H), 3.83 (s, 3H), 2.79 (t, J=5.8 Hz, 2H).

Example 110B 5-methoxy-N-(naphthalene-1-sulfonyl)-3,4-dihydro-1H-2-benzopyran-1-carboxamide A solution of Example 110A (5-methoxyisochromane-1-carboxylic acid) (20 mg, 0.096 mmol) in CH$_2$Cl$_2$ (0.5 mL) at room temperature was treated with N,N'-carbonyldiimidazole (21.81 mg, 0.134 mmol), stirred at room temperature for 30 minutes, treated with naphthalene-1-sulfonamide (39.8 mg, 0.192 mmol) and 1,8-diazabicyclo[5.4.0]undec-7-ene (29.0 μl, 0.192 mmol), stirred at room temperature overnight and partitioned between tert-butyl methyl ether (~30 mL) and 1 M aqueous HCl (~15 mL). The layers were separated and the tert-butyl methyl ether layer was washed with brine, dried (MgSO$_4$), filtered, and concentrated. The residue was dissolved in CH$_2$Cl$_2$ (2 mL), diluted with heptanes (5 mL), and a solid formed. The solid was removed by filtration. The filtrate was concentrated and the residue was chromatographed on silica gel, eluting with a gradient of 50% to 100% [1:1 CH$_2$Cl$_2$:ethyl acetate] in heptanes to provide the title compound. $^1$H NMR (400 MHz, dimethylsulfoxide-d$_6$) δ 12.75 (bs, 1H), 8.65 (d, J=8.4 Hz, 1H), 8.28-8.19 (m, 2H), 8.09 (d, J=8.0 Hz, 1H), 7.77-7.61 (m, 3H), 6.87 (t, J=8.0 Hz, 1H), 6.75 (d, J=8.1 Hz, 1H), 6.48 (bs, 1H), 5.08 (s, 1H), 3.91-3.87 (m, 1H), 3.72 (s, 3H), 3.72-3.65 (m, 1H), 2.62-2.44 (m, 2H). MS (ESI+) m/z 398 (M+H)$^+$.

Determination of Biological Activity

Cell Surface Expression-Horse Radish Peroxidase (CSE-HRP) Assay

A cellular assay for measuring the F508delCFTR cell surface expression after correction with test compounds either without or with a co-corrector (2 μM of 3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid), was developed in human lung derived epithelial cell line (CFBE4lo–) (Veit G et al, (2012) Mol Biol Cell. 23(21): 4188-4202). The development was achieved by expressing the F508delCFTR mutation along with a horseradish peroxidase (HRP) in the fourth exofacial loop, and then measuring the HRP activity using luminescence readout from these cells, CFBE4lo-F508delCFTR-HRP, that were incubated overnight with the test corrector compounds, either without or with the co-corrector. For this primary assay, the CFBE4lo-F508delCFTR-HRP cells were plated in 384-well plates (Greiner Bio-one; Cat 781080) at 4,000 cells/well along with 0.5 μg/mL doxycycline to induce the F508delCFTR-HRP expression and further incubated at 37° C., 5% CO$_2$ for 72 hours. The test compounds were then added either without or with a co-corrector at the required concentrations and further incubated for 18-24 hours at 33° C. The highest concentration tested was 20 μM with an 8-point concentration response curve using a 3-fold dilution in both the test compound without or with the co-corrector. Three replicate plates were run to determine one EC$_{50}$. All plates contained negative controls (dimethyl sulfoxide, DMSO) and positive control (2 μM of 3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid) as well as on-plate concentration response of the positive control. Post incubation, the plates were washed 5× times with Dulbecco's phosphate buffered saline (DPBS), followed by the addition of the HRP substrate, luminol (50 μL), and measuring the HRP activity using luminescence readout on EnVision® Multilabel Plate Reader (Perkin Elmer; product number 2104-0010). The raw counts from the experiment were analyzed using Accelrys® Assay Explorer v3.3.

Z' greater than 0.5 was used as passing quality control criteria for the plates.

The Z' is defined as:

1−[3*SDPositive Control+3*SDNegative Control/
Absolute(Meanpostivie Control−MeanNegative
Control)]

wherein "SD" is standard deviation.

The % activity measured at each of the 8 test concentrations of the test compound added either without or with a co-corrector (2 µM of 3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid) was normalized to the on-plate positive control using the following formulae:

% activity(Test compound without co-corrector)= [(test compound without co-corrector response−DMSO response)/(positive control response−DMSO response)]*100

% activity(Test compound with co-corrector)=[(test compound with co-corrector response−DMSO response)/(positive control response−DMSO response)]*100

The maximum % activity achieved for the test compound either without or with a co-corrector at any tested concentration is presented in Table 1 along with the respective $EC_{50}$'s calculated using the following general sigmoidal curve with variable Hill slope equation (described as Model 42 in the Accelrys® Assay Explorer v3.3 software):

$$y=(a-d)/(1+(x/c)\char`\^b)+d$$

General sigmoidal curve with concentration, response, top, bottom, $EC_{50}$ and Hill slope. This model describes a sigmoidal curve with an adjustable baseline, a. The equation can be used to fit curves where response is either increasing or decreasing with respect to the independent variable, "x".
"x" is a concentration of drug under test.
"y" is the response.
"a" is the maximum response, and "d" is the minimum response
"c" is the inflection point ($EC_{50}$) for the curve. That is, "y" is halfway between the lower and upper asymptotes when x=c.
"b" is the slope-factor or Hill coefficient. The sign of b is positive when the response increases with increasing dose and is negative when the response decreases with increasing dose (inhibition).
The data is presented with the qualifiers shown below:

| Without/with co-corrector | EC50 (µM) |
|---|---|
| | <3 +++ |
| | ≥3 and <10 ++ |
| | ≥10 + |

| Without co-corrector | Maximum % activity (%) |
|---|---|
| | <50 + |
| | ≥50 and <150 ++ |
| | ≥150 +++ |

| With co-corrector | Maximum % activity (%) |
|---|---|
| | <150 + |
| | ≥150 and <350 ++ |
| | ≥350 +++ |

TABLE 1

| Example | EC50 (without co-corrector) (µM) | Maximum % activity (without co-corrector) (%) | EC50 (with co-corrector) (µM) | Maximum % activity (with co-corrector) (%) |
|---|---|---|---|---|
| 1 | +++ | +++ | +++ | +++ |
| 2 | +++ | ++ | +++ | +++ |
| 3 | +++ | +++ | +++ | +++ |
| 4 | +++ | ++ | +++ | +++ |
| 5 | +++ | +++ | +++ | +++ |
| 6 | +++ | ++ | +++ | +++ |
| 7 | ++ | +++ | ++ | +++ |
| 8 | ++ | +++ | +++ | +++ |
| 9 | ++ | +++ | ++ | +++ |
| 10 | +++ | +++ | +++ | +++ |
| 11 | +++ | +++ | +++ | +++ |
| 12 | ++ | +++ | ++ | +++ |
| 13 | +++ | +++ | +++ | +++ |
| 14 | +++ | +++ | +++ | +++ |
| 15 | ++ | ++ | ++ | +++ |
| 16 | + | + | + | + |
| 17 | + | + | + | + |
| 18 | ++ | ++ | +++ | +++ |
| 19 | ++ | +++ | ++ | +++ |
| 20 | ++ | + | +++ | ++ |
| 21 | ++ | ++ | ++ | ++ |
| 22 | ++ | +++ | ++ | +++ |
| 23 | +++ | + | +++ | ++ |
| 24 | ++ | ++ | ++ | +++ |
| 25 | ++ | + | ++ | ++ |
| 26 | + | + | + | + |
| 27 | + | + | + | + |
| 28 | + | + | + | + |
| 29 | + | + | + | + |
| 30 | + | + | ++ | + |
| 31 | + | + | ++ | ++ |
| 32 | ++ | + | ++ | ++ |
| 33 | + | + | + | ++ |
| 34 | + | + | + | + |
| 35 | ++ | ++ | ++ | +++ |
| 36 | +++ | +++ | +++ | +++ |
| 37 | ++ | +++ | +++ | +++ |
| 38 | +++ | +++ | +++ | +++ |
| 39 | +++ | +++ | +++ | +++ |
| 40 | +++ | +++ | +++ | +++ |
| 41 | +++ | +++ | +++ | +++ |
| 42 | ++ | ++ | +++ | +++ |
| 43 | ++ | + | ++ | ++ |
| 44 | ++ | ++ | ++ | +++ |
| 45 | ++ | ++ | ++ | ++ |
| 46 | +++ | +++ | +++ | +++ |
| 47 | ++ | + | ++ | ++ |
| 48 | ++ | +++ | ++ | +++ |
| 49 | ++ | +++ | +++ | +++ |
| 50 | ++ | ++ | +++ | +++ |
| 51 | +++ | +++ | +++ | +++ |
| 52 | +++ | +++ | +++ | +++ |
| 53 | +++ | +++ | +++ | +++ |
| 54 | ++ | +++ | +++ | +++ |
| 55 | ++ | +++ | ++ | +++ |
| 56 | +++ | +++ | +++ | +++ |
| 57 | ++ | +++ | +++ | +++ |
| 58 | +++ | +++ | +++ | +++ |
| 59 | ++ | +++ | ++ | +++ |
| 60 | +++ | +++ | +++ | +++ |
| 61 | ++ | +++ | ++ | +++ |
| 62 | ++ | +++ | ++ | +++ |
| 63 | ++ | +++ | +++ | +++ |
| 64 | ++ | +++ | +++ | +++ |
| 65 | ++ | +++ | ++ | +++ |
| 66 | +++ | +++ | +++ | +++ |
| 67 | ++ | +++ | +++ | +++ |
| 68 | ++ | +++ | +++ | +++ |
| 69 | ++ | ++ | ++ | ++ |
| 70 | +++ | +++ | +++ | +++ |
| 71 | ++ | +++ | +++ | +++ |
| 72 | +++ | +++ | +++ | +++ |
| 73 | ++ | ++ | ++ | ++ |
| 74 | +++ | +++ | +++ | +++ |
| 75 | ++ | +++ | +++ | +++ |
| 76 | ++ | +++ | ++ | +++ |
| 77 | ++ | +++ | +++ | +++ |

TABLE 1-continued

| Example | EC50 (without co-corrector) (μM) | Maximum % activity (without co-corrector) (%) | EC50 (with co-corrector) (μM) | Maximum % activity (with co-corrector) (%) |
|---|---|---|---|---|
| 78 | +++ | +++ | +++ | +++ |
| 79 | ++ | +++ | +++ | +++ |
| 80 | +++ | +++ | +++ | +++ |
| 81 | ++ | +++ | +++ | +++ |
| 82 | ++ | +++ | ++ | +++ |
| 83 | +++ | +++ | +++ | +++ |
| 85 | +++ | +++ | +++ | +++ |
| 86 | +++ | +++ | +++ | +++ |
| 87 | +++ | +++ | +++ | +++ |
| 88 | ++ | +++ | +++ | +++ |
| 90 | ++ | +++ | +++ | +++ |
| 91 | ++ | +++ | ++ | +++ |
| 92 | +++ | +++ | +++ | +++ |
| 93 | +++ | +++ | +++ | +++ |
| 94 | ++ | ++ | +++ | +++ |
| 95 | +++ | +++ | +++ | +++ |
| 96 | +++ | +++ | +++ | +++ |
| 97 | +++ | +++ | +++ | +++ |
| 98 | ++ | ++ | ++ | +++ |
| 99 | +++ | +++ | +++ | +++ |
| 100 | ++ | ++ | ++ | +++ |
| 101 | +++ | +++ | +++ | +++ |
| 102 | +++ | +++ | +++ | +++ |
| 103 | ++ | +++ | +++ | +++ |
| 104 | +++ | +++ | +++ | +++ |
| 105 | ++ | +++ | +++ | +++ |
| 106 | +++ | +++ | +++ | +++ |
| 107 | ++ | + | ++ | ++ |
| 108 | ++ | ++ | +++ | +++ |
| 109 |  |  | ++ | ++ |
| 110 | + | + | ++ | ++ |

The data provided in the present application demonstrate that the compounds of the invention demonstrate activity in vitro, and may be useful in vivo in the treatment of cystic fibrosis.

Further benefits of Applicants' invention will be apparent to one skilled in the art from reading this patent application.

It is to be understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

What is claimed:

1. A compound of Formula I, or a pharmaceutically acceptable salt thereof,

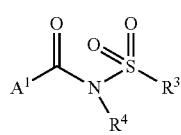

(I)

wherein $A^1$ is selected from the group consisting of

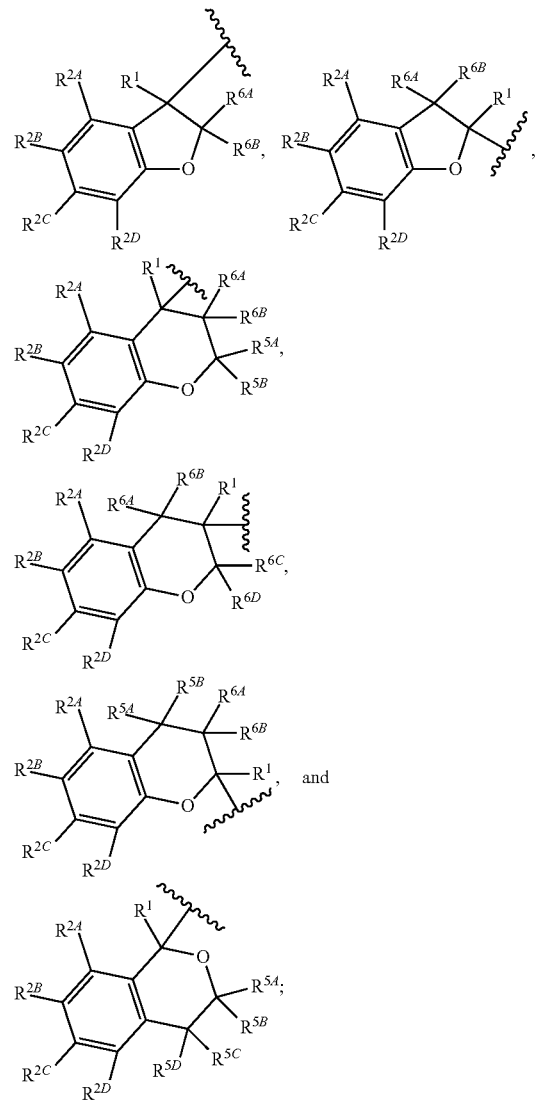

$R^1$ is selected from the group consisting of hydrogen, OH, CN, $C_1$-$C_6$ alkyl, $C_2$-$C_6$ alkenyl, $C_2$-$C_6$ alkynyl, $C_1$-$C_6$ alkoxy, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^1$ $C_1$-$C_6$ alkyl, $C_2$-$C_6$ alkenyl, $C_2$-$C_6$ alkynyl, and $C_1$-$C_6$ alkoxy are optionally substituted with one or more substituents independently selected from the group consisting of $R^7$, $OR^7$, $SR^7$, $NHR^7$, $N(R^7)_2$, $NH_2$, C(O)OH, OH, CN, $NO_2$, F, Cl, Br and I; wherein the $R^1$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $C_1$-$C_6$ alkyl, $C_1$-$C_6$ haloalkyl, $C_1$-$C_6$ alkoxy, $C_1$-$C_6$ haloalkoxy, C(O)OH, OH, oxo, CN, $NO_2$, F, Cl, Br and I;

one of $R^{2A}$, $R^{2B}$, $R^{2C}$ and $R^{2D}$ is hydrogen, and the remaining are independently selected from the group consisting of hydrogen, $R^8$, $OR^8$, $C(O)R^8$, $C(O)OR^8$, $SO_2R^8$, $NHR^8$, $N(R^8)_2$, $NH_2$, $C(O)OH$, OH, CN, $NO_2$, F, Cl, Br and I; or two of $R^{2A}$, $R^{2B}$, $R^{2C}$, and $R^{2D}$ a on adjacent carbons form a fused ring selected from the group consisting of phenyl, 5-6 membered heteroaryl, $C_3$-$C_7$ cycloalkyl, $C_4$-$C_7$ cycloalkenyl, and 4-7 membered heterocyclyl; and the remaining are independently selected from the group consisting of hydrogen, $R^8$, $OR^8$, $C(O)R^8$, $OC(O)R^8$, $C(O)OR^8$, $SO_2R^8$, $NHR^8$, $N(R^8)_2$, $NH_2$, $C(O)OH$, OH, CN, $NO_2$, F, Cl, Br and I; wherein the phenyl, 5-6 membered heteroaryl, $C_3$-$C_7$ cycloalkyl, $C_4$-$C_7$ cycloalkenyl, and 4-7 membered heterocyclyl are optionally substituted with one or more substituents independently selected from the group consisting of $R^8$, $OR^8$, $C(O)R^8$, $OC(O)R^8$, $C(O)OR^8$, $SO_2R^8$, $NHR^8$, $N(R^8)_2$, $NH_2$, $C(O)OH$, OH, CN, $NO_2$, F, Cl, Br and I;

$R^3$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^3$ $C_2$-$C_6$ alkyl, $C_2$-$C_6$ alkenyl, and $C_2$-$C_6$ alkynyl are optionally substituted with one or more substituents independently selected from the group consisting of $C_1$-$C_6$ alkoxy, phenyl, OH, oxo, CN, $NO_2$, F, Cl, Br and I; wherein the $R^3$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^9$, $OR^9$, $C(O)R^9$, $OC(O)R^9$, $C(O)OR^9$, $SO_2R^9$, $C(O)NH_2$, $C(O)NHR^9$, $C(O)N(R^9)_2$, $NHC(O)R^9$, $NHR^9$, $N(R^9)_2$, $NH_2$, $C(O)OH$, OH, oxo, CN, $NO_2$, F, Cl, Br and I;

$R^4$ is selected from the group consisting of hydrogen and $C_1$-$C_6$ alkyl; wherein the $R^4$ $C_1$-$C_6$ alkyl is optionally substituted with one or more substituents independently selected from the group consisting of $R^{10}$, $OR^{10}$, $SR^{10}$, $NHR^{10}$, $N(R^{10})_2$, $NH_2$, $C(O)OH$, OH, oxo, CN, $NO_2$, F, Cl, Br and I;

$R^{5A}$, $R^{5B}$, $R^{5C}$, and $R^{5D}$ are each independently selected from the group consisting of hydrogen, $C_1$-$C_6$ alkyl, $C_2$-$C_6$ alkenyl, $C_2$-$C_6$ alkynyl, $C_1$-$C_6$ alkoxy, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^{5A}$, $R^{5B}$, $R^{5C}$, and $R^{5D}$ $C_1$-$C_6$ alkyl, $C_2$-$C_6$ alkenyl, $C_2$-$C_6$ alkynyl, and $C_1$-$C_6$ alkoxy are optionally substituted with one or more substituents independently selected from the group consisting of 6-10 membered aryl, 5-11 membered heteroaryl, $C_3$-$C_{11}$ cycloalkyl, $C_4$-$C_{11}$ cycloalkenyl, 4-12 membered heterocyclyl, $C_1$-$C_6$ thioalkyl, OH, oxo, CN, $NO_2$, F, Cl, Br and I; wherein the $R^{5A}$, $R^{5B}$, $R^{5C}$, and $R^{5D}$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $C_1$-$C_6$ alkyl, $C(O)OH$, $NH_2$, OH, oxo, CN, $NO_2$, F, Cl, Br and I; or $R^{5A}$ and $R^{5B}$, together with the carbon atom to which they are attached, form a $C_3$-$C_7$ monocyclic cycloalkyl or a 4-7 membered monocyclic heterocycle; wherein the $C_3$-$C_7$ monocyclic cycloalkyl and the 4-7 membered monocyclic heterocycle are each optionally substituted with one or more substituents independently selected from the group consisting of $C_1$-$C_6$ alkyl, $C(O)OH$, $NH_2$, OH, oxo, CN, $NO_2$, F, Cl, Br and I; and $R^{5C}$ and $R^{5D}$ are each independently selected from the group consisting of hydrogen, $C_1$-$C_6$ alkyl, $C_2$-$C_6$ alkenyl, $C_2$-$C_6$ alkynyl, $C_1$-$C_6$ alkoxy, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^{5C}$ and $R^{5D}$ $C_1$-$C_6$ alkyl, $C_2$-$C_6$ alkenyl, $C_2$-$C_6$ alkynyl, and $C_1$-$C_6$ alkoxy are optionally substituted with one or more substituents independently selected from the group consisting of 6-10 membered aryl, 5-11 membered heteroaryl, $C_3$-$C_{11}$ cycloalkyl, $C_4$-$C_{11}$ cycloalkenyl, 4-12 membered heterocyclyl, $C_1$-$C_6$ thioalkyl, OH, oxo, CN, $NO_2$, F, Cl, Br and I; wherein the $R^{5C}$ and $R^{5D}$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $C_1$-$C_6$ alkyl, $C(O)OH$, $NH_2$, OH, oxo, CN, $NO_2$, F, Cl, Br and I; or $R^{5C}$ and $R^{5D}$, together with the carbon atom to which they are attached, form a $C_3$-$C_7$ monocyclic cycloalkyl or a 4-7 membered monocyclic heterocycle; wherein the $C_3$-$C_7$ monocyclic cycloalkyl and the 4-7 membered monocyclic heterocycle are each optionally substituted with one or more substituents independently selected from the group consisting of $C_1$-$C_6$ alkyl, $C(O)OH$, $NH_2$, OH, oxo, CN, $NO_2$, F, Cl, Br and I; and $R^{6A}$, $R^{6B}$, $R^{6C}$, and $R^{6D}$ are each independently hydrogen;

$R^7$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^7$ $C_1$-$C_6$ alkyl, $C_2$-$C_6$ alkenyl, and $C_2$-$C_6$ alkynyl is optionally substituted with one or more substituents independently selected from the group consisting of $C_1$-$C_6$ alkoxy, OH, oxo, CN, $NO_2$, F, Cl, Br and I; wherein each $R^7$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, oxo, OH, CN, $NO_2$, F, Cl, Br and I;

$R^8$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of $R^{11}$, $OR^{11}$, $C(O)OR^{11}$, $NHR^{11}$, $N(R^{11})_2$, $NH_2$, $C(O)OH$, $OH$, $CN$, $NO_2$, F, Cl, Br and I; wherein each $R^8$ $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{12}$, $OR^{12}$, $C(O)OR^{12}$, $NHR^{12}$, $N(R^{12})_2$, $NH_2$, $C(O)OH$, OH, oxo, CN, $NO_2$, F, Cl, Br and I;

$R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{13}$, $OR^{13}$, $SR^{13}$, $C(O)R^{13}$, $NHR^{13}$, $N(R^{13})_2$, $C(O)OH$, OH, CN, $NO_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^{14}$, $OR^{14}$, $C(O)R^{14}$, $OC(O)R^{14}$, $C(O)OR^{14}$, $SO_2R^{14}$, $NHR^{14}$, $N(R^{14})_2$, $NH_2$, $C(O)OH$, OH, oxo, CN, $NO_2$, F, Cl, Br and I;

$R^{10}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{10}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{10}$ $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I;

$R^{11}$, at each occurrence, is independently selected from the group consisting of $C_1$-$C_6$ alkyl, $C_1$-$C_6$ alkoxy, $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl; wherein each $R^{11}$ $C_1$-$C_6$ alkyl and $C_1$-$C_6$ alkoxy is optionally substituted with one or more substituents independently selected from the group consisting of OH, oxo, CN, $NO_2$, F, Cl, Br and I; wherein each $R^{11}$ $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl is optionally substituted with one or more substituents independently selected from the group consisting of $C_1$-$C_6$ alkyl, $C_1$-$C_6$ alkoxy, F, Cl, Br and I;

$R^{12}$, at each occurrence, is independently selected from the group consisting of $C_1$-$C_6$ alkyl, $C_1$-$C_6$ alkoxy, $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl; wherein each $R^{12}$ $C_1$-$C_6$ alkyl and $C_1$-$C_6$ alkoxy is optionally substituted with one or more substituents independently selected from the group consisting of OH, oxo, CN, $NO_2$, F, Cl, Br and I; wherein each $R^{12}$ $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl is optionally substituted with one or more substituents independently selected from the group consisting of $C_1$-$C_6$ alkyl, $C_1$-$C_6$ alkoxy, F, Cl, Br and I;

$R^{13}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{13}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{13}$ $C_6$-$C_{10}$ membered aryl, 5-11 membered heteroaryl, cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I; and $R^{14}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, cycloalkyl, $C_4$-$C_{11}$ cycloalkenyl, and 4-12 membered heterocyclyl; wherein each $R^{14}$ $C_1$-$C_6$ alkyl, $C_2$-$C_6$ alkenyl, and $C_2$-$C_6$ alkynyl is optionally substituted with one or more substituents independently selected from the group consisting of $C_1$-$C_6$ alkyl, $C_1$-$C_6$ alkoxy, 5-6 membered heteroaryl, 4-12 membered heterocyclyl, OH, oxo, CN, $NO_2$, F, Cl, Br and I;

with the proviso that $R^3$ is not $C_1$-alkyl or thienyl;

with the proviso that, when $R^{2A}$, $R^{2B}$, $R^{2C}$, and $R^{2D}$ are each hydrogen, $R^1$ is not hydrogen;

with the proviso that, when $R^3$ is imidazolyl, $R^9$ is not $CH_2CH(CH_3)_2$;

with the proviso that when $R^{2B}$ is Cl, $R^3$ is not 2,4-dimethyl-5-thiazolyl or 2-cyano-3-fluorophenyl;

with the proviso that, when $R^3$ is cyclohexyl, n-butyl or isopropyl, $R^{2C}$ is not $OCH_3$;

with the proviso that, when $R^3$ is 3-pyridinyl, $R^{2C}$ is not Cl; and with the proviso that, when $R^3$ is phenyl, $R^{13}$ is not $C(O)CH_3$.

2. The compound of claim 1, or a pharmaceutically acceptable salt thereof, wherein
$R^4$ is hydrogen.

3. The compound of claim 2, or a pharmaceutically acceptable salt thereof, wherein
$A^1$ is 4. The compound of claim 2, or a pharmaceutically acceptable salt thereof, wherein A¹ is

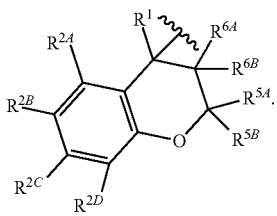

5. The compound of claim 4, or a pharmaceutically acceptable salt thereof, wherein
two of $R^{2A}$, $R^{2B}$, $R^{2C}$, and $R^{2D}$ are hydrogen and the remaining are independently selected from the group consisting of $R^8$ and $OR^8$; wherein $R^8$, at each occurrence, is independently selected from the group consisting of $C_1$-$C_6$ alkyl and $C_3$-$C_{11}$ cycloalkyl.

6. The compound of claim 5, or a pharmaceutically acceptable salt thereof, wherein
$R^1$ is hydrogen.

7. The compound of claim 6, or a pharmaceutically acceptable salt thereof, wherein
$R^{5A}$, $R^{5B}$, $R^{6A}$, and $R^{6B}$ are hydrogen.

8. The compound of claim 7, or a pharmaceutically acceptable salt thereof, wherein
$R^3$ is quinolinyl; wherein the $R^3$ quinolinyl is optionally substituted with one or more $R^9$; and $R^9$ is $C_1$-$C_6$ alkyl.

9. The compound of claim 1, or a pharmaceutically acceptable salt thereof, wherein
A¹ is

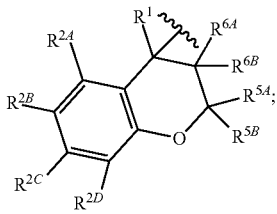

$R^1$ is hydrogen;
two of $R^{2A}$, $R^{2B}$, $R^{2C}$, and $R^{2D}$ are hydrogen and the remaining are independently selected from the group consisting of $R^8$ and $OR^8$;
$R^3$ is 5-11 membered heteroaryl; wherein the $R^3$ 5-11 membered heteroaryl is optionally substituted with one or more $R^9$;
$R^4$ is hydrogen;
$R^{5A}$ and $R^{5B}$ are each independently hydrogen;
$R^{6A}$ and $R^{6B}$ are each independently hydrogen;
$R^8$, at each occurrence, is independently selected from the group consisting of $C_1$-$C_6$ alkyl and $C_3$-$C_{11}$ cycloalkyl; and
$R^9$, at each occurrence, is independently $C_1$-$C_6$ alkyl.

10. A compound, or a pharmaceutically acceptable salt thereof, wherein the compound is selected from the group consisting of:
6-bromo-N-(naphthalene-1-sulfonyl)-4-phenyl-3,4-dihydro-2H-1-benzopyran-4-carboxamide;
(2R,4R)-2-[(ethylsulfanyl)methyl]-N-(naphthalene-1-sulfonyl)-4-phenyl-3,4-dihydro-2H-1-benzopyran-4-carboxamide;
6-methoxy-2,2-dimethyl-N-(naphthalene-1-sulfonyl)-4-phenyl-3,4-dihydro-2H-1-benzopyran-4-carboxamide;
6-methoxy-N-(naphthalene-1-sulfonyl)-4-phenyl-3,4-dihydro-2H-1-benzopyran-4-carboxamide;
6-benzoyl-5,7-dimethyl-N-(naphthalene-1-sulfonyl)-3,4-dihydro-2H-1-benzopyran-4-carboxamide;
N-(naphthalene-1-sulfonyl)-3-phenyl-2,3-dihydro-1-benzofuran-3-carboxamide;
8-chloro-N-(naphthalene-1-sulfonyl)-3,4-dihydro-2H-1-benzopyran-4-carboxamide;
3-ethyl-4-methoxy-N-(naphthalene-1-sulfonyl)-2,3-dihydro-1-benzofuran-3-carboxamide;
5-methoxy-N-(naphthalene-1-sulfonyl)-3,4-dihydro-2H-1-benzopyran-4-carboxamide;
4-ethyl-5-methoxy-N-(naphthalene-1-sulfonyl)-3,4-dihydro-2H-1-benzopyran-4-carboxamide;
8-bromo-5-methoxy-N-(naphthalene-1-sulfonyl)-3,4-dihydro-2H-1-benzopyran-4-carboxamide;
6,8-dibromo-5-methoxy-N-(naphthalene-1-sulfonyl)-3,4-dihydro-2H-1-benzopyran-4-carboxamide;
8-cyclobutyl-5-methoxy-N-(naphthalene-1-sulfonyl)-3,4-dihydro-2H-1-benzopyran-4-carboxamide;
8-cyclopentyl-5-methoxy-N-(naphthalene-1-sulfonyl)-3,4-dihydro-2H-1-benzopyran-4-carboxamide;
3-ethyl-7-methoxy-N-(naphthalene-1-sulfonyl)-2,3-dihydro-1-benzofuran-3-carboxamide;
2-methyl-N-(2-methylbenzene-1-sulfonyl)-2,3-dihydro-1-benzofuran-2-carboxamide;
N-(2-methylbenzene-1-sulfonyl)-2,3-dihydro-1-benzofuran-2-carboxamide;
6-methyl-N-(naphthalene-1-sulfonyl)-4-phenyl-3,4-dihydro-2H-1-benzopyran-4-carboxamide;
6-chloro-N-(naphthalene-1-sulfonyl)-4-phenyl-3,4-dihydro-2H-1-benzopyran-4-carboxamide;
4-methoxy-N-(naphthalene-1-sulfonyl)-2,3-dihydro-1-benzofuran-3-carboxamide;
7-bromo-N-(naphthalene-1-sulfonyl)-2,3-dihydro-1-benzofuran-3-carboxamide;
7-bromo-3-ethyl-N-(naphthalene-1-sulfonyl)-2,3-dihydro-1-benzofuran-3-carboxamide;
3-ethyl-N-(naphthalene-1-sulfonyl)-2,3-dihydro-1-benzofuran-3-carboxamide;
N-(naphthalene-1-sulfonyl)-3,4-dihydro-2H-1-benzopyran-4-carboxamide;
7-methoxy-N-(naphthalene-1-sulfonyl)-2,3-dihydro-1-benzofuran-3-carboxamide;
2-methyl-N-[4-(propan-2-yl)benzene-1-sulfonyl]-2,3-dihydro-1-benzofuran-2-carboxamide;
5-chloro-N-(2-methylbenzene-1-sulfonyl)-2,3-dihydro-1-benzofuran-3-carboxamide;
5-chloro-N-(propane-1-sulfonyl)-2,3-dihydro-1-benzofuran-3-carboxamide;
N-(2-methylbenzene-1-sulfonyl)-2,3-dihydro-1-benzofuran-3-carboxamide;
N-(2-methylbenzene-1-sulfonyl)-3,4-dihydro-2H-1-benzopyran-4-carboxamide;
(2S)—N-(naphthalene-1-sulfonyl)-4-phenyl-2-[(pyrrolidin-1-yl)methyl]-3,4-dihydro-2H-1-benzopyran-4-carboxamide;
(7S)-2,2-difluoro-7-methyl-N-(naphthalene-1-sulfonyl)-6,7-dihydro-2H-furo[2,3-f][1,3]benzodioxole-7-carboxamide;
(7R)-2,2-difluoro-7-methyl-N-(naphthalene-1-sulfonyl)-6,7-dihydro-2H-furo[2,3-f][1,3]benzodioxole-7-carboxamide;
N-(naphthalene-1-sulfonyl)-2,3-dihydro-1-benzofuran-3-carboxamide;

(4S)-8-bromo-5-methoxy-N-(naphthalene-1-sulfonyl)-3,4-dihydro-2H-1-benzopyran-4-carboxamide;
(4R)-8-bromo-5-methoxy-N-(naphthalene-1-sulfonyl)-3,4-dihydro-2H-1-benzopyran-4-carboxamide;
4-bromo-7-methoxy-N-(naphthalene-1-sulfonyl)-2,3-dihydro-1-benzofuran-3-carboxamide;
5-methoxy-N-(naphthalene-1-sulfonyl)-3,4-dihydrospiro[1-benzopyran-2,1'-cyclohexane]-4-carboxamide;
7-bromo-4-methoxy-N-(naphthalene-1-sulfonyl)-2,3-dihydro-1-benzofuran-3-carboxamide;
4-methoxy-N-(naphthalene-1-sulfonyl)-5-(trifluoromethyl)-2,3-dihydro-1-benzofuran-3-carboxamide and 4-methoxy-N-(naphthalene-1-sulfonyl)-7-(trifluoromethyl)-2,3-dihydro-1-benzofuran-3-carboxamide;
8-bromo-5-methoxy-N-(naphthalene-1-sulfonyl)-3,4-dihydrospiro[1-benzopyran-2,1'-cyclohexane]-4-carboxamide;
8-bromo-5-methoxy-N-(quinoline-8-sulfonyl)-3,4-dihydro-2H-1-benzopyran-4-carboxamide;
7-chloro-N-(naphthalene-1-sulfonyl)-2,3-dihydro-1-benzofuran-3-carboxamide;
7-chloro-3-ethyl-N-(naphthalene-1-sulfonyl)-2,3-dihydro-1-benzofuran-3-carboxamide;
N-(naphthalene-1-sulfonyl)-7-(trifluoromethyl)-2,3-dihydro-1-benzofuran-3-carboxamide;
8-bromo-5-methoxy-2,2-dimethyl-N-(quinoline-5-sulfonyl)-3,4-dihydro-2H-1-benzopyran-4-carboxamide;
5-methoxy-2,2-dimethyl-N-(quinoline-8-sulfonyl)-3,4-dihydro-2H-1-benzopyran-4-carboxamide;
5-methoxy-2,2-dimethyl-N-(quinoline-5-sulfonyl)-3,4-dihydro-2H-1-benzopyran-4-carboxamide;
5-methoxy-2,2-dimethyl-N-(naphthalene-1-sulfonyl)-3,4-dihydro-2H-1-benzopyran-4-carboxamide;
8-cyano-5-methoxy-2,2-dimethyl-N-(naphthalene-1-sulfonyl)-3,4-dihydro-2H-1-benzopyran-4-carboxamide;
8-chloro-5-methoxy-2,2-dimethyl-N-(naphthalene-1-sulfonyl)-3,4-dihydro-2H-1-benzopyran-4-carboxamide;
8-bromo-5-methoxy-2,2-dimethyl-N-(naphthalene-1-sulfonyl)-3,4-dihydro-2H-1-benzopyran-4-carboxamide;
5-methoxy-N-(naphthalene-1-sulfonyl)-8-(trifluoromethyl)-3,4-dihydro-2H-1-benzopyran-4-carboxamide;
8-cyclobutyl-5-methoxy-N-(quinoline-5-sulfonyl)-3,4-dihydro-2H-1-benzopyran-4-carboxamide;
(4S)-8-cyclobutyl-5-methoxy-N-(naphthalene-1-sulfonyl)-3,4-dihydro-2H-1-benzopyran-4-carboxamide;
(4R)-8-cyclobutyl-5-methoxy-N-(naphthalene-1-sulfonyl)-3,4-dihydro-2H-1-benzopyran-4-carboxamide;
(4S)-5-methoxy-N-(naphthalene-1-sulfonyl)-8-(trifluoromethyl)-3,4-dihydro-2H-1-benzopyran-4-carboxamide;
(4R)-5-methoxy-N-(naphthalene-1-sulfonyl)-8-(trifluoromethyl)-3,4-dihydro-2H-1-benzopyran-4-carboxamide;
(4S)-8-cyclobutyl-5-methoxy-N-(quinoline-5-sulfonyl)-3,4-dihydro-2H-1-benzopyran-4-carboxamide;
(4R)-8-cyclobutyl-5-methoxy-N-(quinoline-5-sulfonyl)-3,4-dihydro-2H-1-benzopyran-4-carboxamide;
3-ethyl-N-(naphthalene-1-sulfonyl)-7-(trifluoromethyl)-2,3-dihydro-1-benzofuran-3-carboxamide;
4,7-dimethoxy-N-(naphthalene-1-sulfonyl)-2,3-dihydro-1-benzofuran-3-carboxamide;
7-chloro-4-methoxy-N-(naphthalene-1-sulfonyl)-2,3-dihydro-1-benzofuran-3-carboxamide;
8-cyclopropyl-5-methoxy-N-(naphthalene-1-sulfonyl)-3,4-dihydro-2H-1-benzopyran-4-carboxamide;
(3S)-7-cyclobutyl-4-methoxy-N-(naphthalene-1-sulfonyl)-2,3-dihydro-1-benzofuran-3-carboxamide;
(3R)-7-cyclobutyl-4-methoxy-N-(naphthalene-1-sulfonyl)-2,3-dihydro-1-benzofuran-3-carboxamide;
(3R)-7-chloro-4-methoxy-N-(naphthalene-1-sulfonyl)-2,3-dihydro-1-benzofuran-3-carboxamide;
(3S)-7-chloro-4-methoxy-N-(naphthalene-1-sulfonyl)-2,3-dihydro-1-benzofuran-3-carboxamide;
(4S)-8-bromo-5-methoxy-N-(1-methyl-1H-indazole-7-sulfonyl)-3,4-dihydro-2H-1-benzopyran-4-carboxamide;
(4R)-8-bromo-5-methoxy-N-(1-methyl-1H-indazole-7-sulfonyl)-3,4-dihydro-2H-1-benzopyran-4-carboxamide;
(4S)-8-bromo-5-methoxy-2,2-dimethyl-N-(quinoline-5-sulfonyl)-3,4-dihydro-2H-1-benzopyran-4-carboxamide;
(4R)-8-bromo-5-methoxy-2,2-dimethyl-N-(quinoline-5-sulfonyl)-3,4-dihydro-2H-1-benzopyran-4-carboxamide;
(3R)-7-bromo-4-methoxy-N-(1-naphthylsulfonyl)-2,3-dihydrobenzofuran-3-carboxamide;
(3S)-7-bromo-4-methoxy-N-(1-naphthylsulfonyl)-2,3-dihydrobenzofuran-3-carboxamide;
8-cyclobutyl-5-methoxy-N-(2-methylquinoline-5-sulfonyl)-3,4-dihydro-2H-1-benzopyran-4-carboxamide;
(4S)-8-cyclobutyl-5-methoxy-N-(2-methylquinoline-5-sulfonyl)-3,4-dihydro-2H-1-benzopyran-4-carboxamide;
(4R)-8-cyclobutyl-5-methoxy-N-(2-methylquinoline-5-sulfonyl)-3,4-dihydro-2H-1-benzopyran-4-carboxamide;
5-bromo-8-methoxy-N-(naphthalene-1-sulfonyl)-3,4-dihydro-1H-2-benzopyran-1-carboxamide;
5-cyclobutyl-8-methoxy-N-(naphthalene-1-sulfonyl)-3,4-dihydro-1H-2-benzopyran-1-carboxamide;
7-cyclobutyl-4-methoxy-N-(quinoline-5-sulfonyl)-2,3-dihydro-1-benzofuran-3-carboxamide;
5-cyclobutyl-8-methoxy-N-(quinoline-5-sulfonyl)-3,4-dihydro-1H-2-benzopyran-1-carboxamide;
(3R)-7-cyclobutyl-4-methoxy-N-(quinoline-5-sulfonyl)-2,3-dihydro-1-benzofuran-3-carboxamide;
(3S)-7-cyclobutyl-4-methoxy-N-(quinoline-5-sulfonyl)-2,3-dihydro-1-benzofuran-3-carboxamide;
5-cyclobutyl-8-methoxy-1-methyl-N-(naphthalene-1-sulfonyl)-3,4-dihydro-1H-2-benzopyran-1-carboxamide;
8-cyclobutyl-5-methoxy-N-(1,2,3,4-tetrahydroquinoline-5-sulfonyl)-3,4-dihydro-2H-1-benzopyran-4-carboxamide;
(4R)-8-cyclobutyl-5-methoxy-2,2-dimethyl-N-(quinoline-5-sulfonyl)-3,4-dihydro-2H-1-benzopyran-4-carboxamide;
7-cyclobutyl-4-methoxy-N-(1-methyl-1H-benzimidazole-7-sulfonyl)-2,3-dihydro-1-benzofuran-3-carboxamide;
7-cyclobutyl-4-methoxy-N-(pyrazolo[1,5-a]pyridine-4-sulfonyl)-2,3-dihydro-1-benzofuran-3-carboxamide;
7-cyclobutyl-4-methoxy-N-(1,2,3,4-tetrahydroquinoline-5-sulfonyl)-2,3-dihydro-1-benzofuran-3-carboxamide;
7-cyclobutyl-4-methoxy-N-(1,2,3,4-tetrahydroquinoline-8-sulfonyl)-2,3-dihydro-1-benzofuran-3-carboxamide;
(4S)-8-cyclobutyl-5-methoxy-N-(1,2,3,4-tetrahydroquinoline-5-sulfonyl)-3,4-dihydro-2H-1-benzopyran-4-carboxamide;
(4R)-8-cyclobutyl-5-methoxy-N-(1,2,3,4-tetrahydroquinoline-5-sulfonyl)-3,4-dihydro-2H-1-benzopyran-4-carboxamide;

8-cyclobutyl-5-methoxy-2,2-dimethyl-N-(1,2,3,4-tetrahydroquinoline-5-sulfonyl)-3,4-dihydro-2H-1-benzopyran-4-carboxamide;
(3R)-7-cyclobutyl-4-methoxy-N-(1-methyl-1H-indazole-7-sulfonyl)-2,3-dihydro-1-benzofuran-3-carboxamide;
(3S)-7-cyclobutyl-4-methoxy-N-(1-methyl-1H-indazole-7-sulfonyl)-2,3-dihydro-1-benzofuran-3-carboxamide;
(4S)-8-cyclobutyl-5-methoxy-2,2-dimethyl-N-(1,2,3,4-tetrahydroquinoline-5-sulfonyl)-3,4-dihydro-2H-1-benzopyran-4-carboxamide;
(4R)-8-cyclobutyl-5-methoxy-2,2-dimethyl-N-(1,2,3,4-tetrahydroquinoline-5-sulfonyl)-3,4-dihydro-2H-1-benzopyran-4-carboxamide;
(3R)-7-cyclobutyl-4-methoxy-N-(1,2,3,4-tetrahydroquinoline-8-sulfonyl)-2,3-dihydro-1-benzofuran-3-carboxamide;
(3S)-7-cyclobutyl-4-methoxy-N-(1,2,3,4-tetrahydroquinoline-8-sulfonyl)-2,3-dihydro-1-benzofuran-3-carboxamide;
(3R)-7-cyclobutyl-4-methoxy-N-(1,2,3,4-tetrahydroquinoline-5-sulfonyl)-2,3-dihydro-1-benzofuran-3-carboxamide;
(3S)-7-cyclobutyl-4-methoxy-N-(1,2,3,4-tetrahydroquinoline-5-sulfonyl)-2,3-dihydro-1-benzofuran-3-carboxamide;
8-cyclobutyl-N-(1H-indole-4-sulfonyl)-5-methoxy-3,4-dihydro-2H-1-benzopyran-4-carboxamide;
(4S)-8-cyclobutyl-N-(1H-indole-4-sulfonyl)-5-methoxy-3,4-dihydro-2H-1-benzopyran-4-carboxamide;
(4R)-8-cyclobutyl-N-(1H-indole-4-sulfonyl)-5-methoxy-3,4-dihydro-2H-1-benzopyran-4-carboxamide;
5-cyclobutyl-8-methoxy-N-(quinoline-5-sulfonyl)-3,4-dihydro-2H-1-benzopyran-4-carboxamide;
(4R)-5-cyclobutyl-8-methoxy-N-(quinoline-5-sulfonyl)-3,4-dihydro-2H-1-benzopyran-4-carboxamide;
(4S)-5-cyclobutyl-8-methoxy-N-(quinoline-5-sulfonyl)-3,4-dihydro-2H-1-benzopyran-4-carboxamide;
8-bromo-5-methoxy-N-(naphthalene-1-sulfonyl)-3,4-dihydro-1H-2-benzopyran-1-carboxamide;
N-(naphthalene-1-sulfonyl)-7-(trifluoromethoxy)-3,4-dihydro-1H-2-benzopyran-1-carboxamide;
5-methoxy-N-(naphthalene-1-sulfonyl)-3,4-dihydro-1H-2-benzopyran-1-carboxamide; and
pharmaceutically acceptable salts thereof.

11. 8-Cyclobutyl-5-methoxy-N-(2-methylquinoline-5-sulfonyl)-3,4-dihydro-2H-1-benzopyran-4-carboxamide, or a pharmaceutically acceptable salt thereof.

12. (4S)-8-Cyclobutyl-5-methoxy-N-(2-methylquinoline-5-sulfonyl)-3,4-dihydro-2H-1-benzopyran-4-carboxamide; or a pharmaceutically acceptable salt thereof.

13. (4R)-8-Cyclobutyl-5-methoxy-N-(2-methylquinoline-5-sulfonyl)-3,4-dihydro-2H-1-benzopyran-4-carboxamide; or a pharmaceutically acceptable salt thereof.

14. 8-Cyclobutyl-N-(1H-indole-4-sulfonyl)-5-methoxy-3,4-dihydro-2H-1-benzopyran-4-carboxamide; or a pharmaceutically acceptable salt thereof.

15. (4S)-8-Cyclobutyl-N-(1H-indole-4-sulfonyl)-5-methoxy-3,4-dihydro-2H-1-benzopyran-4-carboxamide; or a pharmaceutically acceptable salt thereof.

16. (4R)-8-Cyclobutyl-N-(1H-indole-4-sulfonyl)-5-methoxy-3,4-dihydro-2H-1-benzopyran-4-carboxamide; or a pharmaceutically acceptable salt thereof.

17. 5-Cyclobutyl-8-methoxy-N-(quinoline-5-sulfonyl)-3,4-dihydro-2H-1-benzopyran-4-carboxamide; or a pharmaceutically acceptable salt thereof.

18. (4R)-5-Cyclobutyl-8-methoxy-N-(quinoline-5-sulfonyl)-3,4-dihydro-2H-1-benzopyran-4-carboxamide; or a pharmaceutically acceptable salt thereof.

19. (4S)-5-Cyclobutyl-8-methoxy-N-(quinoline-5-sulfonyl)-3,4-dihydro-2H-1-benzopyran-4-carboxamide; or a pharmaceutically acceptable salt thereof.

* * * * *